US006683055B1

(12) United States Patent
Hillen et al.

(10) Patent No.: US 6,683,055 B1
(45) Date of Patent: Jan. 27, 2004

(54) LOW MOLECULAR WEIGHT INHIBITORS OF COMPLEMENT PROTEASES

(75) Inventors: Heinz Hillen, Hassloch (DE); Martin Schmidt, Bensheim (DE); Helmut Mack, Ludwigshafen (DE); Werner Seitz, Plankstadt (DE); Andreas Haupt, Schwetzingen (DE); Johann-Christian Zechel, Nussloch (DE); Andreas Kling, Mannheim (DE)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 09/539,811

(22) Filed: Mar. 30, 2000

(30) Foreign Application Priority Data

Apr. 9, 1999 (DE) ......................................... 199 15 930

(51) Int. Cl.$^7$ .............................................. C07K 5/06

(52) U.S. Cl. ........................... 514/19; 530/331; 514/18; 548/100; 548/400; 549/29

(58) Field of Search ........................... 530/331; 514/18, 514/19; 548/100, 400

(56) References Cited

U.S. PATENT DOCUMENTS

| | | | |
|---|---|---|---|
| 4,980,495 A | 12/1990 | Etzbach | 558/451 |
| 5,852,051 A | 12/1998 | Böhm et al. | 549/423 |
| 5,932,567 A | 8/1999 | Seitz et al. | 514/210 |
| 6,030,972 A | 2/2000 | Böhm et al. | 514/257 |
| 6,114,358 A | 9/2000 | Baucke et al. | 514/336 |

FOREIGN PATENT DOCUMENTS

| | | |
|---|---|---|
| CA | 2 193 133 | 12/1995 |
| CA | 2 263 220 | 2/1998 |
| CA | 2 264 723 | 3/1998 |
| EP | 0 601 459 | 6/1994 |
| WO | WO 94/29336 | 12/1994 |
| WO | WO 95/35309 | 12/1995 |
| WO | WO 97/23499 | 7/1997 |
| WO | WO 98/06741 | 2/1998 |
| WO | WO 98/09950 | 3/1998 |
| WO | WO 98/55471 | 12/1998 |

OTHER PUBLICATIONS

Fitzgerald (Coronary Artery Disease 7, 911, 1996).*
Tofukuji M (Annals of Thoracic Surgery 69 (3) 799–807, 2000).*
Stammberger Uz (European Journal of Cardiac–thoracic Surgery 22 (3) 368, 2002).*
Park P (Journal of the American Society of Nephrology 12 (7) 1383–90, 2001).*
Niederau C (International Journal of Pancreatology 17 (2) 189–96, 1995).*
Patston, Peter Gettins (Biochemistry 30(36), 8876–8882, 1991).*
Spath et al. "Inherited and Acquired Deficiencies in C1 Esteres Inhibitors in Humans" The Complement System (1998) pp. 353–410.
Weiser et al. "Reperfusion Injury of Ischemic Skeletal Muscle Is Mediated by Natural Antibody and Complement" J. Exp. Med. vol. 183 (1996) pp. 2343–2348.
Arlaud et al. "The Atypical Serine Proteases of the Complement System" Advances in Immunology vol. 69(1998) pp. 249–305.
Ikari et al. "New Synthetic Inhibitor to the Alternative Complement Pathway" Immunology vol. 149(1983) pp. 685–691.
Torzewski et al. "Process in the atherogenesis: complement activation" Atherosclerosis vol. 132(1997) pp. 131–138.
P. Ward et al., "The Numerous Proinflammatory Functions of $C5_a$," XVII International Complement Workshop Abstract 324 in Molecular Immunology (1998) p. 411.
Yasojuma et al. "Human Heart Generates Complement Proteins that are Upregulated and Activated After Myocardial Infarction" Circulation Research (1998) pp. 860–869.
Makrides "Therapeutic Inhibition of the Complement System", vol. 50, No. 1(1998) pp. 59–85.
Lucchesi et al. "Complement Inhibitors in Myocardial Ischemia/Reperfusion Injury" Immunopharmacology vol. 38(1997) pp. 37–42.
Hagmann et al. "Potential Therapeutic Modifiers of the Complement Cascade" Annual Reports of Medicinal Chem. vol. 27 (1992) pp. 199–208.
Morgan "Physiology and Pathophysiology of Complement: Progress and Trends" Critical Reviews in Clinical Laboratory Sciences vol. 32 No. 3 (1995) pp. 265–298.
Morgan "Intervention in the Complement System: a Therapeutic Strategy in Inflammation" Biochemical Soc. Transactions vol. 24(1996)pp. 224–229.
Liszewski et al. "Novel Complement Inhibitors" Ex. Opin. Invest. Drugs vol. 7 No. 3 (1998) pp. 323–332.
Guerrero et al. "Endotoxin–induced Pulmonary Dysfunction is Prevented by C1–Esterase Inhibitor" J. of Clinical Inv. (1993)pp. 2754–2760.
Buerke et al. "Cardioprotective Effects of a C1 Esterase Inhibitor in Myocardial Ischemia and Reperfusion" Circulation vol. 91, No. 2 (1995) pp. 393–402.
Ostreicher et al. "Proctection of Procine Endothelial Cells From Complement–Mediated Cytotoxicity By The Human Complement Regulators CD59, C1 Inhibitor, and Soluble Complement Receptor Type 1" Transplantation vol. 62, No. 11 (1996) pp. 1693–1696.

(List continued on next page.)

Primary Examiner—Christopher S. F. Low
Assistant Examiner—D. Lukton
(74) Attorney, Agent, or Firm—Wood, Phillips, Katz, Clark & Mortimer

(57) ABSTRACT

Peptide substances, their preparation and their use as complement inhibitors are described. These are in particular substances having a guanidine or amidine radical as a terminal group. In particular, inhibitors of the complement proteases C1s and C1r are described.

16 Claims, No Drawings

OTHER PUBLICATIONS

Horstick et al. "Intracoronary Application of C1 Esterase Inhibitor Improves Cardiac Function and Reduces Myocardial Necrosis in an Experimental Model of Ischemia and Reperfusion" Circulation vol. 95, No. 3 (1997) pp. 701–708.

Salvatierra et al. "$C_1$–Esterase Inhibitor Prevents Early Pulmonary Dysfunction after Lung Transplantation in the Dog" Am. J. Respir Crit Care Med. vol. 155 (1997) pp. 1147–1154.

Nissen et al. "C1–esterase inhibitor blocks T lymphocyte proliferation and cytotoxic T lymphocyte generation in vitro" International Immunology vol. 10 No. 2, (1997) pp. 167–173.

Buerke et al. "Blocking of Classical Complement Pathway Inhibits Endothelial Adhesion Molecule Expression and Preserves Ischemic Myocardium from Reperfusion Injury" J. Pharm & Exp. Therapeutics, vol. 286, No. 1 (1998) pp. 429–438.

Nürnberger et al. "Activity of C1 Esterase Inhibitor In Patients and Vascular Leak Syndrome after Bone Marrow Transplantation" Annals of Hemotology No. 67 (1993) pp. 17–21.

Dalmasso et al. "Prevention of Complement–Mediated Activation of Xenogenic Endothelial Cells in an In Vitro Model of Xenograft Hyperacute Rejection By C1 Inhibitor" Transplantation vol. 56, No. 5(1993) pp. 1171–1176.

Hack et al. "Initial Studies on the Administration of C1–Esterase Inhibitor to Patient with Septic Shock or with a Vascular Leak Syndrome Induced by Interleukin–2 Therapy" Progress in Clinical and Biological Research (1994) pp. 335–357.

Niederau et al. "Effects of C1–Esterase Inhibitor in Three Models of Acute Pancreatitis" Intl J. of Pancreantology vol. 17, No. 2 (1995) pp. 189–196.

Sefat et al. "The Therapeutic Effect of C1–Inhibitor on Gut–Derived Bacterial Translocation After Thermal Injury" Shock vol. 9, No. 2 (1998) pp. 101–108.

Bauernschmitt et al. "Rescue Therapy with C–1 Esterase Inhibitor Concentrate After Emergency Coronary Surgery for Failed PTCA" Intensive Care Medicine No. 24 (1998) pp. 635–638.

Shirai et al. "Intermediate in Sommelet–Hauser Rearrangement of N,N–Dimentylbenzylammonium N–Methylides" J. Org. Chem. vol. 55 (1990) pp. 2676–2770.

Rosowsky et al. "(6R, 6S)–5,8, 10–Trideaza–5,6,7,8–tetrahydrofolate and (6R,6S)–5,8,10–Trideaza–5,6,7,8–tetrahydropteroyl–L–ornithine as Potential Antifolates and Antitumor Agents" J.Med.Chem. No. 32(1989)pp. 709–715.

Kami et al. "Human Complement Proteins D, C2, and B" J. Bio Chem. vol. 262, No. 8, (1987) pp. 3444–3451.

Whaley et al. "Haemolytic assays for whole complement activity and individual components" Oxford University Press, (1997) pp. 20–91.

* cited by examiner

LOW MOLECULAR WEIGHT INHIBITORS OF COMPLEMENT PROTEASES

The present invention relates to peptide substances, their preparation and their use as complement inhibitors. In particular, these are substances having a guanidine or amidine radical as terminal group. In particular, the present invention relates to inhibitors of the complement proteases C1s and C1r.

The activation of the complement system leads, via a cascade of about 30 proteins, finally to, inter alia, the lysis of cells. At the same time, molecules which, like, for example, C5a, can lead to an inflammatory reaction are liberated. Under physiological conditions, the complement system provides defense against foreign bodies, e.g. viruses, fungi, bacteria and cancer cells. The activation by the various routes takes place initially via proteases. Activation enables these proteases to activate other molecules of the complement system, which in turn may be inactive proteases. Under physiological conditions, this system—similarly to blood coagulation—is under the control of regulator proteins which counteract excessive activation of the complement system. In these cases, intervention to inhibit the complement system is not advantageous.

In some cases, however, the complement system overreacts and this contributes to the pathophysiology of disorders. In these cases, therapeutic intervention in the complement system by inhibition or modulation of the overshooting reaction is desirable. Inhibition of the complement system is possible at various levels in the complement system and by inhibition of various effectors. The literature contains examples of the inhibition of the serine proteases at the C1 level with the aid of the C1-esterase inhibitor as well as inhibition at the level of the C3- and C5-convertases with the aid of soluble complement receptor CR1 (sCR1), inhibition at the C5 level with the aid of antibodies and inhibition at the C5a level with the aid of antibodies or antagonists. The tools used for achieving the inhibition in the abovementioned examples are proteins. The present invention describes low molecular weight substances which are used for inhibiting the complement system.

In general activation of the complement system is to be expected in every inflammatory disorder which is associated with intrusion of neutrophilic blood cells. It is therefore expected that an improvement in pathophysiological status will be achieved in all these disorders by inhibiting parts of the complement system.

The activation of the complement is associated with the following disorders or pathophysiological conditions (Liszewski, M. K.; Atkinson, J. P.: Exp. Opin. Invest. Drugs 7(3) (1998): 324–332; Morgan, B. P.: Biochemical Society Transactions 24; (1996), 224–9; Morgan, B. P.: Critical Review in Clinical Laboratory Sciences 32 (3); (1995), 265–298; Hagmann, W. K.; Sindelar, R. D.: Annual reports in medicinal chemistry 27, (1992), 199 et seq.; Lucchesi, B. R.; Kilgore, K. S.: Immunopharmacology 38 (1997), 27–42; Makrides, S. C.: Pharmacological Reviews 50(1)(1998), 59–85)

Reperfusion injuries after ischemias; ischemic conditions, during, for example, operations with the aid of heart-lung machines; operations in which blood vessels are clamped off generally for avoiding major hemorrhages; myocardial infarction; thromboembolic cerebral infarction; pulmonary thrombosis, etc.;

Hyperacute organ rejection; especially in xenotransplantations;

Organ failure, e.g. multiple organ failure or ARDS (adult respiratory distress syndrome);

Disorders due to trauma (cranial trauma) or multiple injury, e.g. thermal injury (burns);

Anaphylactic shock;

Sepsis; "vascular leak syndrome": in the case of sepsis and after treatment with biological agents, such as interleukin-2 or after transplantation;

Alzheimer's disease and other inflammatory neurological disorders, such as myastenia graevis, multiple sclerosis, cerebral lupus, Guillain-Barre syndrome; meningitis; encephalitis;

Systemic lupus erythematosus (SLE);

Rheumatoid arthritis and other inflammatory disorders of the rheumatoid disorder group, e.g. Behcet's Syndrome; Juvenile rheumatoid arthritis;

Renal inflammations of various origin, e.g. Glomerulonephritis, *Lupus nephriti;*

Pancreatitis;

Asthma; chronic bronchitis;

Complications during dialysis in the case of kidney failure;

Vasculitis; thyroiditis;

*Ulcerative colitis* and other inflammatory disorders of the gastrointestinal tract;

Autoimmune diseases.

It is possible that complement plays a role in spontaneous abortions, based on immunological rejection reactions (Giacomucci E., Bulletti C., Polli V., Prefetto R A., Flamigni C., Immunologically mediated abortion (IMA). Journal of Steroid Biochemistry & Molecular Biology, 49(2–3) (1994), 107–21). Here, it is possible that modulation of the immunological rejection reaction is achieved by inhibition of the complement system and hence the rate of abortions is correspondingly reduced.

Complement activation plays a role in the case of side effects of drugs. Liposome-based therapies which are used, for example, in cancer treatment may be mentioned as an example here. Hypersensitive reactions have been observed in patients who have been treated with drug formulations based on liposomes (Transfusion 37 (1997) 150). Activation of the complement system has also been demonstrated for other excipients used in drug formulations, e.g. Cremophor EL (Szebeni, J. et al. Journal of the National Cancer Institute 90 (4); 1998). The complement activation may therefore be responsible for the anaphylactoid reactions observed in some cases. Inhibition of the complement system, for example by the C1s inhibitors mentioned here, should therefore alleviate the side effects of medicaments based on activation of the complement system and reduce resulting hypersensitivity reactions.

In the abovementioned disorders, activation of the complement system has been demonstrated.

The synthesis of complement proteins in special diseased tissues or organs indicates participation of the complement system in the pathophysiology of these disorders. Thus, in the case of myocardial infarction, vigorous further synthesis of many complement proteins in the myocardium was detected (Yasojima, K.; Schwab, C.; McGeer, E. G.; McGeer, P. L.; Circulation Research 83 (1998), 860–869). This was also detected in inflammatory disorders of the brain, e.g. multiple sclerosis and bacterial meningitis, and in colitis.

Evidence that complement activation has taken place can be provided by detecting the cell lysis complex in the tissue and by detecting soluble SC5b-9 or other activation products of complement, e.g. factor Bb, C3a; C4a, C5a; C3b, C3d; etc., in the plasma. By corresponding tests, it was possible to demonstrate, inter alia, participation of the complement system in the atherosclerosis as well as to show a relationship with myocardial infarction, unstable angina pectoris and organ transplantations, to mention but a few examples.

Raised blood levels of complement proteins, such as C3 or C4, are correlated with various cardiovascular disorders, e.g. heart failure, as well as diabetes. A similar relationship has imposulated for an increase in TNF in the case of heart failure. Initial studies on the treatment of heart failure with TNF inhibitors (soluble TNF receptor, antibodies) were rated positively. TNF is secreted, for example, after stimulation by complement factor C5a. It has been possible to show that inhibition of the C5a action prevents release of TNF (XVII International Complement Workshop, P. Ward, Abstract 324 in Molecular Immunology 35 (411 6–7), 1998). Accordingly, a treatment of disorders, in which raised levels of complement proteins are present, with the inhibitors described in this publication is possible, as the treatment of disorders in which raised levels of TNF are present.

Furthermore, the participation of complement has been demonstrated in the case of (Atherosclerosis 132 (1997); 131–138. Particular complications due to rapid atherosclerotic processes occur, for example, in organs after transplantations. These processes are the most frequent reason for the chronic failure of the transplanted organs in clinical medicine. In future, apart from transplantations of human organs (allotransplantations) uses of transplants from other species (xenotransplants) has also been considered.

Accordingly, the treatment of the abovementioned disorders or pathophysiological conditions with complement inhibitors is desirable, in particular the treatment with low molecular weight inhibitors.

FUT and FUT derivatives are amidinophenolic esters and amidinonaphthol esters and are described as complement inhibitors (e.g. Immunology 49(4) (1983), 685–91).

Serine proteases are present in the complement system in the three different activation routes: the traditional, alternative and MBL route (Arlaud, G. J. et al. Advances in Immunology 69; (1998) 249 et seq.). In their respective routes, they play a decisive role at the beginning of the cascade.

Inhibitors of the corresponding serine proteases can intervene here both in a completely inhibitory manner and in a modulating manner (partial inhibition) if the complement has been pathophysiologically activated.

Some proteases of the various activation routes are particularly suitable for inhibiting the complement system. From the class of the thrombin-like serine proteases these are the complement proteases C1r and C1s in the traditional route, factor D and factor B in the alternative route and MASP I and MASP II in the MBL route. Inhibition of these proteases then leads to restoration of physiological control of the complement system in the abovementioned disorders or pathophysiological conditions.

The traditional route of the complement system is usually activated by means of antibodies which have bound to an antigen. In physiological conditions this route of the complement system helps in the defense against foreign bodies which are recognized by antibodies. However, an overreaction leads to injuries in the tissue and the body. These injuries can be prevented by inhibiting of the traditional route. According to present knowledge, activation of the complement system via antibodies is experienced during hyperacute organ rejection and especially in the case of xenotransplantations; in the case of reperfusion injuries after ischemias (possibly via IgM antibodies and a neoepitope; Literature: Journal of Exp. Med. 183, (1996), 2343–8; Carroll, XVII International Complement Workshop, Rhodes 1998), for example in the case of myocardial infarction, other thrombotic disorders or long-term vascular occlusions, as are usual, for example, during operations; in the case of anaphylactic shock; in the case of sepsis; in the case of SLE; in the case of disorders in the area of rheumatoid arthritis, renal inflammations of various origins; vasculitis, all autoimmune diseases and allergies. In general, injuries in various organs due to activation of the complement system are to be expected in the case of every disorder in which circulating immune complexes are present. A part of the invention is to prevent these injuries by the C1-inhibitors described.

Activation of the complement system by the traditional route takes place under pathophysiological conditions partly with circumvention of antibodies. Examples of this are Alzheimer's disease, and the unspecified activation of this route by other proteases, as occur, for example, in the lysis therapy following myocardial infarction. In these cases, too, limitation of the injury to be achieved with the C1 inhibitors described.

The activation of the classical route has been demonstrated, for example, by the detection of the activated proteins, for example C1q in the affected tissue (e.g. Circulation Research 83; (1998) 860). However, the pathophysiological participation of the complement system is more substantial if inhibitors which inhibit only the traditional route in the complement system are used. A physiological inhibitor for this purpose is the C1-esterase inhibitor (protein is described in The Complement System, Rother, Till, H änsch eds.; Springer; 1998; pages 353 et seq.). With the aid of this inhibitor, participation of the traditional route and the possibility of therapeutic intervention have been demonstrated in experiments. Some references are given in more detail below:

1. Bauernschmitt R. Bohrer H. Hagl S. Rescue therapy with C1-esterase inhibitor concentrate after emergency coronary surgery for failed PTCA. Intensive Care Medicine. 24(6): (1998), 635–8.
2. Khorram-Sefat R. Goldmann C. Radke A. Lennartz A. Mottaghy K. Afify M. Kupper W. Klosterhalfen B. The therapeutic effect of C1-inhibitor on gut-derived bacterial translocation after thermal injury. Shock. 9(2): (1998) 101–8.
3. Niederau C. Brinsa R. Niederau M. Luthen R. Strohmeyer G. Ferrell L D. Effects of C1-esterase inhibitor in three models of acute pancreatitis. International Journal of Pancreatology. 17(2): (1995) 189–96.
4. Hack C E. Ogilvie A C. Eisele B. Jansen P M. Wagstaff J. Thijs L G. Initial studies on the administration of C1-esterase inhibitor to patients with septic shock or with a vascular leak syndrome induced by interleukin-2 therapy. Progress in Clinical & Biological Research. 388: (1994), 335–57.
5. Dalmasso A P. Platt J L. Prevention of complement-mediated activation of xenogeneic endothelial cells in an in vitro model of xenograft hyperacute rejection by C1 inhibitor. Transplantation. 56(5): (1993), 1171–6.
6. Nurnberger W. Michelmann I. Petrik K. Holthausen S. Willers R. Lauermann G. Eisele B. Delvos U. Burdach S. Gobel U. Activity of C1 esterase inhibitor in patients with vascular leak syndrome after bone marrow transplantation. Annals of Hematology. 67(1): (1993), 17–21.
7. Buerke M. Prufer D. Dahm M. Oelert H. Meyer J. Darius H. Blocking of classical complement pathway inhibits endothelial adhesion molecule expression and preserves ischemic myocardium from reperfusion injury. Journal of Pharmacology & Experimental Therapeutics. 286(1): (1998), 429–38.

8. Nissen M H. Bregenholt S. Nording J A. Claesson M H. C1-esterase inhibitor blocks T lymphocyte proliferation and cytotoxic T lymphocyte generation in vitro. International Immunology. 10(2): (1998), 167–73.
9. Salvatierra A. Velasco F. Rodriguez M. Alvarez A. Lopez-Pedrera R. Ramirez R. Carracedo J. Lopez-Rubio F. Lopez-Pujol A. Guerrero R. C1-esterase inhibitor prevents early pulmonary dysfunction after lung transplantation in the dog. American Journal of Respiratory & Critical Care Medicine. 155(3): (1997), 1147–54.
10. Horstick G. Heimann A. Gotze O. Hafner G. Berg O. Boehmer P. Becker P. Darius H. Rupprecht H J. Loos M. Bhakdi S. Meyer J. Kempski O. Intracoronary application of C1 esterase inhibitor improves cardiac function and reduces myocardial necrosis in an experimental model of ischemia and reperfusion. Circulation. 95(3): (1997), 701–8.
11. Heckl-Ostreicher B. Wosnik A. Kirschfink M. Protection of porcine endothelial cells from complement-mediated cytotoxicity by the human complement regulators CD59, C1 inhibitor, and soluble complement receptor type 1. Analysis in a pig-to-human in vitro model relevant to hyperacute xenograft rejection. Transplantation. 62(11): (1996), 1693–6.
12. Niederau C. Brinsa R. Niederau M. Luthen R. Strohmeyer G. Ferrell L D. Effects of C1-esterase inhibitor in three models of acute pancreatitis. International Journal of Pancreatology. 17(2): (1995), 189–96.
13. Buerke M. Murohara T. Lefer A M. Cardioprotective effects of a C1 esterase inhibitor in myocardial ischemia and reperfusion circulation. 91(2): (1995), 393–402.
14. Hack C E. Ogilvie A C. Eisele B. Jansen P M. Wagstaff J. Thijs L G. Initial studies on the administration of C1-esterase inhibitor to patients with septic shock or with a vascular leak syndrome induced by interleukin-2 therapy. Progress in Clinical & Biological Research. 388: (1994), 335–57.
15. Dalmasso A P. Platt J L. Prevention of complement-mediated activation of xenogeneic endothelial cells in an in vitro model of xenograft hyperacute rejection by C1 inhibitor. Transplantation. 56(5): (1993), 1171–6.
16. Guerrero R. Velasco F. Rodriguez M. Lopez A. Rojas R. Alvarez M A. Villalba R. Rubio V. Torres A. del Castillo D. Endotoxin-induced pulmonary dysfunction is prevented by C1-esterase inhibitor. Journal of Clinical Investigation. 91(6): (June 1993), 2754–60.

Inhibitors which inhibit C1s and/or C1r but not factor D are desirable. Preferably, MASP-I and lysis enzymes, such as t-PA and plasmin, should not be inhibited.

A hereditary disease, hereditary angioneurotic edema, which is due to a deficiency of C1-esterase inhibitor is usually treated by administering C1-esterase inhibitor. Treatment with the C1 inhibitors described here, under certain circumstances as additional medication, is likewise an application of this invention.

Substances which effectively inhibit $C_{1s}$ and $C_{1r}$ are particularly preferred.

PHARMACOLOGICAL EXAMPLES

Example A
Color Substrate Test for C1r Inhibition

| Reagents: | C1r from human plasma, activated, two-chain form (purity: about. 95% according to SDS gel). No foreign protease activity detectable.<br>Substrate: Cbz-Gly-Arg-S-Bzl, product No.: WBASO12, (from PolyPeptide, D-38304 Wolfenbüttel, Germany) Color reagent: DTNB (5,5'dinitro-bis-2-nitrobenzoic acid) (NO. 43760, Fluka, CH-9470 Buchs, Switzerland) Buffer: 150 mM Tris/HCl pH = 7.50 Color substrate test for C1r inhibition |
|---|---|
| Test procedure: | The color substrate test for determining the C1s activity is carried out in 96-well microtiter plates.<br>10 µl of the inhibitor solution in 20% strength DMSO (DMSO diluted with 15 millimolar Tris/HCl pH = 7.50) are added to 140 µl of test buffer, which contains C1s in a final concentration of 0.013 U/ml and DTNB with a final concentration of 0.27 mM/l. Incubation is carried out for 10 minutes at 20 to 25° C.<br>The test is started by adding 50 µl of 1.5 millimolar substrate solution in 30% strength DMSO (final concentration 0.375 mmol/l). After an incubation time of 30 minutes at from 20 to 25° C., the absorbance of each well at 405 nm is measured in a two-beam microtiter plate photometer against a blank value (without enzyme). |
| Measurement criteria: | $IC_{50}$: required inhibitor concentration to reduce the amidolytic C1r activity to 50%. |
| Statistical evaluation: | The dependence of absorbance on the inhibitor concentration serves as a basis for the calculation. |

Example B
Material and Methods: Color Subrate Test for C1s Inhibition

| Reagents: | C1s from human plasma, activated, two-chain form (purity: about 95% according to SDS gel). No foreign protease activity detectable.<br>Substrate: Cbz-Gly-Arg-S-Bzl, product No.: WBASO12, (from PolyPeptide, D-38304 Wolfenbüttel, Germany) Color reagent: DTNB (5,5'dinitro-bis-2-nitrobenzoic acid) (No. 43760, Fluka, CH-9470 Buchs, Switzerland) Buffer: 150 mM Tris/HCl pH = 7.50 |
|---|---|
| Test procedure: | The color substrate test for determining the C1s-activity is carried out in 96-well microtiter plates.<br>10 µl of the inhibitor solution in 20% strength DMSO (DMSO diluted with 15 millimolar Tris/HCl pH = 7.50) are added to 140 µl of test buffer, which contains C1s in a final concentration of 0.013 U/ml and DTNB with a final concentration of 0.27 mM/l. Incubation is carried out for 10 minutes at from 20 to 25° C. The test is started by adding 50 µl of 1.5 millimolar substrate solution in 30% strength DMSO (final concentration 0.375 mmol/l). After an incubation time of 30 minutes at from 20 to 25° C., the absorbence of each well at 405 nm is measured in a two-beam microtiter plate photometer against a blank value (without enzyme). |
| Measurement criterion: | $IC_{50}$: required inhibitor concentration to reduce the amidolytic C1s activity to 50%. |
| Statistical evaluation: | The dependence of the absorbance on the inhibitor concentration serves as a basis for calculation. |

Example C

Detection of Inhibition of Complement in the Traditional Route by the Hemolytic Test The measurement of potential complement inhibitors is carried out, on the basis of diagnostic tests, using a test for measuring the traditional route (literature: Complement, A practical Approach; Oxford University Press; 1997; page 20 et seq.). For this purpose, human serum is used as a source of complement. However, a test of the same type is also carried out using various sera of other species in analogous manner. Erythrocytes from sheep are used as an indicator system. The antibody-dependent lysis of these cells and the hemoglobin which consequently emerges are a measurement of the complement activity.

Reagents, Biochemicals:

| Veronal | from Merck | #2760500 |
|---|---|---|
| Na Veronal | from Merck | #500538 |
| NaCl | from Merck | #1.06404 |
| $MgCl_2 \times 6H_2O$ | from Baker | #0162 |
| $CaCl_2 \times 6H_2O$ | from Riedel de Haen | #31307 |
| Gelatin | from Merck | #1.04078.0500 |
| EDTA | from Roth | #8043.2 |
| Alsever's solution | from Gibco | #15190-044 |
| Penicillin | from Grünenthal | #P1507 10 Mega |
| Amboceptor | from Behring | #ORLC |

Stock solutions:

| VBS stock solution: | 2.875 g/l of Veronal; 1.875 g/l Na Veronal; 42.5 g/l NaCl |
|---|---|
| Ca/Mg stock solution: | 0.15 M Ca++, 1 M Mg++ |
| EDTA stock solution: | 0.1 M pH 7.5 |

Buffer:

| GVBS buffer: | dilute VBS stock solution 1:5 with Fin Aqua; dissolve 1 g/L of gelatin with a little buffer at elevated temperatures |
|---|---|
| GVBS++ buffer: | dilute Ca/Mg stock solution 1:1000 in GVBS buffer |
| GVBS/EDTA buffer: | dilute EDTA stock solution 1:10 in GVBS buffer |

Biogenic Components:

Sheeps' erythrocytes (SRBC): sheep's blood was mixed 1+1 (v/v) with an Alsevers solution and filtered through glass wool and $\frac{1}{10}$ of the volume of EDTA stock solution +1 pinch of penicillin were added. Human serum: after removal of the coagulated fractions by centrifuging at 4° C., the supernatant was stored in aliquots at −70° C. All measurements were carried out with one batch. No substantial deviations compared with serum of other test subjects were found.

Procedure:

1. Sensitization of the Erythrocytes

SRBC were washed three times with GVBS buffer. The cell count was then set at 5.00E+08 cells/ml in GVBS/EDTA buffer. Amboceptor was added in a dilution of 1:600, and the SRBC was sensitized with antibodies by incubation for 30 minutes at 37° C. with agitation. The cells were then washed three times with GVBS buffer at 4° C., then taken up in GVBS++ buffer and adjusted to a cell count of $5 \times 10^8$.

2. Lysis Experiment:

Inhibitors were preincubated in various concentrations with human serum or serum of other species in suitable dilution (e.g. 1:80 for human serum; a suitable dilution is one at which about 80% maximum lysis which can be achieved by serum is achieved) in GVBS++ for 10 minutes at 37° C. in a volume of 100 $\mu$l. 50 $\mu$l of sensitized SRBC in GVBS++ were then added. After incubation for 1 hour at 37° C. with agitation, the SRBC were separated off by centrifuging (5 minutes; 2500 rpm 4° C.). 130 $\mu$l of the cell-free supernatant were transferred to a 96-well plate. The evaluation was carried out by measurement at 540 nm against GVBS++ buffer.

The absorbencies at 540 nm are used for the evaluation.

(1): Background cells without serum (3): 100% Lysis, cells with serum (x): measured values with test substance Calculation: $\%Lysis = \frac{(x) - (1) \times 100\%}{(3) - (1)}$ Example D Testing of Inhibitors for Inhibition of the Protease Factor D In the alternative route of the complement system, factor D performs a central function. Owing to the low plasma concentration of factor D, the enzymatic step involving the cleavage of factor B by factor D constitutes the rate-determining step in the alternative route of complement activation. Owing to the limiting role which this enzyme plays in the alternative route, factor D is a target for the inhibition of the complement system.

The commercial substrate Z-Lys-SBzl*HCl is converted by the enzyme factor D (literature: Kam, C. M. et al., J. Biol. Chem. 262, 1987, 3444–3451). The detection of the cleaved substrate is effected by reaction with Ellmann's reagent. The product formed is detected spectrophotometrically. The reaction can be monitored online. This permits measurements of enzyme kinetics.

Material:

Chemicals:

| Factor D | Calbiochem | 341273 |
|---|---|---|
| Ellmann's reagent | SIGMA | D 8130 |
| Z-Lys-SBz1*HCl (= substrate) | Bachem | M 1300 50 mg/ml (MeOH) |
| NaCl | Riedel-De-Haen | 13423 |
| Triton-X-100 | Aldrich | 23,472-9 |
| Tris (hydroxymethyl)-aminomethane | MERCK | |
| Dimethylformamide (DMF) | | |

Buffer:

| 50 mM | Tris |
|---|---|
| 150 mM | NaCl |
| 0.01% | Triton-X-100 |
| pH 7.6 | |

Stock solutions:

| Substrate | 20 mM (8.46 mg/ml = 16.92 $\mu$l (50 mg/ml) + 83.1 $\mu$l $H_2O$) |
|---|---|
| Ellmann's reagent | 10 mM (3.963 mg/ml) in DMF |
| Factor D | 0.1 mg/ml |
| Samples (inhibitors) | $10^{-2}$ M in DMSO |

Procedure:

Batches:

| Blank value: | 140 $\mu$l of buffer + 4.5 $\mu$l of substrate (0.6 mM) + 4.5 $\mu$l of Ellmann's reagent (0.3 mM) |
|---|---|
| Positive control: | 140 $\mu$l of buffer + 4.5 $\mu$l of substrate (0.6 mM) + 4.5 $\mu$l of Ellmann's reagent (0.3 mM) + 5 $\mu$l of Factor D |
| Sample measurement: | 140 $\mu$l of buffer + 4.5 $\mu$l of substrate (0.6 mM) + 4.5 $\mu$l of Ellmann's reagent (0.3 mM) + 1.5 $\mu$l of samples ($10^{-4}$ M) + 5 $\mu$l of Factor D |

The batches are pipetted together into microtiter plates. After mixing of buffer, substrate and Ellmann's reagent (possibly inhibitors), the enzyme reaction is started by adding in each case 5 $\mu$l of factor D. Incubation takes place at room temperature for 60 minutes.

Measurement:
Measurement at 405 nm for 1 hour at 3 minute intervals
Evaluation:
The result is plotted graphically. The change in the absorbence per minute (delta OD per minute; slope) is relevant for the comparison of inhibitors so it is possible to determine $K_i$ values of inhibitors therefrom. In this test the serine protease inhibitor FUT-175; Futhan; from Torii; Japan, was also run as an effective inhibitor.

Example E

Detection of the inhibition of complement in the alternative route by the hemolytic test (Literature: Complement, A practical Approach; Oxford University Press; 1997, page 20 et seq.)

The test is carried out similarly to clinical tests. The test can be modified by additional activation by means of, for example, Zymosan or Cobra Venom Factor.

Material:

| EGTA (ethylenebis (oxyethylenenitrilo)-tetracetic acid | Boehringer Mannheim | 1093053 |
|---|---|---|
| $MgCl_2 * 6 H_2O$ | MERCK | 5833.0250 |
| NaCl | MERCK | 1.06404.1000 |
| D-Glucose | Cerestar | |
| Veronal | MERCK | 2760500 |
| Na Veronal | MERCK | 500538 |
| VBS stock solution (5×) | Gelatin Veronal buffer PD Dr. Kirschfink; University of Heidelberg, Inst. for Immunoloqy; | |
| Gelatin | MERCK | 1.04078.0500 |
| Tris (hydroxymethyl) amino-methane | MERCK | 1.08382.0100 |
| $CaCl_2$ | MERCK | Art. 2382 |

Human serum was either bought from various suppliers (e.g. Sigma) or obtained from test subjects in the BASF Sud casualty department.

Guinea pigs' blood was obtained and diluted 2:8 in citrate solution. Several batches without obvious differences were used.

Stock Solutions:

| VBS stock solution: | 2.875 g/l of Veronal<br>1.875 g/l of Na Veronal<br>42.5 g/l of NaCl |
|---|---|
| GVBS: | dilute VBS stock solution 1:5 with water (Finn Aqua) + 0.1% of gelatin<br>heat till gelatin has dissolved and cool |
| 100 mM EGTA: | slowly bring 38.04 mg of EGTA in 500 ml of Finn Aqua to pH 7.5 with 10 M NaOH till dissolved and then make up to 1l |
| Mg-EGTA: | 5 ml or 100 mM EGTA<br>3.5 ml or 100 mM $MgCl_2$<br>10.4 ml of GVBS<br>31.1 ml of 5% glucose solution |
| Saline: | 0.9% of NaCl in water (Finn Aqua) |
| GTB: | 0.15 mM $CaCl_2$<br>141 mM NaCl<br>0.5 mM $MgCl_2 * 6 H_2O$<br>10 mM Tris<br>0.1% of gelatin<br>pH 7.2–7.3 |

Procedure:
1. Cell Preparation:
The erythrocytes from the guinea pig blood washed several times by centrifuging (5 minutes; 1000 rpm) with GTB until the supernatant was clear. The cell count was adjusted to $2*10^9$ cells/ml.

2. Procedure: the individual batches were incubated for 30 minutes at 37° C. with agitation. The incubation was then stopped for 480 μl of ice-cold physiological saline solution and the cells were separated off by centrifuging for 5 minutes at 5000 rpm. 200 μl of supernatant were measured at 405 nm by transfer to a microtiter plate and evaluation in a microtiter plate photometer.

Pipetting Scheme (Stated Amounts in μl)

| | Back-ground (– serum) | 100% Lysis | 100% Lysis + factor D | Background + Factor D (– serum) | Max. lysis (water) |
|---|---|---|---|---|---|
| Cells | 20 | 20 | 20 | 20 | 20 |
| Serum 1:4 | | 20 | 20 | | |
| Mg-EGTA | 480 | 480 | 480 | 480 | |
| Factor D | | | 0.5μg | 0.5μg | |
| Saline (for stopping) | 480 | 480 | 480 | 480 | |
| $H_2O$ | | | | | 980 |

Evaluation:
The OD—values are used for the evaluation.

(1): Background; cells without serum (3): 100% lysis + Factor D; cells with serum (x): measured values with test substances Calculation: $\%Lysis = \frac{(X) - (1) * 100\%}{(3) - (1)}$ The present invention relates to peptide and peptidomimetic substances, their preparation and their use as complement inhibitors. In particular, these are substances having an amidine or guanidine radical as a terminal group.

The present invention also relates to the use of known amidine-containing substances for the preparation of complement inhibitors, specifically of inhibitors of C1s and C1r.

The present invention relates to the use of known and novel substances having an amidine or guanidine terminal group for the preparation of complement inhibitors, specially of inhibitors of C1s and C1r.

The present invention relates in particular to the use of chemically stable substances of the formula I, their tautomers, pharmacologically tolerated salts and prodrugs for the preparation of drugs for the treatment and prophylaxis of disorders which are alleviated or cured by partial or complete inhibition, in particular selective inhibition, of C1s and/or C1r. Formula I has the structure $$A-B-D-E-G-K-L \qquad (I)$$

where
A is
H, $C_{1-6}$-alkyl, $C_{1-6}$-alkyl-$SO_2$, $R^{A1}OCO$ (where $R^{A1}$ is H, $C_{1-12}$-alkyl, $C_{3-8}$-cycloalkyl, $C_{1-3}$-alkyl-$C_{3-8}$-cycloalkyl or $C_{1-3}$-alkylaryl), $R^{A2}R^{A3}NCO$ (where $R^{A2}$ is H—, $C_{1-6}$-alkyl, $C_{0-3}$-alkylaryl or $C_{0-3}$-alkylheteroaryl; $R^{A3}$ is H, $C_{1-6}$-alkyl or $C_{0-3}$-alkylaryl; $R^{A2}$–$R^{A3}$ together may also form a ring of 3 to 7 carbon atoms), $R^{A4}OCO_2$ (where $R^{A4}$ is $C_{1-6}$-alkyl or $C_{1-3}$-alkylaryl), $R^{A4}OCONR^{A2}$, $NO_2$, $R^{A4}CONR^{A2}$, $R^{A1}O$, $R^{A2}R^{A3}N$, $R^{A1}S$, $HO-SO_2$, $R^{A2}R^{A3}N-SO_2$, Cl, phenoxy, Br, F, tetrazolyl, $H_2O_3P$, $R^{A1}$—N(OH)—CO, $R^{A1}R^{A2}NCONR^{A3}$, where aryl in each case may be substituted by up to 2 identical or different radicals from the group consisting of F, Cl, Br, $OCH_3$, $CF_3$, $CH_3$ and $NO_2$;

B is
—$(CH_2)_{l^B}$—$L^B$—$(CH_2)_{m^B}$— where
$l^B$ is 0, 1, 2 or 3;
$m^B$ is 0, 1, 2, 3, 4 or 5;

$L^B$ is

[structures shown]

where, in each of the abovementioned ring systems, a phenyl ring may be fused on, which phenyl ring may be substituted by up to 2 identical or different radicals from the group consisting of $CH_3$, $CF_3$, Br, Cl and F or may be substituted by $R^8OOC$— (where $R^8$ is H or $C_{1-3}$-alkyl);
where
$n^B$ is 0, 1 or 2,
$p^B$ is 0, 1 or 2,
$q^B$ is 1, 2 or 3,
$R^{B1}$ is H, $C_{1-6}$-alkyl, $C_{0-3}$-alkylaryl, $C_{0-3}$-alkylheteroaryl, $C_{0-3}$-alkyl-$C_{3-8}$-cycloalkyl, OH or $OCH_3$;

$R^{B2}$ is H, $C_{1-6}$-alkyl, $C_{0-3}$-alkylaryl or $C_{0-3}$-alkylheteroaryl;

$R^{B3}$ is H, $C_{1-6}$-alkyl, $C_{0-3}$-alkylaryl, $C_{0-3}$-alkylheteroaryl, $R^{B5}OCO$ (where $R^{B5}$ is H, $C_{1-6}$-alkyl or $C_{1-3}$-alkylaryl), $R^{B6}$—O (where $R^{B6}$ is H or $C_{1-6}$-alkyl), F, Cl, Br, $NO_2$ or $CF_3$;

$R^{B4}$ is H, $C_{1-6}$-alkyl, $R^{B6}$—O, Cl, Br, F or $CF_3$;

$R^{B1}$ and $R^{B2}$ may also be bonded together;

$T^B$ is $CH_2$, O, S, NH or N—$C_{1-6}$-alkyl;

$X^B$ is O, S, NH or N—$C_{1-6}$-alkyl;

$Y^B$ is =CH—, =C(—$C_{1-6}$-alkyl)—,

=N— or =C(—Cl)—;

$Z^B$ is =CH—, =C(—$C_{1-6}$-alkyl)—,

=N— or =C(—Cl)—;

$U^B$ is =CH—, =C(—$C_{1-6}$-alkyl)—,

=N— or =C(—O—$C_{1-3}$-alkyl)—;

$V^B$ is =CH—, =C(—$C_{1-6}$-alkyl)—,

=N— or =C(—O—$C_{1-3}$-alkyl)—.

B is furthermore
—$(CH_2)_{l^B}$—$L^B$—$M^B$—$L^B$—$(CH_2)_{m^B}$—, where
$l^B$ and $m^B$ have the abovementioned meanings and the two groups $L^B$, independently of one another, are identical or different radicals from among the stated radicals;
$M^B$ is a single bond, O, S, $CH_2$, $CH_2$—$CH_2$, $CH_2$—O, O—$CH_2$, $CH_2$—S, S—$CH_2$, CO, $SO_2$, CH=CH or C≡C;

may furthermore be
-1-adamantyl-, -2-adamantyl-, -1-adamantyl-$CH_2$—, -2-adamantyl-$CH_2$—,

[structures shown]

A—B may furthermore be

[structures shown]

D is a single bond or
CO, OCO, $NR^{D1}$—CO (where $R^{D1}$ is H, $C_{1-4}$-alkyl or $C_{0-3}$-alkylaryl), $SO_2$ or $NR^{D1}SO_2$;

E is a single bond or

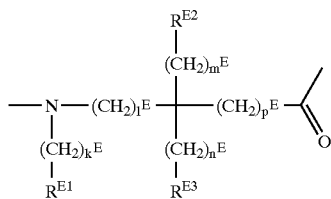

where
$k^E$ is 0, 1 or 2;
$l^E$ is 0, 1 or 2;
$m^E$ is 0, 1, 2 or 3;
$n^E$ is 0, 1 or 2;
$p^E$ is 0, 1 or 2;
$R^{E1}$ is H, $C_{1-6}$-alkyl, $C_{3-8}$-cycloalkyl, aryl (in particular phenyl or naphthyl), heteroaryl (in particular pyridyl, thienyl, imidazolyl or indolyl) or $C_{3-8}$-cycloalkyl having a fused-on phenyl ring, it being possible for the abovementioned radicals to carry up to three identical or different substituents from the group consisting of $C_{1-6}$-alkyl, OH, O—$C_{1-6}$-alkyl, F, Cl and Br;
$R^{E1}$ is furthermore $R^{E4}$OCO—$CH_2$— (where $R^{E4}$ is H, $C_{1-12}$-alkyl or $C_{1-3}$-alkylaryl);
$R^{E2}$ is H, $C_{1-6}$-alkyl, $C_{3-8}$-cycloalkyl, aryl (in particular phenyl or naphthyl), heteroaryl (in particular pyridyl, furyl, thienyl, imidazolyl or indolyl), tetrahydropyranyl, tetrahydrothiopyranyl, $C_{3-8}$-cycloalkyl having a fused-on phenyl ring, it being possible for the abovementioned radicals to carry up to three identical or different substituents from the group consisting of $C_{1-6}$-alkyl, OH, O—$C_{1-6}$-alkyl, F, Cl and Br, or is $CH(CH_3)OH$, $CH(CF_3)_2$;
$R^{E3}$ is H, $C_{1-6}$-alkyl, $C_{3-8}$-cycloalkyl, aryl (in particular phenyl or naphthyl), heteroaryl (in particular pyridyl, thienyl, imidazolyl or indolyl) or $C_{3-8}$-cycloalkyl having a fused-on phenyl ring, it being possible for the abovementioned radicals to carry up to three identical or different substituents from the group consisting of $C_{1-6}$-alkyl, OH, O—$C_{1-6}$-alkyl, F, Cl and Br;
$R^{E2}$ and $R^{B1}$ may together furthermore form a bridge having $(CH_2)_{0-4}$, CH=CH, $CH_2$—CH=CH or CH=CH—$CH_2$ groups; the groups stated under $R^{E1}$ and $R^{E3}$ may be linked to one another via a bond; the groups stated under $R^{E2}$ and $R^{E3}$ may also be linked to one another via a bond;
$R^{E2}$ is furthermore $COR^{E5}$ (where $R^{E5}$ is OH, O—$C_{1-6}$-alkyl or $OC_{1-3}$-alkylaryl), $CONR^{E6}R^{E7}$ (where $R^{E6}$ and $R^{E7}$ are H, $C_{1-6}$-alkyl or $C_{0-3}$-alkylaryl);
E may also be D-Asp, D-Glu, D-Lys, D-Orn, D-His, D-Dab, D-Dap or D-Arg;
G is

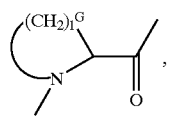

where $l^G$ is 2, 3, 4 and 5, where a $CH_2$ group of the ring may be replaced by O, S, NH, $NC_{1-3}$-alkyl, CHOH, $CHOC_{1-3}$-alkyl, $C(C_{1-3}\text{-alkyl})_2$, $CH(C_{1-3}\text{-alkyl})$, CHF, CHCl or $CF_2$;

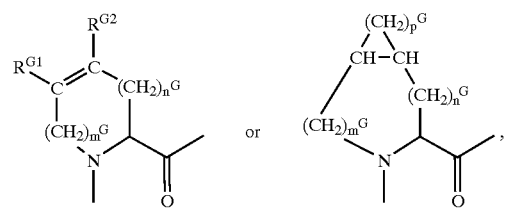

where
$m^G$ is 0, 1 or 2;
$n^G$ is 0, 1 or 2;
$p^G$ is 1, 2, 3 or 4;
$R^{G1}$ is H, $C_1$–$C_6$-alkyl or aryl;
$R^{G2}$ is H, $C_1$–$C_6$-alkyl or aryl;
$R^{G1}$ and $R^{G2}$ together may furthermore form a —CH=CH—CH=CH chain;
G is furthermore

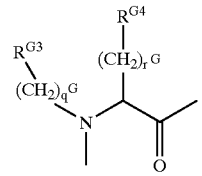

where
$q^G$ is 0, 1 or 2;
$r^G$ is 0, 1 or 2;
$R^{G3}$ is H, $C_1$–$C_6$-alkyl, $C_{3-8}$-cycloalkyl or aryl;
$R^{G4}$ is H, $C_1$–$C_6$-alkyl, $C_{3-8}$-cycloalkyl or aryl (in particular phenyl or naphthyl);
K is
NH—$(CH_2)_{n^K}$—$Q^K$ where
$n^K$ is 0, 1, 2 or 3;
$Q^K$ is $C_{2-6}$-alkyl, it being possible for the chain to be straight-chain or branched and up to two $CH_2$ groups can be replaced by O or S;
$Q^K$ is

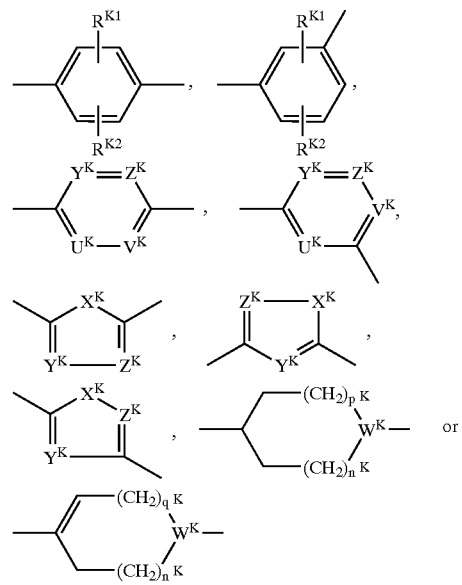

where
$R^{K1}$ is H, $C_{1-3}$-alkyl, OH, O—$C_{1-3}$-alkyl, F, Cl or Br;
$R^{K2}$ is H, $C_{1-3}$-alkyl, O—$C_{1-3}$-alkyl, F, Cl or Br;
$X^K$ is O, S, NH or N—$C_{1-6}$-alkyl;

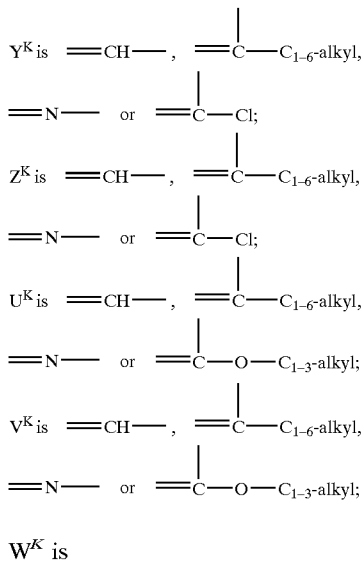

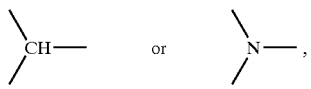

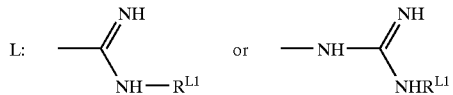

where, in the latter case, L may not be a guanidine group;
$n^K$ is 0, 1 or 2;
$p^K$ is 0, 1 or 2;
$q^K$ is 1 or 2;

L:

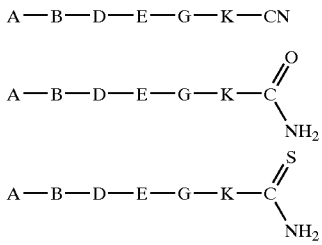

where
$R^{L1}$ is H, OH, O—$C_{1-6}$-alkyl, O—$(CH_2)_{0-3}$-phenyl, CO—$C_{1-6}$-alkyl, $CO_2$—$C_{1-6}$-alkyl or $CO_2$—$C_{1-3}$-alkylaryl.

The term $C_{1-x}$-alkyl includes all straight-chain and branched alkyl chain of up to x-carbon atoms.

The term $C_{3-8}$-cycloalkyl refers to carbocyclic saturated radicals of 3 to 8 carbon atoms.

The term aryl refers to carbocyclic aromatics of 6 to 14 carbon atoms, in particular phenyl, 1-naphthyl or 2-naphthyl.

The term heteroaryl refers to aromatics having a five- or six-membered ring and at least one heteroatom N, O or S, in particular pyridyl, thienyl, furyl, thiazolyl or imidazolyl; furthermore, two aromatic rings may be fused, e.g. indole, N—$C_{1-3}$-alkylindole, benzothiophene, benzothiazole, benzimidazole, quinoline or isoquinoline.

The term $C_{x-y}$-alkylaryl refers to carbocyclic aromatics which are linked to the skeleton via an alkyl group of x, x+1, . . . y−1 or y carbon atoms.

The present invention furthermore relates to compounds which contain the structural element

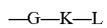

where G, K and L have the abovementioned meanings. Preferably, G—K—L has the meaning of the novel compounds stated below. The structural fragment is valuable as part of complement inhibitors and in particular $C_{1s}$- and/or $C_{1r}$-inhibitors.

The present invention furthermore relates to the intermediates of the following formulae

A—B—D—E—G—K—CN

A—B—D—E—G—K—C(=O)NH$_2$

A—B—D—E—G—K—C(=S)NH$_2$ where A, B, D, E, G and K have the meanings of the following novel compounds of the formula I.

The novel intermediates are used for the preparation of the compounds I and are valuable building blocks for the synthesis of serine protease inhibitors.

The compounds of the formula I may be present as such or in the form of their salts with physiologically tolerated acids. Examples of such acids are: hydrochloric acid, citric acid, tartaric acid, lactic acid, phosphoric acid, methanesulfonic acid, acetic acid, formic acid, maleic acid, fumaric acid, succinic acid, hydroxysuccinic acid, sulfuric acid, glutaric acid, aspartic acid, pyruvic acid, benzoic acid, glucuronic acid, oxalic acid, ascorbic acid and acetylglycine.

The novel compounds of the formula I are competitive inhibitors of the complement system, in particular of $C_{1s}$, and furthermore $C_{1r}$.

The novel compounds can be administered orally or parentally (subcutaneously, intravenously, intramuscularly, intraperitonially or rectally) in the usual manner. The application can also be effected by means of vapors or sprays through the nasopharyngeal space.

The dosage depends on the age, condition and weight of the patient and on the method of application. As a rule, the daily dose of active compound per person is from about 10 to 2000 mg in the case of oral administration and from about 1 to 200 mg in the case of parental administration. This dose can be given in from 2 to 4 single doses once a day as a sustained-release form.

The compounds can be used in the conventional solid or liquid pharmaceutical application forms, for example as tablets, film-coated tablets, capsules, powders, granules, coated tablets, suppositories, solutions, ointments, creams or sprays. These are prepared in a conventional manner. The active compounds can be processed with the conventional pharmaceutical excipients, such as tablet binders, fillers, preservatives, tablet disintegrants, flow regulators, plasticizers, wetting agents, dispersants, emulsifiers, solvents, diffusion coatings, antioxidants and/or propellants (cf. H. Sucker et al.: Pharmazeutische Technologie, Thieme-Verlag, Stuttgart, 1978). The application forms thus obtained usually contain the active compound in an amount of 0.1 to 99% by weight.

Prodrugs are understood as meaning compounds which are converted in vivo (e.g. first pass metabolism) into the pharmacologically active compounds of the formula I.

The present invention also relates to the following novel compounds A—B—D—E—G—K—L and drugs which contain these compounds. Furthermore, these compounds are suitable as particularly good complement inhibitors.

Here:

A is
H, $C_{1-6}$-alkyl, $C_{1-6}$-alkyl-SO$_2$, $R^{A1}$OCO (where $R^{A1}$ is H, $C_{1-12}$-alkyl, $C_{3-8}$-cycloalkyl, $C_{3-8}$-cycloalkyl-$C_{1-3}$-alkyl or $C_{1-3}$-alkylaryl), $R^{A2}R^{A3}$NCO (where $R^{A2}$ is H—, $C_{1-6}$-alkyl, $C_{0-3}$-alkylaryl or $C_{0-3}$-alkylheteroaryl; $R^{A3}$ is H, $C_{1-6}$-alkyl or $C_{0-3}$-alkylaryl); $R^{A4}$OCONR$^{A2}$ (where $R^{A4}$ is $C_{1-6}$-alkyl or $C_{1-3}$-alkylaryl), $R^{A4}$CONR$^{A2}$, $R^{A1}$O, $R^{A2}R^{A3}$N, HO—SO$_2$—, phenoxy, $R^{A2}R^{A3}$N—SO$_2$, Cl, Br, F, tetrazolyl, H$_2$O$_3$P—, NO$_2$, $R^{A1}$—N(OH)—CO— or $R^{A1}R^{A2}$NCONR$^{A3}$, where aryl in each case may be substituted by up to 2 identical or different radicals from the group consisting of F, Cl, Br, CF$_3$, CH$_3$, OCH$_3$ and NO$_2$;

B is
—(CH$_2$)$_{l^B}$—L$^B$—(CH$_2$)$_{m^B}$— where
$l^B$ is 0, 1, 2 or 3;
$m^B$ is 0, 1 or 2;

L$^B$ is

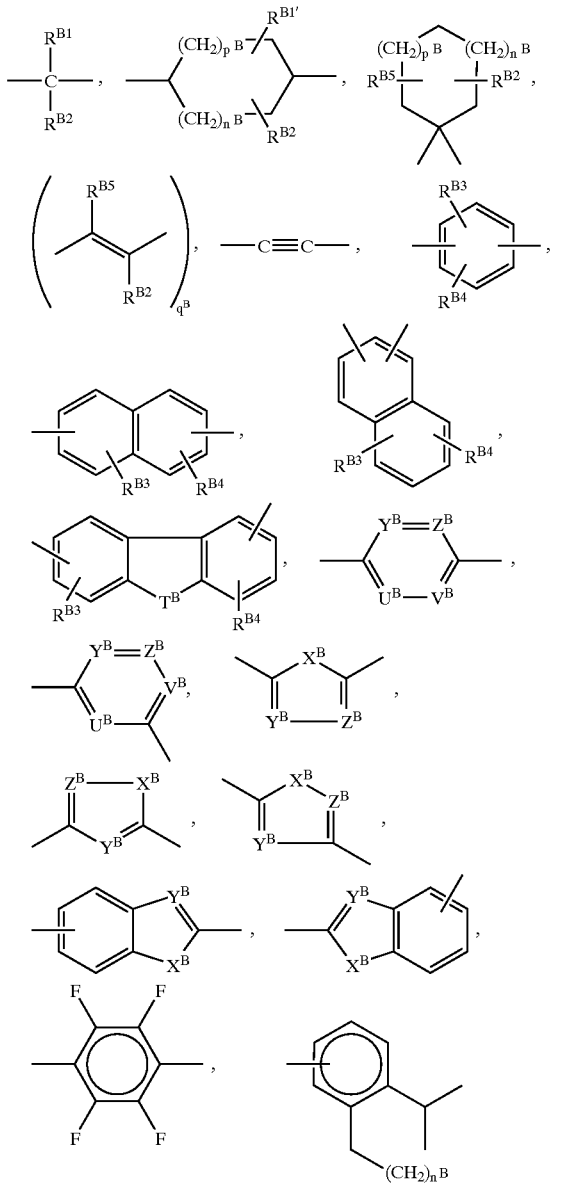

where, in each of the abovementioned ring systems, a phenyl ring can be fused on, which phenyl ring may be substituted by up to 2 identical or different radicals from the group consisting of CH$_3$, CF$_3$, Br, Cl and F or may be substituted by R$^8$OOC— (where R$^8$ is H or $C_{1-3}$-alkyl);

where
$n^B$ is 0, 1 or 2;
$p^B$ is 0, 1 or 2;
$q^B$ is 1, 2 or 3;
$R^{B1}$ is $C_{0-3}$-alkylaryl, $C_{0-3}$-alkylheteroaryl, $C_{0-3}$-alkyl-$C_{3-8}$-cycloalkyl, OH or OCH$_3$;
$R^{B2}$ is H, $C_{1-6}$-alkyl, $C_{0-3}$-alkylaryl or $C_{0-3}$-alkylheteroaryl;
$R^{B3}$ is H, $C_{1-6}$alkyl, $C_{0-3}$-alkylaryl or $C_{0-3}$-alkylheteroaryl; $R^{B5}$OCO (where $R^{B5}$ is H, $C_{1-6}$-alkyl or $C_{1-3}$-alkylaryl), $R^{B6}$—O (where $R^{B6}$ is H or $C_{1-6}$-alkyl), F, Cl, Br, NO$_2$ or CF$_3$;
$R^{B4}$ is H, $C_{1-6}$-alkyl, $R^{B6}$—O, Cl, Br, F or CF$_3$;
$R^{B5}$ is H, $C_{1-6}$-alkyl, $C_{0-3}$-alkylaryl or $C_{0-3}$-alkylheteroaryl;
$T^B$ is CH$_2$, O, S, NH or N—$C_{1-6}$-alkyl;
$R^{B1'}$ is H, $C_{1-6}$-alkyl, $C_{0-3}$-alkylaryl, $C_{0-3}$-alkylheteroaryl or $C_{0-3}$-alkyl-$C_{3-8}$-cycloalkyl;
$R^{B1}$ and $R^{B2}$ may also be bonded together;
$X^B$ is O, S, NH or N—$C_{1-6}$-alkyl;

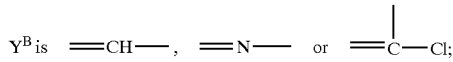

$U^B$ is =CH— or =N—;
$V^B$ is =CH— or =N—;

B is furthermore
—(CH$_2$)$_{l^B}$—L$^B$—M$^B$—L$^B$—(CH$_2$)$_{m^B}$, where $l^B$ and $m^B$ have the abovementioned meanings and the two groups L$^B$, independently of one another, are the radicals stated under L$^B$;

M$^B$ is a single bond, O, S, CH$_2$, CH$_2$—CH$_2$, CH$_2$—O, O—CH$_2$, CH$_2$—S, S—CH$_2$, CO, SO$_2$, CH=CH or C≡C;

B is furthermore
-1-adamantyl-CH$_2$—, -2-adamantyl-CH$_2$—, -1-adamantyl-, -2-adamantyl-,

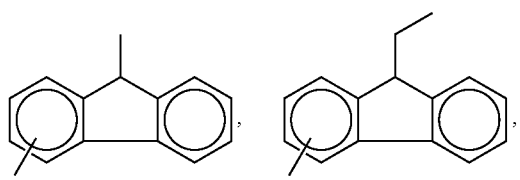

B may furthermore be

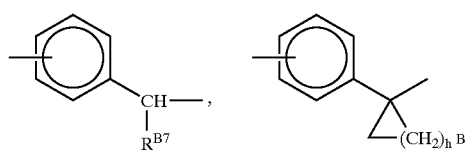

where h$^B$ is 1, 2, 3 or 4
(R$^{B7}$ is $C_{1-6}$-alkyl or $C_{3-8}$-cycloalkyl)

B may furthermore be

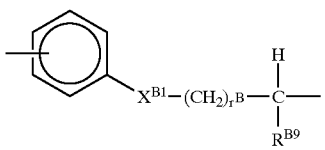

where $X^{B1}$ is a bond, O, S, or

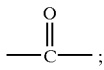

where $r^B$ is 0, 1, 2 or 3;
and $R^{B9}$ is H or $C_{1-3}$-alkyl;

A—B may be

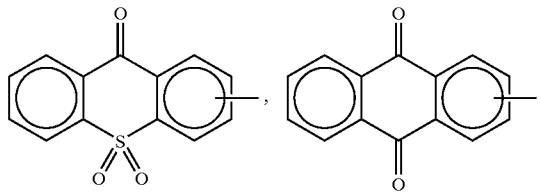

D is a single bond or CO, OCO, $NR^{D1}$—CO (where $R^{D1}$ is H, $C_{1-4}$-alkyl or $C_{0-3}$-alkylaryl), $SO_2$ or $NR^{D1}SO_2$;

E is a single bond or

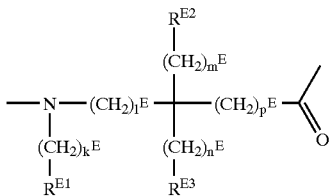

where
$k^E$ is 0, 1 or 2;
$l^E$ is 0, 1 or 2;
$m^E$ is 0, 1, 2 or 3;
$n^E$ is 0, 1 or 2;
$p^E$ is 0, 1 or 2;
$R^{E1}$ is H, $C_{1-6}$-alkyl, $C_{3-8}$-cycloalkyl, aryl (in particular phenyl or naphthyl), pyridyl, thienyl or $C_{3-8}$-cycloalkyl having a fused-on phenyl ring, it being possible for the abovementioned radicals to carry up to three identical or different substituents from the group consisting of $C_{1-6}$-alkyl, O—$C_{1-6}$-alkyl, F, Cl and Br;
$R^{E1}$ is furthermore $R^{E4}$OCO—$CH_2$ (where $R^{E4}$ is H, $C_{1-12}$-alkyl or $C_{1-3}$-alkylaryl);
$R^{E2}$ is H, $C_{1-6}$-alkyl, $C_{3-8}$-cycloalkyl, phenyl, pyridyl, furyl, thienyl, imidazolyl, tetrahydropyranyl or tetrahydrothiopyranyl, it being possible for the abovementioned radicals to carry up to three identical or different substituents from the group consisting of $C_{1-6}$-alkyl, O—$C_{1-6}$-alkyl, F, Cl and Br, or is $CH(CH_3)OH$ or $CH(CF_3)_2$;
$R^{E3}$ is H, $C_{1-6}$-alkyl, $C_{3-8}$-cycloalkyl or phenyl, it being possible for the abovementioned radicals to carry up to three identical or different substituents from the group consisting of $C_{1-6}$-alkyl, O—$C_{1-6}$-alkyl, F, Cl and Br;

$R^{E2}$ and $R^{B1}$ may together furthermore form a bridge having $(CH_2)_{0-4}$, CH=CH, $CH_2$—CH=CH or CH=CH—$CH_2$ groups;

the groups stated under $R^{E1}$ and $R^{E3}$ may be linked to one another via a bond; the groups stated under $R^{E2}$ and $R^{E3}$ may also be linked to one another via a bond;

$R^{E2}$ is furthermore $COR^{E5}$ (where $R^{E5}$ is OH, O—$C_{1-6}$-alkyl or O—$C_{1-3}$-alkylaryl);

if it is asymmetrically substituted, the building block E is preferably present in the R configuration;

E may also be D-Asp, D-Glu, D-Lys, D-Orn, D-His, D-Dab, D-Dap, D-Arg;

G is

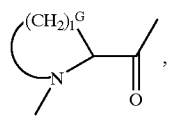

where $l^G$ is 2, 3, 4 and 5, where a $CH_2$ group of the ring may be replaced by O, S, NH, $CF_2$, CHF or CH($C_{1-3}$-alkyl);

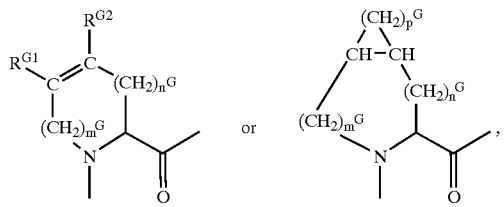

where
$m^G$ is 0, 1 or 2;
$n^G$ is 0, 1 or 2;
$p^G$ is 1 or 3;
$R^{G1}$ and $R^{G2}$ are each H;
$R^{G1}$ and $R^{G2}$ together may furthermore form a CH=CH—CH=CH chain;

G is furthermore

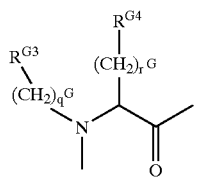

where
$q^G$ is 0, 1 or 2;
$r^G$ is 0, 1 or 2;
$R^{G3}$ is H, $C_1$–$C_6$-alkyl or $C_{3-8}$-cycloalkyl;
$R^{G4}$ is H, $C_1$–$C_6$-alkyl, $C_{3-8}$-cycloalkyl or phenyl;

K is
  NH—(CH$_2$)$_{n^K}$—Q$^K$ where
    n$^K$ is 1 or 2;
  Q$^K$ is

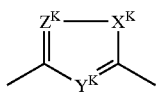 or 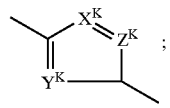 ;

X$^K$ is O, S, NH or N—C$_{1-6}$-alkyl;

Y$^K$ is 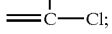

Z$^K$ is 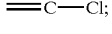

L: 
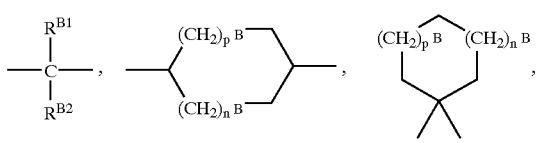

where
  R$^{L1}$ is H, OH, O—C$_{1-6}$-alkyl, O—(CH$_2$)$_{0-3}$-phenyl, CO—C$_{1-6}$-alkyl, CO$_2$—C$_{1-6}$-alkyl or CO$_2$—C$_{1-3}$-alkylaryl.

The present invention also relates to the following novel compounds, their tautomers, physiologically tolerable salts and prodrugs of the formula A—B—D—E—G—K—L and drugs which contain these compounds. These compounds are furthermore suitable as particularly good complement inhibitors.

Here:

A is
  H, C$_{1-6}$-alkyl, C$_{1-6}$-alkyl-SO$_2$, R$^{A1}$OCO (where R$^{A1}$ is H, C$_{1-12}$-alkyl, C$_{3-8}$-cycloalkyl, C$_{1-3}$-alkyl-C$_{3-8}$-cycloalkyl or C$_{1-3}$-alkylaryl), R$^{A2}$R$^{A3}$NCO (where R$^{A2}$ is H, C$_{1-6}$-alkyl, C$_{0-3}$-alkylaryl or C$_{0-3}$-alkylheteroaryl; R$^{A3}$ is H, C$_{1-6}$-alkyl or C$_{0-3}$-alkylaryl), R$^{A4}$OCONR$^{A2}$, R$^{A4}$CONR$^{A2}$ (where R$^{A4}$ is C$_{1-6}$-alkyl or C$_{1-3}$-alkylaryl), R$^{A1}$O, phenoxy, R$^{A2}$R$^{A3}$N, HO—SO$_2$, R$^{A2}$R$^{A3}$N—SO$_2$, Cl, Br, F, tetrazolyl, H$_2$O$_3$P, NO$_2$, R$^{A1}$—N(OH)—CO or R$^{A1}$R$^{A2}$NCONR$^{A3}$, where aryl in each case may be substituted by up to 2 identical or different radicals from the group consisting of F, Cl, Br, OCH$_3$, CH$_3$, CF$_3$ and NO$_2$;

B is
  —(CH$_2$)$_{l^B}$—L$^B$—(CH$_2$)$_{m^B}$— where
    l$^B$ is 0, 1, 2 or 3;
    m$^B$ is 0, 1, 2 or 3;
  L$^B$ is

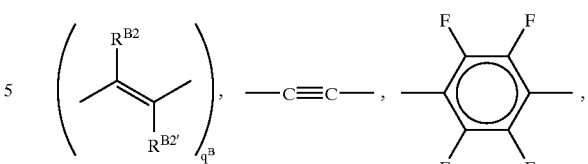

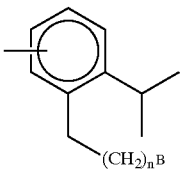

where, in each of the abovementioned ring systems, a phenyl ring may be fused on, which phenyl ring may be substituted by up to 2 identical or different radicals from the group consisting of CH$_3$, CF$_3$, Br, Cl and F or may be substituted by R$^8$OOC— (where R$^8$ is H or C$_{1-3}$-alkyl);
where
  n$^B$ is 0, 1 or 2;
  p$^B$ is 0, 1 or 2;
  q$^B$ is 1, 2 or 3;
  R$^{B1}$ is C$_{0-3}$-alkylaryl, C$_{0-3}$-alkylheteroaryl, C$_{0-3}$-alkyl-C$_{3-8}$-cycloalkyl, OH or OCH$_3$;
  R$^{B2}$ is H, C$_{1-6}$-alkyl, C$_{0-3}$-alkylaryl or C$_{0-3}$-alkylheteroaryl;
  R$^{B1}$ and R$^{B2}$ may also be bonded together;
  R$^{B2'}$ is H, C$_{1-6}$-alkyl, C$_{0-3}$-alkylaryl, C$_{0-3}$-alkylheteroaryl or C$_{0-3}$-alkyl-C$_{3-8}$-cycloalkyl;
  B is furthermore -1-adamantyl-, -1-adamantyl-CH$_2$—,
  -2-adamantyl- or -2-adamantyl-CH$_2$—,

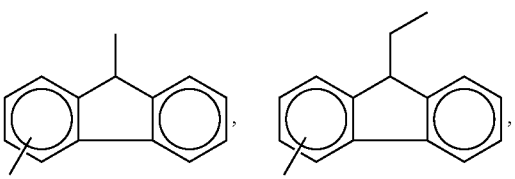

B is furthermore —(CH$_2$)$_{l^B}$—L$^{B1}$—M$^B$—LB$^2$—(CH$_2$)$_{m^B}$—, where l$^B$ and m$^B$ have the abovementioned meanings and the two groups L$^{B1}$ and L$^{B2}$, independently of one another, are the following radical:

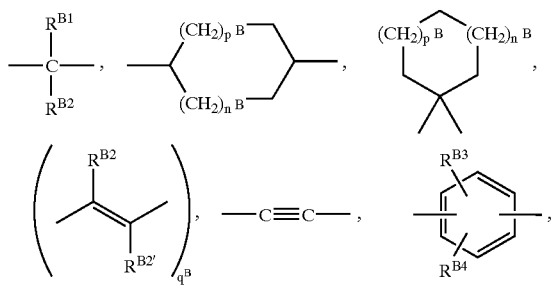

-continued

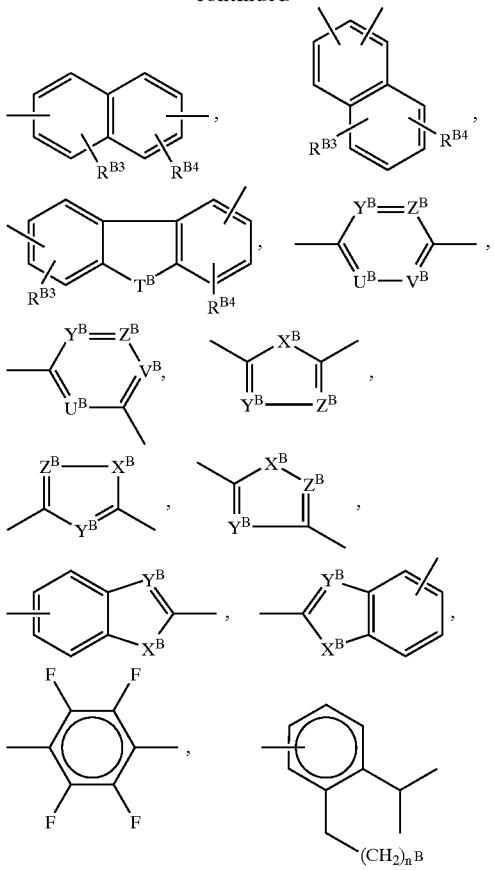

where, in each of the abovementioned ring systems, a phenyl ring may be fused on;
where
$n^B$ is 0, 1 or 2;
$p^B$ is 0, 1 or 2;
$q^B$ is 1, 2 or 3;
$R^{B1}$ is H (only for $L^{B2}$), $C_{1-6}$-alkyl (only for $L^{B2}$), $C_{0-3}$-alkylaryl, $C_{0-3}$-alkylheteroaryl, $C_{0-3}$-alkyl-$C_{3-8}$-cycloalkyl, OH or $OCH_3$;
$R^{B2}$ is H, $C_{1-6}$-alkyl, $C_{0-3}$-alkylaryl or $C_{0-3}$-alkylheteroaryl;
$R^{B2'}$ is H, $C_{1-6}$-alkyl, $C_{0-3}$-alkylaryl, $C_{0-3}$-alkylheteroaryl or $C_{0-3}$-alkyl-$C_{3-8}$-cycloalkyl;
$R^{B3}$ is H, $C_{1-6}$-alkyl, $C_{0-3}$-alkylaryl, $C_{0-3}$-alkylheteroaryl, $R^{B5}OCO$ (where $R^{B5}$ is H, $C_{1-6}$-alkyl or $C_{1-3}$-alkylaryl), $R^{B6}$—O (where $R^{B6}$ is H or $C_{1-6}$-alkyl), F, Cl, Br, $NO_2$ or $CF_3$;
$R^{B4}$ is H, $C_{1-6}$-alkyl, $R^{B6}$—O, Cl, Br, F or $CF_3$;
$T^B$ is $CH_2$, O, S, NH or N—$C_{1-6}$-alkyl;
$X^B$ is O, S, NH or N—$C_{1-6}$-alkyl;

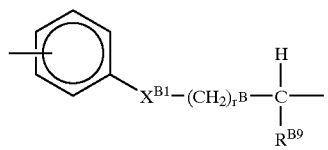

$U^B$ is =CH—, =C—$C_{1-6}$-alkyl, =N— or =C—O—$C_{1-3}$-alkyl;

$V^B$ is =CH—, =C—$C_{1-6}$-alkyl, =N— or =C—O—$C_{1-3}$-alkyl.

$R^{B1}$ and $R^{B2}$ may also be bonded together;
$M^B$ is a single bond, O, S, $CH_2$, $CH_2$—$CH_2$, $CH_2$—O, O—$CH_2$, $CH_2$—S, S—$CH_2$, CO, $SO_2$, CH=CH or C≡C;

B may furthermore be

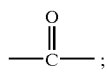

where $X^{B1}$ is a bond, O, S or

—C(=O)—;

$r^B$ is 0, 1, 2 or 3;
$R^{B9}$ is H or $C_{1-3}$-alkyl;
A—B may be

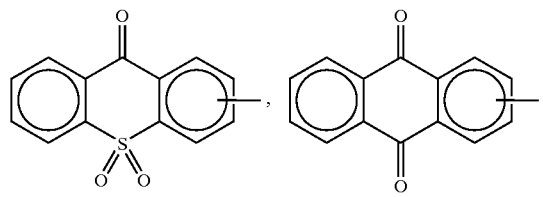

D is a single bond or CO, OCO, $NR^{D1}$—CO (where $R^{D1}$ is H, $C_{1-4}$-alkyl or $C_{0-3}$-alkylaryl), $SO_2$ or $NR^{D1}SO_2$;
B—D may be

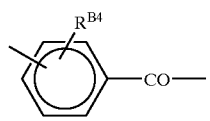

E is a single bond or

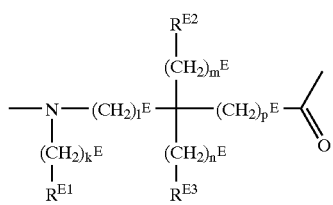

$k^E$ is 0, 1 or 2;
$l^E$ is 0, 1 or 2;

$m^E$ is 0, 1, 2 or 3;
$n^E$ is 0, 1 or 2;
$p^E$ is 0, 1 or 2;
$R^{E1}$ is H, $C_{1-6}$-alkyl, $C_{3-8}$-cycloalkyl, phenyl, naphthyl, pyridyl, thienyl, $C_{3-8}$-cycloalkyl having a fused-on phenyl ring, it being possible for the abovementioned radicals to carry up to three identical or different substituents from the group consisting of $C_{1-6}$-alkyl, O—$C_{1-6}$-alkyl, F, Cl and Br;
$R^{E1}$ is furthermore $R^{E4}OCO$—$CH_2$ (where $R^{E4}$ is H, $C_{1-12}$-alkyl or $C_{1-3}$-alkylaryl);
$R^{E2}$ is H, $C_{1-6}$-alkyl, $C_{3-8}$-cycloalkyl, phenyl, pyridyl, thienyl, furyl, imidazolyl, tetrahydropyranyl or tetrahydrothiopyranyl, it being possible for the abovementioned radicals to carry up to three identical or different substituents from the group consisting of $C_{1-6}$-alkyl, OH, O—$C_{1-6}$-alkyl, F, Cl and Br, or is $CH(CH_3)OH$ or $CH(CF_3)_2$;
$R^{E3}$ is H, $C_{1-6}$-alkyl, $C_{3-8}$-cycloalkyl or phenyl, it being possible for the abovementioned radicals to carry up to three identical or different substituents from the group consisting of $C_{1-6}$-alkyl, O—$C_{1-6}$-alkyl, F, Cl and Br;
$R^{E2}$ and $R^{B1}$ together may furthermore form a bridge having $(CH_2)_{0-4}$, CH=CH, $CH_2$—CH=CH or CH=CH—$CH_2$ groups;
the groups stated under $R^{E1}$ and $R^{E3}$ may be linked to one another via a bond; the groups stated under $R^{E2}$ and $R^{E3}$ may also be linked to one another via a bond;
$R^{E2}$ is furthermore $COR^{E5}$ (where $R^{E5}$ is OH, O—$C_{1-6}$-alkyl or O—$C_{1-3}$-alkylaryl);
if it is asymmetrically substituted, the building block E is preferably present in the R configuration;
E may also be D-Asp, D-Glu, D-Lys, D-Orn, D-His, D-Dab, D-Dap, D-Arg;
G is

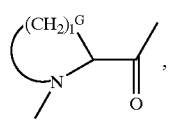

where $l^G$=2, 3, 4 and 5, where a $CH_2$ group of the ring may be replaced by O, S, NH, CHF or $CH(C_{1-3}$-alkyl);

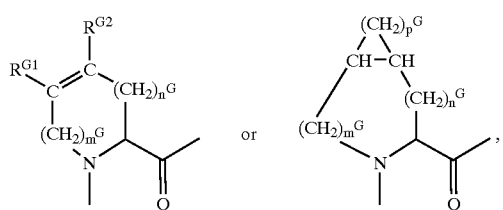

where
$m^G$ is 0, 1 or 2;
$n^G$ is 0, 1 or 2;
$p^G$ is 1 or 3;
$R^{G1}$ is H;
$R^{G2}$ is H;

$R^{G1}$ and $R^{G2}$ together may also be a CH=CH—CH=CH chain;
G is furthermore

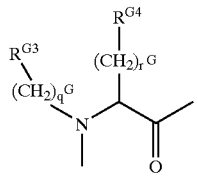

where
$q^G$ is 0, 1 or 2;
$r^G$ is 0, 1 or 2;
$R^{G3}$ is H, $C_1$–$C_6$-alkyl or $C_{3-8}$-cycloalkyl;
$R^{G4}$ is H, $C_1$–$C_6$-alkyl, $C_{3-8}$-cycloalkyl or phenyl;
K is
NH—$(CH_2)_{n^K}$—$Q^K$ where
$n^K$ is 1 or 2;
$Q^K$ is

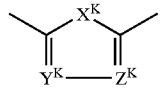

$X^K$ is O, S, NH or N—$C_{1-6}$-alkyl;

$Y^K$ is =CH—, =C—$C_{1-3}$-alkyl, =N— or =C—Cl;

$Z^K$ is =CH—, =C—$C_{1-3}$-alkyl, =N— or =C—Cl;

L: 
$$-C(=NH)-NH-R^{L1} \quad \text{or} \quad -NH-C(=NH)-NHR^{L1}$$

where
$R^{L1}$ is H, OH, O—$C_{1-6}$-alkyl, O—$(CH_2)_{0-3}$-phenyl, CO—$C_{1-6}$-alkyl, $CO_2$—$C_{1-6}$-alkyl or $CO_2$—$C_{1-5}$-alkylaryl.

The present invention also relates to the following novel compounds, their tautomers, physiologically tolerable salts and prodrugs of the formula A—B—D—E—G—K—L and drugs which contain these compounds. These compounds are furthermore suitable as particularly good complement inhibitors.
Here,
A is
H, $C_{1-6}$-alkyl, $C_{1-6}$-alkyl-$SO_2$, $R^{A1}OCO$ (where $R^{A1}$ is H, $C_{1-12}$-alkyl, $C_{3-8}$-cycloalkyl, $C_{1-3}$-alkyl-$C_{3-8}$-cycloalkyl or $C_{1-3}$-alkylaryl), $R^{A2}R^{A3}NCO$ (where $R^{A2}$ is H, $C_{1-6}$-alkyl, $C_{0-3}$-alkylaryl or $C_{0-3}$-alkylheteroaryl; $R^{A3}$ is H, $C_{1-6}$-alkyl or $C_{0-3}$-alkylaryl), $R^{A4}OCONR^{A2}$, $R^{A4}CONR^{A2}$ (where $R^{A4}$ is $C_{1-6}$-alkyl or $C_{1-3}$-alkylaryl), $R^{A1}O$, phenoxy, $R^{A2}R^{A3}N$, HO—$SO_2$, $R^{A2}R^{A3}N$—$SO_2$, Cl, Br, F, tetrazolyl, $H_2O_3P$, $NO_2$, $R^{A1}$—N(OH)—CO— or $R^{A1}R^{A2}NCONR^{A3}$, where aryl in each case may be substituted by up to 2 identical or different substituents from the group consisting of F, Cl, Br, $CH_3$, $CF_3$, $OCH_3$ and $NO_2$;

B is

—(CH$_2$)$_{l^B}$—L$^B$—(CH$_2$)$_{m^B}$— where l$^B$ is 0, 1, 2 or 3;

m$^B$ is 0, 1, 2, 3, 4 or 5;

L$^B$ is

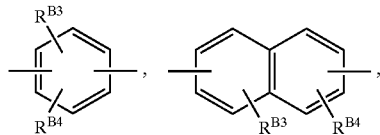

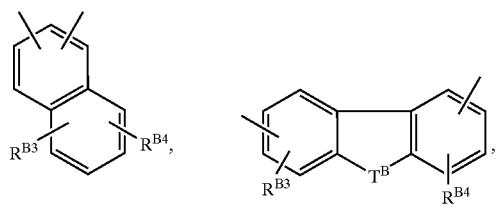

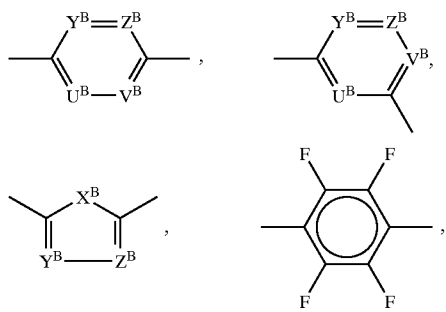

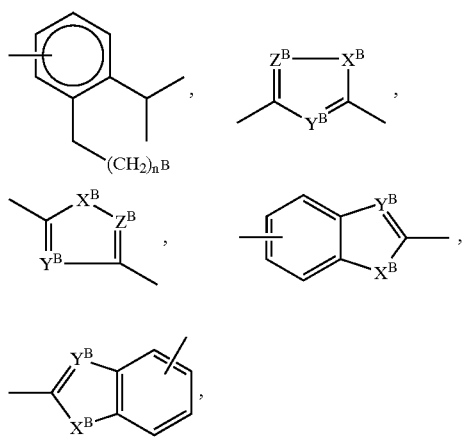

where, in each of the abovementioned ring systems, a phenyl ring may be fused on, which phenyl ring may be substituted by up to 2 identical or different radicals from the group consisting of CH$_3$, CF$_3$, F, Cl and Br or may be substituted by R$^8$OOC— (where R$^8$ is H or C$_{1-3}$-alkyl);

R$^{B3}$ is H, C$_{1-6}$-alkyl, C$_{0-3}$-alkylaryl, C$_{0-3}$-alkylheteroaryl, R$^{B5}$OCO (where R$^{B5}$ is H, C$_{1-6}$-alkyl or C$_{1-3}$-alkylaryl), R$^{B6}$—O (where R$^{B6}$ is H or C$_{1-6}$-alkyl), F, Cl, Br, NO$_2$ or CF$_3$;

R$^{B4}$ is H, C$_{1-6}$-alkyl, R$^{B6}$—O, Cl, Br, F or CF$_3$;

T$^B$ is CH$_2$, O, S, NH or N—C$_{1-6}$-alkyl;

X$^B$ is O, S, NH or N—C$_{1-6}$-alkyl;

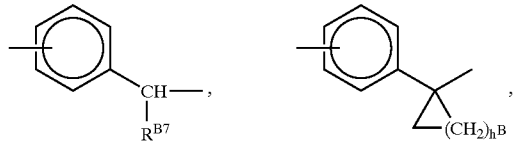

U$^B$ is =CH— or =N—;

V$^B$ is =CH— or =N—;

B may furthermore be

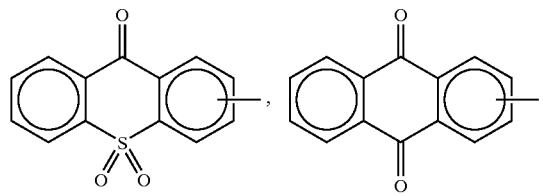

where h$^B$ is 1, 2, 3 or 4

(R$^{B7}$ is C$_{1-6}$-alkyl or C$_{3-8}$-cycloalkyl)

A—B may be

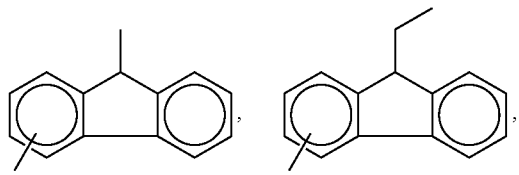

B may furthermore be

-1-adamantyl-, -2-adamantyl-, -1-adamantyl-CH$_2$—, -2-adamantyl-CH$_2$,

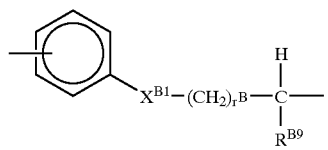

B may furthermore be where X$^{B1}$ is a bond, O, S, or

—C(=O)—;

r$^B$ is 0, 1, 2 or 3;

R$^{B9}$ is H or C$_{1-3}$-alkyl;

D is a single bond or

—NR$^{D1}$—CO (where R$^{D1}$ is H, C$_{1-4}$-alkyl or C$_{0-3}$-alkylaryl) or

—NR$^{D1}$SO$_2$;

E is a single bond or

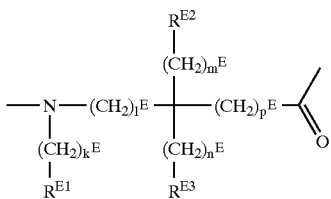

where
$k^E$ is 0, 1 or 2;
$l^E$ is 0, 1 or 2;
$m^E$ is 0, 1, 2 or 3;
$n^E$ is 0, 1 or 2;
$p^E$ is 0, 1 or 2;
$R^{E1}$ is H, $C_{1-6}$-alkyl, $C_{3-8}$-cycloalkyl, aryl (in particular phenyl or naphthyl), pyridyl, thienyl, $C_{3-8}$-cycloalkyl having a fused-on phenyl ring, it being possible for the abovementioned radicals to carry up to three identical or different substituents from the group consisting of $C_{1-6}$-alkyl, O—$C_{1-6}$-alkyl, F, Cl and Br;
$R^{E1}$ is furthermore $R^{E4}$OCO—$CH_2$ (where $R^{E4}$ is H, $C_{1-12}$-alkyl or $C_{1-3}$-alkylaryl);
$R^{E2}$ is H, $C_{1-6}$-alkyl, $C_{3-8}$-cycloalkyl, phenyl, pyridyl, furyl, thienyl, imidazolyl, tetrahydropyranyl or tetrahydrothiopyranyl, it being possible for the abovementioned radicals to carry up to three identical or different substituents from the group consisting of $C_{1-6}$-alkyl, O—$C_{1-6}$-alkyl, F, Cl and Br, or is $CH(CH_3)OH$ or $CH(CF_3)_2$;
$R^{E3}$ is H, $C_{1-6}$-alkyl or $C_{3-8}$-cycloalkyl, it being possible for the abovementioned radicals to carry up to three identical or different substituents from the group consisting of $Cl_6$-alkyl, O—$C_{1-6}$-alkyl, F, Cl and Br;
$R^{E2}$ and $R^{B1}$ together may furthermore form a bridge having $(CH_2)_{0-4}$, CH=CH, $CH_2$—CH=CH or CH=CH-$CH_2$ groups;
the groups stated under $R^{E1}$ and $R^{E3}$ may be linked to one another via a bond; the groups stated under $R^{E2}$ and $R^{E3}$ may also be linked to one another via a bond;
$R^{E2}$ is furthermore $COR^{E5}$ (where $R^{E5}$ is OH, O—$C_{1-6}$-alkyl or $OC_{1-3}$-alkylaryl);
if it is asymmetrically substituted, the building block E is preferably present in the R configuration;
E may also be D-Asp, D-Glu, D-Lys, D-Orn, D-His, D-Dab, D-Dap or D-Arg;
G is

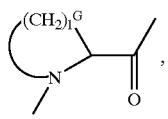

where $l^G$=2, 3, 4 and 5, where a $CH_2$ group of the ring may be replaced by O, S, NH, CHF, $CF_2$ or $CH(C_{1-3}$-alkyl);

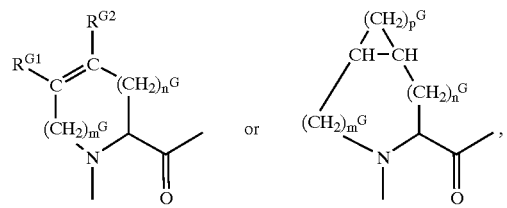

where
$m^G$ is 0, 1 or 2;
$n^G$ is 0, 1 or 2;
$p^G$ is 1 or 3;
$R^{G1}$ is H;
$R^{G2}$ is H;
$R^{G1}$ and $R^{G2}$ together may furthermore form a CH=CH—CH=CH chain;
G is furthermore

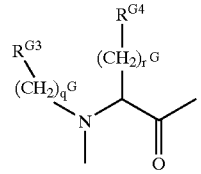

where
$q^G$ is 0, 1 or 2;
$r^G$ is 0, 1 or 2;
$R^{G3}$ is H, $C_1$–$C_6$-alkyl or $C_{3-8}$-cycloalkyl;
$R^{G4}$ is H, $C_1$–$C_6$-alkyl, $C_{3-8}$-cycloalkyl or phenyl;
K is
NH—$(CH_2)_{n^K}$—$Q^K$ where
$n^K$ is 1 or 2;
$Q^K$ is

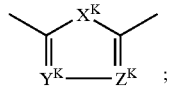

$X^K$ is O, S, NH or N—$C_{1-6}$-alkyl;

$Y^K$ is =CH—, =C—$C_{1-6}$-alkyl,
=N— or =C—Cl;

$Z^K$ is =CH—, =C—$C_{1-6}$-alkyl,
=N— or =C—Cl;

L: —C(=NH)—NH—$R^{L1}$ or —NH—C(=NH)—NH$R^{L1}$ where
$R^{L1}$ is —H, —OH, —O—$C_{1-6}$-alkyl, —O—$(CH_2)_{0-3}$-phenyl, —CO—$C_{1-6}$-alkyl, —$CO_2$—$C_{1-6}$-alkyl or $CO_2$—$C_{1-3}$-alkylaryl.

The present invention also relates to the following novel preferred compounds, their tautomers, physiologically tolerable salts and prodrugs of the formula A—B—D—E—

G—K—L and drugs which contain these compounds. Furthermore, these compounds are suitable as particularly good complement inhibitors.

Here:

A is

H, $C_{1-6}$-alkyl, $C_{1-6}$-alkyl-SO$_2$, $R^{A1}$OCO (where $R^{A1}$ is H, $C_{1-12}$-alkyl, $C_{3-8}$-cycloalkyl, $C_{3-8}$-cycloalkyl-$C_{1-3}$-alkyl or $C_{1-3}$-alkylaryl), $R^{A2}R^{A3}$NCO (where $R^{A2}$ is H—, $C_{1-6}$-alkyl, $C_{0-3}$-alkylaryl or $C_{0-3}$-alkylheteroaryl; $R^{A3}$ is H, $C_{1-6}$-alkyl or $C_{0-3}$-alkylaryl); $R^{A4}$OCONR$^{A2}$ (where RA$^4$ is $C_{1-6}$-alkyl or $C_{1-3}$-alkylaryl), $R^{A4}$CONR$^{A2}$, $R^{A1}$O, $R^{A2}R^{A3}$N, HO—SO$_2$—, phenoxy, $R^{A2}R^{A3}$N—SO$_2$, Cl, Br, F, tetrazolyl, H$_2$O$_3$P—, NO$_2$, $R^{A1}$—N(OH)—CO— or $R^{A1}R^{A2}$NCONR$^{A3}$, where aryl in each case may be substituted by up to 2 identical or different radicals from the group consisting of F, Cl, Br, CF$_3$, CH$_3$, OCH$_3$ and NO$_2$;

B is

—(CH$_2$)$_{l^B}$—L$^B$—(CH$_2$)$_{m^B}$— where
$l^B$ is 0, 1, 2 or 3;
$m^B$ is 0, 1 or 2;

L$^B$ is

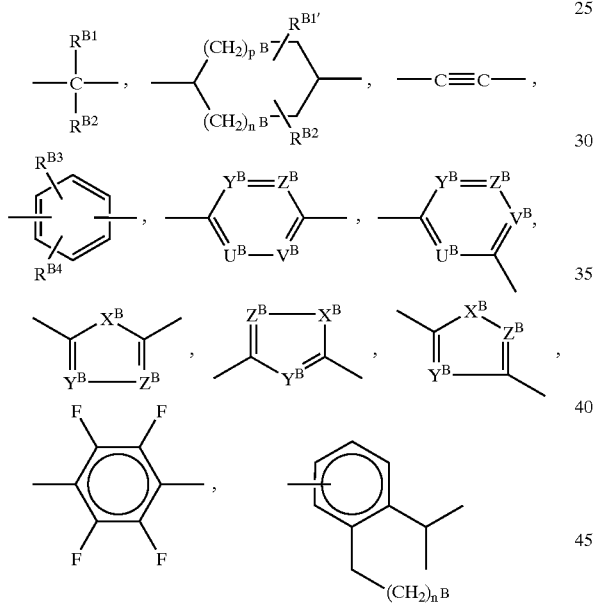

where, in each of the abovementioned ring systems, a phenyl ring can be fused on, which phenyl ring may be substituted by up to 2 identical or different radicals from the group consisting of CH$_3$, CF$_3$, Br, Cl and F or may be substituted by R$^8$OOC— (where R8 is H or $C_{1-3}$-alkyl);

where
$n^B$ is 0, 1 or 2;
$p^B$ is 0, 1 or 2;

$R^{B1}$ is $C_{0-3}$-alkylaryl, $C_{0-3}$-alkylheteroaryl, $C_{0-3}$-alkyl-$C_{3-8}$-cycloalkyl, OH or OCH$_3$;

$R^{B2}$ is H, $C_{1-6}$-alkyl, $C_{0-3}$-alkylaryl or $C_{0-3}$-alkylheteroaryl;

$R^{B3}$ is H, $C_{1-6}$-alkyl, $C_{0-3}$-alkylaryl or $C_{0-3}$-alkylheteroaryl; $R^{B5}$OCO (where $R^{B5}$ is H, $C_{1-6}$-alkyl or $C_{1-3}$-alkylaryl), $R^{B6}$—O (where $R^{B6}$ is H or $C_{1-6}$-alkyl), F, Cl, Br, NO$_2$ or CF$_3$;

$R^{B4}$ is H, $C_{1-6}$-alkyl, $R^{B6}$—O, Cl, Br, F or CF$_3$;

$R^{B1'}$ is H, $C_{1-6}$-alkyl, $C_{0-3}$-alkylaryl, $C_{0-3}$-alkylheteroaryl or $C_{0-3}$-alkyl-$C_{3-8}$-cycloalkyl;

$R^{B1}$ and $R^{B2}$ may also be bonded together;

$X^B$ is O, S, NH or N—$C_{1-6}$-alkyl;
$Y^B$ is =CH— or =N—;
$Z^B$ is =CH— or =N—;
$U^B$ is =CH— or =N—;
$V^B$ is =CH— or =N—;

B is furthermore —(CH$_2$)$_{l^B}$—L$^B$—M$^B$—L$^B$—(CH$_2$)$_{m^B}$—, where $l^B$ and $m^B$ have the abovementioned meanings and the two groups L$^B$, independently of one another, are the radicals stated under L$^B$;

M$^B$ is a single bond, O, S, CH$_2$, CH$_2$—CH$_2$, CH$_2$—O, O—CH$_2$, CH$_2$—S, S—CH$_2$, CO, SO$_2$, CH=CH or C≡C;

B is furthermore -1-adamantyl-CH$_2$—, -2-adamantyl-CH$_2$—, -1-adamantyl-, -2-adamantyl-,

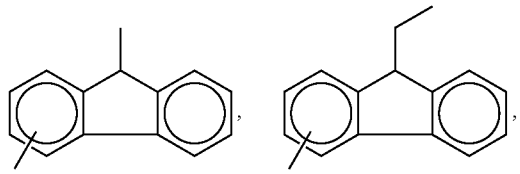

B may furthermore be

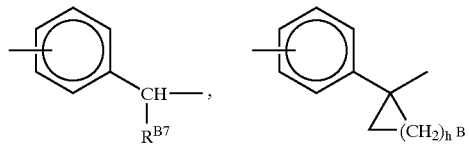

where h$^B$ is 1, 2, 3 or 4
(RB$^7$ is $C_{1-6}$-alkyl or $C_{3-8}$-cycloalkyl)

B may furthermore be

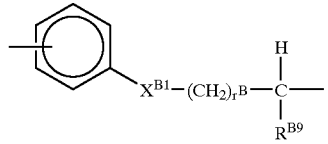

where $X^{B1}$ is a bond, O, S, or

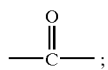

$r^B$ is 0, 1, 2 or 3;
$R^{B9}$ is H or $C_{1-3}$-alkyl;

A—B may be

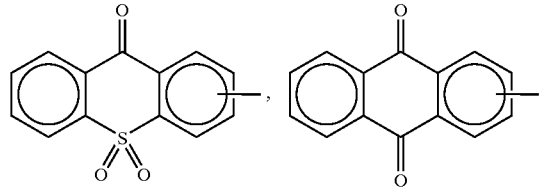

D is a single bond or CO, OCO or NR$^{D1}$—CO (where $R^{D1}$ is H, $C_{1-4}$-alkyl or $C_{0-3}$-alkylaryl), SO$_2$ or NR$^{D1}$SO$_2$;

E is

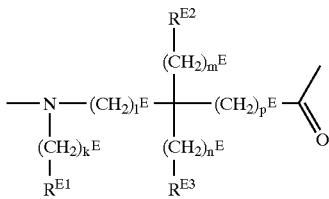

where
$k^E$ is 0 or 1;
$l^E$ is 0 or 1;
$m^E$ is 0 or 1;
$n^E$ is 0 or 1;
$p^E$ is 0 or 1;
$R^{E1}$ is H, $C_{1-6}$-alkyl, $C_{3-8}$-cycloalkyl, aryl (in particular phenyl or naphthyl), pyridyl, thienyl or $C_{3-8}$-cycloalkyl having a fused-on phenyl ring;
$R^{E1}$ is furthermore $R^{E4}OCO-CH_2$ (where $R^{E4}$ is H, $C_{1-12}$-alkyl or $C_{1-3}$-alkylaryl);
$R^{E2}$ is H, $C_{1-6}$-alkyl, $C_{3-8}$-cycloalkyl, phenyl, pyridyl, furyl, thienyl, imidazolyl, tetrahydropyranyl or tetrahydrothiopyranyl, where the abovementioned radicals may carry up to three identical or different substituents from the group consisting of $C_{1-6}$-alkyl, $O-C_{1-6}$-alkyl, F, Cl and Br, or is $CH(CH_3)OH$ or $CH(CF_3)_2$;
$R^{E3}$ is H, $C_{1-6}$-alkyl, $C_{3-8}$-cycloalkyl or phenyl;
$R^{E2}$ and $R^{B1}$ together may also form a bridge with $(CH_2)_{0-4}$, $CH=CH$, $CH_2-CH=CH$ or $CH=CH-CH_2$ groups;
the groups stated under $R^{E1}$ and $R^{E2}$ may be linked to one another via a bond; the groups stated under $R^{E2}$ and $R^{E3}$ may also be linked to one another via a bond;
if it is asymmetrically substituted, the building block E is preferably present in the R configuration;
E may also be D-Asp, D-Glu, D-Lys, D-Orn, D-His, D-Dab, D-Dap or D-Arg;
G is

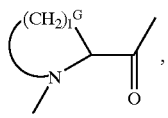

where $l^G$ is 2, 3 or 4, where a $CH_2$ group of the ring may be replaced by O, S, $CF_2$, CHF or $CH(C_{1-3}$-alkyl);

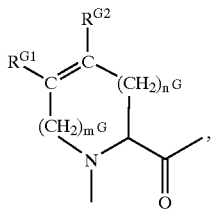

where
$m^G$ is 0, 1 or 2;
$n^G$ is 0, 1 or 2;
$R^{G1}$ and $R^{G2}$ are each H;

G is furthermore

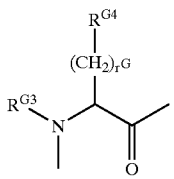

where $r^G$ is 0 or 1;
$R^{G3}$ is H, $C_1-C_6$-alkyl or $C_{3-8}$-cycloalkyl;
$R^{G4}$ is H, $C_1-C_6$-alkyl, $C_{3-8}$-cycloalkyl or phenyl;
K is
$NH-(CH_2)_{n^K}-Q^K$, where
$n^K$ is 1 or 2;
QK is

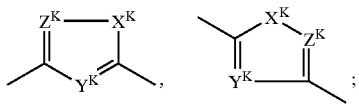

$X^K$ is O or S;

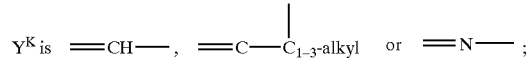

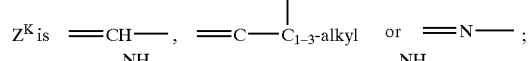

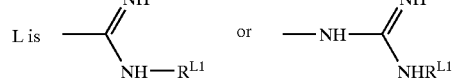

where
$R^{L1}$ is H, OH, $O-C_{1-6}$-alkyl, $O-(CH_2)_{0-3}$-phenyl, $CO-C_{1-6}$-alkyl, $CO_2-C_{1-6}$-alkyl or $CO_2-C_{1-3}$-alkylaryl.

The present invention also relates to the following particularly preferred novel compounds, their tautomers, physiologically tolerable salts and prodrugs of the formula A—B—D—E—G—K—L and drugs which contain these compounds. Furthermore, these compounds are suitable as particularly good complement inhibitors.

Here:
A is
H, $C_{1-6}$-alkyl, $C_{1-6}$-alkyl-$SO_2$ or $R^{A1}OCO$ (where $R^{A1}$ is H, $C_{1-12}$-alkyl, $C_{3-8}$-cycloalkyl, $C_{3-8}$-cycloalkyl-$C_{1-3}$-alkyl or $C_{1-3}$-alkylaryl), $R^{A2}R^{A3}NCO$ (where $R^{A2}$ is H—, $C_{1-6}$-alkyl, $C_{0-3}$-alkylaryl or $C_{0-3}$-alkylheteroaryl; $R^{A3}$ is H, $C_{1-6}$-alkyl or $C_{0-3}$-alkylaryl); $R^{A4}OCONR^{A2}$ (where $R^{A4}$ is $C_{1-6}$-alkyl or $C_{1-3}$-alkylaryl), $R^{A4}CONR^{A2}$, $R^{A1}O$, $R^{A2}R^{A3}N$, $HO-SO_2-$, phenoxy, $R^{A2}R^{A3}N-SO_2$, Cl, Br, F, tetrazolyl, $H_2O_3P-$, $NO_2$, $R^{A1}-N(OH)-CO-$ or $R^{A1}R^{A2}NCONR^{A3}$, where aryl in each case may be substituted by up to 2 identical or different radicals from the group consisting of F, Cl, Br, $CF_3$, $CH_3$, $OCH_3$ and $NO_2$;
B is
$-(CH_2)_{l^B}-L^B-(CH_2)_{m^B}-$ where
$l^B$ is 0, 1 or 2;
$m^B$ is 0, 1 or 2;

$L^B$ is

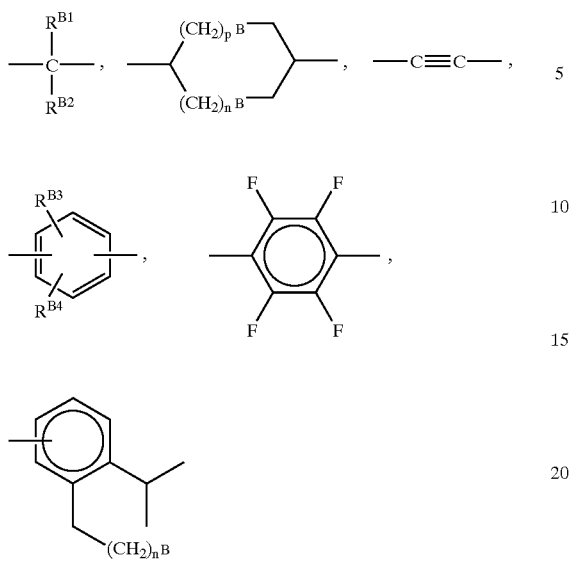

where, in each of the abovementioned ring systems, a phenyl ring can be fused on, which phenyl ring may be substituted by up to 2 identical or different radicals from the group consisting of $CH_3$, $CF_3$, Br, Cl and F or may be substituted by $R^8OOC-$ (where $R^8$ is H or $C_{1-3}$-alkyl);

where $n^B$ is 0 or 1;

$p^B$ is 0 or 1;

$R^{B1}$ is $C_{0-3}$-alkylaryl, $C_{0-3}$-alkylheteroaryl, $C_{03}$-alkyl-$C_{3-8}$-cycloalkyl, OH or $OCH_3$;

$R^{B2}$ is H, $C_{1-6}$-alkyl, $C_{0-3}$-alkylaryl or $C_{0-3}$-alkylheteroaryl;

$R^{B3}$ is H, $C_{1-6}$-alkyl; $R^{B5}OCO$ (where $R^{B5}$ is H, $C_{1-6}$-alkyl), $R^{B6}-O$ (where $R^{B6}$ is H or $C_{1-6}$-alkyl), F, Cl, Br, $NO_2$ or $CF_3$;

$R^{B4}$ is H, $C_{1-6}$-alkyl, $R^{B6}-O$, Cl, Br, F or $CF_3$;

$R^{B1}$ and $R^{B2}$ may also be bonded together;

B is furthermore $-(CH_2)_{l^B}-L^B-M^B-L^B-(CH_2)_{m^B}$, where $l^B$ and $m^B$ have the abovementioned meanings and the two groups $L^B$, independently of one another, are the radicals stated under $L^B$;

$M^B$ is a single bond, O, S, $CH_2$, $CH_2-CH_2$, $CH_2-O$, $O-CH_2$, $CH_2-S$, $S-CH_2$, $CH=CH$ or $C\equiv C$;

B is furthermore

-1-adamantyl-$CH_2-$, -2-adamantyl-$CH_2-$,

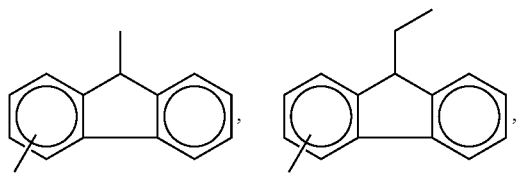

B may furthermore be

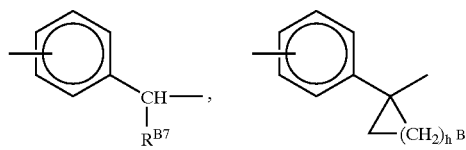

where $h^B$ is 1, 2, 3 or 4

($R^{B7}$ is $C_{1-6}$-alkyl or $C_{3-8}$-cycloalkyl)

B may furthermore be

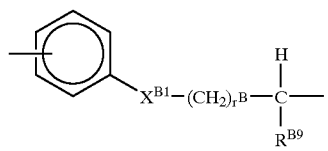

where $X^{B1}$ is a bond, O, S or

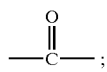

$r^B$ is 0, 1, 2 or 3;

$R^{B9}$ is H or $C_{1-3}$-alkyl;

A—B may be

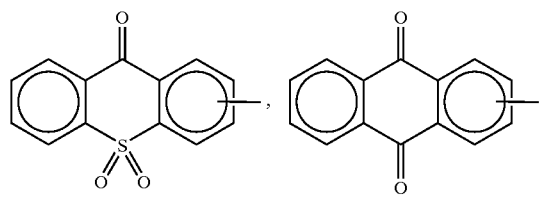

D is a single bond or CO, OCO or $NR^{D1}-CO$ (where $R^{D1}$ is H, $C_{1-4}$-alkyl or $C_{0-3}$-alkylaryl), $SO_2$ or $NR^{D1}SO_2$;

E is

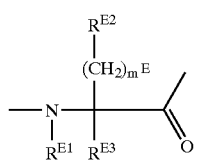

where $m^E$ is 0 or 1;

$R^{E1}$ is H or $C_{1-6}$-alkyl;

$R^{E2}$ is H, $C_{1-6}$-alkyl or $C_{3-8}$-cycloalkyl, where the abovementioned radicals may carry up to three substituents from the group consisting of $C_{1-6}$-alkyl and F, or is $CH(CH_3)OH$ or $CH(CF_3)_2$;

$R^{E3}$ is H; the groups stated under $R^{E1}$ and $R^{E2}$ may be linked to one another via a bond;

if it is asymmetrically substituted, the building block E is preferably present in the R configuration;

E may also be D-Asp, D-Glu, D-Lys, D-Orn, D-His, D-Dab, D-Dap or D-Arg;

G is

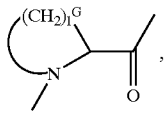

where $l^G$ is 2 or 3, where a $CH_2$ group of the ring may be replaced by S or $CHCH_3$;

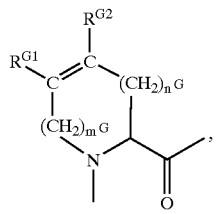

where
$m^G$ is 1;
$n^G$ is 0;
$R^{G1}$ and $R^{G2}$ are each H;

K is
$NH-(CH_2)_{n^K}-Q^K$, where
$n^K$ is 1;
$Q^K$ is

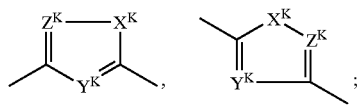

$X^K$ is S;
$Y^K$ is =CH— or =N—;
$Z^K$ is =CH— or =N—;

L is

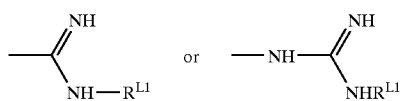

where
$R^{L1}$ is H, OH, CO—$C_{1-6}$-alkyl, $CO_2$—$C_{1-6}$-alkyl or $CO_2$—$C_{1-3}$-alkylaryl.

The present invention also relates to the following very particularly preferred novel compounds, their tautomers, physiologically tolerable salts and prodrugs of the formula A—B—D—E—G—K—L and drugs which contain these compounds. Furthermore, these compounds are suitable as particularly good complement inhibitors.
Here:

A is
H, $C_{1-6}$-alkyl, $C_{1-6}$-alkyl-$SO_2$ or $R^{A1}OCO$ (where $R^{A1}$ is H, $C_{1-12}$-alkyl, $C_{3-8}$-cycloalkyl, $C_{3-8}$-cycloalkyl-$C_{1-3}$-alkyl or $C_{1-3}$-alkylaryl), $R^{A2}R^{A3}NCO$ (where $R^{A2}$ is H—, $C_{1-6}$-alkyl, $C_{0-3}$-alkylaryl or $C_{0-3}$-alkylheteroaryl; $R^{A3}$ is H, $C_{1-6}$-alkyl or $C_{0-3}$-alkylaryl); $R^{A4}OCONR^{A2}$ (where $R^{A4}$ is $C_{1-6}$-alkyl or $C_{1-3}$-alkylaryl), $RA^4CONR^{A2}$, $R^{A1}O$, $R^{A2}R^{A3}N$, HO—$SO_2$—, phenoxy, $R^{A2}R^{A3}N$—$SO_2$, Cl, Br, F, tetrazolyl, $H_2O_3P$—, $NO_2$, $R^{A1}$—N(OH)—CO— or $R^{A1}R^{A2}NCONR^{A3}$, where aryl in each case may be substituted by up to 2 identical or different radicals from the group consisting of F, Cl, Br, $CF_3$, $CH_3$, $OCH_3$ and $NO_2$;

B is
—$(CH_2)_{l^B}$—$L^B$—$(CH_2)_{m^B}$— where
$l^B$ is 0 or 1;
$m^B$ is 0, 1 or 2;

$L^B$ is

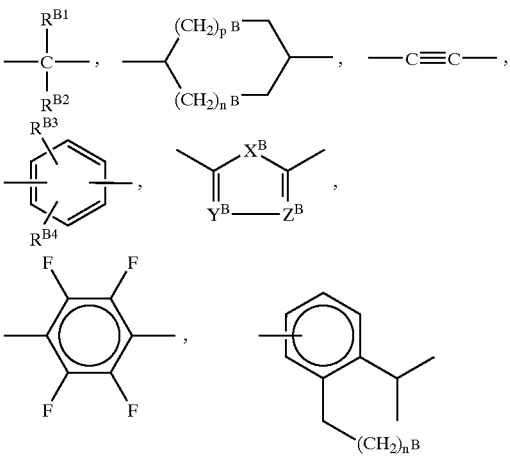

where, in each of the abovementioned ring systems, a phenyl ring can be fused on, which phenyl ring may be substituted by up to 2 identical or different radicals from the group consisting of $CH_3$, $CF_3$, Br, Cl and F or may be substituted by $R^8OOC$— (where $R^8$ is H or $C_{1-3}$-alkyl);
where
$n^B$ is 0 or 1;
$p^B$ is 0 or 1;
$R^{B1}$ is $C_{0-3}$-alkylaryl, $C_{0-3}$-alkylheteroaryl, $C_{0-3}$-alkyl-$C_{3-8}$-cycloalkyl, OH or $OCH_3$;
$R^{B2}$ is H, $C_{1-6}$-alkyl, $C_{0-3}$-alkylaryl or $C_{0-3}$-alkylheteroaryl;
$R^{B3}$ is H, $C_{1-6}$-alkyl;
$R^{B5}OCO$ (where $R^{B5}$ is H or $C_{1-6}$-alkyl), RB6—O (where $R^{B6}$ is H or $C_{1-6}$-alkyl), F, Cl, Br, $NO_2$ or $CF_3$;
$R^{B4}$ is H, $C_{1-6}$-alkyl, $R^{B6}$—O, Cl, Br, F or $CF_3$;
$R^{B1}$ and $R^{B2}$ may also be bonded together;
$X^B$ is O or S;
$Y^B$ is =CH— or =N—;
$Z^B$ is =CH— or =N—;

B is furthermore —$(CH_2)_{l^B}$—$L^B$—$M^B$—$L^B$—$(CH_2)_{m^B}$, where $l^B$ and $m^B$ have the abovementioned meanings and the two groups $L^B$, independently of one another, are the radicals —C≡C— stated under $L^B$,

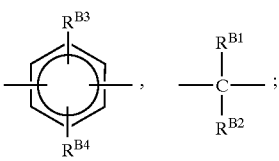

$M^B$ is a single bond, O, $CH_2$—S, S—$CH_2$, CO, $SO_2$ or $CH_2$—O;

B may furthermore be

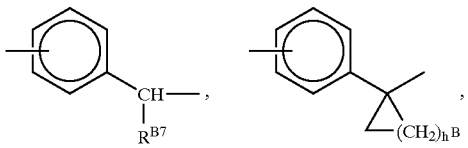

where $h^B$ is 1, 2, 3 or 4
($R^{B7}$ is $C_{1-6}$-alkyl or $C_{3-8}$-cycloalkyl)

B may furthermore be 1-fluorenyl-, 1-adamantyl- or 1-adamantyl-$CH_2$—,

A—B may be 2-pyridyl-$CH_2$—, 2-benzothienyl-, 3-benzothienyl-,

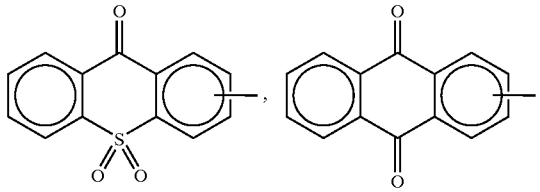

D is a single bond or CO or $SO_2$;

E is

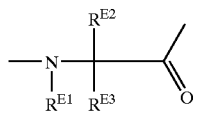

where
$R^{E1}$ is H or $CH_3$;
$R^{E2}$ is H, $C_{1-6}$-alkyl, $C_{3-8}$-cycloalkyl, thienyl, $CH(CH_3)OH$ or $CH(CF_3)_2$;
$R^{E3}$ is H;
the groups stated under $R^{E1}$ and $R^{E2}$ may be linked to one another via a bond; the groups stated under $R^{E2}$ and $R^{E3}$ may also be linked to one another via a bond;
if it is asymmetrically substituted, the building block E is preferably present in the R configuration;

E may also be D-Lys, D-Orn, D-Dab, D-Dap or D-Arg;

G is

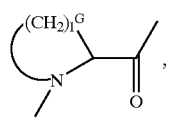

where $l^G$ is 2 or 3, where a $CH_2$ group of the ring may be replaced by $CHCH_3$;

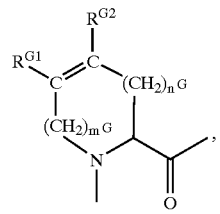

where
$m^G$ is 1;
$n^G$ is 0;
$R^{G1}$ and $R^{G2}$ are each H;

K is
NH—$(CH_2)_{n^K}$—$Q^K$, where
$n^K$ is 1;
$Q^K$ is

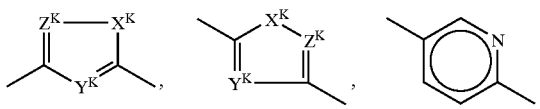

$X^K$ is S;
$Y^K$ is =CH— or =N—;
$Z^K$ is =CH— or =N—;

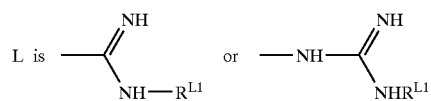

where
$R^{L1}$ is H or OH.

The present invention also relates to the following preferred novel compounds, their tautomers, physiologically tolerable salts and prodrugs of the formula A—B—D—E—G—K—L and drugs which contain these compounds. Furthermore, these compounds are suitable as particularly good complement inhibitors.

Here:

A is
H, $C_{1-6}$-alkyl, $C_{1-6}$-alkyl-$SO_2$ or $R^{A1}OCO$ (where $R^{A1}$ is H, $C_{1-12}$-alkyl, $C_{3-8}$-cycloalkyl, $C_{1-3}$-alkyl-$C_{3-8}$-cycloalkyl or $C_{1-3}$-alkylaryl), $R^{A2}R^{A3}NCO$ (where $R^{A2}$ is H, $C_{1-6}$-alkyl, $C_{0-3}$-alkylaryl or $C_{0-3}$-alkylheteroaryl; $R^{A3}$ is H, $C_{1-6}$-alkyl or $C_{0-3}$-alkylaryl), $R^{A4}OCONR^{A2}$, $R^{A4}CONR^{A2}$ (where $R^{A4}$ is $C_{1-6}$-alkyl or $C_{1-3}$-alkylaryl), $R^{A1}O$, phenoxy, $R^{A2}R^{A3}N$, HO—$SO_2$, $R^{A2}R^{A3}N$—$SO_2$, Cl, Br, F, tetrazolyl, $H_2O_3P$, $NO_2$, $R^{A1}$—N(OH)—CO or $R^{A1}R^{A2}NCONR^{A3}$, where aryl in each case may be substituted by up to 2 identical or different radicals from the group consisting of F, Cl, Br, $OCH_3$, $CH_3$, $CF_3$ and $NO_2$;

B is
—$(CH_2)_{l^B}$—$L^B$—$(CH_2)_{m^B}$—, where
$l^B$ is 0, 1 or 2;
$m^B$ is 0, 1 or 2;

$L^B$ is

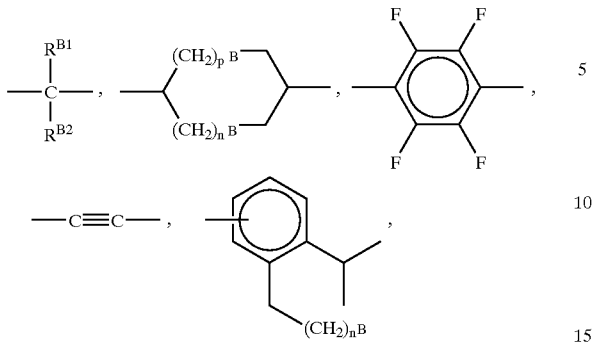

where, in each of the abovementioned ring systems, a phenyl ring can be fused on, which phenyl ring may be substituted by up to 2 identical or different radicals from the group consisting of $CH_3$, $CF_3$, Br, Cl and F or may be substituted by $R^8OOC$— (where $R^8$ is H or $C_{1-3}$-alkyl);

where $n^B$ is 0, 1 or 2;

$p^B$ is 0, 1 or 2;

$R^{B1}$ is $C_{0-3}$-alkylaryl, $C_{0-3}$-alkylheteroaryl, $C_{0-3}$-alkyl-$C_{3-8}$-cycloalkyl, OH or $OCH_3$;

$R^{B2}$ is H, $C_{1-6}$-alkyl, $C_{0-3}$-alkylaryl or $C_{0-3}$-alkylheteroaryl;

$R^{B1}$ and $R^{B2}$ may also be bonded together;

B is furthermore -1-adamantyl-$CH_2$—, -2-adamantyl-$CH_2$—,

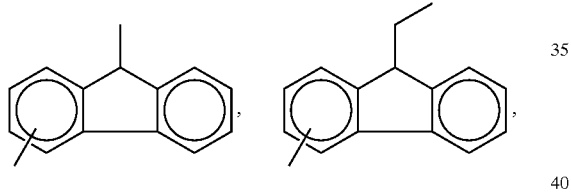

B is furthermore —$(CH_2)_{l^B}$—$L^{B1}$—$M^B$—$L^{B2}$—$(CH_2)_{m^B}$—, where $l^B$ and $m^B$ have the abovementioned meanings and the two groups $L^{B1}$ and $L^{B2}$, independently of one another, are the following radicals:

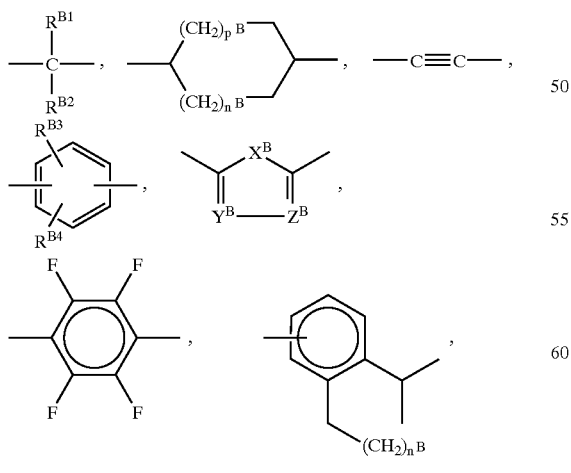

where, in each of the abovementioned ring systems, a phenyl ring can be fused on;

where $n^B$ is 0, 1 or 2;

$p^B$ is 0, 1 or 2;

$R^{B1}$ is H (only for $L^{B2}$), $C_{1-6}$-alkyl (only for $L^{B2}$), $C_{0-3}$-alkylaryl, $C_{0-3}$-alkylheteroaryl, $C_{0-3}$-alkyl-$C_{3-8}$-cycloalkyl, OH or $OCH_3$;

$R^{B2}$ is H, $C_{1-6}$-alkyl, $C_{0-3}$-alkylaryl or $C_{0-3}$-alkylheteroaryl;

$R^{B3}$ is H, $C_{1-6}$-alkyl, aryl, heteroaryl, $R^{B5}OCO$ (where $R^{B5}$ is H or $C_{1-6}$-alkyl), $R^{B6}$—O (where $R^{B6}$ is H or $C_{1-6}$-alkyl), F, Cl, Br, $NO_2$ or $CF_3$;

$R^{B4}$ is H, $C_{1-6}$-alkyl, $R^{B6}$—O, Cl, Br, F or $CF_3$;

$X^B$ is O or S;

$Y^B$ is =CH— or =N—;

$Z^B$ is =CH— or =N—;

$R^{B1}$ and $R^{B2}$ may also be bonded together;

$M^B$ is a single bond, O, S, $CH_2$, $CH_2$—$CH_2$, $CH_2$—O, O—$CH_2$, $CH_2$—S, S—$CH_2$, CO, $SO_2$, CH=CH or C≡C;

B may furthermore be

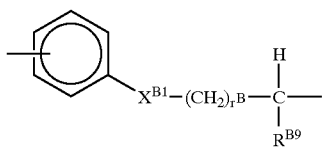

where $X^{B1}$ is a bond, O, S or

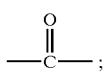;

$r^B$ is 0, 1, 2 or 3;

$R^{B9}$ is H or $C_{1-3}$-alkyl;

A—B may be

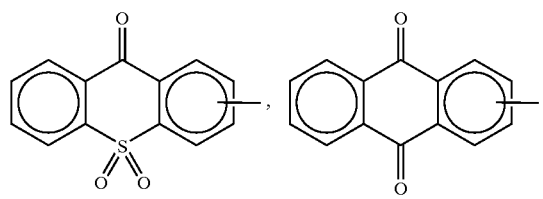

D is a single bond or CO, OCO, $NR^{D1}$—CO (where $R^{D1}$ is H, $C_{1-4}$-alkyl or $C_{0-3}$-alkylaryl), $SO_2$ or $NR^{D1}SO_2$;

B—D may be

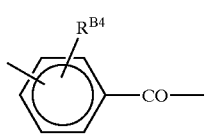

E is

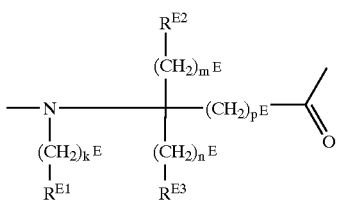

$k^E$ is 0 or 1;
$m^E$ is 0 or 1;
$n^E$ is 0 or 1;
$p^E$ is 0 or 1;
$R^{E1}$ is H, $C_{1-6}$-alkyl, $C_{3-8}$-cycloalkyl, phenyl, naphthyl, pyridyl, thienyl or $C_{3-8}$-cycloalkyl having a fused-on phenyl ring;
$R^{E2}$ is H, $C_{1-6}$-alkyl, $C_{3-8}$-cycloalkyl, phenyl, pyridyl, thienyl, furyl, imidazolyl, tetrahydropyranyl, tetrahydrothiopyranyl, $CH(CH_3)OH$ or $CH(CF_3)_2$;
$R^{E3}$ is H, $C_{1-6}$-alkyl, $C_{3-8}$-cycloalkyl or phenyl;
the groups stated under $R^{E1}$ and $R^{E2}$ may be linked to one another via a bond; the groups stated under $R^{E2}$ and $R^{E3}$ may also be linked to one another via a bond;
if it is asymmetrically substituted, the building block E is preferably present in the R configuration;
E may also be D-Asp, D-Glu, D-Lys, D-Orn, D-His, D-Dab, D-Dap or D-Arg;
G is

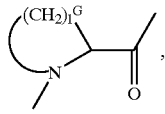

where $l^G$ is 2, 3 or 4, where a $CH_2$ group of the ring may be replaced by $CHCH_3$;

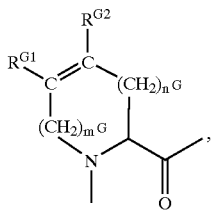

where
$m^G$ is 1;
$n^G$ is 0 or 1;
$R^{G1}$ is H;
$R^{G2}$ is H;
G is furthermore

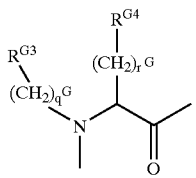

where
$q^G$ is 0 or 1;
$r^G$ is 0 or 1;

$R^{G3}$ is H, $C_1$–$C_6$-alkyl or $C_{3-8}$-cycloalkyl;
$R^{G4}$ is H, $C_1$–$C_6$-alkyl, $C_{3-8}$-cycloalkyl or phenyl;
K is
$NH$—$(CH_2)_{n^K}$—$Q^K$, where
$n^K$ is 1;
$Q^K$ is

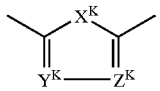

$X^K$ is O or S;
$Y^K$ is =CH— or =N—;
$Z^K$ is =CH— or =N—;
L is

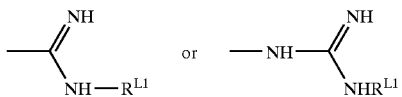

where
$R^{L1}$ is H, OH, CO—$C_{1-6}$-alkyl, $CO_2$—$C_{1-6}$-alkyl or $CO_2$—$C_{1-5}$-alkylaryl.

The present invention also relates to the following particularly preferred novel compounds, their tautomers, physiologically tolerable salts and prodrugs of the formula A—B—D—E—G—K—L and drugs which contain these compounds. Furthermore, these compounds are suitable as particularly good complement inhibitors.

Here:

A is
H, $C_{1-6}$-alkyl, $C_{1-6}$-alkyl-$SO_2$, $R^{A1}OCO$ (where $R^{A1}$ is H, $C_{1-12}$-alkyl, $C_{3-8}$-cycloalkyl, $C_{1-3}$-alkyl-$C_{3-8}$-cycloalkyl or $C_{1-3}$-alkylaryl), $R^{A2}R^{A3}NCO$ (where $R^{A2}$ is H, $C_{1-6}$-alkyl, $C_{0-3}$-alkylaryl or $C_{0-3}$-alkylheteroaryl; $R^{A3}$ is H, $C_{1-6}$-alkyl or $C_{0-3}$-alkylaryl), $R^{A4}OCONR^{A2}$, $R^{A4}CONR^{A2}$ (where $R^{A4}$ is $C_{1-6}$-alkyl or $C_{1-3}$-alkylaryl), $R^{A1}O$, phenoxy, $R^{A2}R^{A3}N$, HO—$SO_2$, $R^{A2}R^{A3}N$—$SO_2$, Cl, Br, F, tetrazolyl, $H_2O_3P$, $NO_2$, $R^{A1}$—$N(OH)$—CO or $R^{A1}R^{A2}NCONR^{A3}$, where aryl in each case may be substituted by up to 2 identical or different radicals from the group consisting of F, Cl, Br, $OCH_3$, $CH_3$, $CF_3$ and $NO_2$;

B is
—$(CH_2)_{l^B}$—$L^B$—$(CH_2)_{m^B}$—, where
$l^B$ is 0 or 1;
$m^B$ is 0, 1 or 2;
$L^B$ is

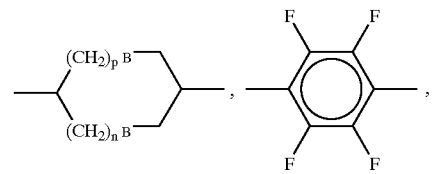

-continued

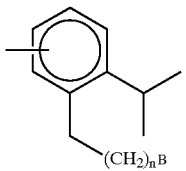

where, in each of the abovementioned ring systems, a phenyl ring can be fused on, which phenyl ring may be substituted by up to 2 identical or different radicals from the group consisting of $CH_3$, $CF_3$, Br, Cl and F or may be substituted by $R^8OOC—$ (where $R^8$ is H or $C_{1-3}$-alkyl);
where
$n^B$ is 0 or 1;
$p^B$ is 0 or 1;
B is furthermore -1-adamantyl-$CH_2$—, -2-adamantyl-$CH_2$—,

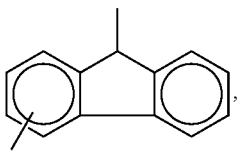

B is furthermore —$(CH_2)_{l^B}$—$L^{B1}$—$M^B$—$L^{B2}$—$(CH_2)_{m^B}$—, where $l^B$ and $m^B$ have the abovementioned meanings and the two groups $L^{B1}$ and $L^{B2}$, independently of one another, are the following radicals:

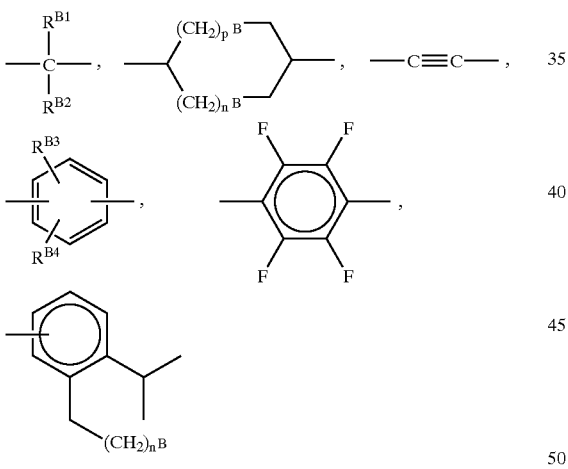

where, in each of the abovementioned ring systems, a phenyl ring can be fused on;
where
$n^B$ is 1;
$p^B$ is 0 or 1;
$R^{B1}$ is H (only for $L^{B2}$), $C_{1-6}$-alkyl (only for $L^{B2}$), $C_{0-3}$-alkylaryl, $C_{0-3}$-alkylheteroaryl, $C_{0-3}$-alkyl-$C_{3-8}$-cycloalkyl, OH or $OCH_3$;
$R^{B2}$ is H, $C_{1-6}$-alkyl, $C_{0-3}$-alkylaryl or $C_{0-3}$-alkylheteroaryl;
$R^{B3}$ is H, $C_{1-6}$-alkyl, $R^{B6}$—O (where $R^{B6}$ is H, $C_{1-6}$-alkyl), F, Cl, Br, $NO_2$ or $CF_3$;
$R^{B4}$ is H, $C_{1-6}$-alkyl, $R^{B6}$—O, Cl, Br, F or $CF_3$;
$R^{B1}$ and $R^{B2}$ may also be bonded together;
$M^B$ is a single bond, O, S, $CH_2$, $CH_2$—$CH_2$, $CH_2$—O, O—$CH_2$, $CH_2$—S, S—$CH_2$, CO or $SO_2$;

A—B may be 2-pyridyl-$CH_2$—, 2-benzothienyl-,

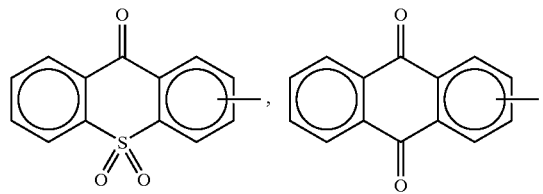

D is a single bond or CO or $SO_2$;
B—D may be

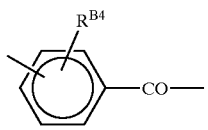

E is

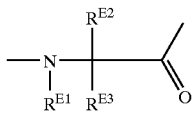

$R^{E1}$ is H;
$R^{E2}$ is H, $C_{1-6}$-alkyl, $C_{3-8}$-cycloalkyl, phenyl, pyridyl, thienyl, furyl, imidazolyl, tetrahydropyranyl, tetrahydrothiopyranyl, $CH(CH_3)OH$ or $CH(CF_3)_2$;
$R^{E3}$ is H; the groups stated under $R^{E1}$ and $R^{E2}$ may be linked to one another via a bond;
E may also be D-Lys, D-Orn, D-Dab, D-Dap or D-Arg;
G is

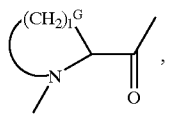

where $l^G$ is 2 or 3, where a $CH_2$ group of the ring may be replaced by $CHCH_3$;

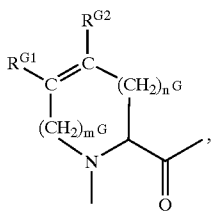

where
$m^G$ is 1;
$n^G$ is 0;
$R^{G1}$ is H;
$R^{G2}$ is H;

K is
    NH—(CH$_2$)$_{n^K}$—Q$^K$, where
    n$^K$ is 1;
    Q$^K$ is

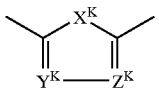

X$^K$ is S;
Y$^K$ is =CH— or =N—;
Z$^K$ is =CH— or =N—;

L is

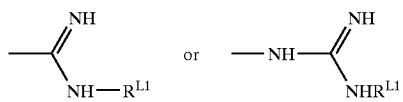

where
R$^{L1}$ is H or OH.

The present invention also relates to the following preferred novel compounds, their tautomers, physiologically tolerable salts and prodrugs of the formula A—B—D—E—G—K—L and drugs which contain these compounds. Furthermore, these compounds are suitable as particularly good complement inhibitors.

Here:

A is
    H, C$_{1-6}$-alkyl, C$_{1-6}$-alkyl-SO$_2$, R$^{A1}$OCO (where R$^{A1}$ is H, C$_{1-12}$-alkyl, C$_{3-8}$-cycloalkyl, C$_{1-3}$-alkyl-C$_{3-8}$-cycloalkyl or C$_{1-3}$-alkylaryl), R$^{A2}$R$^{A3}$NCO (where R$^{A2}$ is H, C$_{1-6}$-alkyl, C$_{0-3}$-alkylaryl or C$_{0-3}$-alkylheteroaryl; R$^{A3}$ is H, C$_{1-6}$-alkyl or C$_{0-3}$-alkylaryl), R$^{A4}$OCONR$^{A2}$, R$^{A4}$CONR$^{A2}$ (where R$^{A4}$ is C$_{1-6}$-alkyl or C$_{1-3}$-alkylaryl), R$^{A1}$O, phenoxy, R$^{A2}$R$^{A3}$N, HO—SO$_2$, R$^{A2}$R$^{A3}$N—SO$_2$, Cl, Br, F, tetrazolyl, H$_2$O$_3$P, NO$_2$, R$^{A1}$—N(OH)—CO— or R$^{A1}$R$^{A2}$NCONR$^{A3}$, where aryl in each case may be substituted by up to 2 identical or different substituents from the group consisting of F, Cl, Br, CH$_3$, CF$_3$, OCH$_3$ and NO$_2$;

B is
    —(CH$_2$)$_{l^B}$—L$^B$—(CH$_2$)$_{m^B}$, where
    l$^B$ is 0 or 1;
    m$^B$ is 0, 1 or 2;

L$^B$ is

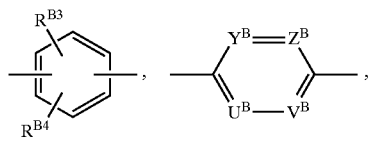

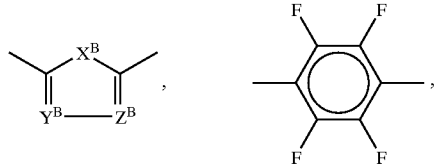

where, in each of the abovementioned ring systems, a phenyl ring can be fused on;

R$^{B3}$ is H, C$_{1-6}$-alkyl, aryl, R$^{B5}$OCO (where R$^{B5}$ is H, C$_{1-6}$-alkyl or C$_{1-3}$-alkylaryl), R$^{B6}$—O (where R$^{B6}$ is H or C$_{1-6}$-alkyl), F, Cl, Br, NO$_2$ or CF$_3$;

R$^{B4}$ is H, C$_{1-6}$-alkyl, R$^{B6}$—O, Cl, Br, F or CF$_3$;

X$^B$ is O or S;

Y$^B$ is =CH— or =N—;
Z$^B$ is =CH— or =N—;
U$^B$ is =CH— or =N—;
V$^B$ is =CH— or =N—;

B may furthermore be

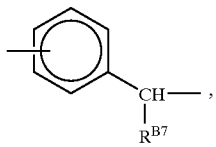

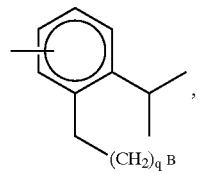

where q$^B$ is 0, 1 or 2
(R$^{B7}$ is C$_{1-6}$-alkyl or C$_{3-8}$-cycloalkyl)

A—B may be

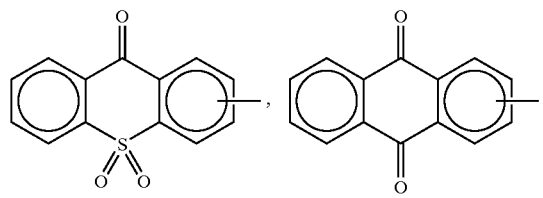

D is a single bond;

E is

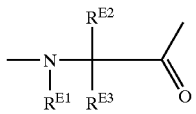

where
R$^{E1}$ is H;
R$^{E2}$ is H, C$_{1-6}$-alkyl, C$_{3-8}$-cycloalkyl, phenyl, pyridyl, furyl, thienyl, imidazolyl, tetrahydropyranyl or tetrahydrothiopyranyl, where the abovementioned radicals may carry up to three identical or different substituents from the group consisting of O—C$_{1-6}$-alkyl and F, or is CH(CH$_3$)OH or CH(CF$_3$)$_2$;
R$^{E3}$ is H;
    the groups stated under R$^{E1}$ and R$^{E2}$ may be linked to one another via a bond;
    if it is asymmetrically substituted, the building block E is preferably present in the R configuration;

E may also be D-Lys, D-Orn, D-Dab, D-Dap or D-Arg;

G is

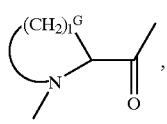

where l$^G$ is 2 or 3, where a CH$_2$ group of the ring may be replaced by CHCH$_3$;

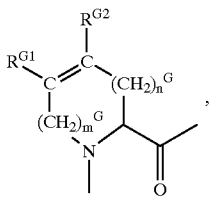

where
$m^G$ is 1;
$n^G$ is 0;
$R^{G1}$ is H;
$R^{G2}$ is H;
K is
NH—(CH$_2$)$_{n^K}$—Q$^K$, where
$n^K$ is 1;
QK is

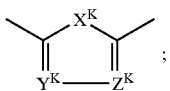

$X^K$ is O or S;
$Y^K$ is =CH— or =N—;
$Z^K$ is =CH— or =N—;

L is 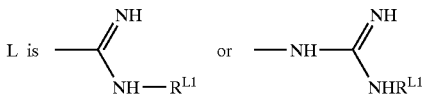

where
$R^{L1}$ is —H or —OH.

If $R^{L1}$ is not hydrogen in the compounds of the formula I, these substances are prodrugs from which the free amidine/guanidine compounds form under in vivo conditions. If the compounds of the formula I contain ester functions, these compounds can act in vivo as prodrugs from which the corresponding carboxylic acids form.

In addition to the substances stated in the examples, the following compounds are very particularly preferred and can be prepared by the stated preparation methods:

1. C$_6$H$_5$—C≡C—CO—(D)Cpg-Pyr-NH—CH$_2$-5-(3-am)-thioph
2. C$_6$H$_5$—C≡C—CO—(D)Ile-Pyr-NH—CH$_2$-5-(3-am)-thioph
3. C$_6$H$_5$—C≡C—CO—(D)allo-Ile-Pyr-NH—CH$_2$-5-(3-am)-thioph
4. C$_6$H$_5$—C≡C—CO—(D)Pro-Pyr-NH—CH$_2$-5-(3-am)-thioph
5. C$_6$H$_5$—C≡C—CO—(D)(2-(2-Thienyl))gly-Pyr-NH—CH$_2$-5-(3-am)-thioph
6. C$_6$H$_5$—C≡C—CO—(D)(2-(3-Thienyl))gly-Pyr-NH—CH$_2$-5-(3-am)-thioph
7. C$_6$H$_5$—C≡C—CO—(D)Phg-Pyr-NH—CH$_2$-5-(3-am)-thioph
8. C$_6$H$_5$—C≡C—CO—(D)(2-Me)Chg-Pyr-NH—CH$_2$-5-(3-am)-thioph
9. C$_6$H$_5$—C≡C—CO—Aib-Pyr-NH—CH$_2$-5-(3-am)-thioph
10. C$_6$H$_5$—C≡C—CO—Acpc-Pyr-NH—CH$_2$-5-(3-am)-thioph
11. C$_6$H$_5$—C≡C—CO—Achc-Pyr-NH—CH$_2$-5-(3-am)-thioph
12. C$_6$H$_5$—C≡C—CO—(D)(2-(2-Furanyl))gly-Pyr-NH—CH$_2$-5-(3-am)-thioph
13. C$_6$H$_5$—C≡C—CO—(D)(N-Me)Val-Pyr-NH—CH$_2$-5-(3-am)-thioph
14. C$_6$H$_5$—C≡C—CO—(D)Nva-Pyr-NH—CH$_2$-5-(3-am)-thioph
15. C$_6$H$_5$—C≡C—CO—(D)Thr-Pyr-NH—CH$_2$-5-(3-am)-thioph
16. C$_6$H$_5$—C≡C—CO—(D)(Tetrahydro-4-thiopyranyl)gly-Pyr-NH—CH$_2$-5-(3-am)-thioph
17. 4-HOOC—C$_6$H$_4$—CH$_2$—(D)Cpg-Pyr-NH—CH$_2$-5-(3-am)-thioph
18. 4-HOOC—C$_6$H$_4$—CH$_2$—(D)2-(2-Thienyl)gly-Pyr-NH—CH$_2$-5-(3-am)-thioph
19. 4-HOOC—C$_6$H$_4$—CH$_2$—(D)2-(3-Thienyl)gly-Pyr-NH—CH$_2$-5-(3-am)-thioph
20. 4-HOOC—C$_6$H$_4$—CH$_2$—(D)Phg-Pyr-NH—CH$_2$-5-(3-am)-thioph
21. 4-HOOC—C$_6$H$_4$—CH$_2$—(D)(2-Me)Chg-Pyr-NH—CH$_2$-5-(3-am)-thioph
22. 4-HOOC—C$_6$H$_4$—CH$_2$—Aib-Pyr-NH—CH$_2$-5-(3-am)-thioph
23. 4-HOOC—C$_6$H$_4$—CH$_2$—Achc-Pyr-NH—CH$_2$-5-(3-am)-thioph
24. 4-HOOC—C$_6$H$_4$—CH$_2$—(D)(2-(2-Furanyl))gly-Pyr-NH—CH$_2$-5-(3-am)-thioph
25. 4-HOOC—C$_6$H$_4$—CH$_2$—(D)Thr-Pyr-NH—CH$_2$-5-(3-am)-thioph
26. 4-HOOC—C$_6$H$_4$—CH$_2$—(D)(Tetrahydro-4-thiopyranyl)-gly-Pyr-NH—CH$_2$-5-(3-am)-thioph
27. C$_6$H$_5$—C≡C—CO—(D)Cpg-Pro-NH—CH$_2$-5-(3-am)-thioph
28. C$_6$H$_5$—C≡C—CO—(D)Ile-Pro-NH—CH$_2$-5-(3-am)-thioph
29. C$_6$H$_5$—C≡C—CO—(D)allo-Ile-Pro-NH—CH$_2$-5-(3-am)-thioph
30. C$_6$H$_5$—C≡C—CO—(D)Pro-Pro-NH—CH$_2$-5-(3-am)-thioph
31. C$_6$H$_5$—C≡C—CO—(D)(2-(2-Thienyl))gly-Pro-NH—CH$_2$-5-(3-am)-thioph
32. C$_6$H$_5$—C≡C—CO—(D)(2-(3-Thienyl))gly-Pro-NH—CH$_2$-5-(3-am)-thioph
33. C$_6$H$_5$—C≡C—CO—(D)Phg-Pro-NH—CH$_2$-5-(3-am)-thioph
34. C$_6$H$_5$—C≡C—CO—(D)(2-Me)Chg-Pro-NH—CH$_2$-5-(3-am)-thioph
35. C$_6$H$_5$—C≡C—CO—Aib-Pro-NH—CH$_2$-5-(3-am)-thioph
36. C$_6$H$_5$—C≡C—CO—Acpc-Pro-NH—CH$_2$-5-(3-am)-thioph
37. C$_6$H$_5$—C≡C—CO—Achc-Pro-NH—CH$_2$-5-(3-am)-thioph
38. C$_6$H$_5$—C≡C—CO—(D)(2-(2-Furanyl))gly-Pro-NH—CH$_2$-5-(3-am)-thioph
39. C$_6$H$_5$—C≡C—CO—(D)(N-Me)Val-Pro-NH—CH$_2$-5-(3-am)-thioph
40. C$_6$H$_5$—C≡C—CO—(D)Abu-Pro-NH—CH$_2$-5-(3-am)-thioph
41. C$_6$H$_5$—C≡C—CO—(D)Nva-Pro-NH—CH$_2$-5-(3-am)-thioph
42. C$_6$H$_5$—C≡C—CO—(D)Thr-Pro-NH—CH$_2$-5-(3-am)-thioph
43. C$_6$H$_5$—C≡C—CO—(D)(Tetrahydro-4-thiopyranyl)gly-Pro-NH—CH$_2$-5-(3-am)-thioph
44. C$_6$H$_5$—C≡C—CO—(D)Cpg-(3S)-MePro-NH—CH$_2$-5-(3-am)-thioph
45. C$_6$H$_5$—C≡C—CO—(D)Ile-L-(3S)-3-MePro-NH—CH$_2$-5-(3-am)-thioph
46. C$_6$H$_5$—C≡C—CO—(D)2-(2-Thienyl)gly-((3S)-3-Me)Pro-NH—CH$_2$-5-(3-am)-thioph
47. C$_6$H$_5$—C≡C—CO—(D)2-(3-Thienyl)gly-((3S)-3-Me)Pro-NH—CH$_2$-5-(3-am)-thioph
48. C$_6$H$_5$—C≡C—CO—(D)Chg-((3S)-3-Me)Pro-NH—CH$_2$-5-(3-am)-thioph
49. C$_6$H$_5$—C≡C—CO—(D)(Tetrahydro-4-thiopyranyl)gly-((3S)-3-Me)-Pro-NH—CH$_2$-5-(3-am)-thioph
50. C$_6$H$_5$—C≡C—CO—(D)Cpg-(trans-4-F)Pro-NH—CH$_2$-5-(3-am)-thioph
51. C$_6$H$_5$—C≡C—CO—(D)Val-(trans-4-F)Pro-NH—CH$_2$-5-(3-am)-thioph
52. C$_6$H$_5$—C≡C—CO—(D)2-(2-Thienyl)gly-(trans-4-F)Pro-NH—CH$_2$-5-(3-am)-thioph
53. C$_6$H$_5$—C≡C—CO—(D)2-(3-Thienyl)gly-(trans-4-F)Pro-NH—CH$_2$-5-(3-am)-thioph
54. C$_6$H$_5$—C≡C—CO—(D)Chg-(trans-4-F)Pro-NH—CH$_2$-5-(3-am)-thioph -continued 55. C$_6$H$_5$—C≡C—CO—(D)Cpg-(cis-4-F)-Pro-NH—CH$_2$-5-(3-am)-thioph
56. C$_6$H$_5$—C≡C—CO—(D)Val-(cis-4-F)Pro-NH—CH$_2$-5-(3-am)-thioph
57. C$_6$H$_5$—C≡C—CO—(D)(2-(2-Thienyl))gly-(cis-4-F)Pro-NH—CH$_2$-5-(3-am)-thioph
58. C$_6$H$_5$—C≡C—CO—(D)(2-(3-Thienyl))gly-(cis-4-F)Pro-NH—CH$_2$-5-(3-am)-thioph
59. C$_6$H$_5$—C≡C—CO—(D)Chg-(cis-4-F)Pro-NH—CH$_2$-5-(3-am)-thioph
60. C$_6$H$_5$—C≡C—CO—(D)Cpg-(5-Me)Pro-NH—CH$_2$-5-(3-am)-thioph
61. C$_6$H$_5$—C≡C—CO—(D)Val-(5-Me)Pro-NH—CH$_2$-5-(3-am)-thioph
62. C$_6$H$_5$—C≡C—CO—(D)(2-(2-Thienyl))gly-(5-Me)Pro-NH—CH$_2$-5-(3-am)-thioph
63. C$_6$H$_5$—C≡C—CO—(D)(2-(3-Thienyl))gly-(5-Me)Pro-NH—CH$_2$-5-(3-am)-thioph
64. C$_6$H$_5$—C≡C—CO—(D)Chg-(5-Me)Pro-NH—CH$_2$-5-(3-am)-thioph
65. C$_6$H$_5$—C≡C—CO—(D)Cpg-Ohii-1-CO—NH—CH$_2$-5-(3-am)-thioph
66. C$_6$H$_5$—C≡C—CO—(D)Val-Ohii-1-CO—NH—CH$_2$-5-(3-am)-thioph
67. C$_6$H$_5$—C≡C—CO—(D)(2-(2-Thienyl))gly-Ohii-1-CO—NH—CH$_2$-5-(3-am)-thioph
68. C$_6$H$_5$—C≡C—CO—(D)(2-(3-Thienyl))gly-Ohii-1-CO—NH—CH$_2$-5-(3-am)-thioph
69. C$_6$H$_5$—C≡C—CO—(D)Chg-Ohii-1-CO—NH—CH$_2$-5-(3-am)-thioph
70. C$_6$H$_5$—C≡C—CO—(D)Cpg-Ohi-2-CO—NH—CH$_2$-5-(3-am)-thioph
71. C$_6$H$_5$—C≡C—CO—(D)Val-Ohi-2-CO—NH—CH$_2$-5-(3-am)-thioph
72. C$_6$H$_5$—C≡C—CO—(D)(2-(2-Thienyl))gly-Ohi-2-CO—NH—CH$_2$-5-(3-am)-thioph
73. C$_6$H$_5$—C≡C—CO—(D)(2-(3-Thienyl))gly-Ohi-2-CO—NH—CH$_2$-5-(3-am)-thioph
74. C$_6$H$_5$—C≡C—CO—(D)Chg-Ohi-2-CO—NH—CH$_2$-5-(3-am)-thioph
75. C$_6$H$_5$—C≡C—CO—(D)Cpg-Ind-2-CO—NH—CH$_2$-5-(3-am)-thioph
76. C$_6$H$_5$—C≡C—CO—(D)Val-Ind-2-CO—NH—CH$_2$-5-(3-am)-thioph
77. C$_6$H$_5$—C≡C—CO—(D)(2-(2-Thienyl))gly-Ind-2-CO—NH—CH$_2$-5-(3-am)-thioph
78. C$_6$H$_5$—C≡C—CO—(D)(2-(3-Thienyl))gly-Ind-2-CO—NH—CH$_2$-5-(3-am)-thioph
79. C$_6$H$_5$—C≡C—CO—(D)Chg-Ind-2-CO—NH—CH$_2$-5-(3-am)-thioph
80. C$_6$H$_5$—C≡C—CO—(D)Cpg-Dhi-1-CO—NH—CH$_2$-5-(3-am)-thioph
81. C$_6$H$_5$—C≡C—CO—(D)Val-Dhi-1-CO—NH—CH$_2$-5-(3-am)-thioph
82. C$_6$H$_5$—C≡C—CO—(D)(2-(2-Thienyl))gly-Dhi-1-CO—NH—CH$_2$-5-(3-am)-thioph
83. C$_6$H$_5$—C≡C—CO—(D)(2-(3-Thienyl))gly-Dhi-1-CO—NH—CH$_2$-5-(3-am)-thioph
84. C$_6$H$_5$—C≡C—CO—(D)Chg-Dhi-1-CO—NH—CH$_2$-5-(3-am)-thioph
85. C$_6$H$_5$—C≡C—CO—(D)Cpg-Ohii-1-CO—NH—CH$_2$-5-(3-am)-thioph
86. C$_6$H$_5$—C≡C—CO—(D)Val-Ohii-1-CO—NH—CH$_2$-5-(3-am)-thioph
87. C$_6$H$_5$—C≡C—CO—(D)(2-(2-Thienyl))gly-Ohii-1-CO—NH—CH$_2$-5-(3-am)-thioph
88. C$_6$H$_5$—C≡C—CO—(D)(2-(3-Thienyl))gly-Ohii-1-CO—NH—CH$_2$-5-(3-am)-thioph
89. C$_6$H$_5$—C≡C—CO—(D)Chg-Ohii-1-CO—NH—CH$_2$-5-(3-am)-thioph
90. (D)HOOC—CH(CH$_2$—C$_6$H$_5$)-Gly-Pyr-NH—CH$_2$-5-(3-am)-thioph
91. HOOC—CH(CH$_2$—C$_6$H$_5$)-Gly-Pyr-NH—CH$_2$-5-(3-am)-thioph
92. (D)HOOC—CH(CH$_2$—C$_6$H$_5$)-(D)Val-Pyr-NH—CH$_2$-5-(3-am)-thioph
93. HOOC—CH(CH$_2$—C$_6$H$_5$)-(D)Val-Pyr-NH—CH$_2$-5-(3-am)-thioph
94. (D)HOOC—CH(CH$_2$—C$_6$H$_{10}$)-Gly-Pyr-NH—CH$_2$-5-(3-am)-thioph
95. HOOC—CH(CH$_2$—C$_6$H$_{10}$)-Gly-Pyr-NH—CH$_2$-5-(3-am)-thioph
96. (D)HOOC—CH(CH$_2$—C$_6$H$_{10}$)-(D)Val-Pyr-NH—CH$_2$-5-(3-am)-thioph
97. HOOC—CH(CH$_2$—C$_6$H$_{10}$)-(D)Val-Pyr-NH—CH$_2$-5-(3-am)-thioph
98. (D)HOOC—CH(CH$_2$—C$_6$H$_5$)-Gly-Pro-NH—CH$_2$-5-(3-am)-thioph
99. HOOC—CH(CH$_2$—C$_6$H$_5$)-Gly-Pro-NH—CH$_2$-5-(3-am)-thioph
100. (D)HOOC—CH(CH$_2$—C$_6$H$_5$)-(D)Val-Pro-NH—CH$_2$-5-(3-am)-thioph
101. HOOC—CH(CH$_2$—C$_6$H$_5$)-(D)Val-Pro-NH—CH$_2$-5-(3-am)-thioph
102. (D)HOOC—CH(CH$_2$—C$_6$H$_{10}$)-Gly-Pro-NH—CH$_2$-5-(3-am)-thioph
103. HOOC—CH(CH$_2$—C$_6$H$_{10}$)-Gly-Pro-NH—CH$_2$-5-(3-am)-thioph
104. (D)HOOC—CH(CH$_2$—C$_6$H$_{10}$)-(D)Val-Pro-NH—CH$_2$-5-(3-am)-thioph
105. HOOC—CH(CH$_2$—C$_6$H$_{10}$)-(D)Val-Pro-NH—CH$_2$-5-(3-am)-thioph
106. (D)HOOC—CH(C$_6$H$_5$)-Gly-Pyr-NH—CH$_2$-5-(3-am)-thioph
107. HOOC—CH(C$_6$H$_5$)-Gly-Pyr-NH—CH$_2$-5-(3-am)-thioph
108. (D)HOOC—CH(C$_6$H$_{10}$)-Gly-Pyr-NH—CH$_2$-5-(3-am)-thioph
109. HOOC—CH(C$_6$H$_{10}$)-Gly-Pyr-NH—CH$_2$-5-(3-am)-thioph
110. (D)HOOC—CH(C$_6$H$_{10}$)-Gly-Pro-NH—CH$_2$-5-(3-am)-thioph
111. HOOC—CH(C$_6$H$_{10}$)-Gly-Pro-NH—CH$_2$-5-(3-am)-thioph
112. HOOC—(CH$_2$)$_5$—(N-CH$_2$—C$_6$H$_5$)Gly-Pyr-NH—CH$_2$-5-(3-am)-thioph
113. HOOC—(CH$_2$)$_5$—(N-CH$_2$—C$_6$H$_{10}$)Gly-Pyr-NH—CH$_2$-5-(3-am)-thioph
114. HOOC—(CH$_2$)$_4$—(N-CH$_2$—C$_6$H$_5$)Gly-Pyr-NH—CH$_2$-5-(3-am)-thioph
115. HOOC—(CH$_2$)$_4$—(N-CH$_2$—C$_6$H$_{10}$)Gly-Pyr-NH—CH$_2$-5-(3-am)-thioph
116. HOOC—(CH$_2$)$_5$—(N-C$_6$H$_5$)Gly-Pyr-NH—CH$_2$-5-(3-am)-thioph
117. HOOC—(CH$_2$)$_5$—(N-C$_6$H$_{10}$)Gly-Pyr-NH—CH$_2$-5-(3-am)-thioph
118. HOOC—(CH$_2$)$_4$—(N-C$_6$H$_5$)Gly-Pyr-NH—CH$_2$-5-(3-am)-thioph
119. HOOC—(CH$_2$)$_4$—(N-C$_6$H$_{10}$)Gly-Pyr-NH—CH$_2$-5-(3-am)-thioph
120. HOOC—(CH$_2$)$_4$—SO$_2$—(N-CH$_2$—C$_6$H$_5$)Gly-Pyr-NH—CH$_2$-5-(3-am)-thioph
121. HOOC—(CH$_2$)$_4$—SO$_2$—(N-CH$_2$—C$_6$H$_{10}$)Gly-Pyr-NH—CH$_2$-5-(3-am)-thioph
122. HOOC—(CH$_2$)$_3$—SO$_2$—(N-CH$_2$—C$_6$H$_5$)Gly-Pyr-NH—CH$_2$-5-(3-am)-thioph
123. HOOC—(CH$_2$)$_3$—SO$_2$—(N-CH$_2$—C$_6$H$_{10}$)Gly-Pyr-NH—CH$_2$-5-(3-am)-thioph
124. 4-HOOC—C$_6$H$_4$—SO$_2$—Gly-Pyr-NH—CH$_2$-5-(3-am)-thioph
125. 3-HOOC—C$_6$H$_4$—SO$_2$—Gly-Pyr-NH—CH$_2$-5-(3-am)-thioph
126. 4-HOOC—C$_6$H$_4$—SO$_2$—D-Val-Pyr-NH—CH$_2$-5-(3-am)-thioph
127. 3-HOOC—C$_6$H$_4$—SO$_2$—D-Val-Pyr-NH—CH$_2$-5-(3-am)-thioph
128. 4-HOOC—C$_6$H$_4$—SO$_2$—Gly-Pro-NH—CH$_2$-5-(3-am)-thioph
129. 3-HOOC—C$_6$H$_4$—SO$_2$—Gly-Pro-NH—CH$_2$-5-(3-am)-thioph
130. 4-HOOC—C$_6$H$_4$—SO$_2$—D-Val-Pro-NH—CH$_2$-5-(3-am)-thioph
131. 3-HOOC—C$_6$H$_4$—SO$_2$—D-Val-Pro-NH—CH$_2$-5-(3-am)-thioph
132. MeHNOC-p-C$_6$H$_4$CH$_2$—(D)Chg-Pyr-NH—CH$_2$-5-(3-am)-thioph
133. H$_2$NO$_2$S-p-C$_6$H$_4$CH$_2$—(D)Chg-Pyr-NH—CH$_2$-5-(3-am)-thioph
134. BzHNO$_2$S-p-C$_6$H$_4$CH$_2$—(D)Chg-Pyr-NH—CH$_2$-5-(3-am)-thioph -continued

| | | |
|---|---|---|
| 135. | 5-Tetrazolyl-p-C$_6$H$_4$CH$_2$—(D)Chg-Pyr-NH—CH$_2$-5-(3-am)-thioph | |
| 136. | HO—CH$_2$-p-C$_6$H$_4$CH$_2$—(D)Chg-Pyr-NH—CH$_2$-5-(3-am)-thioph | |
| 137. | HOOC-p-C$_6$H$_4$CH$_2$—(D)Chg-Pyr-NH—CH$_2$-5-(4-Me-3-am)-thioph | |
| 138. | HOOC-p-C$_6$H$_4$CH$_2$—(D)Chg-Pyr-NH—CH$_2$-5-(3-Me-2-am)-thioph | |
| 139. | HOOC-p-C$_6$H$_4$CH$_2$—(D)Chg-Pyr-NH-3-(6-am)-pico | |
| 140. | HOOC-p-C$_6$H$_4$CH$_2$—(D)Chg-Pyr-NH—CH$_2$-5-(2-am)-thioph | |
| 141. | HOOC-p-C$_6$H$_4$CH$_2$—(D)Chg-Pyr-NH—CH$_2$-5-(2-am)-fur | |
| 142. | HOOC-p-C$_6$H$_4$CH$_2$—(D)Chg-Pyr-NH—CH$_2$-2-(4-am)-thiaz | |
| 143. | HOOC-p-C$_6$H$_4$CH$_2$—(D)Chg-Pyr-NH—CH$_2$-5-(3-am-4-Cl)-thioph | |
| 144. | HOOC-p-C$_6$H$_4$CH$_2$—(D)Chg-Pyr-NH—CH$_2$-5-(2-am-3-Cl)-thioph | |
| 145. | HOOC-p-C$_6$H$_4$CH$_2$—(D)Chg-Pyr-NH—CH$_2$-5-(3-am)-fur | |
| 146. | HOOC-m-C$_6$H$_4$CH$_2$—(D)Chg-Pyr-NH—CH$_2$-5-(2-am)-thioph | |
| 147. | HOOC-m-C$_6$H$_4$CH$_2$—(D)Chg-Pyr-NH—CH$_2$-5-(3-am)-thioph | |
| 148. | HOOC-m-C$_6$H$_4$CH$_2$—(D)Chg-Pyr-NH-3-(6-am)-pico | |
| 149. | MeOOC-m-C$_6$H$_4$CH$_2$—(D)Chg-Pyr-NH—CH$_2$-2-(4-am)-thiaz | |
| 150. | H$_2$NCO-m-C$_6$H$_4$CH$_2$—(D)Chg-Pyr-NH—CH$_2$-5-(3-am)-thioph | |
| 151. | HO$_3$S-m-C$_6$H$_4$CH$_2$—(D)Chg-Pyr-NH—CH$_2$-5-(3-am)-thioph | |
| 152. | H$_2$NO$_2$S-m-C$_6$H$_4$CH$_2$—(D)Cha-Pyr-NH—CH$_2$-5-(2-am)-thioph | |
| 153. | HO$_3$S-m-C$_6$H$_4$CH$_2$—(D)Cha-Pyr-NH—CH$_2$-5-(2-am)-thioph | |
| 154. | (5-Tetrazolyl)-m-C$_6$H$_4$CH$_2$—(D)Chg-Pyr-NH—CH$_2$-5-(3-am)-thioph | |
| 155. | trans-(4-HOOC—C$_6$H$_{10}$CH$_2$)—(D)Val-Pyr-NH—CH$_2$-5-(3-am)-thioph | |
| 156. | HOOC-o-C$_6$H$_4$CH$_2$—Gly-Pyr-NH—CH$_2$-5-(3-am)-thioph | |
| 157. | 4-Benzyloxyphenyl-NH—C(O)—(D)-Ala-Pyr-NH—CH$_2$-5-(3-am)-thioph | |
| 158. | 4-Phenoxyphenyl-NH—C(O)—(D)-Ala-Pyr-NH—CH$_2$-5-(3-am)-thioph | |
| 159. | 4-(6'-Methyl-2'-benzothiazolyl)-phenyl-NH—C(O)—(D)-Ala-Pyr-NH—CH$_2$-5-(3-am)-thioph | |
| 160. | MeOC(O)—(CH$_2$)$_5$—NHC(O)—(D)-Ala-Pyr-5-(3-am)-thioph | |
| 161. | 4-Benzyloxyphenyl-NH—C(O)—Gly-Pyr-NH—CH$_2$-5-(3-am)-thioph | |
| 162. | 4-Phenoxyphenyl-NH—C(O)—Gly-Pyr-NH—CH$_2$-5-(3-am)-thioph | |
| 163. | 4-(6'-Methyl-2'-benzothiazolyl)-phenyl-NH—C(O)—Gly-Pro-NH—CH$_2$-5-(3-am)-thioph | |
| 164. | MeOC(O)—(CH$_2$)$_5$—NHC(O)—Gly-Pyr-5-(3-am)-thioph | |
| 165. | 4-Carboxybenzenesulfonyl-(D)-Ala-Pyr-NH—CH$_2$-5-(3-am)-thioph | |
| 166. | 3-Carboxybenzenesulfonyl-(D)-Ala-Pyr-NH—CH$_2$-5-(3-am)-thioph | |
| 167. | 4-Methoxycarbonylbenzenesulfonyl-(D)-Ala-Pyr-NH—CH$_2$-5-(3-am)-thioph | |
| 168. | 3-Methoxycarbonylbenzenesulfonyl-(D)-Ala-Pyr-NH—CH$_2$-5-(3-am)-thioph | |
| 169. | 4-Acetamidobenzenesulfonyl-(D)-Ala-Pyr-NH—CH$_2$-5-(3-am)-thioph | |
| 170. | 3-Acetamidobenzenesulfonyl-(D)-Ala-Pyr-NH—CH$_2$-5-(3-am)-thioph | |
| 171. | 4-Phenylbenzenesulfonyl-(D)-Ala-Pro-NH—CH$_2$-5-(3-am)-thioph | |
| 172. | 4-Carboxybenzenesulfonyl-(D)-Ala-Pro-NH—CH$_2$-5-(3-am)-thioph | |
| 173. | 3-Carboxybenzenesulfonyl-(D)-Ala-Pro-NH—CH$_2$-5-(3-am)-thioph | |
| 174. | 4-Methoxycarbonylbenzenesulfonyl-(D)-Ala-Pro-NH—CH$_2$-5-(3-am)-thioph | |
| 175. | 3-Methoxycarbonylbenzenesulfonyl-(D)-Ala-Pro-NH—CH$_2$-5-(3-am)-thioph | |
| 176. | 4-Acetamidobenzenesulfonyl-(D)-Ala-Pro-NH—CH$_2$-5-(3-am)-thioph | |
| 177. | 3-Acetamidobenzenesulfonyl-(D)-Ala-Pro-NH—CH$_2$-5-(3-am)-thioph | |
| 178. | 4-Carboxybenzenesulfonyl-Ala-Pyr-NH—CH$_2$-5-(3-am)-thioph | |
| 179. | 3-Carboxybenzenesulfonyl-Ala-Pyr-NH—CH$_2$-5-(3-am)-thioph | |
| 180. | 4-Methoxycarbonylbenzenesulfonyl-Gly-Pyr-NH—CH$_2$-5-(3-am)-thioph | |
| 181. | 3-Methoxycarbonylbenzenesulfonyl-Gly-Pyr-NH—CH$_2$-5-(3-am)-thioph | |
| 182. | 4-Acetamidobenzenesulfonyl-Gly-Pyr-NH—CH$_2$-5-(3-am)-thioph | |
| 183. | 3-Acetamidobenzenesulfonyl-Gly-Pyr-NH—CH$_2$-5-(3-am)-thioph | |
| 184. | 4-Phenylbenzenesulfonyl-Gly-Pro-NH—CH$_2$-5-(3-am)-thioph | |
| 185. | 4-Carboxybenzenesulfonyl-Ala-Pro-NH—CH$_2$-5-(3-am)-thioph | |
| 186. | 3-Carboxybenzenesulfonyl-Ala-Pro-NH—CH$_2$-5-(3-am)-thioph | |
| 187. | 4-Methoxycarbonylbenzenesulfonyl-Gly-Pro-NH—CH$_2$-5-(3-am)-thioph | |
| 188. | 3-Methoxycarbonylbenzenesulfonyl-Gly-Pro-NH—CH$_2$-5-(3-am)-thioph | |
| 189. | 4-Acetamidobenzenesulfonyl-Gly-Pro-NH—CH$_2$-5-(3-am)-thioph | |
| 190. | 3-Acetamidobenzenesulfonyl-Gly-Pro-NH—CH$_2$-5-(3-am)-thioph | |
| 191. | 3-Benzoylbenzoyl-(D)-Ala-Pyr-NH—CH$_2$-5-(3-am)-thioph | |
| 192. | 4-Phenylbenzoyl-(D)-Ala-Pyr-NH—CH$_2$-5-(3-am)-thioph | |
| 193. | 4-Phenylphenylacetyl-(D)-Ala-Pyr-NH—CH$_2$-5-(3-am)-thioph | |
| 194. | 2-(Benzylthio)-benzoyl-(D)-Ala-Pyr-NH—CH$_2$-5-(3-am)-thioph | |
| 195. | 3-Phenylpropionyl-(D)-Ala-Pyr-NH—CH$_2$-5-(3-am)-thioph | |
| 196. | 4-Phenylbutyryl-(D)-Ala-Pyr-NH—CH$_2$-5-(3-am)-thioph | |
| 197. | 5-Phenylvaleryl-(D)-Ala-Pyr-NH—CH$_2$-5-(3-am)-thioph | |
| 198. | (3-Phenyl)-acryloyl-(D)-Ala-Pyr-NH—CH$_2$-5-(3-am)-thioph | |
| 199. | 3-Benzyloxycarbonylpropionyl-(D)-Ala-Pyr-NH—CH$_2$-5-(3-am)-thioph | |
| 200. | 3-(4-Methoxycarbonyl(-phenyl)-acryloyl-(D)-Ala-Pyr-NH—CH$_2$-5-(3-am)-thioph | |
| 201. | 4-Methoxycarbonylbenzoyl-(D)-Ala-Pyr-NH—CH$_2$-5-(3-am)-thioph | |
| 202. | 6-(Acetylamino)-pyridyl-3-carbonyl-(D)-Ala-Pyr-NH—CH$_2$-5-(3-am)-thioph | |
| 203. | 3-(3'-Pyridyl)-acryloyl-(D)-Ala-Pyr-NH—CH$_2$-5-(3-am)-thioph | |
| 204. | HOOC-p-C$_6$H$_4$—C≡C—CO—(D)-Ala-Pyr-NH—CH$_2$-5-(3-am)-thioph | |
| 205. | HOOC-m-C$_6$H$_4$—C≡C—CO—(D)-Ala-Pyr-NH—CH$_2$-5-(3-am)-thioph | |
| 206. | 4-(4'-Aminophenoxy)-benzoyl-(D)-Ala-Pyr-NH—CH$_2$-5-(3-am)-thioph | |
| 207. | 3-(4'-Aminophenoxy)-benzoyl-(D)-Ala-Pyr-NH—CH$_2$-5-(3-am)-thioph | |
| 208. | 4-(2'-Chloro-4'-aminophenoxy)-benzoyl-(D)-Ala-Pyr-NH—CH$_2$-5-(3-am)-thioph | |
| 209. | 5-Phenylethynyl-nicotinoyl-(D)-Ala-Pyr-NH—CH$_2$-5-(3-am)-thioph | |
| 210. | 4-Phenylethynyl-benzoyl-(D)-Ala-Pyr-NH—CH$_2$-5-(3-am)-thioph | |
| 211. | 3-Phenylethynyl-benzoyl-(D)-Ala-Pyr-NH—CH$_2$-5-(3-am)-thioph | |
| 212. | 3-Benzoylbenzoyl-Ala-Pyr-NH—CH$_2$-5-(3-am)-thioph | |
| 213. | 4-Benzoylbenzoyl-Ala-Pyr-NH—CH$_2$-5-(3-am)-thioph | |
| 214. | 4-Phenylbenzoyl-Ala-Pyr-NH—CH$_2$-5-(3-am)-thioph | |
| 215. | 4-Phenylphenylacetyl-Ala-Pyr-NH—CH$_2$-5-(3-am)-thioph | |
| 216. | 2-(Benzylthio)-benzoyl-Ala-Pyr-NH—CH$_2$-5-(3-am)-thioph | |
| 217. | 3-Phenylpropionyl-Ala-Pyr-NH—CH$_2$-5-(3-am)-thioph | |
| 218. | 4-Phenylbutyryl-Ala-Pyr-NH—CH$_2$-5-(3-ant)-thioph | |
| 219. | 5-Phenylvaleryl-Ala-Pyr-NH—CH$_2$-5-(3-am)-thioph | |
| 220. | Cinnamoyl-Ala-Pyr-NH—CH$_2$-5-(3-am)-thioph | |
| 221. | C$_6$H$_5$—C≡C—CO—Ala-Pyr-NH—CH$_2$-5-(3-am)-thioph | |
| 222. | 3-Benzyloxycarbonylpropionyl-Ala-Pyr-NH—CH$_2$-5-(3-am)-thioph | |
| 223. | 4-Methoxycarbonylcinnamoyl-Ala-Pyr-NH—CH$_2$-5-(3-am)-thioph | |

| | |
|---|---|
| 224. | 4-Methoxycarbonylbenzoyl-Ala-Pyr-NH—CH$_2$-5-(3-am)-thioph |
| 225. | 6-(Acetylamino)-pyridyl-3-carbonyl-Ala-Pyr-NH—CH$_2$-5-(3-am)-thioph |
| 226. | 3-(3'-Pyridyl)-acryloyl-Ala-Pyr-NH—CH$_2$-5-(3-am)-thioph |
| 227. | HOOC-p-C$_6$H$_4$—C≡C—CO—Ala-Pyr-NH—CH$_2$-5-(3-am)-thioph |
| 228. | HOOC-m-C$_6$H$_4$—C≡C—CO—Ala-Pyr-NH—CH$_2$-5-(3-am)-thioph |
| 229. | 4-(4'-Aminophenoxy)-benzoyl-Ala-Pyr-NH—CH$_2$-5-(3-am)-thioph |
| 230. | 3-(4'-Aminophenoxy)-benzoyl-Ala-Pyr-NH—CH$_2$-5-(3-am)-thioph |
| 231. | 4-(2'-Chloro-4'-aminophenoxy)-benzoyl-Ala-Pyr-NH—CH$_2$-5-(3-am)-thioph |
| 232. | 5-Phenylethynyl-nicotinoyl-Ala-Pyr-NH—CH$_2$-5-(3-am)-thioph |
| 233. | 4-Phenylethynyl-benzoyl-Ala-Pyr-NH—CH$_2$-5-(3-am)-thioph |
| 234. | 3-Phenylethynyl-benzoyl-Ala-Pyr-NH—CH$_2$-5-(3-am)-thioph |
| 235. | 3-Benzoylbenzoyl-(D)-Ala-Pyr-NH—CH$_2$-5-(2-am)-thioph |
| 236. | 4-Phenylbenzoyl-(D)-Ala-Pyr-NH—CH$_2$-5-(2-am)-thioph |
| 237. | 4-Phenylphenylacetyl-(D)-Ala-Pyr-NH—CH$_2$-5-(2-am)-thioph |
| 238. | 4-Phenylphenylacetyl-(D)-Ala-Pro-NH—CH$_2$-5-(2-am)-thioph |
| 239. | 3-Benzoylbenzoyl-(D)-Ala-Pro-NH—CH$_2$-5-(2-am)-thioph |
| 240. | 4-Benzoylbenzoyl-(D)-Ala-Pro-NH—CH$_2$-5-(2-am)-thioph |
| 241. | 4-Phenylbenzoyl-(D)-Ala-Pro-NH—CH$_2$-5-(2-am)-thioph |
| 242. | 3-Benzoylbenzoyl-(D)-Asp-Pro-NH—CH$_2$-5-(2-am)-thioph |
| 243. | 4-Phenylbenzoyl-(D)-Asp-Pro-NH—CH$_2$-5-(3-am)-thioph |
| 244. | 4-Phenylphenylacetyl-(D)-Asp-Pyr-NH—CH$_2$-5-(3-am)-thioph |
| 245. | 3-(3'-Pyridyl)-acryloyl-(D)-Asp-Pyr-NH—CH$_2$-5-(3-am)-thioph |
| 246. | 4-(4'-Aminophenoxy)-benzoyl-(D)-Asp-Pyr-NH—CH$_2$-5-(3-am)-thioph |
| 247. | 3-(4'-Aminophenoxy)-benzoyl-(D)-Asp-Pyr-NH—CH$_2$-5-(3-am)-thioph |
| 248. | 4-(2'-Chloro-4'-aminophenoxy)-benzoyl-(D)-Asp-Pyr-NH—CH$_2$-5-(3-am)-thioph |
| 249. | 3-Benzoylbenzoyl-Asp-Pyr-NH—CH$_2$-5-(3-am)-thioph |
| 250. | 4-Benzoylbenzoyl-Asp-Pyr-NH—CH$_2$-5-(3-am)-thioph |
| 251. | 4-Phenylbenzoyl-Asp-Pyr-NH—CH$_2$-5-(3-am)-thioph |
| 252. | 4-Phenylphenylacetyl-Asp-Pyr-NH—CH$_2$-5-(3-am)-thioph |
| 253. | C$_6$H$_5$—C≡C—CO—Asp-Pyr-NH—CH$_2$-5-(3-am)-thioph |
| 254. | 3-Benzoylbenzoyl-(D)-Ala-Pyr-NH-3-(6-am)-pico |
| 255. | 4-Benzoylbenzoyl-(D)-Ala-Pyr-NH-3-(6-am)-pico |
| 256. | 4-Phenylbenzoyl-(D)-Ala-Pyr-NH-3-(6-am)-pico |
| 257. | 4-Phenylphenylacetyl-(D)-Ala-Pyr-NH-3-(6-am)-pico |
| 258. | C$_6$H$_5$—C≡C—CO—(D)-Ala-Pyr-NH-3-(6-am)-pico |
| 259. | 3-Benzoylbenzoyl-(D)-Arg-Pyr-NH—CH$_2$-5-(3-am)-thioph |
| 260. | 4-Phenylphenylacetyl-(D)-Arg-Pyr-NH—CH$_2$-5-(3-am)-thioph |
| 261. | 3-Benzoylbenzoyl-Arg-Pyr-NH—CH$_2$-5-(3-am)-thioph |
| 262. | 4-Benzoylbenzoyl-Arg-Pyr-NH—CH$_2$-5-(3-am)-thioph |
| 263. | 4-Phenylbenzoyl-Arg-Pyr-NH—CH$_2$-5-(3-am)-thioph |
| 264. | 4-Phenylphenylacetyl-Arg-Pyr-NH—CH$_2$-5-(3-am)-thioph |
| 265. | C$_6$H$_5$—C≡C—CO—Arg-Pyr-NH—CH$_2$-5-(3-am)-thioph |
| 266. | 3-Benzoylbenzoyl-(D)-Val-Pyr-NH—CH$_2$-5-(3-am)-thioph |
| 267. | 4-Phenylbenzoyl-(D)-Val-Pyr-NH—CH$_2$-5-(3-am)-thioph |
| 268. | 4-Phenylphenylacetyl-(D)-Val-Pyr-NH—CH$_2$-5-(3-am)-thioph |
| 269. | 2-(Benzylthio)-benzoyl-(D)-Val-Pyr-NH—CH$_2$-5-(3-am)-thioph |
| 270. | 3-Phenylpropionyl-(D)-Val-Pyr-NH—CH$_2$-5-(3-am)-thioph |
| 271. | 4-Phenylbutyryl-(D)-Val-Pyr-NH—CH$_2$-5-(3-am)-thioph |
| 272. | 5-Phenylvaleryl-(D)-Val-Pyr-NH—CH$_2$-5-(3-am)-thioph |
| 273. | Cinnamoyl-(D)-Val-Pyr-NH—CH$_2$-5-(3-am)-thioph |
| 274. | 3-Benzyloxycarbonylpropionyl-(D)-Val-Pyr-NH—CH$_2$-5-(3-am)-thioph |
| 275. | 4-Methoxycarbonylcinnamoyl-(D)-Val-Pyr-NH—CH$_2$-5-(3-am)-thioph |
| 276. | 4-Methoxycarbonylbenzoyl-(D)-Val-Pyr-NH—CH$_2$-5-(3-am)-thioph |
| 277. | 6-(Acetylamino)-pyridyl-3-carbonyl-(D)-Val-Pyr-NH—CH$_2$-5-(3-am)-thioph |
| 278. | 3-(3'-Pyridyl)-acryloyl-(D)-Val-Pyr-NH—CH$_2$-5-(3-am)-thioph |
| 279. | HOOC-p-C$_6$H$_4$—C≡C—CO—(D)-Val-Pyr-NH—CH$_2$-5-(3-am)-thioph |
| 280. | HOOC-m-C$_6$H$_4$—C≡C—CO—(D)-Val-Pyr-NH—CH$_2$-5-(3-am)-thioph |
| 281. | 4-(4'-Aminophenoxy)-benzoyl-(D)-Val-Pyr-NH—CH$_2$-5-(3-am)-thioph |
| 282. | 3-(4'-Aminophenoxy)-benzoyl-(D)-Val-Pyr-NH—CH$_2$-5-(3-am)-thioph |
| 283. | 4-(2'-Chloro-4'-aminophenoxy)-benzoyl-(D)-Val-Pyr-NH—CH$_2$-5-(3-am)-thioph |
| 284. | 5-Phenylethynyl-nicotinoyl-(D)-Val-Pyr-NH—CH$_2$-5-(3-am)-thioph |
| 285. | 4-Phenylethynyl-benzoyl-(D)-Val-Pyr-NH—CH$_2$-5-(3-am)-thioph |
| 286. | 3-Phenylethynyl-benzoyl-(D)-Val-Pyr-NH—CH$_2$-5-(3-am)-thioph |
| 287. | 3-Benzoylbenzoyl-(D)-Val-Pyr-NH—CH$_2$-5-(2-am)-thioph |
| 288. | 4-Phenylbenzoyl-(D)-Val-Pyr-NH—CH$_2$-5-(2-am)-thioph |
| 289. | 4-Phenylphenylacetyl-(D)-Val-Pyr-NH—CH$_2$-5-(2-am)-thioph |
| 290. | 4-Phenylphenylacetyl-(D)-Val-Pro-NH—CH$_2$-5-(2-am)-thioph |
| 291. | 3-Benzoylbenzoyl-(D)-Val-Pro-NH—CH$_2$-5-(2-am)-thioph |
| 292. | 4-Benzoylbenzoyl-(D)-Val-Pro-NH—CH$_2$-5-(2-am)-thioph |
| 293. | 4-Phenylbenzoyl-(D)-Val-Pro-NH—CH$_2$-5-(2-am)-thioph |
| 294. | C$_6$H$_5$—C≡C—CO—(D)-Lys-Pyr-NH—CH$_2$-5-(2-am)-thioph |
| 295. | 3-Benzoylbenzoyl-(D)-Lys-Pyr-NH—CH$_2$-5-(3-am)-thioph |
| 296. | 4-Phenylbenzoyl-(D)-Lys-Pyr-NH—CH$_2$-5-(3-am)-thioph |
| 297. | 4-Phenylphenylacetyl-(D)-Lys-Pyr-NH—CH$_2$-5-(3-am)-thioph |
| 298. | 3-(3'-Pyridyl)-acryloyl-(D)-Lys-Pyr-NH—CH$_2$-5-(3-am)-thioph |
| 299. | 4-(4'-Aminophenoxy)-benzoyl-(D)-Lys-Pyr-NH—CH$_2$-5-(3-am)-thioph |
| 300. | 3-(4'-Aminophenoxy)-benzoyl-(D)-Lys-Pyr-NH—CH$_2$-5-(3-am)-thioph |
| 301. | 4-(2'-Chloro-4'-aminophenoxy)-benzoyl-(D)-Lys-Pyr-NH—CH$_2$-5-(3-am)-thioph |
| 302. | 3-Benzoylbenzoyl-Gly-Pyr-NH—CH$_2$-5-(3-am)-thioph |
| 303. | 4-Phenylbenzoyl-Gly-Pyr-NH—CH$_2$-5-(3-am)-thioph |
| 304. | 4-Phenylphenylacetyl-Gly-Pyr-NH—CH$_2$-5-(3-am)-thioph |
| 305. | 2-(Benzylthio)-benzoyl-Gly-Pyr-NH—CH$_2$-5-(3-am)-thioph |
| 306. | 3-Phenylpropionyl-Gly-Pyr-NH—CH$_2$-5-(3-am)-thioph |
| 307. | 4-Phenylbutyryl-Gly-Pyr-NH—CH$_2$-5-(3-am)-thioph |
| 308. | 5-Phenylvaleryl-Gly-Pyr-NH—CH$_2$-5-(3-am)-thioph |
| 309. | (3-Phenyl)-acryloyl-Gly-Pyr-NH—CH$_2$-5-(3-am)-thioph |
| 310. | 3-Benzyloxycarbonylpropionyl-Gly-Pyr-NH—CH$_2$-5-(3-am)-thioph |
| 311. | 3-(4-Methoxycarbonyl-phenyl)-acryloyl-Gly-Pyr-NH—CH$_2$-5-(3-am)-thioph |
| 312. | 4-Methoxycarbonylbenzoyl-Gly-Pyr-NH—CH$_2$-5-(3-am)-thioph |
| 313. | 6-(Acetylamino)-pyridyl-3-carbonyl-Gly-Pyr-NH—CH$_2$-5-(3-am)-thioph |
| 314. | 3-(3'-Pyridyl)-acryloyl-Gly-Pyr-NH—CH$_2$-5-(3-am)-thioph |
| 315. | HOOC-p-C$_6$H$_4$—C≡C—CO—Gly-Pyr-NH—CH$_2$-5-(3-am)-thioph |
| 316. | HOOC-m-C$_6$H$_4$—C≡C—CO—Gly-Pyr-NH—CH$_2$-5-(3-am)-thioph |
| 317. | 4-(4'-Aminophenoxy)-benzoyl-Gly-Pyr-NH—CH$_2$-5-(3-am)-thioph |
| 318. | 3-(4'-Aminophenoxy)-benzoyl-Gly-Pyr-NH—CH$_2$-5-(3-am)-thioph |
| 319. | 4-(2'-Chloro-4'-aminophenoxy)-benzoyl-Gly-Pyr-NH—CH$_2$-5-(3-am)-thioph |
| 320. | 5-Phenylethynyl-nicotinoyl-Gly-Pyr-NH—CH$_2$-5-(3-am)-thioph |
| 321. | 4-Phenylethynyl-benzoyl-Gly-Pyr-NH—CH$_2$-5-(3-am)-thioph |
| 322. | 3-Phenylethynyl-benzoyl-Gly-Pyr-NH—CH$_2$-5-(3-am)-thioph |
| 323. | HOOC-p-C$_6$H$_4$—C≡C—CO—Gly-Pro-NH—CH$_2$-5-(3-am)-thioph |
| 324. | HOOC-m-C$_6$H$_4$—C≡C—CO—Gly-Pro-NH—CH$_2$-5-(3-am)-thioph |

325. 5-Phenylethynyl-nicotinoyl-Gly-Pro-NH—CH$_2$-5-(3-am)-thioph
326. 4-Phenylethynyl-benzoyl-Gly-Pro-NH—CH$_2$-5-(3-am)-thioph
327. 3-Phenylethynyl-benzoyl-Gly-Pro-NH—CH$_2$-5-(3-am)-thioph
328. 3-Benzoylbenzoyl-(D)-Val-Pyr-NH—CH$_2$-2-(4-am)-thiaz
329. 4-Benzoylbenzoyl-(D)-Val-Pyr-NH—CH$_2$-2-(4-am)-thiaz
330. 4-Phenylbenzoyl-(D)-Val-Pyr-NH—CH$_2$-2-(4-am)-thiaz
331. 4-Phenylphenylacetyl-(D)-Val-Pyr-NH—CH$_2$-2-(4-am)-thiaz
332. 3-Benzoylbenzoyl-(D)-Ala-Pyr-NH—CH$_2$-2-(4-am)-thiaz
333. 4-Benzoylbenzoyl-(D)-Ala-Pyr-NH—CH$_2$-2-(4-am)-thiaz
334. 4-Phenylbenzoyl-(D)-Ala-Pyr-NH—CH$_2$-2-(4-am)-thiaz
335. 4-Phenylphenylacetyl-(D)-Ala-Pyr-NH—CH$_2$-2-(4-am)-thiaz
336. 3-Benzoylbenzoyl-Gly-Pyr-NH—CH$_2$—2-(4-am)-thiaz
337. 4-Benzoylbenzoyl-Gly-Pyr-NH—CH$_2$-2-(4-am)-thiaz
338. 4-Phenylbenzoyl-Gly-Pyr-NH—CH$_2$-2-(4-am)-thiaz
339. 4-Phenylphenylacetyl-Gly-Pyr-NH—CH$_2$-2-(4-am)-thiaz
340. 3-Benzoylbenzoyl-Val-Pyr-NH—CH$_2$-5-(3-am)-thioph
341. 4-Benzoylbenzoyl-Val-Pyr-NH—CH$_2$-5-(3-am)-thioph
342. 4-Phenylbenzoyl-Val-Pyr-NH—CH$_2$-5-(3-am)-thioph
343. 4-Phenylphenylacetyl-Val-Pyr-NH—CH$_2$-5-(3-am)-thioph
344. 2-(Benzylthio)-benzoyl-Val-Pyr-NH—CH$_2$-5-(3-am)-thioph
345. 3-Phenylpropionyl-Val-Pyr-NH—CH$_2$-5-(3-am)-thioph
346. 4-Phenylbutyryl-Val-Pyr-NH—CH$_2$-5-(3-am)-thioph
347. 5-Phenylvaleryl-Val-Pyr-NH—CH$_2$-5-(3-am)-thioph
348. (3-Phenyl)-acryloyl-Val-Pyr-NH—CH$_2$-5-(3-am)-thioph
349. C$_6$H$_5$—C≡C—CO—Val-Pyr-NH—CH$_2$-5-(3-am)-thioph
350. 3-Benzyloxycarbonylpropionyl-Val-Pyr-NH—CH$_2$-5-(3-am)-thioph
351. 3-(4-Methoxycarbonyl-phenyl)-acryloyl-Val-Pyr-NH—CH$_2$-5-(3-am)-thioph
352. 4-Methoxycarbonylbenzoyl-Val-Pyr-NH—CH$_2$-5-(3-am)-thioph
353. 6-(Acetylamino)-pyridine-3-carbonyl-Val-Pyr-NH—CH$_2$-5-3-am)-thioph
354. 3-(3'-Pyridyl)-acryloyl-Val-Pyr-NH—CH$_2$-5-(3-am)-thioph
355. HOOC-p-C$_6$H$_4$—C≡C—CO—Val-Pyr-NH—CH$_2$-5-(3-am)-thioph
356. HOOC-m-C$_6$H$_4$—C≡C—CO—Val-Pyr-NH—CH$_2$-5-(3-am)-thioph
357. 4-(4'-Aminophenoxy)-benzoyl-Val-Pyr-NH—CH$_2$-5-(3-am)-thioph
358. 3-(4'-Aminophenoxy)-benzoyl-Val-Pyr-NH—CH$_2$-5-(3-am)-thioph
359. 4-(2'-Chloro-4'-aminophenoxy)-benzoyl-Val-Pyr-NH—CH$_2$-5-(3-am)-thioph
360. 5-Phenylethynyl-nicotinoyl-Val-Pyr-NH—CH$_2$-5-(3-am)-thioph
361. 4-Phenylethynyl-benzoyl-Val-Pyr-NH—CH$_2$-5-(3-am)-thioph
362. 3-Phenylethynyl-benzoyl-Val-Pyr-NH—CH$_2$-5-(3-am)-thioph
363. 3-Benzoylbenzoyl-Sar-Pyr-NH—CH$_2$-5-(3-am)-thioph
364. 4-Benzoylbenzoyl-Sar-Pyr-NH—CH$_2$-5-(3-am)-thioph
365. 4-Phenylphenylacetyl-Sar-Pyr-NH—CH$_2$-5-(3-am)-thioph
366. 3-Phenylpropionyl-Sar-Pyr-NH—CH$_2$-5-(3-am)-thioph
367. 4-Phenylbutyryl-Sar-Pyr-NH—CH$_2$-5-(3-am)-thioph
368. 5-Phenylvaleryl-Sar-Pyr-NH—CH$_2$-5-(3-am)-thioph
369. 3-Benzyloxycarbonylpropionyl-Sar-Pyr-NH—CH$_2$-5-(3-am)-thioph
370. 6-(Acetylamino)-pyridyl-3-carbonyl-Sar-Pyr-NH—CH$_2$-5-(3-am)-thioph
371. 3-(3'-Pyridyl)-acryloyl-Sar-Pyr-NH—CH$_2$-5-(3-am)-thioph
372. 4-(4'-Aminophenoxy)-benzoyl-Sar-Pyr-NH—CH$_2$-5-(3-am)-thioph
373. 3-(4'-Aminophenoxy)-benzoyl-Sar-Pyr-NH—CH$_2$-5-(3-am)-thioph
374. 4-(2'-Chloro-4'-aminophenoxy)-benzoyl-Sar-Pyr-NH—CH$_2$-5-(3-am)-thioph
375. 3-Benzoylbenzoyl-Sar-Pro-NH—CH$_2$-5-(3-am)-thioph
376. 4-Benzoylbenzoyl-Sar-Pro-NH—CH$_2$-5-(3-am)-thioph
377. 4-Phenylbenzoyl-Sar-Pro-NH—CH$_2$-5-(3-am)-thioph
378. 4-Phenylphenylacetyl-Sar-Pro-NH—CH$_2$-5-(3-am)-thioph
379. 3-Phenylpropionyl-Sar-Pro-NH—CH$_2$-5-(3-am)-thioph
380. 4-Phenylbutyryl-Sar-Pro-NH—CH$_2$-5-(3-am)-thioph
381. 5-Phenylvaleryl-Sar-Pro-NH—CH$_2$-5-(3-am)-thioph
382. C$_6$H$_5$—C≡C—CO—Sar-Pro-NH—CH$_2$-5-(3-am)-thioph
383. 3-Benzyloxycarbonylpropionyl-Sar-Pro-NH—CH$_2$-5-(3-am)-thioph
384. 6-(Acetylamino)-pyridine-3-carbonyl-Sar-Pro-NH—CH$_2$-5-(3-am)-thioph
385. 3-(3'-Pyridyl)-acryloyl-Sar-Pro-NH—CH$_2$-5-(3-am)-thioph
386. 4-(4'-Aminophenoxy)-benzoyl-Sar-Pro-NH—CH$_2$-5-(3-am)-thioph
387. 3-(4'-Aminophenoxy)-benzoyl-Sar-Pro-NH—CH$_2$-5-(3-am)-thioph
388. 4-(2'-Chloro-4'-aminophenoxy)-benzoyl-Sar-Pro-NH—CH$_2$-5-(3-am)-thioph
389. 3-Benzoylbenzoyl-(D)-(N-Me)Ala-Pyr-NH—CH$_2$-5-(3-am)-thioph
390. 4-Benzoylbenzoyl-(D)-(N-Me)Ala-Pyr-NH—CH$_2$-5-(3-am)-thioph
391. 4-Phenylbenzoyl-(D)-(N-Me)Ala-Pyr-NH—CH$_2$-5-(3-am)-thioph
392. 4-Phenylphenylacetyl-(D)-(N-Me)Ala-Pyr-NH—CH$_2$-5-(3-am)-thioph
393. 3-Phenylpropionyl-(D)-(N-Me)Ala-Pyr-NH—CH$_2$-5-(3-am)-thioph
394. 4-Phenylbutyryl-(D)-(N-Me)Ala-Pyr-NH—CH$_2$-5-(3-am)-thioph
395. 5-Phenylvaleryl-(D)-(N-Me)Ala-Pyr-NH—CH$_2$-5-(3-am)-thioph
396. C$_6$H$_5$—C≡C—CO—(D)-(N-Me)Ala-Pyr-NH—CH$_2$-5-(3-am)-thioph
397. 3-Benzyloxycarbonylpropionyl-(D)-(N-Me)Ala-Pyr-NH—CH$_2$-5-(3-am)-thioph
398. 6-(Acetylamino)-pyridyl-3-carbonyl-(D)-(N-Me)Ala-Pyr-NH—CH$_2$-5-(3-am)-thioph
399. 3-(3'-Pyridyl)-acryloyl-(D)-(N-Me )Ala-Pyr-NH—CH$_2$-5-(3-am)-thioph
400. 4-(4'-Aminophenoxy)-benzoyl-(D)-(N-Me)Ala-Pyr-NH—CH$_2$-5-(3-am)-thioph
401. 3-(4'-Aminophenoxy)-benzoyl-(D)-(N-Me)Ala-Pyr-NH—CH$_2$-5-(3-am)-thioph
402. 4-(2'-Chloro-4'-aminophenoxy)-benzoyl-(D)-(N-Me)Ala-Pyr-NH—CH$_2$-5-(3-am)-thioph
403. 3-Benzoylbenzoyl-(D)-(N-Me)Ala-Pro-NH—CH$_2$-5-(3-am)-thioph
404. 4-Benzoylbenzoyl-(D)-(N-Me)Ala-Pro-NH—CH$_2$-5-(3-am)-thioph
405. 4-Phenylbenzoyl-(D)-(N-Me)Ala-Pro-NH—CH$_2$-5-(3-am)-thioph
406. 4-Phenylphenylacetyl-(D)-(N-Me)Ala-Pro-NH—CH$_2$-5-3-am)-thioph
407. 3-Phenylpropionyl-(D)-(N-Me)Ala-Pro-NH—CH$_2$-5-(3-am)-thioph
408. 4-Phenylbutyryl-(D)-(N-Me)Ala-Pro-NH—CH$_2$-5-(3-am)-thioph
409. 5-Phenylvaleryl-(D)-(N-Me)Ala-Pro-NH—CH$_2$-5-(3-am)-thioph
410. C$_6$H$_5$—C≡C—CO—(D)-(N-Me)Ala-Pro-NH—CH$_2$-5-(3-am)-thioph
411. 3-Benzyloxycarbonylpropionyl-(D)-(N-Me)Ala-Pro-NH—CH$_2$-5-(3-am)-thioph
412. 6-(Acetylamino)-pyridyl-3-carbonyl-(D)-(N-Me)Ala-Pro-NH—CH$_2$-5-(3-am)-thioph
413. 3-(3'-Pyridyl)-acryloyl-(D)-(N-Me)Ala-Pro-NH—CH$_2$-5-(3-am)-thioph
414. 4-(4'-Aminophenoxy)-benzoyl-(D)-(N-Me)Ala-Pro-NH—CH$_2$-5-(3-am)-thioph
415. 3-(4'-Aminophenoxy)-benzoyl-(D)-(N-Me)Ala-Pro-NH—CH$_2$-5-(3-am)-thioph
416. 4-(2'-Chloro-4'-aminophenoxy)-benzoyl-(D)-(N-Me)Ala-Pro-NH—CH$_2$-5-(3-am)-thioph
417. 3-Benzoylbenzoyl-β-Ala-Pro-NH—CH$_2$-5-(3-am)-thioph
418. Cinnamoyl-β-Ala-Pro-NH—CH$_2$-5-(3-am)-thioph
419. C$_6$H$_5$—C≡C—CO—β-Ala-Pro-NH—CH$_2$-5-(3-am)-thioph
420. 3-Benzyloxycarbonylpropionyl-β-Ala-Pro-NH—CH$_2$-5-(3-am)-thioph
421. 4-Methoxycarbonylcinnamoyl-β-Ala-Pro-NH—CH$_2$-5-(3-am)-thioph
422. 4-Methoxycarbonylbenzoyl-β-Ala-Pro-NH—CH$_2$-5-(3-am)-thioph -continued

| | |
|---|---|
| 423. | 6-(Acetylamino)-pyridyl-3-carbonyl-β-Ala-Pro-NH—CH₂-5-(3-am)-thioph |
| 424. | 3-(3'-Pyridyl)-acryloyl-β-Ala-Pro-NH—CH₂-5-(3-am)-thioph |
| 425. | HOOC-p-C₆H₄—C≡C—CO—β-Ala-Pro-NH—CH₂-5-(3-am)-thioph |
| 426. | HOOC-m-C₆H₄—C≡C—CO—β-Ala-Pro-NH—CH₂-5-(3-am)-thioph |
| 427. | 4-(4'-Aminophenoxy)-benzoyl-β-Ala-Pro-NH—CH₂-5-(3-am)-thioph |
| 428. | 3-(4'-Aminophenoxy)-benzoyl-β-Ala-Pro-NH—CH₂-5-(3-am)-thioph |
| 429. | 4-(2'-Chloro-4'-aminophenoxy)-benzoyl-β-Ala-Pro-NH—CH₂-5-(3-am)-thioph |
| 430. | 5-Phenylethynyl-nicotinoyl-β-Ala-Pro-NH—CH₂-5-(3-am)-thioph |
| 431. | 4-Phenylethynyl-benzoyl-β-Ala-Pro-NH—CH₂-5-(3-am)-thioph |
| 432. | 3-Phenylethynyl-benzoyl-β-Ala-Pro-NH—CH₂-5-(3-am)-thioph |
| 433. | 3-Benzoylbenzoyl-β-Ala-Pyr-NH—CH₂-5-(3-am)-thioph |
| 434. | 4-Phenylbenzoyl-β-Ala-Pyr-NH—CH₂-5-(3-am)-thioph |
| 435. | 4-Phenylphenylacetyl-β-Ala-Pyr-NH—CH₂-5-(3-am)-thioph |
| 436. | 2-(Benzylthio)-benzoyl-β-Ala-Pyr-NH—CH₂-5-(3-am)-thioph |
| 437. | 3-Phenylpropionyl-β-Ala-Pyr-NH—CH₂-5-(3-am)-thioph |
| 438. | 4-Phenylbutyryl-β-Ala-Pyr-NH—CH₂-5-(3-am)-thioph |
| 439. | 5-Phenylvaleryl-β-Ala-Pyr-NH—CH₂-5-(3-am)-thioph |
| 440. | 3-Benzyloxycarbonylpropionyl-β-Ala-Pyr-NH—CH₂-5-(3-am)-thioph |
| 441. | 4-Methoxycarbonylcinnamoyl-β-Ala-Pyr-NH—CH₂-5-(3-am)-thioph |
| 442. | 4-Methoxycarbonylbenzoyl-β-Ala-Pyr-NH—CH₂-5-(3-am)-thioph |
| 443. | 6-(Acetylamino)-pyridyl-3-carbonyl-β-Ala-Pyr-NH—CH₂-5-(3-am)-thioph |
| 444. | 3-(3'-Pyridyl)-acryloyl-β-Ala-Pyr-NH—CH₂-5-(3-am)-thioph |
| 445. | HOOC-p-C₆H₄—C≡C—CO—β-Ala-Pyr-NH—CH₂-5-(3-am)-thioph |
| 446. | HOOC-m-C₆H₄—C≡C—CO—β-Ala-Pyr-NH—CH₂-5-(3-am)-thioph |
| 447. | 4-(4'-Aminophenoxy)-benzoyl-β-Ala-Pyr-NH—CH₂-5-(3-am)-thioph |
| 448. | 3-(4'-Aminophenoxy)-benzoyl-β-Ala-Pyr-NH—CH₂-5-(3-am)-thioph |
| 449. | 4-(2'-Chloro-4'-aminophenoxy)-benzoyl-β-Ala-Pyr-NH—CH₂-5-(3-am)-thioph |
| 450. | 5-Phenylethynyl-nicotinoyl-β-Ala-Pyr-NH—CH₂-5-(3-am)-thioph |
| 451. | 4-Phenylethynyl-benzoyl-β-Ala-Pyr-NH—CH₂-5-(3-am)-thioph |
| 452. | 3-Phenylethynyl-benzoyl-β-Ala-Pyr-NH—CH₂-5-(3-am)-thioph |
| 453. | 4-HOOC—C₆H₄—CH₂—(D)Cpg-Dhi-1-CO—NH—CH₂-5-(3-am)-thioph |
| 454. | 4-HOOC—C₆H₄—CH₂—(D)Cpg-Ohii-1-CO—NH—CH₂-5-(3-am)-thioph |
| 455. | 4-HOOC—C₆H₄—CH₂—(D)Cpg-(5-Me)Pro-NH—CH₂-5-(3-am)-thioph |
| 456. | 4-HOOC—C₆H₄—CH₂—(D)Cpg-Cis-(4-F)Pro-NH—CH₂-5-(3-am)-thioph |
| 457. | 4-HOOC—C₆H₄—CH₂—(D)Cpg-trans-(4-F)Pro-NH—CH₂-5-(3-am)-thioph |
| 458. | 4-HOOC—C₆H₄—CH₂—(D)Cpg-(3S)(3-Me)Pro-NH—CH₂-5-(3-am)-thioph |
| 459. | 4-HOOC—C₆H₄—CH₂—(D)Cpg-Pyr-NH—CH₂-5-(2-am)-thioph |
| 460. | 4-HOOC—C₆H₄—CH(CH₃)—(D)Cpg-Pyr-NH—CH₂-5-(3-am)-thioph |
| 461. | 4-HOOC—C₆H₄—CO—(D)Cpg-Pyr-NH—CH₂-5-(3-am)-thioph |
| 462. | 4-HOOC—C₆H₄—CH(CH₃)—(D)Chg-Pyr-NH—CH₂-5-(3-am)-thioph |
| 463. | 4-HOOC—C₆H₄—CH₂—(N-Me)(D)Chg-Pyr-NH—CH₂-5-(3-am)-thioph |
| 464. | 4-HOOC—C₆H₄—C(CH₃)₂—(D)Chg-Pyr-NH—CH₂-5-(3-am)-thioph |
| 465. | 4-HOOC-3-Me—C₆H₄—CH₂—(D)Chg-Pyr-NH—CH₂-5-(3-am)-thioph |
| 466. | 4-HOOC-2-Me—C₆H₄—CH₂—(D)Chg-Pyr-NH—CH₂-5-(3-am)-thioph |
| 467. | 4-HOOC—CH₂—C₆H₄—CH₂—(D)Chg-Pyr-NH—CH₂-5-(3-am)-thioph |
| 468. | 3-HOOC—CH₂—C₆H₄—CH₂—(D)Chg-Pyr-NH—CH₂-5-(3-am)-thioph |
| 469. | 4-HOOC—C₆H₄—CH(CH₃)—(D)Cpg-Pyr-NH—CH₂-5-(3-am)-thioph |
| 470. | 4-HOOC—C₆H₄—CH₂—(N-Me)(D)Cpg-Pyr-NH—CH₂-5-(3-am)-thioph |
| 471. | 4-HOOC—C₆H₄—C(CH₃)₂—(D)Cpg-Pyr-NH—CH₂-5-(3-am)-thioph |
| 472. | 4-HOOC-3-Me—C₆H₄—CH₂—(D)Cpg-Pyr-NH—CH₂-5-(3-am)-thioph |
| 473. | 4-HOOC-2-Me—C₆H₄—CH₂—(D)Cpg-Pyr-NH—CH₂-5-(3-am)-thioph |
| 474. | 4-HOOC—CH₂—C₆H₄—CH₂—(D)Cpg-Pyr-NH—CH₂-5-(3-am)-thioph |
| 475. | 3-HOOC—CH₂—C₆H₄—CH₂—(D)Cpg-Pyr-NH—CH₂-5-(3-am)-thioph |
| 476. | 4-HOOC—C₆H₄—CH(CH₃)—(D)Chg-Pyr-NH—CH₂-5-(2-am)-thioph |
| 477. | 4-HOOC—C₆H₄—CH₂—(N-Me)(D)Chg-Pyr-NH—CH₂-5-(2-am)-thioph |
| 478. | 4-HOOC—C₆H₄—C(CH₃)₂—(D)Chg-Pyr-NH—CH₂-5-(2-am)-thioph |
| 479. | 4-HOOC-3-Me—C₆H₄—CH₂—(D)Chg-Pyr-NH—CH₂-5-(2-am)-thioph |
| 480. | 4-HOOC-2-Me—C₆H₄—CH₂—(D)Chg-Pyr-NH—CH₂-5-(2-am)-thioph |
| 481. | 4-HOOC—CH₂—C₆H₄—CH₂—(D)Chg-Pyr-NH—CH₂-5-(2-am)-thioph |
| 482. | 3-HOOC—CH₂—C₆H₄—CH₂—(D)Chg-Pyr-NH—CH₂-5-(2-am)-thioph |
| 483. | 4-HOOC—C₆H₄—CH(CH₃)—(D)Cpg-Pyr-NH—CH₂-5-(2-am)-thioph |
| 484. | 4-HOOC—C₆H₄—CH₂—(N-Me)(D)Cpg-Pyr-NH—CH₂-5-(2-am)-thioph |
| 485. | 4-HOOC—C₆H₄—C(CH₃)₂—(D)Cpg-Pyr-NH—CH₂-5-(2-am)-thioph |
| 486. | 4-HOOC-3-Me—C₆H₄—CH₂—(D)Cpg-Pyr-NH—CH₂-5-(2-am)-thioph |
| 487. | 4-HOOC-2-Me—C₆H₄—CH₂—(D)Cpg-Pyr-NH—CH₂-5-(2-am)-thioph |
| 488. | 4-HOOC—CH₂—C₆H₄—CH₂—(D)Cpg-Pyr-NH—CH₂-5-(2-am)-thioph |
| 489. | 3-HOOC—CH₂—C₆H₄—CH₂—(D)Cpg-Pyr-NH—CH₂-5-(2-am)-thioph |
| 490. | HOOC-p-C₆H₄—CH(CH₃)—D-Val-Pyr-NH—CH₂-5-(3-am)-thioph |
| 491. | HOOC-p-C₆H₄—(CH₂)₂—D-Val-Pyr-NH—CH₂-5-(3-am)-thioph |
| 492. | HOOC-p-CH₂—C₆H₄—CH₂—D-Val-Pyr-NH—CH₂-5-(3-am)-thioph |
| 493. | p-Carboxy-tetrafluorobenzyl-D-Val-Pyr-NH—CH₂-5-(3-am)-thioph |
| 494. | p-Carboxy-2'-F-benzyl-D-Val-Pyr-NH—CH₂-5-(3-am)-thioph |
| 495. | p-Carboxy-2'-methoxy-benzyl-D-Val-Pyr-NH—CH₂-5-(3-am)-thioph |
| 496. | p-Carboxy-3'-methoxy-benzyl-D-Val-Pyr-NH—CH₂-5-(3-am)-thioph |
| 497. | H₂O₃P-p-C₆H₄—CH₂—D-Val-Pyr-NH—CH₂-5-(3-am)-thioph |
| 498. | 5-COOH-indan-1-yl-D-Val-Pyr-NH-5-(3-am)-thioph |
| 499. | 6-COOH-indan-1-yl-D-Val-Pyr-NH-5-(3-am)-thioph |
| 500. | HOOC-p-C₆H₄—CH₂—D-Val-Pyr-NH-4-amb |
| 501. | HOOC-p-C₆H₄—CH₂—D-Val-Pyr-NH—CH₂-5-(2-am)-thioph |
| 502. | HOOC-p-C₆H₄—CH₂—D-Val-Pyr-NH—CH₂-4-(2-am)-thioph |
| 503. | HOOC-p-C₆H₄—CH₂—D-Val-Pyr-NH-3-(6-am)pico |
| 504. | HOOC-p-C₆H₄—CH₂—D-Val-Pyr-NH—CH₂-5-(2-am)-fur |
| 505. | HOOC-p-C₆H₄—CH₂—D-Val-Pyr-NH—CH₂-5-(3-am-4-Cl)-thioph |
| 506. | HOOC-p-C₆H₄—CH₂—D-Val-Pyr-NH—CH₂-5-(2-am-3-Cl)-thioph |

-continued

| | |
|---|---|
| 507. | HOOC-p-C$_6$H$_4$—CH$_2$—D-Val-Pyr-NH—CH$_2$-2-(4-am)-thiaz |
| 508. | HOOC-p-C$_6$H$_4$—CH$_2$—D-Val-Pyr-NH—CH$_2$-2-(5-am)-thiaz |
| 509. | HOOC-p-C$_6$H$_4$—CH$_2$—D-Val-Pyr-NH—CH$_2$-5-(2-am)-thiaz |
| 510. | HOOC-p-C$_6$H$_4$—CH$_2$—D-Val-Pyr-NH—CH$_2$-4-(2-am)-thiaz |
| 511. | HOOC-p-C$_6$H$_4$—CH$_2$—D-Val-Pyr-NH—CH$_2$-5-(3-am-4-Me)-thioph |
| 512. | HOOC-p-C$_6$H$_4$—CH$_2$—D-Val-Pyr-NH—CH$_2$-5-(2-am-4-Me)-thioph |
| 513. | HOOC-p-C$_6$H$_4$—CH$_2$—D-Val-Pyr-NH—CH$_2$-2-(4-guan)-thiaz |
| 514. | HOOC-p-C$_6$H$_4$—CH$_2$—D-Val-Pyr-NH—CH$_2$-2-(5-guan)-thiaz |
| 515. | HOOC-p-C$_6$H$_4$—CH$_2$—D-Val-Pyr-NH—CH$_2$-5-(3-guan)-thioph |
| 516. | HOOC-p-C$_6$H$_4$—CH$_2$—D-Val-Pyr-NH—CH$_2$-5-(2-guan)-thioph |
| 517. | HOOC-p-C$_6$H$_4$—CH$_2$—D-Val-Pyr-NH—(4-guan)benzyl |
| 518. | HOOC-p-C$_6$H$_4$—CH$_2$—D-Val-Pyr-NH—(CH$_2$)$_4$-am |
| 519. | HOOC-p-C$_6$H$_4$—CH$_2$—D-Val-Pyr-NH—(CH$_2$)$_5$-am |
| 520. | HOOC-p-C$_6$H$_4$—CH$_2$—D-Val-Pyr-NH—(CH$_2$)$_3$-am |
| 521. | HOOC-p-C$_6$H$_4$—CH$_2$—D-Val-Pyr-NH—(CH$_2$)$_4$-guan |
| 522. | HOOC-p-C$_6$H$_4$—CH$_2$—D-Val-Pyr-NH—(CH$_2$)$_5$-guan |
| 523. | HOOC-p-C$_6$H$_4$—CH$_2$—D-Val-Pyr-NH—(CH$_2$)$_3$-guan |
| 524. | HOOC-p-C$_6$H$_4$—CH$_2$—D-Val-Pyr-NH-3-amb |
| 525. | HOOC-p-C$_6$H$_4$—CH$_2$—D-Val-Pyr-NH—CH$_2$-5-(3-C(NHCH$_3$)=NCH$_3$)-thioph |
| 526. | HOOC-p-C$_6$H$_4$—CH$_2$—D-Val-Pyr-NH—CH$_2$-5-(3-C(NH$_2$)=NCH$_3$)-thioph |
| 527. | HOOC-p-C$_6$H$_4$—CH$_2$—D-Val-Pic-NH—CH$_2$-5-(3-am)-thioph |
| 528. | HOOC-p-C$_6$H$_4$—CH$_2$—D-Val-Aze-NH—CH$_2$-5-(3-am)-thioph |
| 529. | HOOC-p-C$_6$H$_4$—CH$_2$—D-Val-N-Me-Ala-NH—CH$_2$-5-(3-am)-thioph |
| 530. | HOOC-p-C$_6$H$_4$—CH$_2$—D-Val-4,4-Difluoro-Pro-NH—CH$_2$-5-(3-am)-thioph |
| 531. | HOOC-p-C$_6$H$_4$—CH$_2$—D-Val-Thz-4-CO—NH—CH$_2$-5-(3-am)-thioph |
| 532. | HOOC-p-C$_6$H$_4$—CH$_2$—D-(2-CF$_3$)Gly-Pyr-NH—CH$_2$-5-(3-am)-thioph |
| 533. | HOOC-p-C$_6$H$_4$—CH$_2$—D-(3-CF$_3$)Ala-Pyr-NH—CH$_2$-5-(3-am)-thioph |
| 534. | HOOC-p-C$_6$H$_4$—CH$_2$—D-3,3-(CF$_3$)$_2$-Ala-Pyr-NH—CH$_2$-5-(3-am)-thioph |
| 535. | HOOC-p-C$_6$H$_4$—CH$_2$—D-2-Methyl-Val-Pyr-NH—CH$_2$-5-(3-am)-thioph |
| 536. | (p-CH$_3$)-Benzoyl-D-Val-Pyr-NH—CH$_2$-5-(3-am)-thioph |
| 537. | (p-Ethyl)-benzoyl-D-Val-Pyr-NH—CH$_2$-5-(3-am)-thioph |
| 538. | (p-Propyl)-benzoyl-D-Val-Pyr-NH—CH$_2$-5-(3-am)-thioph |
| 539. | (p-Butyl)-benzoyl-D-Val-Pyr-NH—CH$_2$-5-(3-am)-thioph |
| 540. | (p-Isopropyl)benzoyl-D-Val-Pyr-NH—CH$_2$-5-(3-am)-thioph |
| 541. | (p-tBu)Benzoyl-D-Val-Pyr-NH—CH$_2$-5-(3-am)-thioph |
| 542. | (p-Pentyl)benzoyl-D-Val-Pyr-NH—CH$_2$-5-(3-am)-thioph |
| 543. | (p-Hexyl)benzoyl-D-Val-Pyr-NH—CH$_2$-5-(3-am)-thioph |
| 544. | (p-Trifluoromethyl)benzoyl-D-Val-Pyr-NH—CH$_2$-5-(3-am)-thioph |
| 545. | (o-Methyl)pyr-benzoyl-D-Val-Pyr-NH—CH$_2$-5-(3-am)-thioph |
| 546. | (o-Trifluoromethyl)benzoyl-D-Val-Pyr-NH—CH$_2$-5-(3-am)-thioph |
| 547. | (o-Methoxy)benzoyl-D-Val-Pyr-NH—CH$_2$-5-(3-am)-thioph |
| 548. | (o-Dimethyl)benzoyl-D-Val-Pyr-NH—CH$_2$-5-(3-am)-thioph |
| 549. | (o-Dimethoxy)benzoyl-D-Val-Pyr-NH—CH$_2$-5-(3-am)-thioph |
| 550. | (p-Methoxy)benzoyl-D-Val-Pyr-NH—CH$_2$-5-(3-am)-thioph |
| 551. | (p-Ethoxy)benzoyl-D-Val-Pyr-NH—CH$_2$-5-(3-am)-thioph |
| 552. | (p-Propoxy)benzoyl-D-Val-Pyr-NH—CH$_2$-5-(3-am)-thioph |
| 553. | (p-Isopropoxy)benzoyl-D-Val-Pyr-NH—CH$_2$-5-(3-am)-thioph |
| 554. | (p-Butyloxy)benzoyl-D-Val-Pyr-NH—CH$_2$-5-(3-am)-thioph |
| 555. | (p-tert-Butoxy)benzoyl-D-Val-Pyr-NH—CH$_2$-5-(3-am)-thioph |
| 556. | (p-Aminomethyl)benzoyl-D-Val-Pyr-NH—CH$_2$-5-(3-am)-thioph |
| 557. | 2,6-Dichlorophenyl-CH$_2$CO—D-Ala-Pyr-NH—CH$_2$-5-(3-am)-thioph |

-continued

| | |
|---|---|
| 558. | 2,6-Dichlorophenyl-CH$_2$CO—D-Ile-Pyr-NH—CH$_2$-5-(3-am)-thioph |
| 559. | 2,6-Dichlorophenyl-CH$_2$CO—D-allo-Ile-Pyr-NH—CH$_2$-5-(3-am)-thioph |
| 560. | 2,6-Dichlorophenyl-CH$_2$CO—D-tLeu-Pyr-NH—CH$_2$-5-(3-am)-thioph |
| 561. | 2,6-Dichlorophenyl-CH$_2$CO—D-hexafluoro-Val-Pyr-NH—CH$_2$-5-(3-am)-thioph |
| 562. | 2,6-Dichlorophenyl-CH$_2$CO—D-Thr-Pyr-NH—CH$_2$-5-(3-am)-thioph |
| 563. | 2,6-Dichlorophenyl-CH$_2$CO—D-Cpg-Pyr-NH—CH$_2$-5-(3-am)-thioph |
| 564. | 2,6-Dichlorophenyl-CH$_2$CO—D-2-methyl-Val-Pyr-NH—CH$_2$-5-(3-am)-thioph |
| 565. | 2,6-Dichlorophenyl-CH$_2$CO—D-Val-Pyr-NH-4-amb |
| 566. | 2,6-Dichlorophenyl-CH$_2$CO—D-Val-Pyr-NH—CH$_2$-5-(2-am)-thioph |
| 567. | 2,6-Dichlorophenyl-CH$_2$CO—D-Val-Pyr-NH-3-(6-am)-pico |
| 568. | 2,6-Dichlorophenyl-CH$_2$CO—D-Val-Pyr-NH—CH$_2$-5-(2-am)-fur |
| 569. | 2,6-Dichlorophenyl-CH$_2$CO—D-Val-Pyr-NH—CH$_2$-5-(3-am-4-Cl)-thioph |
| 570. | 2,6-Dichlorophenyl-CH$_2$CO—D-Val-Pyr-NH—CH$_2$-5-(2-am-3-Cl)-thioph |
| 571. | 2,6-Dichlorophenyl-CH$_2$CO—D-Val-Pyr-NH—CH$_2$-2-(4-am)-thiaz |
| 572. | 2,6-Dichlorophenyl-CH$_2$CO—D-Val-Pyr-NH—CH$_2$-2-(5-am)-thiaz |
| 573. | 2,6-Dichlorophenyl-CH$_2$CO—D-Val-Pyr-NH—CH$_2$-5-(2-am)-thiaz |
| 574. | 2,6-Dichlorophenyl-CH$_2$CO—D-Val-Pyr-NH—CH$_2$-4-(2-am)-thiaz |
| 575. | 2,6-Dichlorophenyl-CH$_2$CO—D-Val-Pyr-NH—CH$_2$-2-(4-guan)-thiaz |
| 576. | 2,6-Dichlorophenyl-CH$_2$CO—D-Val-Pyr-NH—CH$_2$-2-(5-guan)-thiaz |
| 577. | 2,6-Dichlorophenyl-CH$_2$CO—D-Val-Pyr-NH—CH$_2$-5-(3-guan)-thioph |
| 578. | 2,6-Dichlorophenyl-CH$_2$CO—D-Val-Pyr-NH—CH$_2$-5-(2-guan)-thioph |
| 579. | 2,6-Dichlorophenyl-CH$_2$CO—D-Val-Pyr-NH—CH$_2$-4-(2-am)-thioph |
| 580. | 2,6-Dichlorophenyl-CH$_2$CO—D-Val-Pyr-NH—(4-guan)-benzyl |
| 581. | 2,6-Dichlorophenyl-CH$_2$CO—D-Val-Pyr-NH—(CH$_2$)$_4$-am |
| 582. | 2,6-Dichlorophenyl-CH$_2$CO—D-Val-Pyr-NH—(CH$_2$)$_5$-am |
| 583. | 2,6-Dichlorophenyl-CH$_2$CO—D-Val-Pyr-NH—(CH$_2$)$_3$-am |
| 584. | 2,6-Dichlorophenyl-CH$_2$CO—D-Val-Pyr-NH—(CH$_2$)$_4$-guan |
| 585. | 2,6-Dichlorophenyl-CH$_2$CO—D-Val-Pyr-NH—(CH$_2$)$_5$-guan |
| 586. | 2,6-Dichlorophenyl-CH$_2$CO—D-Val-Pyr-NH—(CH$_2$)$_3$-guan |
| 587. | 2,6-Dichlorophenyl-CH$_2$CO—D-Val-Pyr-NH-3-amb |
| 588. | 2,6-Dichlorophenyl-CH$_2$CO—D-Val-Pyr-NH—CH$_2$-5-(3-C(NHCH$_3$)=NCH$_3$)-thioph |
| 589. | 2,6-Dichlorophenyl-CH$_2$CO—D-Val-Pyr-NH—CH$_2$-5-(3-C(NH$_2$)=NCH$_3$)-thioph |
| 590. | 1R-Indanyl-D-Cpg-Pyr-NH—CH$_2$-5-(3-am)-thioph |
| 591. | 1R-Indanyl-D-Ala-Pyr-NH—CH$_2$-5-(3-am)-thioph |
| 592. | 1R-Indanyl-D-Thr-Pyr-NH—CH$_2$-5-(3-am)-thioph |
| 593. | 1R-Indanyl-D-allo-Ile-Pyr-NH—CH$_2$-5-(3-am)-thioph |
| 594. | 1R-Indanyl-D-tLeu-Pyr-NH—CH$_2$-5-(3-am)-thioph |
| 595. | 1R-Indanyl-D-hexafluoro-Val-Pyr-NH—CH$_2$-5-(3-am)-thioph |
| 596. | 1R-Indanyl-D-2-methyl-Val-Pyr-NH—CH$_2$-5-(3-am)-thioph |
| 597. | 1R-Indanyl-CO—D-Cpg-Pyr-NH—CH$_2$-5-(3-am)-thioph |
| 598. | 1R-Indanyl-CO—D-Ala-Pyr-NH—CH$_2$-5-(3-am)-thioph |
| 599. | 1R-Indanyl-CO—D-allo-Ile-Pyr-NH—CH$_2$-5-(3-am)-thioph |
| 600. | 1R-Indanyl-CO—D-tLeu-Pyr-NH—CH$_2$-5-(3-am)-thioph |
| 601. | 1S-Indanyl-D-Cpg-Pyr-NH—CH$_2$-5-(3-am)-thioph |
| 602. | 1S-Indanyl-D-Ala-Pyr-NH—CH$_2$-5-(3-am)-thioph |
| 603. | 1S-Indanyl-D-Thr-Pyr-NH—CH$_2$-5-(3-am)-thioph |
| 604. | 1S-Indanyl-D-allo-Ile-Pyr-NH—CH$_2$-5-(3-am)-thioph |
| 605. | 1S-Indanyl-D-tLeu-Pyr-NH—CH$_2$-5-(3-am)-thioph |
| 606. | 1S-Indanyl-D-hexafluoro-Val-Pyr-NH—CH$_2$-5-(3-am)-thioph |

-continued

| | |
|---|---|
| 607. | 1S-Indanyl-D-2-methyl-Val-Pyr-NH—CH$_2$-5-(3-am)-thioph |
| 608. | 1S-Indanyl-CO—D-Cpg-Pyr-NH—CH$_2$-5-(3-am)-thioph |
| 609. | 1S-Indanyl-CO—D-Ala-Pyr-NH—CH$_2$-5-(3-am)-thioph |
| 610. | 1S-Indanyl-CO—D-allo-Ile-Pyr-NH—CH$_2$-5-(3-am)-thioph |
| 611. | 1S-Indanyl-CO—D-tLeu-Pyr-NH—CH$_2$-5-(3-am)-thioph |
| 612. | (5,6-Dimethyl)-1-indanyl-CO—D-Val-Pyr-NH—CH$_2$-5-(3-am)-thioph |
| 613. | (5,7-Dimethyl)-1-indanyl-CO—D-Val-Pyr-NH—CH$_2$-5-(3-am)-thioph |
| 614. | (p-Aminomethyl)-benzyl-CO—D-Val-Pyr-NH—CH$_2$-5-(3-am)-thioph |
| 615. | (o-Carboxy)-benzyl-CO—D-Val-Pyr-NH—CH$_2$-5-(3-am)-thioph |
| 616. | (m-Carboxy)-benzyl-CO—D-Val-Pyr-NH—CH$_2$-5-(3-am)-thioph |
| 617. | (p-Carboxy)-benzyl-CO—D-Val-Pyr-NH—CH$_2$-5-(3-am)-thioph |
| 618. | (p-Carboxy-methyl)-benzyl-CO—D-Val-Pyr-NH—CH$_2$-5-(3-am)-thioph |
| 619. | 2-Indanyl-CO—D-Val-Pyr-NH—CH$_2$-5-(3-am)-thioph |
| 620. | (2,4,6-Trimethoxy)-benzyl-CO—D-Val-Pyr-NH—CH$_2$-5-(3-am)-thioph |
| 621. | Tetrahydronaphthyl(1S)-CO—D-Val-Pyr-NH—CH$_2$-5-(3-am)-thioph |
| 622. | Tetrahydronaphthyl(1R)-CO—D-Val-Pyr-NH—CH$_2$-5-(3-am)-thioph |
| 623. | 2,6-Dibromophenyl-CH$_2$CO—D-Val-Pyr-NH—CH$_2$-5-(3-am)-thioph |
| 624. | 2,6-Ditrifluoromethyl-phenyl-CH$_2$CO—D-Val-Pyr-NH—CH$_2$-5-(3-am)-thioph |
| 625. | 3-Indolyl-CO—D-Val-Pyr-NH—CH$_2$-5-(3-am)-thioph |
| 626. | N-Methyl-3-indolyl-CO—D-Val-Pyr-NH—CH$_2$-5-(3-am)-thioph |
| 627. | 3-Benzothienyl-CO—D-Val-Pyr-NH—CH$_2$-5-(3-am)-thioph |
| 628. | (5-Carboxy)-1R-indanyl-D-Val-Pyr-NH—CH$_2$-5-(3-am)-thioph |
| 629. | (6-Carboxy)-1R-indanyl-D-Val-Pyr-NH—CH$_2$-5-(3-am)-thioph |
| 630. | (4-Carboxy-2,6-dichloro)benzyl-CO—D-Val-Pyr-NH—CH$_2$-5-(3-am)-thioph |
| 631. | (5-Carboxy)-1S-indanyl-D-Val-Pyr-NH—CH$_2$-5-(3-am)-thioph |
| 632. | (6-Carboxy)-1S-indanyl-D-Val-Pyr-NH—CH$_2$-5-(3-am)-thioph |
| 633. | (5-Carboxy)-1R-indanyl-CO—D-Val-Pyr-NH—CH$_2$-5-(3-am)-thioph |
| 634. | (6-Carboxy)-1R-indanyl-CO—D-Val-Pyr-NH—CH$_2$-5-(3-am)-thioph |
| 635. | (5-Carboxy)-1S-indanyl-CO—D-Val-Pyr-NH—CH$_2$-5-(3-am)-thioph |
| 636. | (6-Carboxy)-1S-indanyl-CO—D-Val-Pyr-NH—CH$_2$-5-(3-am)-thioph |
| 637. | (p-CH$_3$)-Benzyl-CO—D-Val-Pyr-NH—CH$_2$-5-(3-am)-thioph |
| 638. | (p-Ethyl)-benzyl-CO—D-Val-Pyr-NH—CH$_2$-5-(3-am)-thioph |
| 639. | (p-Propyl)-benzyl-CO—D-Val-Pyr-NH—CH$_2$-5-(3-am)-thioph |
| 640. | (p-Butyl)-benzyl-CO—D-Val-Pyr-NH—CH$_2$-5-(3-am)-thioph |
| 641. | (p-Isopropyl)-benzyl-CO—D-Val-Pyr-NH—CH$_2$-5-(3-am)-thioph |
| 642. | (p-tBu)Benzyl-CO—D-Val-Pyr-NH—CH$_2$-5-(3-am)-thioph |
| 643. | (p-Pentyl)-benzyl-CO—D-Val-Pyr-NH—CH$_2$-5-(3-am)-thioph |
| 644. | (p-Hexyl)benzyl-CO—D-Val-Pyr-NH—CH$_2$-5-(3-am)-thioph |
| 645. | (p-Trifluoromethyl)benzyl-CO—D-Val-Pyr-NH—CH$_2$-5-(3-am)-thioph |
| 646. | (o-Methyl)benzyl-CO—D-Val-Pyr-NH—CH$_2$-5-(3-am)-thioph |
| 647. | (o-Trifluoromethyl)benzyl-CO—D-Val-Pyr-NH—CH$_2$-5-(3-am)-thioph |
| 648. | (o-Methoxy)benzyl-CO—D-Val-Pyr-NH—CH$_2$-5-(3-am)-thioph |
| 649. | (o-Dimethyl)benzyl-CO—D-Val-Pyr-NH—CH$_2$-5-(3-am)-thioph |
| 650. | (o-Dimethoxy)benzyl-CO—D-Val-Pyr-NH—CH$_2$-5-(3-am)-thioph |
| 651. | (p-Methoxy)benzyl-CO—D-Val-Pyr-NH—CH$_2$-5-(3-am)-thioph |
| 652. | (p-Ethoxy)benzyl-CO—D-Val-Pyr-NH—CH$_2$-5-(3-am)-thioph |
| 653. | (p-Propoxy)benzyl-CO—Val-Pyr-NH—CH$_2$-5-(3-am)-thioph |
| 654. | (p-Isopropoxy)benzyl-CO—D-Val-Pyr-NH—CH$_2$-5-(3-am)-thioph |
| 655. | (p-Butoxy)benzyl-CO—D-Val-Pyr-NH—CH$_2$-5-(3-am)-thioph |
| 656. | (p-tert-Butoxy)benzyl-CO—D-Val-Pyr-NH—CH$_2$-5-(3-am)-thioph |
| 657. | (p-CN)-Benzyl-D-Val-Pyr-NH—CH$_2$-5-(3-am)-thioph |
| 658. | (p-Dimethylamino)-benzyl-D-Val-Pyr-NH—CH$_2$-5-(3-am)-thioph |
| 659. | (p-Methoxy)-benzyl-D-Val-Pyr-NH—CH$_2$-5-(3-am)-thioph |
| 660. | (p-Ethoxy)-benzyl-D-Val-Pyr-NH—CH$_2$-5-(3-am)-thioph |
| 661. | (p-Propoxy)benzyl-D-Val-Pyr-NH—CH$_2$-5-(3-am)-thioph |
| 662. | (p-Isopropoxy)benzyl-D-Val-Pyr-NH—CH$_2$-5-(3-am)-thioph |
| 663. | (p-Butoxy)benzyl-D-Val-Pyr-NH—CH$_2$-5-(3-am)-thioph |
| 664. | (p-tert-Butoxy)benzyl-D-Val-Pyr-NH—CH$_2$-5-(3-am)-thioph |
| 665. | (p-Pentoxy)benzyl-D-Val-Pyr-NH—CH$_2$-5-(3-am)-thioph |
| 666. | (p-Trifluoromethyl)benzyl-D-Val-Pyr-NH—CH$_2$-5-(3-am)-thioph |
| 667. | (p-Ethyl)benzyl-D-Val-Pyr-NH—CH$_2$-5-(3-am)-thioph |
| 668. | (p-Propyl)benzyl-D-Val-Pyr-NH—CH$_2$-5-(3-am)-thioph |
| 669. | (p-Butyl)benzyl-D-Val-Pyr-NH—CH$_2$-5-(3-am)-thioph |
| 670. | (p-tert-Butyl)benzyl-D-Val-Pyr-NH—CH$_2$-5-(3-am)-thioph |
| 671. | (p-Pentyl)benzyl-D-Val-Pyr-NH—CH$_2$-5-(3-am)-thioph |
| 672. | (p-Hexyl)benzyl-D-Val-Pyr-NH—CH$_2$-5-(3-am)-thioph |
| 673. | (p-MeSO$_2$)Benzyl-D-Val-Pyr-NH—CH$_2$-5-(3-am)-thioph |
| 674. | (p-Nitro)benzyl-D-Val-Pyr-NH—CH$_2$-5-(3-am)-thioph |
| 675. | (p-Carboxy)benzyl-D-Val-Pyr-NH—CH$_2$-5-(3-ham)-thioph |
| 676. | (p-Carboxy)benzyl-D-Ala-Pyr-NH—CH$_2$-5-(3-ham)-thioph |
| 677. | (p-Carboxy)benzyl-D-Abu-Pyr-NH—CH$_2$-5-(3-ham)-thioph |
| 678. | (p-Carboxy)benzyl-D-Nva-Pyr-NH—CH$_2$-5-(3-ham)-thioph |
| 679. | (p-Carboxy)benzyl-D-tLeu-Pyr-NH—CH$_2$-5-(3-ham)-thioph |
| 680. | (p-Carboxy)benzyl-D-Ile-Pyr-NH—CH$_2$-5-(3-ham)-thioph |
| 681. | (p-Carboxy)benzyl-D-allo-Ile-Pyr-NH—CH$_2$-5-(3-ham)-thioph |
| 682. | (p-Carboxy)benzoyl-D-Val-Pyr-NH—CH$_2$-5-(3-ham)-thioph |
| 683. | (p-Carboxy)benzyl-D-Cpg-Pyr-NH—CH$_2$-5-(3-ham)-thioph |
| 684. | 2,6-Dichlorobenzyl-CO—D-Val-Pyr-NH—CH$_2$-5-(3-ham)-thioph |
| 685. | 2,6-Dichlorobenzyl-CO—D-Ala-Pyr-NH—CH$_2$-5-(3-ham)-thioph |
| 686. | 2,6-Dichlorobenzyl-CO—D-Abu-Pyr-NH—CH$_2$-5-(3-ham)-thioph |
| 687. | 2,6-Dichlorobenzyl-CO—D-Nva-Pyr-NH—CH$_2$-5-(3-ham)-thioph |
| 688. | 2,6-Dichlorobenzyl-CO—D-tLeu-Pyr-NH—CH$_2$-5-(3-ham)-thioph |
| 689. | 2,6-Dichlorobenzyl-CO—D-Ile-Pyr-NH—CH$_2$-5-(3-ham)-thioph |
| 690. | 2,6-Dichlorobenzyl-CO—D-alloIle-Pyr-NH—CH$_2$-5-(3-ham)-thioph |
| 691. | 2,6-Dichlorobenzyl-CO—D-Cpg-Pyr-NH—CH$_2$-5-(3-ham)-thioph |
| 692. | p-Benzoyl-benzoyl-D-Val-Pyr-NH—CH$_2$-5-(3-ham)-thioph |
| 693. | (p-Phenyl-NH—CO—NH)benzoyl-D-Val-Pyr-NH—CH$_2$-5-(3-ham)-thioph |
| 694. | 2,4,6-Trimethyl-benzyl-CO—D-Val-Pyr-NH—CH$_2$-5-(3-ham)-thioph |
| 695. | Benzhydryl-CO—D-Val-Pyr-NH—CH$_2$-5-(3-ham)-thioph |
| 696. | (p-Carboxy)benzyl-CO—D-Val-Pyr-NH—CH$_2$-5-(3-ham)-thioph |
| 697. | (p-COOMe)Benzyl-D-Val-Pyr-NH—CH$_2$-5-(3-ham)-thioph |
| 698. | (p-COOEt)Benzyl-D-Val-Pyr-NH—CH$_2$-5-(3-ham)-thioph |
| 699. | (p-COOPr)Benzyl-D-Val-Pyr-NH—CH$_2$-5-(3-ham)-thioph |
| 700. | (p-COOiPr)Benzyl-D-Val-Pyr-NH—CH$_2$-5-(3-ham)-thioph |
| 701. | (p-COOtBu)Benzyl-D-Val-Pyr-NH—CH$_2$-5-(3-ham)-thioph |
| 702. | (p-COOCyclohexyl)benzyl-D-Val-Pyr-NH—CH$_2$-5-(3-ham)-thioph |

| # | Compound |
|---|---|
| 703. | (p-COOCyclopentyl)benzyl-D-Val-Pyr-NH—CH$_2$-5-(3-ham)-thioph |
| 704. | (p-COOMe)Benzyl-D-Ala-Pyr-NH—CH$_2$-5-(3-ham)-thioph |
| 705. | (p-COOEt)Benzyl-D-Ala-Pyr-NH—CH$_2$-5-(3-ham)-thioph |
| 706. | (p-COOPr)Benzyl-D-Ala-Pyr-NH—CH$_2$-5-(3-ham)-thioph |
| 707. | (p-COOiPr)Benzyl-D-Ala-Pyr-NH—CH$_2$-5-(3-ham)-thioph |
| 708. | (p-COOtBu)Benzyl-D-Ala-Pyr-NH—CH$_2$-5-(3-ham)-thioph |
| 709. | (p-COOCyclohexyl)benzyl-D-Ala-Pyr-NH—CH$_2$-5-(3-ham)-thioph |
| 710. | (p-COOCyclopentyl)benzyl-D-Ala-Pyr-NH—CH$_2$-5-(3-ham)-thioph |
| 711. | (p-COOMe)Benzyl-D-Abu-Pyr-NH—CH$_2$-5-(3-ham)-thioph |
| 712. | (p-COOEt)Benzyl-D-Abu-Pyr-NH—CH$_2$-5-(3-ham)-thioph |
| 713. | (p-COOPr)Benzyl-D-Abu-Pyr-NH—CH$_2$-5-(3-ham)-thioph |
| 714. | (p-COOiPr)Benzyl-D-Abu-Pyr-NH—CH$_2$-5-(3-ham)-thioph |
| 715. | (p-COOtBu)Benzyl-D-Abu-Pyr-NH—CH$_2$-5-(3-ham)-thioph |
| 716. | (p-COOCyclohexyl)benzyl-D-Abu-Pyr-NH—CH$_2$-5-(3-ham)-thioph |
| 717. | (p-COOCyclopentyl)benzyl-D-Abu-Pyr-NH—CH$_2$-5-(3-ham)-thioph |
| 718. | (p-COOMe)Benzyl-D-Ile-Pyr-NH—CH$_2$-5-(3-ham)-thioph |
| 719. | (p-COOEt)Benzyl-D-Ile-Pyr-NH—CH$_2$-5-(3-ham)-thioph |
| 720. | (p-COOPr)Benzyl-D-Ile-Pyr-NH—CH$_2$-5-(3-ham)-thioph |
| 721. | (p-COOiPr)Benzyl-D-Ile-Pyr-NH—CH$_2$-5-(3-ham)-thioph |
| 722. | (p-COOtBu)Benzyl-D-Ile-Pyr-NH—CH$_2$-5-(3-ham)-thioph |
| 723. | (p-COOCyclohexyl)benzyl-D-Ile-Pyr-NH—CH$_2$-5-(3-ham)-thioph |
| 724. | (p-COOCyclopentyl)benzyl-D-Ile-Pyr-NH—CH$_2$-5-(3-ham)-thioph |
| 725. | (p-COOMe)Benzoyl-D-Val-Pyr-NH—CH$_2$-5-(3-ham)-thioph |
| 726. | (p-COOEt)Benzoyl-D-Val-Pyr-NH—CH$_2$-5-(3-ham)-thioph |
| 727. | (p-COOPr)Benzoyl-D-Val-Pyr-NH—CH$_2$-5-(3-ham)-thioph |
| 728. | (p-COOiPr)Benzoyl-D-Val-Pyr-NH—CH$_2$-5-(3-ham)-thioph |
| 729. | (p-COOtBu)Benzoyl-D-Val-Pyr-NH—CH$_2$-5-(3-ham)-thioph |
| 730. | (p-COOCyclohexyl)benzoyl-D-Val-Pyr-NH—CH$_2$-5-(3-ham)-thioph |
| 731. | (p-COOCyclopentyl)benzoyl-D-Val-Pyr-NH—CH$_2$-5-(3-ham)-thioph |
| 732. | (p-COOMe)Benzoyl-D-Ala-Pyr-NH—CH$_2$-5-(3-ham)-thioph |
| 733. | (p-COOEt)Benzoyl-D-Ala-Pyr-NH—CH$_2$-5-(3-ham)-thioph |
| 734. | (p-COOPr)Benzoyl-D-Ala-Pyr-NH—CH$_2$-5-(3-ham)-thioph |
| 735. | (p-COOiPr)Benzoyl-D-Ala-Pyr-NH—CH$_2$-5-(3-ham)-thioph |
| 736. | (p-COOtBu)Benzoyl-D-Ala-Pyr-NH—CH$_2$-5-(3-ham)-thioph |
| 737. | (p-COOCyclohexyl)benzoyl-D-Ala-Pyr-NH—CH$_2$-5-(3-ham)-thioph |
| 738. | (p-COOCyclopentyl)benzoyl-D-Ala-Pyr-NH—CH$_2$-5-(3-ham)-thioph |
| 739. | (p-COOMe)Benzoyl-D-Abu-Pyr-NH—CH$_2$-5-(3-ham)-thioph |
| 740. | (p-COOEt)Benzoyl-D-Abu-Pyr-NH—CH$_2$-5-(3-ham)-thioph |
| 741. | (p-COOPr)Benzoyl-D-Abu-Pyr-NH—CH$_2$-5-(3-ham)-thioph |
| 742. | (p-COOiPr)Benzoyl-D-Abu-Pyr-NH—CH$_2$-5-(3-ham)-thioph |
| 743. | (p-COOtBu)Benzoyl-D-Abu-Pyr-NH—CH$_2$-5-(3-ham)-thioph |
| 744. | (p-COOCyclohexyl)benzoyl-D-Abu-Pyr-NH—CH$_2$-5-(3-ham)-thioph |
| 745. | (p-COOCyclopentyl)benzoyl-D-Abu-Pyr-NH—CH$_2$-5-(3-ham)-thioph |
| 746. | (p-COOMe)Benzoyl-D-Ile-Pyr-NH—CH$_2$-5-(3-ham)-thioph |
| 747. | (p-COOEt)Benzoyl-D-Ile-Pyr-NH—CH$_2$-5-(3-ham)-thioph |
| 748. | (p-COOPr)Benzoyl-D-Ile-Pyr-NH—CH$_2$-5-(3-ham)-thioph |
| 749. | (p-COOiPr)Benzoyl-D-Ile-Pyr-NH—CH$_2$-5-(3-ham)-thioph |
| 750. | (p-COOtBu)Benzoyl-D-Ile-Pyr-NH—CH$_2$-5-(3-ham)-thioph |
| 751. | (p-COOCyclohexyl)benzoyl-D-Ile-Pyr-NH—CH$_2$-5-(3-ham)-thioph |
| 752. | (p-COOCyclopentyl)benzoyl-D-Ile-Pyr-NH—CH$_2$-5-(3-ham)-thioph |
| 753. | (p-COOMe)Benzyl-CO—D-Val-Pyr-NH—CH$_2$-5-(3-ham)-thioph |
| 754. | (p-COOEt)Benzyl-CO—D-Val-Pyr-NH—CH$_2$-5-(3-ham)-thioph |
| 755. | (p-COOPr)Benzyl-CO—D-Val-Pyr-NH—CH$_2$-5-(3-ham)-thioph |
| 756. | (p-COOiPr)Benzyl-CO—D-Val-Pyr-NH—CH$_2$-5-(3-ham)-thioph |
| 757. | (p-COOtBu)Benzyl-CO—D-Val-Pyr-NH—CH$_2$-5-(3-ham)-thioph |
| 758. | (p-COOCyclohexyl)benzyl-CO—D-Val-Pyr-NH—CH$_2$-5-(3-ham)-thioph |
| 759. | (p-COOCyclopentyl)benzyl-CO—D-Val-Pyr-NH—CH$_2$-5-(3-ham)-thioph |
| 760. | (p-COOMe)Benzyl-CO—D-Ala-Pyr-NH—CH$_2$-5-(3-ham)-thioph |
| 761. | (p-COOEt)Benzyl-CO—D-Ala-Pyr-NH—CH$_2$-5-(3-ham)-thioph |
| 762. | (p-COOPr)Benzyl-CO—D-Ala-Pyr-NH—CH$_2$-5-(3-ham)-thioph |
| 763. | (p-COOiPr)Benzyl-CO—D-Ala-Pyr-NH—CH$_2$-5-(3-ham)-thioph |
| 764. | (p-COOtBu)Benzyl-CO—D-Ala-Pyr-NH—CH$_2$-5-(3-ham)-thioph |
| 765. | (p-COOCyclohexyl)benzyl-CO—D-Ala-Pyr-NH—CH$_2$-5-(3-ham)-thioph |
| 766. | (p-COOCyclopentyl)benzyl-CO—D-Ala-Pyr-NH—CH$_2$-5-(3-ham)-thioph |
| 767. | (p-COOMe)Benzyl-CO—D-Abu-Pyr-NH—CH$_2$-5-(3-ham)-thioph |
| 768. | (p-COOEt)Benzyl-CO—D-Abu-Pyr-NH—CH$_2$-5-(3-ham)-thioph |
| 769. | (p-COOPr)Benzyl-CO—D-Abu-Pyr-NH—CH$_2$-5-(3-ham)-thioph |
| 770. | (p-COOiPr)Benzyl-CO—D-Abu-Pyr-NH—CH$_2$-5-(3-ham)-thioph |
| 771. | (p-COOtBu)benzyl-CO—D-Abu-Pyr-NH—CH$_2$-5-(3-ham)-thioph |
| 772. | (p-COOCyclohexyl)benzyl-CO—D-Abu-Pyr-NH—CH$_2$-5-(3-ham)-thioph |
| 773. | (p-COOCyclopentyl)benzyl-CO—D-Abu-Pyr-NH—CH$_2$-5-(3-ham)-thioph |
| 774. | (p-COOMe)Benzyl-CO—D-Ile-Pyr-NH—CH$_2$-5-(3-ham)-thioph |
| 775. | (p-COOEt)Benzyl-CO—D-Ile-Pyr-NH—CH$_2$-5-(3-ham)-thioph |
| 776. | (p-COOPr)Benzyl-CO—D-Ile-Pyr-NH—CH$_2$-5-(3-ham)-thioph |
| 777. | (p-COOiPr)Benzyl-CO—D-Ile-Pyr-NH—CH$_2$-5-(3-ham)-thioph |
| 778. | (p-COOtBu)Benzyl-CO—D-Ile-Pyr-NH—CH$_2$-5-(3-ham)-thioph |
| 779. | (p-COOCyclohexyl)benzyl-CO—D-Ile-Pyr-NH—CH$_2$-5-(3-ham)-thioph |
| 780. | (p-COOCyclopentyl)benzyl-CO—D-Ile-Pyr-NH—CH$_2$-5-(3-ham)-thioph |
| 781. | 5-EtOOC-1R-Indanyl-CO—D-Val-Pyr-NH—CH$_2$-5-(3-ham)-thioph |
| 782. | 6-EtOOC-1R-Indanyl-CO—D-Val-Pyr-NH—CH$_2$-5-(3-ham)-thioph |
| 783. | 5-EtOOC-1R-Indanyl-D-Val-Pyr-NH—CH$_2$-5-(3-ham)-thioph |
| 784. | 6-EtOOC-1R-Indanyl-D-Val-Pyr-NH—CH$_2$-5-(3-ham)-thioph |
| 785. | 5-EtOOC-1S-Indanyl-CO—D-Val-Pyr-NH—CH$_2$-5-(3-ham)-thioph |
| 786. | 6-EtOOC-1S-Indanyl-CO—D-Val-Pyr-NH—CH$_2$-5-(3-ham)-thioph |
| 787. | 5-EtOOC-1S-Indanyl-D-Val-Pyr-NH—CH$_2$-5-(3-ham)-thioph |
| 788. | 6-EtOOC-1S-Indanyl-D-Val-Pyr-NH—CH$_2$-5-(3-ham)-thioph |
| 789. | 4-(Benzylamino-methyl)-benzoyl-D-Val-Pyr-NH—CH$_2$-5-(3-am)-thioph |
| 790. | 4-(Cyclohexylmethylamino-methyl)-benzoyl-D-Val-Pyr-NH—CH$_2$-5-(3-am)-thioph |
| 791. | 4-(Isobutylamino-methyl)-benzoyl-D-Val-Pyr-NH—CH$_2$-5-(3-am)-thioph |

792. 4-(Isopropylamino-methyl)-benzoyl-D-Val-Pyr-NH—CH$_2$-5-(3-am)-thioph
793. 4-(Benzylamino-methyl)-benzoyl-D-Ala-Pyr-NH—CH$_2$-5-(3-am)-thioph
794. 4-(Cyclohexylmethylamino-methyl)-benzoyl-D-Ala-Pyr-NH—CH$_2$-5-(3-am)-thioph
795. 4-(Isobutylamino-methyl)-benzoyl-D-Ala-Pyr-NH—CH$_2$-5-(3-am)-thioph
796. 4-(Isopropylamino-methyl)-benzoyl-D-Ala-Pyr-NH—CH$_2$-5-(3-am)-thioph
797. 4-(Cyclohexylmethylamino-methyl)-benzoyl-D-Abu-Pyr-NH—CH$_2$-5-(3-am)-thioph
798. 4-(Benzylamino-methyl)-benzoyl-D-Abu-Pyr-NH—CH$_2$-5-(3-am)-thioph
799. 3-(Benzylamino-methyl)-benzoyl-D-Val-Pyr-NH—CH$_2$-5-(3-am)-thioph
800. 3-(Cyclohexylmethylamino-methyl)-benzoyl-D-Val-Pyr-NH—CH$_2$-5-(3-am)-thioph
801. 3-(Isobutylamino-methyl)-benzoyl-D-Val-Pyr-NH—CH$_2$-5-(3-am)-thioph
802. 3-(Isopropylamino-methyl)-benzoyl-D-Val-Pyr-NH—CH$_2$-5-(3-am)-thioph
803. 3-(Benzylamino-methyl)-benzoyl-D-Ala-Pyr-NH—CH$_2$-5-(3-am)-thioph
804. 3-(Cyclohexylmethylamino-methyl)-benzoyl-D-Ala-Pyr-NH—CH$_2$-5-(3-am)-thioph
805. 3-(Isobutylamino-methyl)-benzoyl-D-Ala-Pyr-NH—CH$_2$-5-(3-am)-thioph
806. 3-(Isopropylamino-methyl)-benzoyl-D-Ala-Pyr-NH—CH$_2$-5-(3-am)-thioph
807. 4-(Benzylamino-methyl)-phenylacetyl-D-Val-Pyr-NH—CH$_2$-5-(2-am)-thioph
808. 4-(Cyclohexylmethylamino-methyl)-phenylacetyl-D-Val-Pyr-NH—CH$_2$-5-(2-am)-thioph
809. 4-(Isobutylamino-methyl)-phenylacetyl-D-Val-Pyr-NH—CH$_2$-5-(2-am)-thioph
810. 4-(Isopropylamino-methyl)-phenylacetyl-D-Val-Pyr-NH—CH$_2$-5-(2-am)-thioph
811. 4-(Benzylamino-methyl)-phenylacetyl-D-Ala-Pyr-NH—CH$_2$-5-(2-am)-thioph
812. 4-(Cyclohexylmethylamino-methyl)-phenylacetyl-D-Ala-Pyr-NH—CH$_2$-5-(2-am)-thioph
813. 4-(Isobutylamino-methyl)-phenylacetyl-D-Ala-Pyr-NH—CH$_2$-5-(2-am)-thioph
814. 4-(Isopropylamino-methyl)-phenylacetyl-D-Ala-Pyr-NH—CH$_2$-5-(2-am)-thioph
815. 4-(Benzylamino-methyl)-phenylacetyl-D-Abu-Pyr-NH—CH$_2$-5-(2-am)-thioph
816. 4-(Cyclohexylmethylamino-methyl)-phenylacetyl-D-Abu-Pyr-NH—CH$_2$-5-(2-am)-thioph
817. 4-(Benzylamino-methyl)-phenylacetyl-D-Val-Pyr-NH—CH$_2$-5-(3-am)-thioph
818. 4-(Cyclohexylmethylamino-methyl)-phenylacetyl-D-Val-Pyr-NH—CH$_2$-5-(3-am)-thioph
819. 4-(Isobutylamino-methyl)-phenylacetyl-D-Val-Pyr-NH—CH$_2$-5-(3-am)-thioph
820. 4-(Isopropylamino-methyl)-phenylacetyl-D-Val-Pyr-NH—CH$_2$-5-(3-am)-thioph
821. 4-(Benzylamino-methyl)-phenylacetyl-D-Ala-Pyr-NH—CH$_2$-5-(3-am)-thioph
822. 4-(Cyclohexylmethylamino-methyl)-phenylacetyl-D-Ala-Pyr-NH—CH$_2$-5-(3-am)-thioph
823. 4-(Isobutylamino-methyl)-phenylacetyl-D-Ala-Pyr-NH—CH$_2$-5-(3-am)-thioph
824. 4-(Isopropylamino-methyl)-phenylacetyl-D-Ala-Pyr-NH—CH$_2$-5-(3-am)-thioph
825. 4-(Benzylamino-methyl)-phenylacetyl-D-Abu-Pyr-NH—CH$_2$-5-(3-am)-thioph
826. 4-(Cyclohexylmethylamino-methyl)-phenylacetyl-D-Abu-Pyr-NH—CH$_2$-5-(3-am)-thioph
827. 3-[4-(Benzylamino-methyl)-phenyl]-propionyl-D-Val-Pyr-NH—CH$_2$-5-(3-am)-thioph
828. 3-[4-(Cyclohexylmethylamino-methyl)-phenyl]-propionyl-D-Val-Pyr-NH—CH$_2$-5-(3-am)-thioph
829. 3-[4-(Isobutylamino-methyl)-phenyl]-propionyl-D-Val-Pyr-NH—CH$_2$-5-(3-am)-thioph
830. 3-[4-(Isopropylamino-methyl)-phenyl]-propionyl-D-Val-Pyr-NH—CH$_2$-5-(3-am)-thioph
831. 3-[4-(Benzylamino-methyl)-phenyl]-propionyl-D-Ala-Pyr-NH—CH$_2$-5-(3-am)-thioph
832. 3-[4-(Cyclohexylmethylamino-methyl)-phenyl]-propionyl-D-Ala-Pyr-NH—CH$_2$-5-(3-am)-thioph
833. 3-[4-(Isobutylamino-methyl)-phenyl]-propionyl-D-Ala-Pyr-NH—CH$_2$-5-(3-am)-thioph
834. 3-[4-(Isopropylamino-methyl)-phenyl]-propionyl-D-Ala-Pyr-NH—CH$_2$-5-(3-am)-thioph
835. 3-[4-(Benzylamino-methyl)-phenyl]-propionyl-D-Abu-Pyr-NH—CH$_2$-5-(3-am)-thioph
836. 3-[4-(Isopropylylamino-methyl)-phenyl]-propionyl-D-Abu-Pyr-NH—CH$_2$-5-(3-am)-thioph
837. 3-[4-(Cyclohexylmethylamino-methyl)-phenyl]-propionyl-D-Abu-Pyr-NH—CH$_2$-5-(3-am)-thioph
838. 3-[4-(Benzylamino-methyl)-phenyl]-propionyl-D-Abu-Pyr-NH—CH$_2$-5-(2-am)-thioph
839. 3-[4-(Isopropylylamino-methyl)-phenyl]-propionyl-D-Abu-Pyr-NH—CH$_2$-5-(2-am)-thioph
840. 3-[4-(Cyclohexylmethylamino-methyl)-phenyl]-propionyl-D-Abu-Pyr-NH—CH$_2$-5-(2-am)-thioph
841. 3-[4-(Benzylamino-methyl)-phenyl]-propionyl-D-Ala-Pyr-NH—CH$_2$-5-(2-am)-thioph
842. 3-[4-(Isopropylamino-methyl)-phenyl]-propionyl-D-Val-Pyr-NH—CH$_2$-5-(2-am)-thioph List of Abbreviations:

| | |
|---|---|
| Abu: | 2-Aminobutyric acid |
| AIBN: | Azobisisobutyronitrile |
| Ac: | Acetyl |
| Acpc: | 1-Aminocyclopentane-1-carboxylic acid |
| Achc: | 1-Aminocyclohexane-1-carboxylic acid |
| Aib: | 2-Aminoisobutyric acid |
| Ala: | Alanine |
| β-Ala: | β-Alanine (3-Aminopropionic acid) |
| am: | Amidino |
| amb: | Amidinobenzyl |
| 4-amb: | 4-Amidinobenzyl (p-amidinobenzyl) |
| Arg: | Arginine |
| Asp: | Aspartic acid |
| Aze: | Azetidine-2-carboxylic acid |
| Bn: | Benzyl |
| Boc: | tert-Butoxycarbonyl |
| Bu: | Butyl |
| Cbz: | Benzyloxycarbonyl |
| Cha: | Cyclohexylalanine |
| Chea: | Cycloheptylalanine |
| Cheg: | Cycloheptylglycine |
| Chg: | Cyclohexylglycine |
| Cpa: | Cyclopentylalanine |
| Cpg: | Cyclopentylglycine |
| d: | Doublet |

-continued

| | |
|---|---|
| Dab: | 2,4-diaminobutyric acid |
| Dap: | 2,3-diaminopropionic acid |
| TLC: | Thin-layer chromatography |
| DCC: | Dicyclohexylcarbodiimide |
| Dcha: | Dicyclohexylamine |
| DCM: | Dichloromethane |
| Dhi-1-COOH: | 2,3-Dihydro-1H-isoindole-1-carboxylic acid |
| DMF: | Dimethylformamide |
| DIPEA: | Diisopropylethylamine |
| EDC: | N'-(3-Dimethylaminopropyl)-N-ethylcarbodiimide |
| Et: | Ethyl |
| Eq: | Equivalents |
| Gly: | Glycine |
| Glu: | Glutamic acid |
| fur: | Furan |
| guan: | Guanidino |
| ham: | Hydroxyamidino |
| HCha | Homocyclohexylalanine, 2-amino-4-cyclohexylbutyric acid |
| His: | Histidine |
| HOBT: | Hydroxybenzotriazole |
| HOSucc: | Hydroxysuccinimide |
| HPLc: | High-performance liquid chromatography |
| Hyp: | Hydroxyproline |
| Ind-2-COOH: | Indoline-2-carboxylic acid |
| iPr: | Isopropyl |
| Leu: | Leucine |
| Soln: | Solution |
| Lys: | Lysine |
| m: | Multiplet |
| Me: | Methyl |
| MPLC: | Medium-pressure liquid chromatography |
| MTBE: | Methyl-tert-butyl-ether |
| NBS: | N-Bromosuccinimide |
| Nva: | Norvaline |
| Ohi-2-COOH: | Octahydroindole-2-carboxylic acid |
| Ohii-1-COOH: | Octahydroisoindole-1-carboxylic acid |
| Orn: | Ornithine |
| Oxaz: | Oxazole |
| p-amb: | p-Amidinobenzyl |
| Ph: | Phenyl |
| Phe: | Phenylalanine |
| Phg: | Phenylglycine |
| Pic: | Pipecolinic acid |
| pico: | Picolyl |
| PPA: | Propylphosphonic anhydride |
| Pro: | Proline |
| Py: | Pyridine |
| Pyr: | 3,4-Dehydroproline |
| q: | Quartet |
| RT: | Room temperature |
| RP-18 | Reversed Phase C-18 |
| s: | Singlet |
| Sar: | Sarcosine (N-methylglycine) |
| sb: | Singlet broad |
| t: | Triplet |
| t: | Tertiary |
| tBu: | tertiary-Butyl |
| tert: | Tertiary |
| TBAB: | Tetrabutylammonium bromide |
| TEA: | Triethylamine |
| TFA: | Trifluoroacetic acid |
| TFFA: | Trifluoroacetic anhydride |
| thiaz: | Thiazole |
| Thz-2-COOH: | 1,3-Thiazolidine-2-carboxylic acid |
| Thz-4-COOH: | 1,3-Thiazolidine-4-carboxylic acid |
| thioph: | Thiophene |
| 1-Tic: | 1-Tetrahydroisoquinolinecarboxylic acid |
| 3-Tic: | 3-Tetrahydroisoquinolinecarboxylic acid |
| TOTU: | O-(Cyano-ethoxycarbonylmethylene)-amino-]-N,N,N',N'-tetramethyluronium tetrafluoroborate |
| Z: | Benzyloxycarbonyl |

EXPERIMENTAL SECTION

The compounds of the formula I can be prepared according to Schemes I–III.

The building blocks A—B—D, E, G and K are preferably synthesized separately and used in suitably protected form (cf. Schemes I–III, is in each case of orthogonal protective groups compatible with the synthesis method used (P or P*).

Scheme I

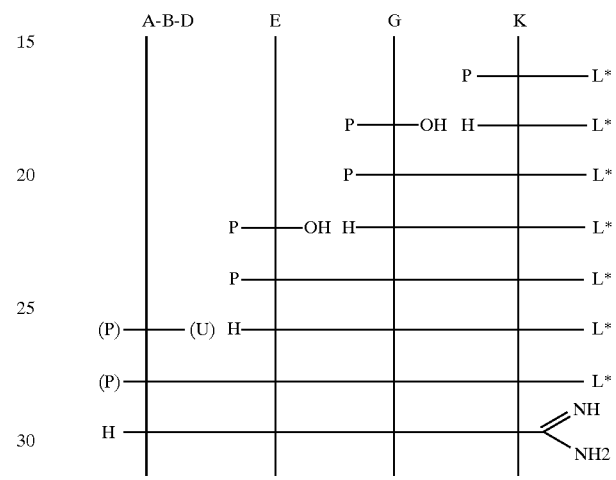

(P = protective group, (P) = protective group or H)

Scheme I describes the linear synthesis of the molecule I by eliminating the protective group from P—K—L* (where L* is CONH$_2$, CSNH$_2$, CN or C(=NH)NH—COOR*; and R* is a protective group or polymeric carrier with a spacer (solid-phase synthesis)), coupling the amine H—K—L* to the N-protected amino acid P—G—OH to give P—G—K—L*, eliminating the N-terminal protective group to give H—G—K—L*, coupling to the N-protected amino acid P—E—OH to give P—E—G—K—L*, eliminating the protective group P to give H—E—G—K—L*, then coupling or alkylating with the unprotected or protected (P)—A—B—D—U building block (where U is a leaving group) or reductive alkylation with (P)—A—B—D'—U (where U is an aldehyde or ketone) or Michael-Addition with a suitable (P)—A—B—D"—C=C derivative to give (P)—A—B—D—E G—K—L*. If L* is an amide function, it can be converted at the respective protected stages by dehydration with trifluoroacetic anhydride into the corresponding nitrile function. Amidine syntheses for the benzamidine, picolylamidine, thienylamidine, furylamidine and thiazolylamidine compounds of the structure type I starting from the corresponding carboxamides, nitriles, carboxylic acid thioamides and hydroxyamidines are described in a number of patent applications (cf. for example WO 95/35309, WO 96/178860, WO 96/24609, WO 96/25426, WO 98/06741 and WO 98/09950). Any protective groups still present are then eliminated. If L* is a C(=NH)NH-spacer-polymeric carrier, these compounds are cleaved from the polymeric carrier in the final step and the active substance thus liberated.

Scheme II

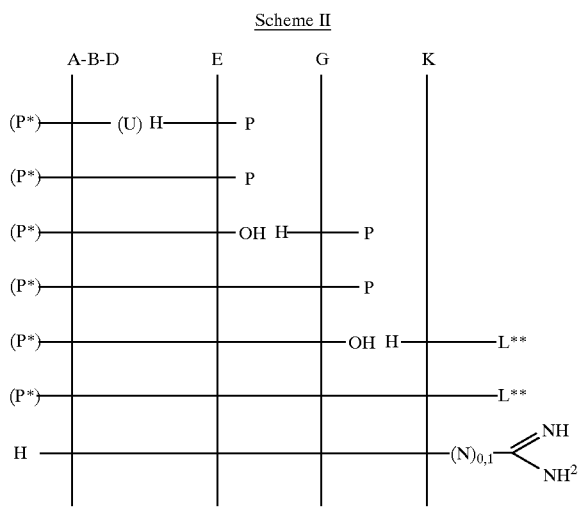

Scheme II describes the linear synthesis of the molecule I by coupling, alkylation, reductive amination or Michael-Addition of H—E—P with suitable unprotected or protected (P*)—A—B—D building blocks [(P*)—A—B—D—U (where U is a leaving group) or (P*)—A—B—D'—U (where U is an aldehyde, ketone) or (P*)—A—B—D"—C=C derivative] to give (P*)—A—B—D—E—P. This is followed by elimination of the C-terminal protective group to give (P*)—A—B—D—E—OH, coupling with H—G—P to give (P*)—A—B—D—E—G—P, further elimination of the C-terminal protective group to give (P*)—A—B—D—E—G—OH and coupling with H—K—L (where L is CONH2, CSNH2, CN, NH—C(=NH)NH$_2$, C(=NH)NH—R and R is a hydrogen atom or protective group) to give (P*)—A—B—D—E—G—K—L**. The conversion of this intermediate into the end product is carried out analogously to scheme I. The synthesis sequence according to scheme II is also suitable for solid-phase synthesis if the A—B—D building block has a corresponding anchor function, e.g. a carboxyl or amino function.

Scheme III

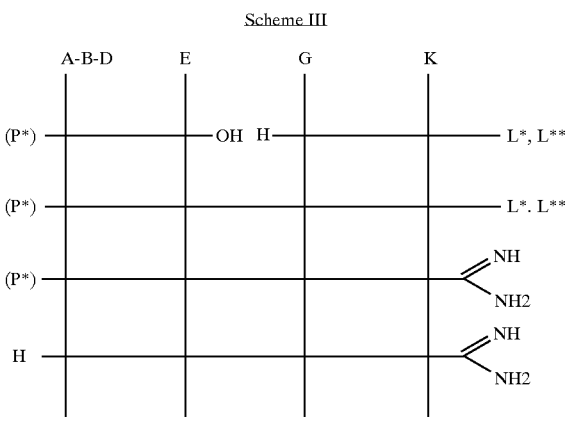

Scheme III describes a very efficient route for preparing the compounds I by a convergent synthesis. The appropriately protected building blocks (P*)—A—B—D—E—OH and H—C—K—L* or H—G—K—L** are coupled to one another and the resulting intermediate (P*)—A—B—D—E—G—K—L* and (P*)—A—B—D—E—G—K—L** respectively, are reacted according to scheme I to give the end product.

The N-terminal protective groups used are Boc, Cbz or Fmoc, and C-terminal protective groups are methyl, tert-butyl and benzyl esters. Amidine protective groups are preferably BOC, Cbz and groups derived therefrom, for the solid-phase synthesis. If the intermediates contain olefinic double bonds, protective groups which are eliminated hydrogenolytically are unsuitable.

The required coupling reactions and the customary reactions for introducing and eliminating protective groups are carried out according to standard conditions of peptide chemistry (cf. M. Bodanszky, A. Bodanszky "The Practice of Peptide Synthesis", $2^{nd}$ edition, Springer Verlag Heidelberg, 1994).

Boc-protective groups are eliminated by means of dioxane/HCl or TFA/DCM, Cbz-protective groups are eliminated hydrogenolytically or with HF, and Fmoc protective groups are eliminated with piperidine. The hydrolysis of ester functions is effected with LiOH in an alcoholic solvent or in dioxane/water. t-Butylester are cleaved using TFA or dioxane/HCl.

The reactions were monitored by TLC, the following were mobile phases usually being used:

| | | |
|---|---|---|
| A. | DCM/MeOH | 95:5 |
| B. | DCM/MeOH | 9:1 |
| C. | DCM/MeOH | 8:2 |
| D. | DCM/MeOH/50% strength HOAc | 40:10:5 |
| E. | DCM/MeOH/50% strength HOAc | 35:15:5 |

Where separation by means of column chromatography are mentioned, these were separations over silica gel, for which the abovementioned mobile phases were used.

Reversed-phase HPLC separation were carried out using acetonitrile/water and HOAc buffer.

The starting compounds can be prepared by the following methods:

A—B—D Building Blocks:

The compounds suitable as A—B—D building blocks are for the most part commercially available, e.g. tert-butyl α-bromoacetate, methylsulfonyl chloride, benzenesulfonyl chloride, 4-chlorosulfonylbenzoic acid, cinnamic acid, hydrocinnamic acid, 5-bromovaleric acid, phenylpropiolic acid, 4-phenylbutyric acid, 5-phenylvaleric acid, 4-phenylbenzoic acid, 4-biphenyl acetic acid, etc. Where these compounds have a plurality of functional groups, protective groups are introduced at the required sites. If necessary, functional groups are converted into reactive or leaving groups (e.g. active esters, mixed anhydrides, sulfonyl chlorides, etc.), in order to permit appropriate chemical linkage with the other building blocks.

The synthesis of the E building blocks was carried out as follows:

The compounds used as E building blocks, i.e. glycine, (D)- and (L)-alanine, (D)- and (L)-valine, (D)-phenylalanine, (D)-cyclohexylalanine, (D)-cycloheptylglycine, etc., are commercially available either as free amino acids, as Boc-protected compounds or as corresponding methyl esters.

The preparation of cycloheptylglycine and cyclopentylglycine was carried out by reacting cycloheptanone and cyclopentanone, respectively, with ethyl isonitriloacetate by known methods (H.-J. Pratorius, J. Flossdorf, M. Kula, Chem. Ber. 108, 1985, 3079 or U. Schöllkopf and R. Meyer, Liebigs Ann. Chem. (1977), 1174).

Said amino acids were provided, as required, with either an N-terminal or a C-terminal protective groups.

The synthesis of the G building blocks was carried out as follows:

The compounds used as G building blocks, i.e. (L)-proline, (L)-4,4-difluoroproline, (L)-3-methylproline, (L)-5-methylproline, (L)-3,4-dehydroproline, (L)-octahydroindole-2-carboxylic acid, (L)-thiazolidine-4-carboxylic acid and (L)-azetidinecarboxylic acid, are commercially available either as free amino acids, as Boc-protective compounds or as corresponding methyl esters. Methyl (−)-thiazolidine-2-carboxylate was prepared according to R. L. Johnson, E. E. Smissman, J. Med. Chem. 21, (1978) 165.

The synthesis of K building blocks was carried as follows:

p-Cyanobenzylamine

This building block was prepared as described in WO 95/35309.

3-(6-Cyano)-picolylamine

This building block was prepared as described in WO 96/25426 or WO 96/24609.

5-Aminomethyl-2-cyanothiophene

This building block was prepared as described in WO 95/23609.

5-Aminomethyl-3-cyanothiophene

This building block was prepared as described in WO 96/17860.

2-Aminomethyl-thiazole-4-thiocarboxamide

The preparation was carried out according to G. Videnov, D. Kaier, C. Kempter and G. Jung, Angew. Chemie 108 (1996), 1604, the protective group being eliminated from the N-Boc-protected compound described there by means of ethereal hydrochloric acid in methylene chloride.

5-Aminomethyl-2-cyanofuran

This building block was prepared as described in WO 96/17860.

5-Aminomethyl-3-cyanofuran

This building block was prepared as described in WO 96/17860.

5-Aminomethyl-3-methylthiophene-2-carbonitrile
a) 5-Formyl-3-methylthiophene-2-carbonitrile:

112 ml (179 mmol) of a 1.6 molar solution of n-butyllithium in n-hexane were added in the course of 20 minutes to a solution, cooled to −78° C., of 25.1 ml (179 mmol) of diisopropylamine in 400 ml of tetrahydrofuran. The solution was allowed to reach −35° C. and was cooled again to −78° C., and a solution of 20.0 g (162 mmol) of 2-cyano-3-methylthiophene in 80 ml of tetrahydrofuran was slowly added dropwise at this temperature. The solution acquired a dark red color. Stirring was continued for 45 minutes, 63 ml (811 mmol) of dimethylformamide were slowly added dropwise and stirring was carried out for a further 30 minutes. For working up, a solution of 27 g of citric acid and 160 ml of water was added at −70° C. Evaporating down was carried out in a rotary evaporator, 540 ml of saturated sodium chloride solution were added and extraction was effected with three times 250 ml of diethyl ether. The combined organic extracts were dried over magnesium sulfate. After the drying agent had been filtered off, the solvent was distilled off under reduced pressure from a water jet pump and the residue was purified by column chromatography (mobile phase: 4/1 hexane/ethyl acetate). 23 g (94%) of the title compound were obtained.

$^1$H-NMR (270 MHz, DMSO-$d_6$): δ=2.4 (s, 3H), 8.0 (s, 1H), 9.8 (s, 1H).
b) 5-Hydroxymethyl-3-methylthiophene-2-carbonitrile:

5.75 g (152 mmol) of sodium borohydride were added a little at a time at room temperature to a solution of 23 g (152 mmol) of 5-formyl-3-methylthiophene-2-carbonitrile. Stirring was carried out for 5 minutes, the reaction mixture was evaporated down under reduced pressure from a waterjet pump, the residue was taken up in ethyl acetate, extraction was carried out with 5% strength citric acid solution and with saturated sodium chloride solution, the organic phase was dried over magnesium sulfate, the drying agent was filtered off and the solvent was distilled off under reduced pressure from a waterjet pump at room temperature. This gave 24 g of the title compound as a dark red oil which still contains solvent and was used in the following reactions without further purification.

$^1$H-NMR (270 MHz, DMSO-$d_6$): δ=2.4 (s, 3H), 4.7 (m, 2H), 5.9 (m, 1H), 7.0 (s, 1H).
c) 5-Bromomethyl-3-methylthiophene-2-carbonitrile:

44 g (167 mmol) of triphenylphosphine were added to a solution of 24 g (152 mmol) of 5-hydroxymethyl-3-methylthiophene-2-carbonitrile in 180 ml of tetrahydrofuran. A solution of 55 g (167 mmol) of tetrabromomethane in 100 ml of tetrahydrofuran was then added. Stirring was carried out for 90 minutes at room temperature. The reaction mixture was evaporated down in a rotary evaporator under reduced pressure from a waterjet pump and the residue was purified by column chromatography (mobile phase: 8:2 hexane, ethyl acetate). 34 g of the title compound, which still contained a little solvent, were obtained.

$^1$H-NMR (270 MHz, DMSO-$d_6$): δ=2.4 (s, 3H), 5.0 (s, 2H), 7.3 (s, 1H).
d) 5-N,N-bis(tert-Butoxycarbonyl)aminomethyl-3-methylthiophene-2-carbonitrile:

5.0 g (167 mmol) of sodium hydride (80% strength suspension in mineral oil) were added a little at a time to a solution, cooled to 0° C., of 33.8 g (152 mmol) of 5-bromomethyl-3-methylthiophene-2-carbonitrile in 255 ml of tetrahydrofuran. A solution of 36.4 g (167 mmol) of di-tert-butyl iminodicarboxylate in 255 ml of tetrahydrofuran was then added dropwise, the temperature not exceeding 5° C. The mixture was allowed to reach room temperature and was stirred overnight. Heating was carried out for a further three hours at 35° C. to complete the reaction, after which the mixture was allowed to cool to room temperature and 510 ml of a saturated ammonium chloride solution was slowly added. The solvent was distilled off under reduced pressure from a waterjet pump, the residue was extracted several times with ethyl acetate and the combined organic phases were washed with saturated sodium chloride solution, dried over magnesium sulfate and evaporated down in a rotary evaporator. 57.6 g of an oily residue which still contained di-tert-butyl iminodicarboxylate were obtained and said residue was used as a crude product in the following reaction.

$^1$H-NMR (270 MHz, DMSO-$d_6$): δ=1.45 (s, 18H), 2.35 (s, 3H), 4.85 (s, 2H), 7.05 (s, 1H).
e) 5-Aminomethyl-3-methylthiophene-2-carbonitrile hydrochloride:

52.6 g of 5-N,N-bis(tert-butoxycarbonyl)aminomethyl-3-methylthiophene-2-carbonitrile (crude product from d), not more than 139 mmol) were dissolved in 950 ml of ethyl acetate and cooled to 0° C. The solution was saturated with hydrogen chloride gas, white precipitate separating out after 10 minutes. Stirring was carried out for two hours at room temperature and for one hour at 30° C., the resulting suspension was then evaporated down in a rotary evaporator, the residue was stirred with diethyl ether and filtered off from the solvent and the solid residue was dried at room temperature under reduced pressure. 24.7 g (94%) of the title compound were obtained as a white powder.

$^1$H-NMR (270 MHz, DMSO-d$_6$): δ=2.4 (s, 3H), 4.25 (s, 2H), 7.3 (S, 1H), 8.8–9.0 (bs, 3H). $^{13}$C-NMR (DMSO-d$_6$): 15.0 (CH$_3$), 36.4 (CH$_2$), 104.8 (C-2), 113.8 (CN), 131.5 (C-4), 142.8 (C-5), 149.6 (C-3).

5-Aminomethyl-3-chlorothiophene-2-carbonitrile Hydrochloride

This compound was prepared analogously to 5-aminomethyl-3-methylthiophene-2-carbonitrile, the 3-chloro-2-cyanothiophene used having been prepared by dehydrating 3-chlorothiophene-2-carboxamide (substances commercially available) with trifluoroacetic anhydride.

5-Aminomethyl-4-methylthiophene-3-thiocarboxamide a) Ethyl 2-Amino-3-cyano-4-methylthiophene-5-carboxylate Ethyl 2-amino-3-cyano-4-methylthiophene-5-carboxylate was prepared according to "Organikum", 19$^{th}$ edition, Dt. Verlag der Wissenschaften, Leipzig, Heidelberg, Berlin, 1993, Chapter 6, pages 374–375, starting from 130 g (1.0 mol) of 45 ethyl acetoacetate, 66 g (1.0 mol) of malonodinitrile, 32 g (1.0 mol) of sulfur and 80 g (0.92 mol) of morpholine.

$^1$H-NMR (270 MHz, DMSO-d$_6$): δ=1.25 (t, 3H), 2.3 (s, 3H), 4.2 (q, 2H), 7.9 (bs, 2H).

b) Ethyl-4-cyano-3-methylthiophene-2-carboxylate

A solution of 20.5 g (97.5 mmol) of ethyl 2-amino-3-cyano-4-methylthiophene-5-carboxylate in 600 ml of a 1:1 mixture of acetonitrile and dimethylformamide was cooled to 5° C., and 15.7 g (146 mmol) of tert-butyl nitrite were added dropwise, the reaction mixture heating up and vigorous gas evolution beginning. Stirring was carried out for seven hours at room temperature, the mixture was evaporated down in a rotary evaporator and under greatly reduced pressure, the residue was purified by column chromatography (mobile phase: dichloromethane) and 9.1 g (48%) of the desired compound were obtained as a yellow oil.

$^1$H-NMR (270 MHz, DMSO-d$_6$): δ=1.3 (t, 3H), 2.55 (s, 3H), 4.3 (q, 2H), 8.8 (s, 1H).

c) 5-Hydroxymethyl-4-methylthiophene-3-carbonitrile:

2.44 g (64 mmol) of lithium aluminum hydride were added a little at a time at 0° C. to a solution of 25.1 g (129 mmol) of ethyl 3-cyano-4-methylthiophene-5-carboxylate in 400 ml of tetrahydrofuran. Stirring was carried out for five hours at room temperature, excess reducing agent was destroyed by adding 0.5 N hydrochloric acid, and the reaction mixture was evaporated down under reduced pressure from a waterjet pump, diluted with water and extracted three times with ethyl acetate. The combined organic phases were then washed once with 0.5 N hydrochloric acid and once with saturated sodium chloride solution. The organic phase was dried over magnesium sulfate, the drying agent was filtered off and the solvent was distilled off under reduced pressure from a waterjet pump at room temperature. The residue was purified by column chromatography (mobile phase: 95:5 dichloromethane/methanol) and 16.1 g (83%) of the desired compound were obtained as light yellow oil.

$^1$H-NMR (270 MHz, DMSO-d$_6$): δ=2.2 (s, 3H), 4.6 (d, 2H), 5.7 (m, 1H), 8.35 (s, 1H).

d) 5-Bromomethyl-4-methylthiophene-3-carbonitrile:

30 g (115 mmol) of triphenylphosphine were added at 5° C. to a 45 solution of 16 g (104 mmol) of 5-hydroxymethyl-4-methylthiophene-3-carbonitrile in 300 ml of tetrahydrofuran. A solution of 38 g (115 mmol) of tetrabromomethane in 100 ml of tetrahydrofuran was then added. Stirring was carried out overnight at room temperature. The reaction mixture was evaporated down in a rotary evaporator under reduced pressure from a waterjet pump and the residue was purified by column chromatography (mobile phase: 1:1 petroleum ether: dichloromethane). 17 g (76%) of the title compound were obtained as a yellow oil.

$^1$H-NMR (270 MHz, DMSO-d$_6$): δ=2.25 (s, 3H), 5.0 (s, 2H), 8.5 (s, 1H).

e) 5-N,N-bis(tert-Butoxycarbonyl)aminomethyl-4-methylthiophene-3-carbonitrile:

3.5 g (103 mmol) of sodium hydride (oil-free) were added a little at a time to a solution, cooled to 0° C., of 17.2 g (79.5 mmol)of 5-bromomethyl-4-methylthiophene-3-carbonitrile in 250 ml of tetrahydrofuran. A solution of 22.5 g (103 mmol) of di-tert-butyl iminodicarboxylate in 100 ml of tetrahydrofuran was then added dropwise, the temperature not exceeding 5° C. The mixture was allowed to warm up to room temperature and was stirred for two hours. 400 ml of a saturated ammonium chloride solution was slowly added. The solvent was distilled off under reduced pressure from a waterjet pump and the residue was diluted with a little water and extracted three times with ethyl acetate. The combined organic phases were washed with saturated ammonium dichloride solution and with saturated sodium chloride solution, dried over magnesium sulfate and evaporated down in a rotary evaporator. 28 g of an oil which still contained di-tert-butyl iminodicarboxylate were obtained and said oil was used as a crude product in the following reaction.

$^1$H-NMR (270 MHz, DMSO-d$_6$): δ=1.4 (s, 9H), 1.45 (s, 9H), 2.3 (s, 3H), 4.8 (s, 2H), 8.4 (s, 1H).

f) 5-N,N-bis(tert-Butoxycarbonyl)aminomethyl-4-methylthiophene-3-thiocarboxamide The crude product (max. 79 mmol) obtained from e) was dissolved in 280 ml of pyridine and 140 ml of triethylamine and saturated with hydrogen sulfide at room temperature. The previously yellow solution became green. Stirring was carried out overnight at room temperature. To complete the reaction, hydrogen sulfide was passed in for a further 15 minutes and stirring was carried out for a further two hours at room temperature. Excess hydrogen sulfide was expelled with the aid of a stream of nitrogen via a scrubbing tower. Thereafter, the reaction mixture was evaporated down in a rotary evaporator, taken up in ethyl acetate, washed several times with a 20% strength sodium bisulfate solution, dried over magnesium sulfate and evaporated down in a rotary evaporator. 27 g of a light yellow firm foam were obtained, and said foam was used without further purification in the following reaction.

$^1$H-NMR (270 MHz, DMSO-d$_6$): δ=1.4 (s, 18H), 2.15 (s, 3H), 4.8 (s, 2H), 7.5 (s, 1H), 9.3 (bs, 1H), 9.75 (bs, 1H).

g) 5-Aminomethyl-4-methylthiophene-3-thiocarboxamide Hydrochloride 27 g of 5-N,N-bis(tert-butoxycarbonyl)aminomethyl-4-methylthiophene-3-thiocarboxamide (crude product from f), not more than 70 mmol) were dissolved in 400 ml of ethyl acetate and cooled to 0° C. The solution was saturated with hydrogen chloride gas, a white precipitate separating out after 10 minutes. Stirring was carried out after two hours at room temperature, the precipitate was filtered off and washed with ethyl acetate and the solid residue was dried at room temperature under reduced pressure. 13.6 g (87%) of the title compound were obtained as a white powder.

EI-MS: M$^+$=186.

5-Aminomethyl-4-chlorothiophene-3-thiocarboxamide a) 5-Formyl-4-chlorothiophene-3-carbonitrile:

35 g (325 mmol) of tert-butyl nitrite were added dropwise at room temperature to a solution of 53.0 g (250 mmol) of 2-amino-4-chloro-5-formylthiophene-3-carbonitrile (the preparation of this compound is described in the patent DB 3738910) in 600 ml of a 1:1 mixture of acetonitrile and dimethylformamide, the reaction mixture warming up from 20° C. to 37° C. and vigorous gas evolution beginning. The mixture was cooled to 25° C. and stirred for seven hours at room temperature, the black solution was evaporated down in a rotary evaporator and under greatly reduced pressure, the residue was purified by column chromatography (mobile phase: dichloromethane) and 29 g (68%) of the desired compound were obtained as a yellow oil.

$^1$H-NMR (270 MHz, DMSO-d$_6$): δ=9.1 (s, 1H), 10.0 (s, 1H).

b) 5-Hydroxymethyl-4-chlorothiophene-3-carbonitrile:

6.3 g (166 mmol) of sodium borohydride were added a little at a time at 5° C. to a solution of 28.5 g (166 mmol) of 5-formyl-4-chlorothiophene-3-carbonitrile in 400 ml of absolute methanol. The reaction mixture warmed up slightly and acquired a dark red color. Vigorous gas evolution was observed. After ten minutes, the reaction mixture was evaporated down under reduced pressure from a waterjet pump, the residue was taken up in 200 ml of ethyl acetate and the solution was extracted with 200 ml of 1 M hydrochloric acid and the organic phase was washed with twice 250 ml of water and with saturated sodium chloride solution and dried over magnesium sulfate, the drying agent was filtered off and the solvent was distilled off under reduce pressure from a waterjet pump at room temperature. 22 g (76%) of the title compound were obtained as a dark red oil, which was used without further purification in the following reactions.

$^1$H-NMR (270 MHz, DMSO-d$_6$): δ=4.65 (bs, 1H), 5.95 (t, 2H), 8.6 (s, 1H).

c) 5-Bromomethyl-4-chlorothiophene-3-carbonitrile:

36.1 g (137 mmol) of triphenylphosphine were added at 5° C. to a solution of 21.7 g (125 mmol) of 5-hydroxymethyl-4-chlorothiophene-3-carbonitrile in 250 ml of tetrahydrofuran. A solution of 45.6 g (137 mmol) of tetrabromomethane in 100 ml of tetrahydrofuran was then added. Stirring was carried on overnight at room temperature. The precipitate was filtered off, the filtrate was evaporated down in a rotary evaporator under reduced pressure from a waterjet pump and the residue was purified by column chromatography (mobile phase: 1:1 petroleum ether: dichloromethane). 26.0 g (88%) of the title compound were obtained as an oil.

$^1$H-NMR (270 MHz, DMSO-d$_6$): δ=4.95 (s, 2H), 8.8 (s, 1H).

d) 5-N,N-bis(tert-Butoxycarbonyl)aminomethyl-4-chlorothiophene-3-carbonitrile:

6.9 g (159 mmol) of sodium hydride (oil-free) were added a little at a time to a solution, cooled to 0° C., of 25.0 g (106 mmol) of 5-bromomethyl-4-chlorothiophene-3-carbonitrile in 300 ml of tetrahydrofuran. A solution of 34.4 g (159 mmol) of di-tert-butyl iminodicarboxylate in 100 ml of tetrahydrofuran was then added dropwise, the temperature not exceeding 5° C. The mixture was allowed to warm up to room temperature and was stirred for two hours. 300 ml of saturated ammonium chloride solution was slowly added. The solvent was distilled off under reduced pressure from a waterjet pump and the residue was diluted with a little water and extracted three times with ethyl acetate. The combined organic phases were washed with saturated ammonium chloride solution and with saturated sodium chloride solution, dried over magnesium sulfate and evaporated down in a rotary evaporator. 51.3 g of an oil which still contained di-tert-butyl iminodicarboxylate and solvent residues were obtained, and said oil was used as a crude product in the following reaction.

$^1$H-NMR (270 MHz, DMSO-d$_6$): δ=1.4 (s, 9H), 1.45 (s, 9H), 4.8 (s, 2H), 8.65 (s, 1H).

e) 5-N,N-bis(tert-Butoxycarbonyl)aminomethyl-4-methylthiophene-3-thiocarboxamide A part of the crude product (39.4 g, max. 106 mmol) obtained from d) was dissolved in 400 ml of pyridine and 40 ml of triethylamine and saturated with hydrogen sulfide at room temperature. The previously yellow solution acquired a green color. Stirring was carried out overnight at room temperature. Excess hydrogen sulfide was expelled with the aid of a stream of nitrogen via a scrubbing tower. Thereafter the reaction mixture was poured into ice-cooled, 20% strength sodium bisulfate solution and extracted three times with ethyl acetate. The organic phase was then washed several times with 20% strength sodium bisulfate solution, dried over magnesium sulfate and evaporated down in a rotary evaporator. 49.0 g of a solvent-containing residue were obtained, and said residue was used without further purification in the following reaction.

$^1$H-NMR (270 MHz, DMSO-d$_6$): δ=1.4, 1.45 (s, 18H), 4.8 (s, 2H), 7.75 (s, 1H), 9.4 (bs, 1H), 10.0 (bs, 1H).

f) 5-Aminomethyl-4-chlorothiophene-3-thiocarboxamide Hydrochloride 38.0 g of the crude product from e), not more than 93 mmol, were dissolved in 400 ml of ethyl acetate and cooled to 0° C. The solution was saturated with hydrogen chloride gas, white precipitate separating out after 10 minutes. Since the reaction was not yet complete, 200 ml of ethyl acetate were added, the solution was saturated again with hydrogen chloride gas and stirring was carried out overnight at room temperature. The precipitate was filtered off, washed with petroleum ether and dried at room temperature under reduced pressure. 21.1 g of the title compound were obtained as a white powder which contained ammonium chloride as an impurity.

EI-MS: M$^+$=206.

5-Aminomethyl-2-guanidinothiazole Bishydrochloride a) N-Phthaloyl-5-aminomethyl-2-guanidinothiazole A solution of 31 g (130 mmol) of N-phthaloyl-3-amino-2-chloropropionaldehyde (S. Marchais et al., Tetrahedron Letters 39 (1998), 8085–8088) and 15.4 g (130 mmol) of amidinothiourea in 200 ml of butanol was heated at 110° C. for 75 minutes under a nitrogen atmosphere, after which the reaction mixture was evaporated down under reduced pressure (1 mbar, bath temperature up to 50° C.) and methylene chloride and concentrated ammonia were added to the residue. A part of the product was precipitated from water. This was purified, together with the part obtained from the methylene chloride phase after drying and evaporating down, by column chromatography (silica gel; mobile phase: methylene chloride with a methanol content increasing from 0 to 5%). The predominantly pure fractions were then crystallized from acetone, 12.3 g of the title compound being obtained.

b) 5-Aminomethyl-2-guanidinothiazole Bishydrochloride

A solution of 5 g (16.6 mmol) of N-phthaloyl-5-aminomethyl-2-guanidinothiazole and 4.15 g (83 mmol) of hydrazine hydrate in 100 ml of methanol was stirred under a nitrogen atmosphere for one hour at room temperature, after which the reaction mixture was evaporated down under reduced pressure (1 mbar, bath temperature to 50° C.) and 70 ml of water and 20% strength hydrochloric acid were added to the residue until the pH reached 1, phthalylhydrazide being precipitated and then filtered off. The filtrate was evaporated down under reduced pressure and the residue was codistilled three times with methanol, dried at 50° C. under reduced pressure and then recrystallized from ethanol. 3.7 g of the title compound were obtained.

5-Amino-3-amidino-thiophene Bishydrochloride

The synthesis of this compound was carried out starting from 5-aminomethyl-3-cyanothiophene (WO 96/17860) by reaction with $(Boc)_2O$ to give 5-tert-butoxycarbonylaminomethyl-3-cyanothiophene, conversion of the nitrile function into the corresponding thioamide by addition of hydrogen sulfide, methylation of the thioamide function with methyliodide, reaction with ammonium acetate to give the corresponding amidine and subsequent elimination of the protective group with hydrochloric acid and isopropanol to give 5-aminomethyl-3-amidinothiophene bishydrochloride.

3-Amidino-5-[N-1-(4,4-dimethyl-2,6-dioxocyclohexylidene)ethyl]-aminomethylthiophene Hydrochloride 3-Amidino-5-aminomethylthiophene bishydrochloride (1.3 g, 5.7 mmol) in DMF (15 ml) was initially taken and N,N-diisopropylethylamine (0.884 g, 6.84 mmol) was added. Stirring was carried out for 5 minutes at room temperature, after which 2-acetyldimedone (1.25 g, 6.84 mmol) and trimethyl orthoformate (3.02 g, 28.49 mmol) were added. Stirring was carried out for 2.5 hours at room temperature, after which the DMF was removed under greatly reduced pressure and the residue was stirred thoroughly with DCM (5 ml) and petroleum ether (20 ml). The solvent was decanted from slightly yellowish product, and the solid was dried under reduced pressure at 40° C. Yield: 1.84 g (5.2 mmol, 91%).

1H-NMR (400 MHz, $[D_6]$DMSO, 25° C., TMS): δ=0.97 (s, 6H); 2.30 (s, 4H); 2.60 (s, 4H); 4.96 (d, J=7 Hz, 2H); 7.63 (s, 1H); 8.60 (s, 1H); 9.07 (sbr, 2H); 9.37 (sbr, 1H).

Syntheses of Building Blocks:

A—B—D—E—OH (in appropriately protected form):

The E building blocks were partly converted into the corresponding benzyl esters (or methyl esters) and linked to the appropriately protected A—B—D—U building blocks (U is a leaving group). In the case of compounds still having a free N—H-function, this was then protected with a Boc-group, the benzyl ester group was eliminated by hydrogenolysis (or the corresponding methyl ester group was hydrolyzed) and the building block A—B—D—E—OH was purified by crystallization, salt precipitation or column chromatography. This route is described by way of example for tBuOOC—CH$_2$-(Boc)(D)Cha-OH in WO 98/06741.

A—B—D—E—G—OH (in appropriately protected form):

The preparation of the A—B—D—E—G—OH building blocks in appropriately protected form is described by way of example for N-Boc-N-(tert-butoxycarbonylmethylene)-(D)-cyclohexylalanyl-3,4-dehydroproline in WO 98/06741.

H—G—K—CN:

The preparation of the H—G—K—CN building block is described by way of example for prolyl-4-cyanobenzylamide in WO 95/35309, for 3,4-dehydroprolyl-4-cyanobenzylamide in WO 98/06740 and for 3,4-dehydroprolyl-5-(2-cyano)-thienylmethylamide in WO 98/06741.

In the examples which follow, complement inhibitors are mentioned:

EXAMPLE 1

$CF_3$—$CH_2$—$SO_2$-(D)Phe-Pro-NH-p-amb.$CH_3$COOH (WO 96/17860 Example 13)

EXAMPLE 2 n-Octyl-$SO_2$-(D)Phe-Pro-NH-p-amb.$CH_3$COOH (WO 96/17860 Example 14)

EXAMPLE 3

3-Py-$SO_2$-(D)Phe-Pro-NH-p-amb.$CH_3$COOH (WO 96/17860 Example 4)

EXAMPLE 4

$CH_3$—$SO_2$-(D)Cha-Pyr-NH-p-amb.$CH_3$COOH (Preparation analogous to WO 96/17860 Example 1) FAB-MS: (M+H$^+$)=476.

EXAMPLE 5

H-(D)Val-Pro-NH-p-amb.2HCl (WO 95/35309 Example 151)

EXAMPLE 6

Boc-(D)Asp(OBn)-Pro-NH-p-amb.$CH_3$COOH (WO 95/35309, intermediate of Example 179) FAB-MS: (M+H$^+$)=552

EXAMPLE 7

2-$C_6H_{10}$—$CH_2$-Gly-Pro-NH-p-amb.2HCl (Preparation analogous to WO 95/35309 Example 166) FAB-MS: (M+H$^+$)=444.

EXAMPLE 8

$C_6H_5$—$CH_2$—$CH_2$—CO-Gly-Pro-NH-p-amb.HI (Preparation analogous to WO 95/35309 Example 6) FAB-MS: (M+H$^+$)=436.

EXAMPLE 9

$C_6H_5$—$(CH_2)_3$—CO-Gly-Pro-NH-p-amb.HI (Preparation analogous to WO 95/35309 Example 6) FAB-MS: (M+H$^+$)=450.

EXAMPLE 10

(D)(4-Me)Pic-Pro-NH-p-amb.2$CH_3$COOH (Preparation analogous to WO 95/35309 Example 112) FAB-MS: (M+H$^+$)=372.

EXAMPLE 11

H-(D)3-Tic-Pro-NH-p-amb.2CH$_3$COOH (WO 95/35309 Example 112)

EXAMPLE 12

HO$_3$S—(CH$_2$)$_3$-(D)Phe-Pro-NH-p-amb.HCl (The preparation of this compound was carried out by alkylating H-(D)Phe-Pro-NH—CH$_2$—pC$_6$H$_4$—CN with

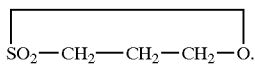

The nitrile function was converted into the amidino group by hydrogenating the hydroxyamidine intermediate.) FAB-MS: (M+H$^+$)=516.

EXAMPLE 13

CH$_3$—SO$_2$-(D)Cha-Pyr-NH-3-(6-am)-pico.CH$_3$COOH (WO 96/24609 Example 8).

EXAMPLE 14

CH$_3$—SO$_2$-(D)Chg-Pro-NH-3-(6-am)-pico.CH$_3$COOH (WO 96/24609 Example 6).

EXAMPLE 15

C$_6$H$_5$—CH$_2$—SO$_2$-(D)Cha-Pyr-NH-3-(6-am)-pico.CH$_3$COOH (Preparation analogous to WO 96/24609 Example 8) FAB-MS: (M+H$^+$)=553.

EXAMPLE 16

HOOC—CH$_2$—SO$_2$-(D)Chg-Pro-NH-3-(6-am)-pico.CH$_3$COOH (WO 96/24609 Example 10).

EXAMPLE 17

CH$_3$OOC—CH$_2$—SO$_2$-(D)Chg-Pro-NH-3-(6-am)-pico.CH$_3$COOH (WO 96/24609, intermediate in the preparation of Example 10) FAB-MS: (M+H$^+$)=523.

EXAMPLE 18

HOOC—CH$_2$-(D)Chg-Pyr-NH-3-(6-am)-pico.CH$_3$COOH (Preparation analogous to WO 96/25426 Example 93; described as a byproduct in the synthesis of Example 95 (WO 96/25426)) FAB-MS: (M+H$^+$)=443.

EXAMPLE 19

HOOC—CH$_2$-HCha-Pyr-NH-3-(6-am)-pico (Preparation analogous to WO 96/25426 Example 93) FAB-MS: (M+H$^+$)=471.

EXAMPLE 20

Boc-NH-p-C$_6$H$_4$CH$_2$—SO$_2$-(D)Cha-Pyr-NH-3-(6-am)-pico-CH$_3$COOH a) Methyl N-(4-Nitrobenzylsulfonyl)-(D)-cyclohexylalanine 2.6 g (25 mmol) of triethylamine, 2.6 g (25 mmol) of N-methylmorpholine and a solution of 5.9 g (25 mmol) of p-nitrobenzylsulfonyl chloride (J. E. Macor et al., THL 33 (1992), 8011) in 50 ml of methylene chloride were added dropwise at 0° C., while stirring, to a solution of 5.53 g (25 mmol) of methyl (D)-cyclohexylalanine hydrochloride in 150 ml of methylene chloride and 10 ml of acetonitrile. Stirring was carried out for a further 30 minutes, after which the yellow reaction solution was washed with water, 5% strength citric acid solution, 5% strength NaHCO$_3$-solution and again with water and was dried over Na$_2$SO$_4$ and the solvent was distilled off under reduced pressure. 10 g of slightly yellowish oil remained.

b) Methyl N-(4-Aminobenzylsulfonyl)-(D)-cyclohexylalanine

The above oil was dissolved in 250 ml of methanol, 1.5 g of 10% strength Pd/C were added and hydrogenation was carried out at room temperature with hydrogen. After the catalyst had been filtered off with suction, the methanol was distilled off under reduced pressure, crystallization beginning toward the end. The methanol-moist residue was substantially free from methanol by dissolving in methylene chloride and evaporating down again and, after dispersing with 1:4 toluene/n-hexane, was filtered off with suction. 8 g of the title compound (90% of theory), based on methyl D-cyclohexylalanine hydrochloride) were isolated as slightly yellowish crystals, m.p. 134–136° C., TLC: (9:1) CH$_2$Cl$_2$/acetone.

c) Methyl N-(4-tert-Butoxycarbonylaminobenzylsulfonyl)-(D)-cyclohexylalanine

A solution of 7.95 g (22.45 mmol) of the above compound and 5.4 g (24.7 mmol) of Boc$_2$O in 80 ml of THF was refluxed for 10 hours under nitrogen. The dark brown residue remaining after the solvent had been stripped off was purified over a silica gel column (eluent: 50:2.5 CH$_2$Cl$_2$/acetone). 8.85 g of the title compound (86.7% of theory) were isolated as white crystals (m.p. 143–144° C., TLC: 47:3 CH$_2$Cl$_2$/acetone) from the uniform fractions after treatment with n-hexane.

d) N-(4-tert-Butoxycarbonylaminobenzylsulfonyl)-(D)-cyclohexyl-alanine 40 ml of 1 n LiOH were added dropwise at 5° C., while stirring, to a solution of 8.85 g (19.5 mmol) of the above ester in 70 ml of dioxane, and stirring was continued for 20 hours at room temperature. According to TLC (9:1 CH$_2$Cl$_2$/acetone) traces of ester were still detectable. After the dropwise addition of 1 N HCl the pH was brought to 8, the dioxane was substantially distilled off and the residue was diluted with 1 liter of water. The aqueous phase was brought to pH 2 by adding KHSO$_4$ solution, covered with a layer of 500 ml of ethyl acetate and stirred for 2 hours. The organic phase was separated off, washed with water and dried over Na$_2$SO$_4$. The residue obtained after the solvent had been distilled off was digested at elevated temperature of 1,2-dichloroethane to remove traces of ester. After filtration with suction and washing with n-hexane, 7.1 g of the title compound were isolated as white crystals (m.p. 186–187° C. (decomposition), TLC: 20:5:1 CH$_2$Cl$_2$/acetone/acetic acid).

BocNH-p-C$_6$H$_4$CH$_2$—SO$_2$-(D)Cha-Pyr-NH-3-(6-CN)-pico 5.8 g of diisopropylamine followed by 11 ml (15 mmol) of a 50% strength solution of propanephosphoric anhydride in ethyl acetate were added dropwise at 0° C. to a suspension of 4.4 g (10 mmol) of N-(4-tert-butoxycarbonylaminobenzylsulfonyl)-(D)-cyclohexylalanine and 2.7 g (10 mmol) of 3,4-dehydroprolyl-(3-(6-cyano)picolyl)amide (prepared from Boc-3,4-dehydroprolyl(3-(6-carboxamido) picolylamide (WO 96/25426) by dehydration by means of trifluoroacetic anhydride and subsequent elimination of the Boc group) in 70 ml of methylene chloride, and stirring was carried out for 3 hours at 0° C.

The organic phase was washed with water, 5% strength NaHCO$_3$ solution and 5% strength citric acid solution, dried over Na$_2$SO$_4$ and evaporated to dryness. The remaining oily residue was purified by column chromatography (eluent: 45:5:4 CH$_2$Cl$_2$/acetone/methanol). The residue remaining after the eluent had been stripped off was converted into 5 g of white powder, m.p. 175–180° C. (decomposition), by treatment with ether.

f) Boc-NH-p-C$_6$H$_4$CH$_2$—SO$_2$-(D)Cha-Pyr-NH-3-(6-am)-pico.CH$_3$COOH

A solution of 3.12 g (4.8 mmol) are Boc-NH-p-C$_6$H$_4$—CH$_2$—SO$_2$-(D)Cha-Pyr-NH-3-(6-CN)-pico and 0.94 g (5.8 mmol) of L-acetylcysteine in 6 ml of methanol was heated at 50° C. for 4 hours while passing in ammonia.

To remove the ammonia, the methanol was distilled off and the residue was taken up again in 50 ml of methanol and converted into the acetate by means of an ion exchanger (acetate on polymeric carrier, Fluka 00402). After the methanol had been stripped off, the residue was purified by column chromatography (eluent: 43:7:1.5 CH$_2$Cl$_2$/methanol/50% strength acetic acid). 2.25 g of the title compound were obtained as the slightly yellowish powder by treating the pure acetate with ethyl acetate. FAB-MS: 668 (M+H$^+$).

EXAMPLE 21

H$_2$N-p-C$_6$H$_4$CH$_2$—SO$_2$-(D)Cha-Pyr-NH-3-(6-am)-pico-HCl 1.7 g (2.3 mmol) of the compound of Example 20 were dissolved in 10 ml of isopropanol and 4.5 ml of 4 N hydrochloric acid and heated at 50° C. for 3 hours. After the solvent had been stripped off, the residue was treated with ether and the precipitated amorphous hydrochloride was filtered off with suction. This was dissolved in 200 ml of isopropanol with the addition of a little water at elevated temperatures, active carbon was added and the solution was filtered and was evaporated down to a volume of about 40 ml. The precipitated hydrochloride of the compound was filtered off with suction, 1.65 g of slightly yellowish crystals being obtained; TLC: 43:7:2 CH$_2$Cl$_2$/methanol/50% strength of acetic acid; FAB-MS: (M+H$^+$)=568.

EXAMPLE 22

Boc-NH-p-C$_6$H$_4$—CH$_2$—SO$_2$-(D)Chg-Pyr-NH-3-(6-am)-pico.CH$_3$COOH (The preparation was carried out analogously to Example 20) FAB-MS (M+H$^+$)=654.

EXAMPLE 23

H$_2$N-p-C$_6$H$_4$—CH$_2$—SO$_2$-(D)Chg-Pyr-NH-CH$_2$-3-(6-am)-pico.HCl (The preparation was carried out starting from Example 22, analogously to Example 21); FAB-MS: (M+H$^+$)=554.

EXAMPLE 24

HOOC—(CH$_2$)$_5$-(D)Chg-Pro-NH-3-(6-am)-pico.CH$_3$COOH (The preparation was carried out analogously to WO 95/35309 Example 221) FAB-MS: (M+H$^+$)=501.

EXAMPLE 25

C$_2$H$_5$OOC—(CH$_2$)$_5$-(D)Chg-Pro-NH-3-(6-am)-pico.CH$_3$COOH (Preparation analogous to WO 95/35309 Example 221) FAB-MS: (M+H$^+$)=529.

EXAMPLE 26

HOOC—(CH$_2$)$_4$-(D)Chg-Pro-NH-3-(6-am)-pico.CH$_3$COOH (Preparation analogous to WO 95/35309 Example 221) FAB-MS: (M+H$^+$)=487.

EXAMPLE 27 t-BUOOC—(CH$_2$)$_3$-(D)Chg-Pro-NH-3-(6-am)-pico.CH$_3$COOH (Preparation analogous to WO 95/35309 Example 221 stage c) FAB-MS: (M+H$^+$)=529.

EXAMPLE 28

(C$_6$H$_5$—CH$_2$)$_2$-Gly-Pyr-NH-3-(6-am)-pico.CH$_3$COOH (Preparation analogous to WO 96/25426 Example 33 from (C$_6$H$_5$—CH$_2$)$_2$-Gly-OH and H-Pyr-NH-CH$_2$-3-(6-CN-pico) FAB-MS: (M+H$^+$)=483.

EXAMPLE 29

HOOC—CH$_2$-(D)Chg-Pyr-NH-CH$_2$-5-(2-am)-thioph.CH$_3$COOH (WO 98/06741 Example 3).

EXAMPLE 30

HOOC—CH$_2$—CH$_2$-(D)Cha-Pro-NH-CH$_2$-5-(2-am)-thioph.CH$_3$COOH (Preparation analogous to WO 98/06741 Example 1) FAB-MS: (M+H$^+$)=479.

EXAMPLE 31

HOOC—CH$_2$-(D)Chg-Aze-NH-CH$_2$-5-(2-am)-thioph (Preparation analogous to WO 98/06741 Example 3) FAB-MS: (M+H$^+$)=436.

EXAMPLE 32

HOOC—CH$_2$-(D)Cha-Pyr-NH—CH$_2$-5-(2-am)-thioph.CH$_3$COOH (WO 98/06741 Example 1).

EXAMPLE 33

HOOC—CH$_2$-(D)Cha-Thz-4-CO—NH—CH$_2$-5-(2-am)-thioph.2HCl (Preparation analogous to WO 98/06741 Example 1) FAB-MS: (M+H$^+$)=482.

EXAMPLE 34

HOOC—CH$_2$-(D)Cha-Pro-NH—CH$_2$-5-(3-am)-fur.CH$_3$COOH (Preparation analogous to WO 98/06741 Example 10) FAB-MS: (M+H$^+$)=448.

EXAMPLE 35

HOOC—CH$_2$-(D)Chg-Pyr-NH—CH$_2$-2-(4-am)-thiaz.2HCl (WO 98/06741 Example 22).

EXAMPLE 36

HOOC—CH$_2$-(D)Chg-Pyr-NH—CH$_2$-5-(2-am-3-Cl)-thioph.2HCl (Preparation analogous to WO 98/06741 Example 3) FAB-MS: (M+H$^+$)=482.

EXAMPLE 37

HOOC—CH$_2$-(D)Cha-Pyr-NH—CH$_2$-5-(2-am-3-Cl)-thioph.2HCl (Preparation analogous to WO 98/06741 Example 1) FAB-MS: (M+H$^+$)=496.

EXAMPLE 38

HOOC—CH$_2$-(D)Cha-Pyr-NH—CH$_2$-5-(3-am)-thioph.CH$_3$COOH (WO 98/06741 Example 5).

EXAMPLE 39

HOOC—CH$_2$-(D)Chg-Aze-NH—CH$_2$-5-(3-am)-thioph (Preparation analogous to WO 98/06741 Example 8) FAB-MS: (M+H$^+$)=436.

EXAMPLE 40

HOOC—CH$_2$(D)Chg-Pyr-NH—CH$_2$-5-(3-am)-thioph.CH$_3$COOH (WO 98/06741 Example 8)

EXAMPLE 41

HOOC—CH$_2$-Cheg-Pyr-NH—CH$_2$-5-(3-am)-thioph.CH$_3$COOH (Preparation analogous to WO 98/06741 Example 8) FAB-MS: (M+H$^+$)=462.

EXAMPLE 42

HOOC—CH$_2$-Cpg-Pyr-NH—CH$_2$-5-(3-am)-thioph.CH$_3$COOH (Preparation analogous to WO 98/06741 Example 8) FAB-MS: (M+H$^+$)=434.

EXAMPLE 43

HOOC—CH$_2$-(D)Chg-Pro-NH—CH$_2$-5-(3-am).thioph.2HCl (Preparation analogous to WO 98/06741 Example 8) FAB-MS: (M+H$^+$)=450.

EXAMPLE 44

HOOC—CH$_2$-(D)Cha-Pyr-NH—CH$_2$-5-(3-am)-fur.CH$_3$COOH (WO 98/0671 Example 13)

EXAMPLE 45

HOOC—CH$_2$-(D)Chg-Thz-2-CO—NH—CH$_2$-5-(3-am)-thioph (Preparation analogous to WO 98/06741 Example 5) FAB-MS: (M+H$^+$)=468.

EXAMPLE 46

HOOC—CH$_2$-(D)Cha-Thz-2-CO—NH—CH$_2$-5-(3-am)-thioph.2HCl (Preparation analogous to WO 98/06741 Example 8) FAB-MS: (M+H$^+$)=482.

EXAMPLE 47

HOOC—CH$_2$-(D)Cha-(L)Ohi-2-CO—NH—CH$_2$-5-(3-am)-thioph.HCl (Preparation analogous to WO 98/06741 Example 8) FAB-MS: (M+H$^+$)=518.

EXAMPLE 48

HOOC—CH$_2$-(D)Chg-(L)Ohi-2-CO—NH—CH$_2$-5-(3-am)-thioph.HCl (Preparation analogous to WO 98/06741 Example 5) FAB-MS: (M+H$^+$)=504.

EXAMPLE 49

HOOC—CH$_2$-(D)Chg-Pyr-NH—CH$_2$-5-(4-Cl-3-am)-thioph.CH$_3$COOH (Preparation analogous to WO 98/06741 Example 5) FAB-MS: (M+H$^+$)=482.

EXAMPLE 50

HOOC—CH$_2$(D)Cha-Pyr-NH—CH$_2$-5-(4-Cl-3-am)-thioph.CH$_3$COOH (Preparation analogous to WO 98/06741 Example 8) FAB-MS: (M+H$^+$)=496.

EXAMPLE 51

HOOC—CH$_2$-(D)Chg-Pyr-NH—CH$_2$-5-(4-Me-3-am)-thioph.CH$_3$COOH (Preparation analogous to WO 98/06741 Example 5) FAB-MS: (M+H$^+$)=462.

EXAMPLE 52

HOOC—CH$_2$-(D,L)Cpg-Pyr-NH—CH$_2$-5-(3-Me-3-am)-thioph.CH$_3$COOH (Preparation analogous to WO 98/06741 Example 5) FAB-MS: (M+H$^+$)=448.

EXAMPLE 53

HOOC—CH$_2$-(D)Cha-Pyr-NH—CH$_2$-5-(3-Me-2-am)-thioph.CH$_3$COOH (Preparation analogous to WO 98/06741 Example 8) FAB-MS: (M+H$^+$)=462.

EXAMPLE 54

N-(Hydroxycarbonyl-methylene)-(D) cyclohexylalanyl- 3,4-dehydroprolyl-[5-(2-guanidino)thiazolylmethyl] amide Bishydrochloride a) N-(tert-Butoxycarbonyl-methylene)-(N-Boc)-(D)-cyclohexylalanyl-3,4-dehydroprolyl-[5-(2-guanidino)-thiazolylmethyl]-amide 7.28 g (15.15 mmol) of N-(t-BuO$_2$C—CH$_2$)-(N-Boc)-(D)-Cha-Pyr-OH, 3.7 g (15.15 mmol) of 5-aminomethyl-2- guanidinothiazole bishydrochloride and 7.8 g (10.3 ml of 60.6 mmol) of diisopropylethylamine in 90 ml of dichloromethane and 6 ml of DMF were initially taken and 6.46 g (19.7 mmol) of TOTU were added a little at a time, the temperature being kept at 20° C. After 90 minutes, (the TLC check indicated complete conversion), the reaction mixture was evaporated down under gentle conditions under a reduced pressure, and the residue was taken up in ethyl acetate, the solution was extracted in succession with water, dilute hydrochloric acid (pH 1.5) and saturated to sodium chloride solution (three times) and the organic phase was dried over magnesium sulfate and was evaporated down under reduced pressure. The crude product (9.3 g) was purified by column chromatography (silica gel; mobile phase, methylene chloride with a methanol content increasing from 0 to 5%). The virtually pure fractions (3.2 g) were further purified by crystallization from a hexane-ether mixture, 2.7 g of the title compound being obtained.

b) N-(Hydroxycarbonyl-methylene)-(D)-cyclohexylalanyl-3,4-dehydroprolyl-[5-(2-guanidino)thiazolylmethyl]amide Bishydrochloride 2.7 g (4.03 mmol) of N-(tert-butoxycarbonyl-methylene)-(N-Boc)-(D)-cyclohexylalanyl-3,4-dehydroprolyl-[5-(2-guanidino)-thiazolylmethyl]-amide were stirred in 190 ml of dichloromethane and 50 ml of 5 M solution of hydrochloric acid in ether for 17 hours at room temperature, a precipitate separating out. The reaction mixture was evaporated down under reduced pressure, codistilled several times with dichloromethane and finally thoroughly stirred in 1:1 ether/dichloromethane, 2.2 g of the title compound being obtained. FAB-MS (M+H$^+$): 478.

EXAMPLE 55

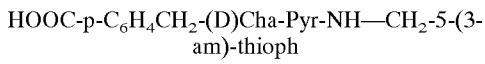

HOOC-p-C$_6$H$_4$CH$_2$-(D)Cha-Pyr-NH—CH$_2$-5-(3-am)-thioph

The compound was prepared analogously to Example 56, starting from methyl D-cyclohexylalanine hydrochloride.

White, amorphous powder, FAB-MS (M–H$^+$)=538. The intermediate N-(tert-butoxycarbonyl)-N-(4-tert-butoxycarbonylbenzyl)-D-cyclohexylamine was obtained in crystalline form, m.p. 119° C.

EXAMPLE 56

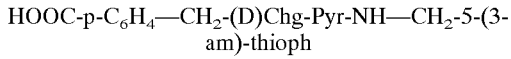

HOOC-p-C$_6$H$_4$—CH$_2$-(D)Chg-Pyr-NH—CH$_2$-5-(3-am)-thioph a) Methyl N-(4-tert-Butoxycarbonylbenzyl)-D-cyclohexylglycine A solution of 10 g (48.2 mmol) of methyl D-cyclohexylglycine hydrochloride, 13.1 g (38.3 mmol) of tert-butyl 4-bromomethyl-benzoate (A. Rosowsky et al. J. Med. Chem. 32 (1989), 709) and 15.6 g (121 mmol) of diisopropylethylamine in 50 ml of dimethylformamide were stirred for 16 hours at room temperature.

After the addition of 300 ml of water, extraction was carried out with methyl-tert-butylether (MTBE) and the organic phase was washed with 5% strength citric acid solution and water, dried over MgSO$_4$ and evaporated to dryness. The oily residue was purified by column chromatography (eluent: 50:1 CH$_2$Cl$_2$/MTBE) and gave 11.5 g (66% of theory) of the title compound as a colorless oil.

b) Methyl N-(tert-Butoxycarbonyl)-N-(4-tert-butoxycarbonylbenzyl)-D-cyclohexylglycine A solution of 11.5 g (31.8 mmol) of the above compound, 10.4 g (47.7 mmol) of di-tert-butyl dicarbonate and 1.5 ml of diisopropylethylamine was stirred for 40 hours at room temperature under nitrogen. The acetonitrile was distilled off, the residue was taken up in MTBE and the solution was washed with 5% strength citric acid solution and water, dried over MgSO$_4$ and evaporated to dryness. After purification by column chromatography (eluent: 99:2 CH$_2$Cl$_2$/acetone), the residue gave 14 g (95% of theory) of the title compound as a colorless oil.

c) N-(tert-Butoxycarbonyl)-N-(4-tert-butoxycarbonylbenzyl)-D-cyclohexylglycine 60 ml of 1 N sodium hydroxide solution were added dropwise at 10° C. to a solution of 14 g (30.3 mmol) of the above compound in 100 ml of dioxane and stirring was carried out for 20 hours at 40° C. The pH of the reaction solution was brought to about 8 by adding citric acid, the dioxin was distilled off and aqueous phase was extracted with MTBE, acidified by further addition of citric acid and extracted several times with MTBE. The combined MTBE extract were dried over MgSO$_4$, the solvent was distilled off and the residue was crystallized by treatment with water-saturated n-hexane.

Yield: 7.2 g of the title compound (53% of theory), m.p. 154° C., R$_f$ 0,39 (95:5 CH$_2$Cl$_2$/methanol).

d) N-(tert-Butoxycarbonyl)-N-(4-tert-butoxycarbonylbenzyl)-D-cyclohexylglycyl-3,4-dehydroproline 5.3 g (40.5 mmol) of diisopropylethylamine, followed by 10 ml of a 50% strength solution of propane phosphonic anhydride in ethyl acetate, were added dropwise at 0° C. to a suspension of 4.1 g (9 mmol) of the above compound and 1.5 g (9 mmol) of methyl 3,4-dehydroproline hydrochloride in 40 ml of CH$_2$Cl$_2$, and stirring was carried out for 2 hours at 0° C. and for 12 hours at room temperature. The working up was carried out analogously to Example 20, stage e). After purification by column chromatography (eluent: 50:5 CH$_2$Cl$_2$/ether), 2.1 g (41.2% of theory) of a slightly yellowish, amorphous powder were isolated. The hydrolysis to the acid was carried out analogously to stage c), a reaction time of 3 hours and a reaction temperature of 10° C. being sufficient. 1.8 g of the title compound were isolated as a white amorphous powder, TLC 50:1 ether/acetic acid.

e) N-Boc-N-(t-BuOOC-p-C$_6$H$_4$CH$_2$)-(D)Chg-Pyr-NH—CH$_2$-5-(3-am)-thio-phacetate 0.68 g (6.6 mmol) of N-methylmorpholine was added at 0° C., under nitrogen, to a suspension of 1.8 g (3.3 mmol) of the above acid and 0.75 g (3.3 mmol) of 5-aminomethyl-3-amidino-thiophene dihydrochloride. Addition of 1.9 g (5.8 mmol) of O-[cyano(ethoxycarbonyl)methyleneamino]-N,N,N',N'-tetra-methyluronium tetrafluoroborate (TOTU) a little at a time gave a clear solution, which was stirred for 3 hours. The yellow reaction solution was evaporated down under reduced pressure at from 35 to 40° C. and the residue was digested three times with diisopropyl ether and, after dissolution in methanol, was converted into the acetate by means of an ion exchanger (acetate on polymeric carrier, Fluka 00402). After the eluent had been evaporated down, the crude acetate was purified by column chromatography (eluent: 40:10:0.5 CH$_2$Cl$_2$/methanol/50% strength acetic acid). 1.8 g of the title compound were isolated as a white amorphous powder, FAB-MS (M–H$^+$)=580.

f) HOOC-p-C$_6$H$_4$CH$_2$-(D)Chg-Pyr-NH—CH$_2$-5-(3-am)-thioph 1.8 g of the above amidine compound were dissolved in 12 ml of glacial acetic acid, 12 ml of 4 N HCl in dioxane and 0.5 ml of water were added and the mixture was left to stand for 2.5 hours at room temperature.

After the solvent had been stripped off, the residue was treated with acetonitrile, the dihydrochloride separating out. This was dissolved in water for conversion into a monohydrochloride and was brought to a pH of 4.5 with a weakly basic ion exchanger (3-X4 Resin, BioRad). The aqueous solution was lyophilized after treatment with active carbon. 1.0 g of the title compound was obtained as lyophilized product, which was converted into a crystalline state by treatment with isopropanol, m.p. 230–233° C. (decomposition), FAB-MS (M+H⁺)=524.

EXAMPLE 57

MeOOC-p-C₆H₄CH₂-(D)Chg-Pyr-NH—CH₂-5-(3-am)-thioph.HCl 0.75 g (20 mmol) of hydrogen chloride was passed into a solution of 1.1 g (2 mmol) of the compound described in Example 56 in 70 ml of methanol and refluxing was then carried out for 8 hours.

The cooled solution was brought to pH 6 with a weakly basic ion exchanger (3-X4 Resin, BioRad), the methanol was distilled off and the viscous, oily residue was converted, by treatment with acetonitrile, into a slightly yellowish monohydrochloride which could be filtered off with suction. By dissolution in methanol, treatment with active carbon and removal of the methanol by distillation, finally with the addition of acetonitrile, 1.9 g of the title compound were isolated as white crystals, m.p. 215–220° C. (decomposition), FAB-MS (M+H⁺)=538; TLC: 20:5:1 CH₂Cl₂/methanol/50% strength acetic acid.

EXAMPLE 58

H₂N—CO-p-C₆H₄CH₂-(D)Chg-Pyr-NH—CH₂-5-(3-am)-thioph.HCl 0.6 g of the above compound (Example 57) was dissolved in 40 ml of methanol and the solution was heated at about 45° C. for 4 days while passing in ammonia. After the solvent had been stripped off, purification was carried out by column chromatography (eluent: 35:15:2.5 CH₂Cl₂/methanol/50% strength acetic acid). The residue was dissolved in water, the solution was brought to pH 2 with 1 N hydrochloric acid and was evaporated to dryness and the residue was again taken up in water, brought to pH 6 with a weakly basic ion exchanger and, after treatment with an active carbon, lyophilized. 0.28 g of the title compound was obtained as white, amorphous powder, FAB-MS M–H⁺)=523.

EXAMPLE 59

HOOC-m-C₆H₄CH₂-D(Chg)-Pyr-NH—CH₂-5-(3-am)-thioph

The title compound was obtained analogously to Example 56, starting from tert-butyl 3-bromomethylbenzoate (N. Shirai et al., J. Org. Chem. 55, (1990), 2767). White, amorphous powder, FAB-MS (M+H⁺)=524.

EXAMPLE 60

HOOC-p-C₆H₄CH₂-(D)Cha-Pyr-NH-3-(6-am)-pico.HCl

The preparation was carried out by reacting N-(tert-butoxycarbonyl)-N-(4-tert-butoxycarbonylbenzyl)-D-cyclohexylalanine (Example 55) with 3,4-dehydroprolyl-(3-(6-cyano)picolyl)amide (Example 20, stage e), then forming the amidine (Example 20, stage f) and eliminating the protective groups (Example 56, stage f).

Colorless, amorphous powder, FAB-MS (M+H⁺)=533.

EXAMPLE 61

HOOC-p-C₆H₄CH₂-(D)Chg-Pyr-NH-3-(6-am)-pico.HCl

The preparation was carried out analogously to Example 60. The starting material N-(tert-butoxycarbonyl)-N-(tert-butoxycarbonylbenzyl)-D-cyclohexylglycine is described in Example 56, stages a) to c).

Colorless, amorphous powder, FAB-MS (M+H⁺)=519.

EXAMPLE 62

N-(4-Hydroxycarbonyl-phenylsulfonyl)-(D)-cyclohexylglycyl-3,4-dehydroprolyl-[5-(3-amidino) thienylmethyl]amide: This compound is prepared by coupling (PPA, dichloromethane) H-Pyr-NH—CH₂-5-(3-CN)-thioph with Boc(D)Chg-OH to give Boc(D)Chg-Pyr-NH—CH₂-5-(3-CN)-thioph, eliminating the protective group (HCl in isopropanol) and then reacting (dichloromethane, DIPEA) with 4-HOOC—C₆H₄-SO₂Cl to give 4-HOOC—C₆H₄-SO₂-(D)Chg-Pyr-NH—CH₂-5-(3-CN)-thioph. After conversion of the nitrile function into the amidine function and purification by MPL chromatography, the title compound was obtained as a white amorphous powder. FAB-MS (M+H⁺): 574.

EXAMPLE 63

N-(3-Hydroxycarbonyl-phenylsulfonyl)-(D)-cyclohexylglycyl-3,4-dehydroprolyl-[5-(3-amidino) thienylmethyl]amide: This compound is prepared by coupling (PPA, dichloromethane) H-Pyr-NH—CH₂-5-(3-CN)-thioph with Boc(D)Chg-OH to give Boc(D)Chg-Pyr-NH—CH₂-5-(3-CN)-thioph, eliminating the protective group (HCl in isopropanol) and then reacting (dichloromethane, DIPEA) with 3-HOOC—C₆H₄-SO₂Cl to give 3-HOOC—C₆H₄—SO₂-(D)Chg-Pyr-NH—CH₂-5-(3-CN)-thioph. After conversion of the nitrile function into the amidine function and purification by MPL chromatography, the title compound was obtained as a white amorphous powder.

FAB-MS (M+H⁺): 574.

EXAMPLE 64

t-BuOOC-p-C₆H₄CH₂-(D)Chg-Pyr-NH—CH₂-5-(3-am)-thiop Acetate a) N-(4-tert-Butoxycarbonylbenzyl)-D-cyclohexylglycine 96.3 ml (96.3 mmol) of 1 N sodium hydroxide solution were added dropwise at 10° C. to a solution of 29 g (80 mmol) of methyl N-(4-tert-butoxycarbonylbenzyl)-D-cyclohexylglycine (Example 56, stage a) and stirring was carried out for 48 hours at room temperature. After the addition of a further 0.3 equivalent of 1 N NaOH, stirring was carried out for a further 10 hours at 50° C. By adding 5% strength citric acid solution, the pH of the solution was brought to about 8, the dioxane was distilled off and the aqueous phase was extracted with MTBE and acidified by further addition of citric acid. The precipitated acid was taken up in ethyl acetate, the aqueous phase was extracted several times with ethyl acetate, the combined ethyl acetate extracts were dried with MgSO₄ and the solvent was then distilled off, the acid crystallizing out toward the end. Yield: 17.5 g of white crystals (63% of theory), m.p.>225° C. (decomposition).

b) N-(tert-Butoxycarbonyl)-3,4-dehydroprolyl-[2-(4-hydroxyamidino)thienylmethyl]amide 8 g of concentrated ammonia were added to a suspension of 15.6 g (224.5 mmol) of hydroxylamine hydrochloride in 300 ml of ethanol, stirring was carried out for 30 minutes, the precipitated NH$_4$Cl was filtered off with suction, 30 g (90 mmol) of N-(tert-butoxycarbonyl)-3,4-dehydroprolyl-[2-(4-cyano)thienylmethyl]amide (WO 98/06741, Examples 1 and 5) were then added and stirring was carried out overnight at room temperature. Thereafter, no starting material was detectable (TLC, mobile phase: CH$_2$Cl$_2$/MeOH, 9/1 or CH$_2$Cl$_2$/MeOH/concentrated ammonia, 4.5/5/0.3).

After the solvent had been distilled off, the residue was taken up in 300 ml of methylene chloride, and the solution was washed with water and aqueous NaHCO$_3$ solution and dried over Na$_2$SO$_4$. After evaporating down, 31.5 g (95.5% of theory) of amorphous residue remained, RF 0.32 (CH$_2$Cl$_2$/MeOH) [lacuna]/1, FAB-MS: 366 (M+).

c) N-(tert-Butoxycarbonyl)-3,4-dehydroprolyl-[2-(4-hydroxyamidino)thienylmethyl]amide 31.5 g (86 mmol) of the above hydroxyamidine compound were dissolved in 300 ml of glacial acetic acid under nitrogen, 17 g of zinc dust (<10 μm) were added a little at a time at from 40 to 50° C. and stirring was carried out for 6 hours at 40° C. Thereafter, no starting material was detectable (TLC, mobile phase: CH$_2$Cl$_2$/methanol, 9/1).

After removal of the solids by filtration with suction and washing with glacial acetic acid, the acetic acid was substantially distilled off, with addition of toluene toward the end. The residue was taken up in 350 ml of water, brought to pH 7 with 1 N sodium hydroxide solution and extracted once with 180 ml of MTBE. After addition of 200 ml of CH$_2$Cl$_2$, the aqueous phase was brought to pH 12, the CH$_2$Cl$_2$ phase was separated off and then extraction was carried out again and the combined CH$_2$Cl$_2$ phases were dried over Na$_2$SO$_4$. After distillation, 28.4 g (94% of theory) of amorphous residue remained, RF 0.35 (CH$_2$Cl$_2$/MeOH/50% strength acetic acid, 12/3/1), FAB-MS: 350 (M$^+$).

c) 3,4-Dehydroprolyl-[2-(4-amidino)thienylmethyl]amide Dihydrochloride 28.4 g (81 mmol) of the above amidine were suspended in 450 ml of isopropanol, and 1215 ml of 4 N HCl in dioxane were added with stirring, a clear solution resulted in a short time, from which the dihydrochloride was slowly precipitated. The reaction mixture was stirred for 3 hours at room temperature and the crystals were filtered off with suction and washed thoroughly with cold isopropanol and finally with MTBE. After drying, 19.5 g (74.4% of theory) of the hygroscopic dihydrochloride remained, RF 0.53 (CH$_2$Cl$_2$/MeOH/H$_2$O/CF$_3$COOH, 24/9/1/0.5), FAB-MS: 250 (M$^+$), m.p. 220–223° C. (decomposition).

d) t-BuOOC-p-C$_6$H$_4$CH$_2$-(D)Chg-Pyr-NH—CH$_2$-5-(3-am)-thioph Acetate

N-(4-t-Butoxycarbonylbenzyl)-D-cyclohexylglycine (stage a) and 3,4-dehydroprolyl-[2-(4-amidino) thienylmethyl]amide dihydrochloride were coupled analogously to Example 56, stage e, to give the end product. White amorphous powder, FAB-MS: 579 (M$^+$).

EXAMPLE 65

HOOC-p-C$_6$H$_4$CH$_2$-(D)Val-Pyr-NH—CH$_2$-5-(3-am)-thioph HCl a) Methyl N-(4-tert-Butoxycarbonylbenzyl)-D-valine Prepared by reaction of methyl D-valine hydrochloride and tert-butyl 4-bromomethylbenzoate analogously to Example 56, stage a. The compound was obtained in 74% yield after chromatographic purification, FAB-MS: 321 (M$^+$).

b) N-(4-tert-Butoxycarbonylbenzyl)-D-valine

The hydrolysis was carried out analogously to Example 64, stage a. White crystals, m.p. 224–226° C. (decomposition), FAB-MS: 307 (M$^+$).

c) t-BuOOC-p-C$_6$H$_4$CH$_2$-(D)Val-Pyr-NH—CH$_2$-5-(3-am)-thioph Acetate

N-(4-t-Butoxycarbonylbenzyl)-D-valine and 3,4-dehydroprolyl-[2-(4-amidino)thienylmethyl]amide dihydrochloride (Example 64, stage c) were coupled analogously to Example 56, stage e. After purification by column chromatography (eluent: CH$_2$Cl$_2$/MeOH/50% strength CH$_3$COOH, 20/5/1), 3.1 g of white amorphous powder were isolated, FAB-MS: 539 (M$^+$).

d) HOOC-p-C$_6$H$_4$CH$_2$-(D)Val-Pyr-NH—CH$_2$-5-(3-am)-thioph HCl

The hydrolysis of the tert-butyl ester was carried out analogously to Example 56, stage f. After freeze-drying, 1.6 g of lyophilized product were isolated, FAB-MS: 483 (M$^+$).

The following compounds were obtained analogously to Examples 56 and 64:

EXAMPLE 66

HOOC-m-C$_6$H$_4$CH$_2$-(D)Val-Pyr-NH—CH$_2$-5-(3-am)-thioph HCl

White amorphous powder, FAB-MS: 483 (M$^+$).

EXAMPLE 67

HOOC-p-C$_6$H$_4$CH$_2$-(D)tBu-Ala-Pyr-NH—CH$_2$-5-(3-am)-thioph Acetate

White amorphous powder, FAB-MS: 511 (M$^+$).

EXAMPLE 68

HOOC-p-C$_6$H$_4$CH$_2$-(D)tBu-Gly-Pyr-NH—CH$_2$-5-(3-am)-thioph HCl

White amorphous powder, FAB-MS: 497 (M$^+$).

EXAMPLE 69

HOOC-p-C$_6$H$_4$CH$_2$-Pyr-NH—CH$_2$-5-(3-am)-thioph HCl

White amorphous powder, FAB-MS: 441 (M$^+$).

EXAMPLE 70

HOOC-m-C$_6$H$_4$CH$_2$-Gly-Pyr-NH—CH$_2$-5-(3-am)-thioph HCl

White amorphous powder, FAB-MS: 441 (M$^+$).

EXAMPLE 71

H$_2$N-p-C$_6$H$_4$CH$_2$—SO$_2$-(D)CHa-Pyr-NH—CH$_2$-(3-am)-thioph HCl

N-(4-tert-Butoxycarbonylaminobenzylsulfonyl)-D-cyclohexylalanine (preparation: Example 20, stage d) and 3,4-dehydroprolyl-[2-(4-amidino)thienylmethyl]amide dihydrochloride (Example 64, stage c) were coupled analogously to Example 56, stage c, and the tert-butoxycarbonyl protective group was then eliminated analogously to Example 21. White, amorphous powder, FAB-MS: 572 (M$^+$).

EXAMPLE 72

H$_2$N-p-C$_6$H$_4$CH$_2$-SO$_2$-(D)Chg-Pyr-NH—CH$_2$-(3-am)-thioph HCl

Preparation analogous to Examples 20 and 21. The intermediates methyl N-(4-nitrobenzylsulfonyl)- and N-(4- aminobenzylsulfonyl)-(D)-cyclohexylglycine were obtained as slightly yellowish crystals, m.p. 137° C. and 181° C., respectively.

White, amorphous powder, FAB-MS: 558 (M⁺).

EXAMPLE 73

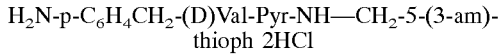
H₂N-p-C₆H₄CH₂-(D)Val-Pyr-NH—CH₂-5-(3-am)-thioph 2HCl

The preparation was carried out analogously to Examples 20 and 21.

Intermediates: methyl N-(4-nitrobenzylsulfonyl)-(D)-valine, slightly yellowish crystals, m.p. 98–100° C., FAB-MS: 330 (M⁺); methyl N-(4-aminobenzylsulfonyl)-(D)-valine, slightly yellowish crystals, m.p. 96–98° C., FAB-MS: 300 (M⁺); methyl N-(4-tert-butoxycarbonylaminobenzylsulfonyl)-D-valine white crystals, m.p. 150–152° C., (i-propanol); N-(4-tert-butoxycarbonylaminobenzylsulfonyl)-D-valine, colorless crystals, m.p. 177–180° C. (decomposition), FAB-MS: 386 M⁺).

The end product was isolated as lyophilized product, FAB-MS: 558 (M⁺).

EXAMPLE 74

H₂N-SO₂-p-C₆H₄CH₂-(D)Chg-Pyr-NH—CH₂-5-(3-am)-thioph HCl a) Methyl N-(4-Sulfonamidobenzyl)-D-cyclohexylglycine 7.3 g of diisopropylethylamine were added dropwise at room temperature to a solution of 5.2 g (25 mmol) of methyl D-cyclohexylglycine hydrochloride and 5.5 g (22 mmol) of 4-bromomethylbenzenesulfonamide (F. Amer. Chem. Soc. 79 (1957), 4232) in 30 ml of DMF, the temperature increasing to 26° C. The colorless solution remained standing overnight at room temperature. Thereafter, no starting material was detectable. (TLC, CH₂Cl₂/ether, 5/2).

After dilution with 100 ml of ice water, the white precipitate which separated out was filtered off with suction, washed with water and dissolved in ethyl acetate. The ethyl acetate phase was washed several times with sodium chloride solution and dried over Na₂SO₄, and the solvent was distilled off. The residue was recrystallized from 50 ml of isopropanol. 4.8 g (64% of theory) of white crystals were obtained, m.p. 113–114° C., FAB-MS: 340 (M⁺).

b) N-(4-Sulfonamidobenzyl)-D-cyclohexylglycine 4.0 g (11.8 mmol) of the above ester were suspended in 50 ml of water, brought into solution by adding 35 ml of 1 N NaOH and allowed to stand overnight at room temperature. A pH of 5 was established by dropwise addition of 10% strength hydrochloric acid, a fine precipitate separating out. A structure which could be readily filtered off with suction was obtained by brief heating to 80°, slow cooling to room temperature and stirring for 30 minutes while cooling in an ice bath. After being filtered off with suction, the precipitate was washed chloride-free with cold water, then digested with 50 ml of acetone, filtered off with suction again and then washed several times with an acetone/ether mixture and dried. 3.6 g (93.5% of theory) of white powder remained, said powder being extremely sparingly soluble.

c) H₂N-SO₂-p-C₆H₄CH₂-(D)Chg-Pyr-NH—CH₂-5-(3-am)-thioph HCl

Coupling to give the end product was carried out analogously to Example 56, stage e. 1 g of a lyophilized product was obtained, FAB MS: 558 (M⁺).

EXAMPLE 75

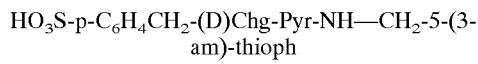
HO₃S-p-C₆H₄CH₂-(D)Chg-Pyr-NH—CH₂-5-(3-am)-thioph

4-Bromomethylbenzenesulfonic acid (F. Med. Chem. 33 (1990), 2437) was reacted with methyl D-cyclohexylglycine hydrochloride analogously to Example 74 and the reaction product was hydrolyzed and was then coupled with 3,4-dehydroprolyl-[2-(4-amidino)thienylmethyl]amide dihydrochloride.

White amorphous powder, FAB-MS: 559 (M⁺).

EXAMPLE 76

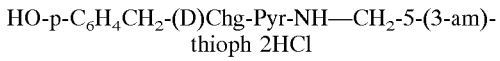
HO-p-C₆H₄CH₂-(D)Chg-Pyr-NH—CH₂-5-(3-am)-thioph 2HCl a) Methyl N-(4-tert-Butoxybenzyl)-D-cyclohexylglycine 5.2 g (25 mmol) of methyl D-cyclohexylglycine hydrochloride were dissolved in 200 ml of toluene with gentle heating, 2.6 g (25.7 mmol) of triethylamine were added and stirring was carried out for 1 hour. The triethylamine hydrochloride was filtered off with suction and washed with toluene, after which the filtrate was evaporated down to 70 ml, 4.5 g (25 mmol) of p-tert-butoxybenzaldehyde and 0.1 ml of glacial acetic acid were added and refluxing was carried out for 2.5 hours under a water separator. The toluene was distilled off under reduced pressure, the residue was dissolved in 50 ml of methanol, 1.5 g (25 mmol) of glacial acetic acid were added and 0.9 g of sodium cyanoborohydride was introduced a little at a time at 5° C. (TLC check: CH₂Cl₂/E₂O, 25/1). The methanol was distilled off, excess 5% strength NaHCO₃ was added to the residue and extraction was carried out with ether. After washing the ether phase with sodium chloride solution, drying over Na₂SO₄ and distilling off the ether, the oily residue was purified by column chromatography (eluent: CH₂Cl₂/E₂O, 25/1).

Yield: 4.3 g (51% of theory), colorless oil; FAB-MS: 333 (M⁺).

Analogously to Example 74, the above ester was hydrolyzed and was coupled with 3,4-dehydroprolyl-[2-(4-amidino)thienylmethyl]amide dihydrochloride, and the tert-butyl group was eliminated by means of hydrochloric acid. Amorphous, white powder, FAB-MS: 495 (M⁺).

EXAMPLE 77

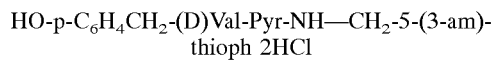
HO-p-C₆H₄CH₂-(D)Val-Pyr-NH—CH₂-5-(3-am)-thioph 2HCl

The preparation was carried out analogously to Example 76. White, amorphous powder, FAB-MS: 455 (M⁺).

EXAMPLE 78

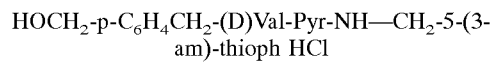
HOCH₂-p-C₆H₄CH₂-(D)Val-Pyr-NH—CH₂-5-(3-am)-thioph HCl

The preparation was carried out starting from 4-(hydroxymethyl)benzyl chloride (J. Org. Chem. 61 (1996), 449), analogously to Example 76.

White, amorphous powder, FAB-MS: 469 (M⁺).

EXAMPLE 79

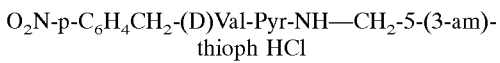
O₂N-p-C₆H₄CH₂-(D)Val-Pyr-NH—CH₂-5-(3-am)-thioph HCl

The preparation was carried out analogously to Example 76. Slightly yellowish, amorphous powder, FAB-MS: 484 (M⁺).

EXAMPLE 80

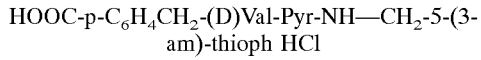
HOOC-p-C₆H₄CH₂-(D)Val-Pyr-NH—CH₂-5-(3-am)-thioph HCl 4-(tert-Butoxycarbonyl)benzylsulfonyl Chloride A suspension of 15 g (55 mol) of tert-butyl 4-bromomethylbenzoate and 6.95 g (55 mol) of sodium sulfite in 28.5 ml of water and 13.5 ml of DMF was heated at 80–90° C. for 4 hours while stirring, after addition of 0.4 g of Adogen®. After cooling to room temperature, 100 ml of water were added, extraction was effected ith twice 100 ml of MTBE, 250 ml of MeOH were added to the aqueous phase, the precipitated salts were filtered off with suction and the filtrate was evaporated down, under reduced pressure from an oil pump toward the end. The residue was digested with 200 ml of MeOH, insoluble solid components were filtered off with suction and the methanol was distilled off, after repeated addition of ethanol/toluene toward the end. The residue (16.1 g) was suspended in 200 ml of $CH_2Cl_2$, 0.8 g of etraethylbenzylammonium chloride was added, 15 g of oxalyl ichloride were added dropwise at 0° C. and refluxing was carried out for 30 minutes. Undissolved matter was filtered off with suction and the $CH_2Cl_2$ phase was washed with 5% strength $NaHCO_3$ solution, dried over $Na_2SO_4$ and distilled off. By treatment with n-hexane, 6.6 g of virtually white crystals were isolated, m.p. 82–83° C. (decomposition).

Analogously to Example 76, reaction was carried out with methyl D-valine hydrochloride, hydrolysis was effected to give the acid, coupling was carried out with 3,4-dehydroprolyl-[2-(4-amidino)thienylmethyl]amide dihydrochloride and the tert-butyl ester group was eliminated.

White, amorphous powder, FAB-MS: 547 ($M^+$).

EXAMPLE 81

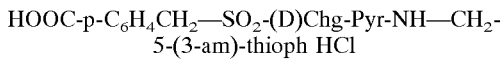

HOOC-p-$C_6H_4CH_2$—$SO_2$-(D)Chg-Pyr-NH—$CH_2$-5-(3-am)-thioph HCl

The preparation was carried out analogously to Examples 80 and 76.

White, amorphous powder, FAB-MS: 587 ($M^+$).

EXAMPLE 82 trans-HOOC-4-Cyclohexylmethyl-Gly-Pyr-NH—$CH_2$-5-(3-am)-thioph 2HCl a) trans-4-[N-(o-Nitrophenylsulfonyl)] aminomethylcyclohexane-carboxylic Acid A solution of 29.9 g (0.135 mol) of o-nitrobenzenesulfonyl chloride in 150 ml of dioxane and 150 ml of 1 N NaOH was added simultaneously and dropwise at 4° C. (ice bath) to a solution of 14.13 g (0.09 mol) of trans-4-(aminomethyl)cyclohexanecarboxylic acid in a two-phase system comprising 90 ml of 1 N NaOH and 90 ml of dioxane. After the slightly exothermic reaction had died down, stirring was carried out for 30 minutes at room temperature, the precipitate which separated out was filtered off with suction and washed with a little ice water and the filtrate was evaporated down under reduced pressure, further precipitation of salt occurring. The combined amounts of salt were digested with ether, suspended in water, acidified with 1 M $KHSO_4$ solution and extracted with ethyl acetate. The ethyl acetate phase was washed with sodium chloride solution, dried over $Na_2SO_4$ and evaporated down under reduced pressure.

The residue was recrystallized from acetonitrile. Yield: 27.4 g (89% of theory), m.p. 179° C.
b) tert-Butyl trans-4-[N-(o-Nitrophenylsulfonyl)] aminomethylcyclohexane Carboxylate 11.3 g (90 mmol) of oxalyl dichloride were added dropwise at 0° to a solution of 20.4 g (60 mmol) of the above compound and 0.1 ml of DMF in 350 ml of $CH_2Cl_2$, and the mixture was then heated until the gas evolution had ended. After the methylene chloride had been distilled off—with the addition of toluene toward the end—the residue was dissolved in ml of methylene chloride and was added dropwise to a solution of 6.1 g (83 mmol) of tert-butanol and 9.4 g (119 mmol) of pyridine in 60 ml of $CH_2Cl_2$ while cooling with ice. The reaction mixture remained standing at room temperature for 24 hours and was then washed with 1 N $KHSO_4$ solution, water and $NaHCO_3$ solution and dried over $Na_2SO_4$, and the solvent was distilled off. The residue was recrystallized from cyclohexane/ethyl acetate (95/5) and gave 9.3 g of slightly yellowish crystals, m.p. 114° C.
c) tert-Butyl trans-4-[N-(o-Nitrophenylsulfonyl)-N-(methoxycarbonylmethyl)] aminomethylcyclohexanecarboxylate A solution of 2.68 g (6.7 mmol) of the above compound and 1.23 g (7.6 mmol) of methyl bromoacetate in 50 ml of DMF was stirred overnight at room temperature with the addition of 1.85 g (13.4 mmol) of $K_2CO_3$ powder (TLC: ethyl acetate/n-hexane, 1/1). 100 ml of water were added to the reaction mixture, extraction was effected several times with ethyl acetate, the combined ethyl acetate extracts were washed with sodium chloride solution and dried over $Na_2SO_4$ and the solvent was distilled off. After purification by column chromatography (eluent: ethyl acetate/n-hexane, 1/1) and crystallization from ether/n-hexane, 2.6 g (82.3% of theory) of yellowish crystals were obtained, m.p. 123–124° C.
d) tert-Butyl trans-4-[N-(o-Nitrophenylsulfonyl)-N-(hydroxycarbonylmethyl)] aminomethylcyclohexanecarboxylate The methyl ester group of the above compound was hydrolyzed analogously to Example 20, stage d. Viscous yellow oil, FAB-MS: 456 ($M^+$), TLC: ethyl acetate/n-hexane/glacial acetic acid, 34/15/1.5.
e) trans-t-BuOOC-4-Cyclohexylmethyl-(o-$NO_2$-$C_6H_4SO_2$) Gly-Pyr-NH—$CH_2$-5-(3-CN)-thioph The above acid was coupled with 3,4-dehydroprolyl-[2-(4-cyano)thienylmethyl]amide hydrochloride analogously to Example 20, stage e. Amorphous, yellowish residue, FAB-MS: 671 ($M^+$), TLC: $CH_2Cl_2$/acetone/methanol, 45/5/1.
f) trans-t-BuOOC-4-Cyclohexylmethyl-Gly-Pyr-NH—$CH_2$-5-(3-N)-thioph A solution of 3.5 g (5.5 mmol) of the above compound and 0.7 g (6.35 mmol) of thiophenol in 10 ml of DMF was stirred overnight at room temperature with the addition of 2.5 g (18.1 mmol) of $K_2CO_3$ powder. 100 ml of ice water were added to the yellow reaction mixture, extraction was effected with 4×35 ml of ethyl acetate, the ethyl acetate extracts were washed with sodium chloride solution and dried over $Na_2SO_4$ and the viscous yellow oil obtained after distilling off the solvent was purified by column chromatography (eluent: $CH_2Cl_2$/methanol, 50/4). 2.3 g of yellowish amorphous residue were obtained, FAB-MS: 486 ($M^+$).
g) trans-HOOC-4-Cyclohexylmethyl-Gly-Pyr-NH-5-(3-am)-thioph 2HCl The amidine formation was carried out analogously to Example 64, stages b and c. The hydrolysis of the tert-butyl ester was carried out with 4 N hydrochloric acid in dioxane. 1.1 g of lyophilized product were obtained, FAB-MS: 447 ($M^+$), TLC: $CH_2Cl_2$/MeOH/50% strength glacial acetic acid, 35/15/6.

EXAMPLE 83

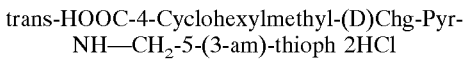

trans-HOOC-4-Cyclohexylmethyl-(D)Chg-Pyr-NH—$CH_2$-5-(3-am)-thioph 2HCl 1.9 ml (11 mmol) of trifluoromethanesulfonic anhydride and then 1.2 g (11 mmol) of 2,6-lutidine were added dropwise at −8° C. to a solution of 1.72 g (10 mmol) of methyl S-hexahydromandelate while stirring. After stirring for 20 minutes at 0° C. (TLC: Et$_2$O/n-hexane, 3/2), a solution of 5.3 g (24.9 mmol) of tert-butyl trans-4-(aminomethyl)cyclohexanecarboxylate and 2.6 g (20 mmol) of diisopropylethylamine in 20 ml of CH$_2$Cl$_2$ was added dropwise and stirring was carried out for a further 2 hours at 0° C. and overnight at room temperature (TLC: CH$_2$Cl$_2$/ether, 25/3).

The reaction solution was washed with water, with twice 10 ml 1 N hydrochloric acid and with 5% strength NaHCO$_3$ solution and dried over Na$_2$SO$_4$, the solvent was distilled off and the residue was purified by column chromatography (eluent: CH$_2$Cl$_2$/ether, 10/1). 2.7 g of a slightly yellowish oil were isolated, which oil was hydrolyzed analogously to Example 56, stage c, to give the acid and then coupled analogously to stage e with 3,4-dehydroprolyl[2-(4-amidino)thienylmethyl]amide dihydrochloride. After hydrolysis of the tert-butyl ester group with 4 N hydrochloric acid in dioxane, the residue was freeze-dried to give a slightly yellowish amorphous powder, FAB-MS: 529 (M$^+$), TLC: CH$_2$Cl$_2$/MeOH/50% strength acetic acid, 35/15/3.

EXAMPLE 84

4-Benzoylbenzoyl-Ala-Pro-5-(3-am)-thioph a) 3 g (1.62 mmol) p-nitrophenyl carbonate Wang resin (Novabiochem, substitution 0.54 mmol/g) were suspended in 20 ml of DMF and shaken with 1.15 g (3.24 mmol) of 4-amidino-2-[N-1-(4,4-dimethyl-2,6-dioxocyclohexylidene)ethyl]aminomethylthiophene hydrochloride and 4.48 ml (32.4 mmol) of triethylamine for 4 days at room temperature. The solid was filtered off with suction and was washed with DMF, CH$_2$Cl$_2$, methanol and CH$_2$Cl$_2$. The resin was then treated with 0.5 M NH$_4$OAc solution in methanol (3×10 min), washed with methanol, DMF and CH$_2$Cl$_2$ and dried under reduced pressure at room temperature. To eliminate the Dde protective group, the resin was treated with 20 ml of a 2% strength solution of hydrazine hydrate in DMF at room temperature for 5 minutes. The solid was filtered off with suction and was washed with DMF. The elimination was repeated twice. Thereafter, the residue was washed with DMF, CH$_2$Cl$_2$, methanol and CH$_2$Cl$_2$ and was dried under reduced pressure at room temperature (weight obtained: 2.84 g).

b) A solution of 0.088 mmol of 2(1H-benzotriazol-1-yl)-1,1,3,3-tetramethyluronium tetrafluoroborate in 0.5 ml of dimethylformamide was added at room temperature to 0.044 mmol of a resin from a), 0.088 mmol of Fmoc-Pro-OH and 0.088 mmol of N,N,-diisopropylethylamine in 1.5 ml of dimethylformamide and stirring was carried out for 2 hours at room temperature. The solid was then filtered off with suction and was washed with dimethylformamide, CH$_2$Cl$_2$, methanol and CH$_2$Cl$_2$. The elimination of the Fmoc-protective group was carried out with 2 ml of a solution of 10% of (1,8-diazabicyclo-[5.4.0.]undec-7-ene), 2% of piperidine and 88% of dimethylformamide (3 min). Thereafter, the resin was filtered off with suction and was washed with dimethylformamide, CH$_2$Cl$_2$, methanol and CH$_2$Cl$_2$.

c) The resin from b) was suspended in a solution of 0.088 mmol of Fmoc-Ala-OH and 0.088 mmol of N,N,-diisopropylethylamine in 1.5 ml of dimethylformamide, a solution of 0.088 mmol of 2-(1H-benzotriazol-1-yl-)-1,1,3,3-tetramethyluronium tetrafluoroborate in 0.5 ml of dimethylformamide was added and stirring was carried out for 2 hours at room temperature. Thereafter, the solid was filtered off with suction and was washed with dimethylformamide, CH$_2$Cl$_2$, methanol and CH$_2$Cl$_2$. The elimination of the Fmoc protective group was carried out with 2 ml of a solution of 10% of (1,8-diazabicyclo [5.4.0.]undec-7-ene), 2% of piperidine and 88% of dimethylformamide (3 min). Thereafter, the resin was filtered off with suction and was washed with dimethylformamide, CH$_2$Cl$_2$, methanol and CH$_2$Cl$_2$.

d) The resin from c) was suspended in a solution of 0.088 mmol of 4-benzoylbenzoic acid in 1 ml of CH$_2$Cl$_2$, and 0.088 mmol of diisopropylcarbodiimide in 0.5 ml of CH$_2$Cl$_2$ was added. Stirring was carried out for 2 hours at room temperature, after which the solid was filtered off with suction and was washed with dimethylformamide, CH$_2$Cl$_2$, methanol and CH$_2$Cl$_2$. The elimination of the product from the carrier was carried out by treatment with 95:5 trifluoroacetic acid/water (1 h/room temperature).

Yield: 13 mg. HPLC-MS: M+H$^+$ 532 (calculated: 532).

The following examples were prepared analogously to Example 84, where, for example, reductive aminations of the resin can be carried out with, for example, 4-carboxybenzaldehyde or other aldehydes under standard conditions with sodium cyanoborohydride in 1% AcOH/DMF instead of the final coupling.

EXAMPLE 85

3-Benzoylbenzoyl-Gly-Pro-NH—CH$_2$-5-(3-am)-thioph

ESI-MS [M+H]$^+$ 518.

EXAMPLE 86

4-Benzoylbenzoyl-Gly-Pro-NH—CH$_2$-5-(3-am)-thioph

ESI-MS [M+H]$^+$ 518.

EXAMPLE 87

4-Phenylbenzoyl-Gly-Pro-NH—CH$_2$-5-(3-am)-thioph

ESI-MS [M+H]$^+$ 490.

EXAMPLE 88

4-Phenylphenylacetyl-Gly-Pro-NH—CH$_2$-5-(3-am)-thioph

ESI-MS [M+H]$^+$ 504.

EXAMPLE 89

2-(Benzylthio)-benzoyl-Gly-Pro-NH—CH$_2$-5-(3-am)-thioph

ESI-MS [M+H]$^+$ 536.

EXAMPLE 90

3-Phenylpropionyl-Gly-Pro-NH—CH$_2$-5-(3-am)-thioph

ESI-MS [M+H]$^+$ 442.

EXAMPLE 91

4-Phenylbutyryl-Gly-Pro-NH—CH$_2$-5-(3-am)-thioph

ESI-MS [M+H]$^+$ 456.

EXAMPLE 92

5-Phenylvaleryl-Gly-Pro-NH—$CH_2$-5-(3-am)-thioph
ESI-MS $[M+H]^+$ 470.

EXAMPLE 93

Cinnamoyl-Gly-Pro-NH—$CH_2$-5-(3-am)-thioph
ESI-MS $[M+H]^+$ 440.

EXAMPLE 94

$C_6H_5$—C≡C—CO-Gly-Pro-NH—$CH_2$-5-(3-am)-thioph
ESI-MS $[M+H]^+$ 438.

EXAMPLE 95

9-Fluorenone-4-carbonyl-Gly-Pro-NH—$CH_2$-5-(3-am)-thioph
ESI-MS $[M+H]^+$ 516.

EXAMPLE 96

3-Benzyloxycarbonylpropionyl-Gly-Pro-NH—$CH_2$-5-(3-am)-thioph
ESI-MS $[M+H]^+$ 500.

EXAMPLE 97

4-Methoxycarbonylcinnamoyl-Gly-Pro-NH—$CH_2$-5-(3-am)-thioph
ESI-MS $[M+H]^+$ 498.

EXAMPLE 98

4-Methoxycarbonylbenzoyl-Gly-Pro-NH—$CH_2$-5-(3-am)-thioph
ESI-MS $[M+H]^+$ 472.

EXAMPLE 99

2-(4'-Chloro-3'-nitrobenzoyl)-benzoyl-Gly-Pro-NH—$CH_2$-5-(3-am)-thioph
ESI-MS $[M+H]^+$ 597.

EXAMPLE 100

6-(Acetylamino)-pyridyl-3-carbonyl-Gly-Pro-NH—$CH_2$-5-(3-am)-thioph
ESI-MS $[M+H]^+$ 472.

EXAMPLE 101

3-(3'-Pyridyl)-acryloyl-Gly-Pro-NH—$CH_2$-5-(3-am)-thioph
ESI-MS $[M+H]^+$ 441.

EXAMPLE 102

4-Acetylaminobenzoyl-Gly-Pro-NH—$CH_2$-5-(3-am)-thioph
ESI-MS $[M+H]^+$ 471.

EXAMPLE 103

4-(4'-Aminophenoxy)-benzoyl-Gly-Pro-NH—$CH_2$-5-(3-am)-thioph
ESI-MS $[M+H]^+$ 521.

EXAMPLE 104

4-(2'-Chloro-4'-aminophenoxy)-benzoyl-Gly-Pro-NH—$CH_2$-5-(3-am)-thioph
ESI-MS $[M+H]^+$ 555.

EXAMPLE 105

4-Aminobenzoyl-Gly-Pro-NH—$CH_2$-5-(3-am)-thioph
ESI-MS $[M+H]^+$ 486.

EXAMPLE 106

(4-Aminophenyl)acetyl-Gly-Pro-NH—$CH_2$-5-(3-am)-thioph
ESI-MS $[M+H]^+$ 443.

EXAMPLE 107

(4-Aminophenylthio)-acetyl-Gly-Pro-NH—$CH_2$-5-(3-am)-thioph
ESI-MS $[M+H]^+$ 475.

EXAMPLE 108

2-(Pyrid-3-yl)-acetyl-Gly-Pro-NH—$CH_2$-5-(3-am)-thioph
ESI-MS $[M+H]^+$ 429.

EXAMPLE 109

3-(4'-Aminobenzoyl)-butyryl-Gly-Pro-NH—$CH_2$-5-(3-am)-thioph
ESI-MS $[M+H]^+$ 499.

EXAMPLE 110

4-Benzoylbenzoyl-(D)-Val-Pro-NH—$CH_2$-5-(3-am)-thioph
ESI-MS $[M+H]^+$ 560.

EXAMPLE 111

4-Phenylphenylacetyl-(D)-Val-Pro-NH—$CH_2$-5-(3-am)-thioph
ESI-MS $[M+H]^+$ 546.

EXAMPLE 112

4-Phenylphenylacetyl-(D)-Ala-Pro-NH—$CH_2$-5-(3-am)-thioph
ESI-MS $[M+H]^+$ 518.

EXAMPLE 113

4-Benzoylbenzoyl-β-Ala-Pro-NH—$CH_2$-5-(3-am)-thioph
ESI-MS $[M+H]^+$ 532.

EXAMPLE 114

4-Benzoylbenzoyl-(D)-Ala-Pro-NH—$CH_2$-5-(3-am)-thioph
ESI-MS $[M+H]^+$ 532.

EXAMPLE 115

2-(Benzylthio)-benzoyl-(D)-Ala-Pro-NH—CH$_2$-5-(3-am)-thioph

ESI-MS [M+H]$^+$ 550.

EXAMPLE 116

5-Phenylvaleryl-(D)-Val-Pro-NH—CH$_2$-5-(3-am)-thioph

ESI-MS [M+H]$^+$ 512.

EXAMPLE 117

5-Phenylvaleryl-(D)-Ala-Pro-NH—CH$_2$-5-(3-am)-thioph

ESI-MS [M+H]$^+$ 484.

EXAMPLE 118

5-Phenylvaleryl-Ala-Pro-NH—CH$_2$-5-(3-am)-thioph

ESI-MS [M+H]$^+$ 484.

EXAMPLE 119

3-Phenylpropionyl-(D)-Val-Pro-NH—CH$_2$-5-(3-am)-thioph

ESI-MS [M+H]$^+$ 484.

EXAMPLE 120

4-Phenylbutyryl-(D)-Val-Pro-NH—CH$_2$-5-(3-am)-thioph

ESI-MS [M+H]$^+$ 498.

EXAMPLE 121

4-Phenylbutyryl-(D)-Ala-Pro-NH—CH$_2$-5-(3-am)-thioph

ESI-MS [M+H]$^+$ 470.

EXAMPLE 122

4-Phenylbenzoyl-(D)-Val-Pro-NH—CH$_2$-5-(3-am)-thioph

ESI-MS [M+H]$^+$ 532.

EXAMPLE 123

4-Phenylbenzoyl-Ala-Pro-NH—CH$_2$-5-(3-am)-thioph

ESI-MS [M+H]$^+$ 504.

EXAMPLE 124

4-Phenylbenzoyl-Val-Pro-NH—CH$_2$-5-(3-am)-thioph

ESI-MS [M+H]$^+$ 532.

EXAMPLE 125

3-Phenylpropionyl-(D)-Ala-Pro-NH—CH$_2$-5-(3-am)-thioph

ESI-MS [M+H]$^+$ 456.

EXAMPLE 126

2-(Benzylthio)-benzoyl-(D)-Val-Pro-NH—CH$_2$-5-(3-am)-thioph

ESI-MS [M+H]$^+$ 578.

EXAMPLE 127

5-Phenylvaleryl-Val-Pro-NH—CH$_2$-5-(3-am)-thioph

ESI-MS [M+H]$^+$ 512.

EXAMPLE 128

4-Phenylphenylacetyl-β-Ala-Pro-NH—CH$_2$-5-(3-am)-thioph

ESI-MS [M+H]$^+$ 518.

EXAMPLE 129

4-Phenylbenzoyl-(D)-Ala-Pro-NH—CH$_2$-5-(3-am)-thioph

ESI-MS [M+H]$^+$ 504.

EXAMPLE 130

4-Phenylphenylacetyl-Val-Pro-NH—CH$_2$-5-(3-am)-thioph

ESI-MS [M+H]$^+$ 546.

EXAMPLE 131

4-Phenylphenylacetyl-Ala-Pro-NH—CH$_2$-5-(3-am)-thioph

ESI-MS [M+H]$^+$ 518.

EXAMPLE 132

3-Phenylpropionyl-Ala-Pro-NH—CH$_2$-5-(3-am)-thioph

ESI-MS [M+H]$^+$ 456.

EXAMPLE 133

3-Phenylpropionyl-β-Ala-Pro-NH—CH$_2$-5-(3-am)-thioph

ESI-MS [M+H]$^+$ 456.

EXAMPLE 134

4-Phenylbutyryl-β-Ala-Pro-NH—CH$_2$-5-(3-am)-thioph

ESI-MS [M+H]$^+$ 470.

EXAMPLE 135

5-Phenylvaleryl-β-Ala-Pro-NH—CH$_2$-5-(3-am)-thioph

ESI-MS [M+H]$^+$ 484.

EXAMPLE 136

4-Benzoylbenzoyl-Val-Pro-NH—CH$_2$-5-(3-am)-thioph

ESI-MS [M+H]$^+$ 560.

EXAMPLE 137

4-Phenylbenzoyl-β-Ala-Pro-NH—CH$_2$-5-(3-am)-thioph

ESI-MS [M+H]$^+$ 504.

EXAMPLE 138

3-Phenylpropionyl-Val-Pro-NH—CH$_2$-5-(3-am)-thioph

ESI-MS [M+H]$^+$ 484.

EXAMPLE 139

4-Phenylbutyryl-Val-Pro-NH—CH$_2$-5-(3-am)-thioph

ESI-MS [M+H]$^+$ 498.

EXAMPLE 140

2-(Benzylthio)-benzoyl-Val-Pro-NH—CH$_2$-5-(3-am)-thioph

ESI-MS [M+H]$^+$ 578.

EXAMPLE 141

2-(Benzylthio)-benzoyl-Ala-Pro-NH—CH$_2$-5-(3-am)-thioph

ESI-MS [M+H]$^+$ 550.

EXAMPLE 142

4-Benzoylbenzoyl-(D)-Ala-Pyr-NH—CH$_2$-5-(3-am)-thioph

ESI-MS [M+H]$^+$ 530.

EXAMPLE 143

4-Benzoylbenzoyl-(D)-Val-Pyr-NH—CH$_2$-5-(3-am)-thioph

ESI-MS [M+H]$^+$ 558.

EXAMPLE 144

4-Benzoylbenzoyl-Sar-Pyr-NH—CH$_2$-5-(3-am)-thioph

ESI-MS [M+H]$^+$ 530.

EXAMPLE 145

C$_6$H$_5$—C≡C—CO-Gly-Pyr-NH—CH$_2$-5-(3-am)-thioph

ESI-MS [M+H]$^+$ 436.

EXAMPLE 146

C$_6$H$_5$—C≡C—CO-Sar-Pyr-NH—CH$_2$-5-(3-am)-thioph

ESI-MS [M+H]$^+$ 450.

EXAMPLE 147

C$_6$H$_5$—C≡C—CO-(D)-Val-Pyr-NH—CH$_2$-5-(3-am)-thioph

ESI-MS [M+H]$^+$ 478.

EXAMPLE 148

C$_6$H$_5$—C≡C—CO-(D)-Ala-Pyr-NH—CH$_2$-5-(3-am)-thioph

ESI-MS [M+H]$^+$ 450.

EXAMPLE 149

4-Phenylbutyryl-Ala-Pro-NH—CH$_2$-5-(3-am)-thioph

ESI-MS [M+H]$^+$ 470.

EXAMPLE 150

MeOC(O)—(CH$_2$)$_5$—NHC(O)-Gly-Pro-NH—CH$_2$-5-(3-am)-thioph a) 0.044 mmol of resin from Example 64/section b), was suspended in a solution of 0.088 mmol of Fmoc-Gly-OH and 0.088 mmol of N,N,-diisopropylethylamine in 1.5 ml of dimethylformamide, 0.088 mmol of 2(1H-benzotriazol-1-yl-)1,1,3,3-tetramethyluronium tetrafluoroborate in 0.5 ml of dimethylformamide was added and stirring was carried out for 2 hours at room temperature. The resin was then filtered off with suction and was washed with dimethylformamide, CH$_2$Cl$_2$, methanol and CH$_2$Cl$_2$. The elimination of the Fmoc protective group was carried out with 2 ml of a solution of 10% of (1,8-diazabicyclo[5.4.0]undec-7-ene), 2% of piperidine and 88% of dimethylformamide (3 min). Thereafter, the resin was filtered off with suction and was washed with dimethylformamide, CH$_2$Cl$_2$, methanol and CH$_2$Cl$_2$.

b) The resin was suspended in 1 ml of CH$_2$Cl$_2$, and 0.088 mmol of methyl 6-isocyanatocaproate in 0.5 ml of CH$_2$Cl$_2$ was added. Stirring was carried out for 2 hours at room temperature, after which the solid was filtered off with suction and was washed with dimethylformamide, CH$_2$Cl$_2$, methanol and CH$_2$Cl$_2$. The elimination of the product from the carrier was carried out by treatment with 95:5 trifluoroacetic acid/water (1 h/room temperature). Yield: 18 mg. HPLC-MS: M+H$^+$ 481 (calculated: 481).

EXAMPLE 151

Phenylsulfonyl-Gly-Pro-NH—CH$_2$-5-(3-am)-thioph 0.01 mmol of resin from Example 150/section a) was suspended in 0.2 ml of 1:1 CH$_2$Cl$_2$/DMF, and 10.4 μl (0.06 mmol) of N,N,-diisopropylethylamine and then a solution of 2.5 μl (0.02 mmol) of benzenesulfonyl chloride in 200 μl of 1:1 CH$_2$Cl$_2$/DMF were added. Stirring was carried out for 2 hours at room temperature after which the solid was filtered off with suction and was washed with dimethylformamide, CH$_2$Cl$_2$, methanol and CH$_2$Cl$_2$. The elimination of the product from the carrier was carried out by treatment with 95:5 trifluoroacetic acid/water (1 h/room temperature).

Yield: 4.6 mg. HPLC-MS: M+H$^+$ 450 (calculated: 450).

EXAMPLE 152

3-[4-(2,5-Dichlorobenzyloxy)phenyl]propionyl(-D-Val-Pyr-NH—CH$_2$-5-(3-am)-thioph a) 0.2 mmol of 2-chlorotrityl 3-(4-hydroxyphenyl)propionic acid resin was suspended in a solution of 262 mg (1 mmol) of triphenylphosphine in 2 ml of THF. After the addition of a solution of 2 mmol of 2,5-dichlorobenzyl alcohol in 2 ml of THF, a solution of 408 μl (2 mmol) of diisopropyl azodicarboxylate in 200 μl of THF was added a little at a time in the course of 30 minutes while stirring. After incubation for 20 hours, the resin was filtered off with suction and washed with THF. Step a) was then repeated.

b) For working up, the resin was filtered off with suction and washed with THF and then with methanol and dichloromethane. The product was cleaved from the substrate with trifluoroethanol, acetic acid and dichloromethane (1:1:3) over 45 minutes. After evaporating down under reduced pressure, the residue was dissolved in acetic acid and freeze-dried. Yield: 31 mg.

Reference:

Krchnak, V., Flegelova, Z., Weichsel, A. S., and Lebl, M. (1995). Tetrahedron Lett., 36, 6193.

c) The acid component was coupled with TBTU on polymer-bound H-D-Val-Pyr-NH—$CH_2$-5-(3-am)-thioph, as described for Example 84. After elimination with TFA-water (95:5) (1 h at room temperature), the product was obtained (ESI-MS $[M+H]^+$ 656).

The following compounds were prepared analogously to the above examples:

153. 4-(2,5-Dichloro-benzyloxy)-benzoyl-D-Val-Pyr-NH—$CH_2$-5-(3-am)-thioph
     ESI-MS $[M + H]^+$ 628
154. 4-(2-Chloro-benzyloxy)-benzoyl-D-Val-Pyr-NH—$CH_2$-5-(3-am)-thioph
     ESI-MS $[M + H]^+$ 594
155. 3-[4-(2-Chloro-benzyloxy)-phenyl]-propionyl-D-Val-Pyr-NH—$CH_2$-5-(3-am)-thioph
     ESI-MS $[M + H]^+$ 622
156. 3-[4-(4-Nitro-benzyloxy)-phenyl]-propionyl-D-Val-Pyr-NH—$CH_2$-5-(3-am)-thioph
     ESI-MS $[M + H]^+$ 633
157. 3-[4-(4-Methoxycarbonyl-benzyloxy)-phenyl]-propionyl-D-Val-Pyr-NH—$CH_2$-5-(3-am)-thioph
     ESI-MS $[M + H]^+$ 646
158. 3-[4-(4-Fluoro-3-trifluoromethyl-benzyloxy)-phenyl]-propionyl-D-Val-Pyr-NH—$CH_2$-5-(3-am)-thioph
     ESI-MS $[M + H]^+$ 674
159. 3-[4-(2-Chloro-3-isopropyl-benzyloxy)-phenyl]-propionyl-D-Val-Pyr-NH—$CH_2$-5-(3-am)-thioph
     ESI-MS $[M + H]^+$ 664
160. 4-(2,5-Dichloro-benzyloxy)-phenylacetyl-D-Val-Pyr-NH—$CH_2$-5-(3-am)-thioph
     ESI-MS $[M + H]^+$ 642
161. 4-(4-Chloro-3-nitro-benzyloxy)-phenylacetyl-D-Val-Pyr-NH—$CH_2$-5-(3-am)-thioph
     ESI-MS $[M + H]^+$ 653
162. 4-(4-Nitro-benzyloxy)-phenylacetyl-D-Val-Pyr-NH—$CH_2$-5-(3-am)-thioph
     ESI-MS $[M + H]^+$ 619
163. 4-(4-Methoxycarbonyl-benzyloxy)-phenylacetyl-D-Val-Pyr-NH—$CH_2$-5-(3-am)-thioph
     ESI-MS $[M + H]^+$ 632
164. 4-(4-Fluoro-3-trifluoromethyl-benzyloxy)-phenylacetyl-D-Val-Pyr-NH—$CH_2$-5-(3-am)-thioph
     ESI-MS $[M + H]^+$ 660
165. 4-(2-Chloro-3-isopropyl-benzyloxy)-phenylacetyl-D-Val-Pyr-NH—$CH_2$-5-(3-am)-thioph
     ESI-MS $[M + H]^+$ 650
166. 4-(4-Chloro-benzyloxy)-phenylacetyl-D-Val-Pyr-NH—$CH_2$-5-(3-am)-thioph
     ESI-MS $[M + H]^+$ 608
167. 5-[4-(2, 5-Dichloro-benzyloxy)-phenyl]-5-oxo-pentanoyl-D-Val-Pyr-NH—$CH_2$-5-(3-am)-thioph
     ESI-MS $[M + H]^+$ 698
168. 5-[4-(4-Chloro-3-nitro-benzyloxy)-phenyl]-5-oxo-pentanoyl-D-Val-Pyr-NH—$CH_2$-5-(3-am)-thioph
     ESI-MS $[M + H]^+$ 709
169. 5-[4-(4-Nitro-benzyloxy)-phenyl]-5-oxo-pentanoyl-D-Val-Pyr-NH—$CH_2$-5-(3-am)-thioph
     ESI-MS $[M + H]^+$ 675
170. 5-[4-(4-Methoxycarbonyl-benzyloxy)-phenyl]-5-oxo-pentanoyl-D-Val-Pyr-NH—$CH_2$-5-(3-am)-thioph
     ESI-MS $[M + H]^+$ 688
171. 5-[4-(4-Fluoro-3-trifluoromethyl-benzyloxy)-phenyl]-5-oxo-pentanoyl-D-Val-Pyr-NH—$CH_2$-5-(3-am)-thioph
     ESI-MS $[M + H]^+$ 715
172. 5-[4-(2-Chloro-3-isopropyl-benzyloxy)-phenyl]-5-oxo-pentanoyl-D-Val-Pyr-NH—$CH_2$-5-(3-am)-thioph
     ESI-MS $[M + H]^+$ 706
173. 5-(4-Benzyloxy-phenyl )-5-oxo-pentanoyl-D-Val-Pyr-NH—$CH_2$-5-(3-am)-thioph
     ESI-MS $[M + H]^+$ 630

-continued 174. 5-[4-(4-Chloro-benzyloxy)-phenyl]-5-oxo-pentanoyl-D-Val-Pyr-NH—CH$_2$-5-(3-am)-thioph
ESI-MS [M + H]$^+$ 664
175. 2-[4-(2, 5-Dichloro-benzyloxy)-phenoxy]-propionyl-D-val-Pyr-NH—CH$_2$-5-(3-am)-thioph
ESI-MS [M + H]$^+$ 672
176. 2-[4-(4-Chloro-3-nitro-benzyloxy)-phenoxy]-propionyl-D-Val-Pyr-NH—CH$_2$-5-(3-am)-thioph
ESI-MS [M + H]$^+$ 683
177. 2-[4-(2-Chloro-benzyloxy)-phenoxy]-propionyl-D-Val-Pyr-NH—CH$_2$-5-(3-am)-thioph
ESI-MS [M + H]$^+$ 638
178. 2-[4-(4-Nitro-benzyloxy)-phenoxy]-propionyl-D-Val-Pyr-NH—CH$_2$-5-(3-am)-thioph
ESI-MS [M + H]$^+$ 649
179. 2-[4-(4-Methoxycarbonyl-benzyloxy)-phenoxy]-propionyl-D-Val-Pyr-NH—CH$_2$-5-(3-am)-thioph
ESI-MS [M + H]$^+$ 662
180. 2-[4-(4-Fluoro-3-trifluoromethyl-benzyloxy)-phenoxy]-propionyl-D-Val-Pyr-NH—CH$_2$-5-(3-am)-thioph
ESI-MS [M + H]$^+$ 690
181. 2-[4-(2-Chloro-3-isopropyl-benzyloxy)-phenoxy]-propionyl-D-Val-Pyr-NH—CH$_2$-5-(3-am)-thioph
ESI-MS [M + H]$^+$ 680
182. 2-(4-Benzyloxy-phenoxy)-propionyl-D-Val-Pyr-NH—CH$_2$-5-(3-am)-thioph
ESI-MS [M + H]$^+$ 604
183. 2-[4-(4-Chloro-benzyloxy)-phenoxy]-propionyl-D-Val-Pyr-NH—CH$_2$-5-(3-am)-thioph
ESI-MS [M + H]$^+$ 638
184. 2-[4-(2,5-Dichloro-benzyloxy)-phenyl]-3-methyl-butyryl-Pyr-NH—CH$_2$-5-(3-am)-thioph
ESI-MS [M + H]$^+$ 585
185. 2-[4-(2,5-Dichloro-benzyloxy)-phenyl]-3-methyl-butyryl-D-Val-Pyr-NH—CH$_2$-5-(3-am)-thioph
ESI-MS [M + H]$^+$ 684
186. 2-[4-(4-Chloro-3-nitro-benzyloxy)-phenyl]-3-methyl-butyryl-D-Val-Pyr-NH—CH$_2$-5-(3-am)-thioph
ESI-MS [M + H]$^+$ 695
187. 2-[4-(4-Nitro-benzyloxy)-phenyl]-3-methyl-butyryl-D-Val-Pyr-NH—CH$_2$-5-(3-am)-thioph
ESI-MS [M + H]$^+$ 661
188. 2-[4-(4-Methoxycarbonyl-benzyloxy)-phenyl]-3-methyl-butyryl-D-Val-Pyr-NH—CH$_2$-5-(3-am)-thioph
ESI-MS [M + H]$^+$ 674
189. 2-[4-(4-Fluoro-3-trifluoromethyl-benzyloxy)-phenyl]-3-methyl-butyryl-D-Val-Pyr-NH—CH$_2$-5-(3-am)-thioph
ESI-MS [M + H]$^+$ 702
190. 2-(4-Benzyloxy-phenyl)-3-methyl-butyryl-D-Val-Pyr-NH—CH$_2$-5-(3-am)-thioph
ESI-MS [M + H]$^+$ 616
191. 2-[4-(4-Chloro-benzyloxy)-phenyl]-3-methyl-butyryl-D-Val-Pyr-NH—CH$_2$-5-(3-am)-thioph
ESI-MS [M + H]$^+$ 650
192. 2-[4-(2, 5-Dichloro-benzyloxy)-phenoxy]-propionyl-Pyr-NH—CH$_2$-5-(3-am)-thioph
ESI-MS [M + H]$^+$ 573
193. 2-[4-(4-Nitro-benzyloxy)-phenoxy]-propionyl-Pyr-NH—CH$_2$-5-(3-am)-thioph
ESI-MS [M + H]$^+$ 550
194. 2-[4-(4-Methoxycarbonyl-benzyloxy)-phenoxy]-propionyl-Pyr-NH—CH$_2$-5-(3-am)-thioph
ESI-MS [M + H]$^+$ 563
195. 2-[4-(2-Chloro-3-isopropyl-benzyloxy)-phenoxy]-propionyl-Pyr-NH—CH$_2$-5-(3-am)-thioph
ESI-MS [M + H]$^+$ 581
196. 2-(4-Benzyloxy-phenoxy)-propionyl-Pyr-NH—CH$_2$-5-(3-am)-thioph
ESI-MS [M + H]$^+$ 505
197. 2-[4-(4-Chloro-benzyloxy)-phenoxy]-propionyl-Pyr-NH—CH$_2$-5-(3-am)-thioph
ESI-MS [M + H]$^+$ 539
198. 2-[4-(4-Chloro-3-nitro-benzyloxy)-phenoxy]-propionyl-Pyr-NH—CH$_2$-5-(3-am)-thioph
ESI-MS [M + H]$^+$ 596
199. 3-(2,5-Dichloro-benzyloxy)-benzoyl-D-Val-Pyr-NH—CH$_2$-5-(3-am)-thioph
ESI-MS [M + H]$^+$ 628

-continued 200. 3-(4-Chloro-3-nitro-benzyloxy)-benzoyl-D-Val-Pyr-NH—
CH$_2$-5-(3-am)-thioph
ESI-MS [M + H]$^+$ 639
201. 3-(2-Naphthylmethoxy)-benzoyl-D-Val-Pyr-NH—
CH$_2$-5-(3-am)-thioph
ESI-MS [M + H]$^+$ 610
202. 3-(4-Methyl-3-nitro-benzyloxy)-benzoyl-D-Val-Pyr-NH—
CH$_2$-5-(3-am)-thioph
ESI-MS [M + H]$^+$ 619
203. 3-(4-Nitro-benzyloxy)-benzoyl-D-Val-Pyr-NH—
CH$_2$-5-(3-am)-thioph
ESI-MS [M + H]$^+$ 605
204. 3-(4-Fluoro-3-trifluoromethyl)-benzyloxy)-benzoyl-D-Val-
Pyr-NH—CH$_2$-5-(3-am)-thioph
ESI-MS [M + H]$^+$ 646
205. 3-(2-Chloro-3-isopropyl-benzyloxy)-benzoyl-D-Val-Pyr-NH—
CH$_2$-5-(3-am)-thioph
ESI-MS [M + H]$^+$ 636
206. 3-Benzyloxybenzoyl-D-Val-Pyr-NH—CH$_2$-5-(3-am)-thioph
ESI-MS [M + H]$^+$ 560
207. 3-(4-Chlorobenzyloxy)-benzoyl-D-Val-Pyr-NH—
CH$_2$-5-(3-am)-thioph
ESI-MS [M + H]$^+$ 594
208. 3-(2,5-Dichloro-benzyloxy)-phenylacetyl-D-Val-Pyr-NH—
CH$_2$-5-(3-am)-thioph
ESI-MS [M + H]$^+$ 642
209. 3-(4-Chloro-3-nitro-benzyloxy)-phenylacetyl-D-Val-Pyr-NH—
CH$_2$-5-(3-am)-thioph
ESI-MS [M + H]$^+$ 653
210. 3-(4-Methyl-3-nitro-benzyloxy)-phenylacetyl-D-Val-Pyr-NH—
CH$_2$-5-(3-am)-thioph
ESI-MS [M + H]$^+$ 633
211. 3-(4-Nitro-benzyloxy)-phenylacetyl-D-Val-Pyr-NH—
CH$_2$-5-(3-am)-thioph
ESI-MS [M + H]$^+$ 619
212. 3-(4-Fluoro-3-trifluoromethyl-benzyloxy)-phenylacetyl-
D-Val-Pyr-NH—CH$_2$-5-(3-am)-thioph
ESI-MS [M + H]$^+$ 660
213. 3-(2-Chloro-3-isopropyl-benzyloxy)-phenylacetyl-D-Val-Pyr-
NH—CH$_2$-5-(3-am)-thioph
ESI-MS [M + H]$^+$ 650
214. 3-Benzyloxy-phenylacetyl-D-Val-Pyr-NH—CH$_2$-5-(3-am)-thioph
ESI-MS [M + H]$^+$ 574
215. 3-(4-Chloro-benzyloxy)-phenylacetyl-D-Val-Pyr-NH—
CH$_2$-5-(3-am)-thioph
ESI-MS [M + H]$^+$ 608
216. 3-[3-(2,5-Dichloro-benzyloxy)-phenyl]-acryloyl-D-Val-Pyr-
NH—CH$_2$-5-(3-am)-thioph
ESI-MS [M + H]$^+$ 654
217. 3-[3-(4-Chloro-3-nitro-benzyloxy)-phenyl]-acryloyl-D-Val-
Pyr-NH—CH$_2$-5-(3-am)-thioph
ESI-MS [M + H]$^+$ 665
218. 3-[3-(4-Methyl-3-nitro-benzyloxy)-phenyl]-acryloyl-D-Val-
Pyr-NH—CH$_2$-5-(3-am)-thioph
ESI-MS [M + H]$^+$ 645
219. 3-(3-(4-Nitro-benzyloxy)-phenyl]-acryloyl-D-Val-Pyr-NH—
CH$_2$-5-(3-am)-thioph
ESI-MS [M + H]$^+$ 631
220. 3-(3-(4-Fluoro-3-trifluoromethyl-benzyloxy)-phenyl]-
acryloyl-D-Val-Pyr-NH—CH$_2$-5-(3-am)-thioph
ESI-MS [M + H]$^+$ 672
221. 3-[3-(2-Chloro-3-isopropyl-benzyloxy)-phenyl]-acryloyl-
D-Val-Pyr-NH—CH$_2$-5-(3-am)-thioph
ESI-MS [M + H]$^+$ 662
222. 3-(3-Benzyloxy-phenyl)-acryloyl-D-Val-Pyr-NH—
CH$_2$-5-(3-am)-thioph
ESI-MS [M + H]$^+$ 586
223. 4-Phenylbenzenesulfonyl-β-Ala-Pyr-NH—CH$_2$-5-(3-am)-thioph
ESI-MS [M + H]$^+$ 538
224. 4-Phenylbenzenesulfonyl-D-Ala-Pyr-NH—CH$_2$-5-3-am)-thioph
ESI-MS [M + H]$^+$ 538
225. 4-Phenylbenzenesulfonyl-Sar-Pyr-NH—CH$_2$-5-(3-am)-thioph
ESI-MS [M + H]$^+$ 538
226. 4-Phenylbenzenesulfonyl-Gly-Pyr-NH—CH$_2$-5-(3-am)-thioph
ESI-MS [M + H]$^+$ 524
227. C$_6$H$_5$—C≡C—CO-β-Ala-Pyr-NH—CH$_2$-5-(3-am)-thioph
ESI-MS [M + H]$^+$ 450
228. C$_6$H$_5$—C≡-C—CO-D-Asp-Pyr-NH—CH$_2$-5-(3-am)-thioph
ESI-MS [M + H]$^+$ 494

-continued

229. C$_6$H$_5$—C≡C—CO-D-Arg-Pyr-NH—CH$_2$-5-(3-am)-thioph
ESI-MS [M + H]$^+$ 535
230. 4-Benzoylbenzoyl-β-Ala-Pyr-NH—CH$_2$-5-(3-am)-thioph
ESI-MS [M + H]$^+$ 530
231. 4-Benzoylbenzoyl-D-Ala-Pyr-NH—CH$_2$-5-(3-am)-thioph
ESI-MS [M + H]$^+$ 574
232. 4-Benzoylbenzoyl-D-Arg-Pyr-NH—CH$_2$-5-(3-am)-thioph
ESI-MS [M + H]$^+$ 615
233. C$_6$H$_5$—C≡C—CO-Gly-Pyr-NH—CH$_2$-5-(2-am)-thioph
ESI-MS [M + H]$^+$ 436
234. C$_6$H$_5$—C≡-C—CO-β-Ala-Pyr-NH—CH$_2$-5-(2-am)-thioph
ESI-MS [M + H]$^+$ 450
235. C$_6$H$_5$—C≡C—CO-D-Ala-Pyr-NH—CH$_2$- 5-(2-am)-thioph
ESI-MS [M + H]$^+$ 450
236. C$_6$H$_5$—C≡C—CO-D-Val-Pyr-NH—CH$_2$- 5-(2-am)-thioph
ESI-MS [M + H]$^+$ 478
237. 4-Benzoylbenzoyl-Gly-Pyr-NH—CH$_2$-5-(2-am)-thioph
ESI-MS [M + H]$^+$ 516
238. 4-Benzoylbenzoyl-β-Ala-Pyr-NH—CH$_2$-5-(2-am)-thioph
ESI-MS [M + H]$^+$ 530
239. 4-Benzoylbenzoyl-D-Ala-Pyr-NH—CH$_2$-5-(2-am)-thioph
ESI-MS [M + H]$^+$ 530
240. 4-Benzoylbenzoyl-D-Val-Pyr-NH—CH$_2$-5-(2-am)-thioph
ESI-MS [M + H]$^+$ 558
241. 4-Benzoylbenzoyl-D-Lys-Pyr-NH—CH$_2$-5-(3-am)-thioph
ESI-MS [M + H]$^+$ 587
242. 4-Benzoylbenzoyl-D-Orn-Pyr-NH—CH$_2$-5-(3-am)-thioph
ESI-MS [M + H]$^+$ 573
243. 4-Benzoylbenzoyl-D-His-Pyr-NH—CH$_2$-5-(3-am)-thioph
ESI-MS [M + H $^+$ 596
244. 4-Benzoylbenzoyl-D-Dab-Pyr-NH—CH$_2$-5-(3-am)-thioph
ESI-MS [M + H $^+$ 559
245. 4-Benzoylbenzoyl-D-Dap-Pyr-NH—CH$_2$-5-(3-am)-thioph
ESI-MS [M + H]$^+$ 545
246. 4-Benzoylbenzoyl-D-Arg-Pyr-NH—CH$_2$-5-(2-am)-thioph
ESI-MS [M + H]$^+$ 615
247. 4-Benzoylbenzoyl-D-Lys-Pyr-NH—CH$_2$-5-(2-am)-thioph
ESI-MS [M + H]$^+$ 587
248. 4-Benzoylbenzoyl-D-Orn-Pyr-NH—CH$_2$-5-(2-am)-thioph
ESI-MS [M + H]$^+$ 573
249. 4-Benzoylbenzoyl-D-His-Pyr-NH—CH$_2$-5-(2-am)-thioph
ESI-MS [M + H]$^+$ 596
250. 4-Benzoylbenzoyl-D-Dab-Pyr-NH—CH$_2$-5-(2-am)-thioph
ESI-MS [M + H]$^+$ 559
251. 4-Benzoylbenzoyl-D-Dap-Pyr-NH—CH$_2$-5-(2-am)-thioph
ESI-MS [M + H]$^+$ 545
252. 9,10,10-Trioxo-9,10-dihydro-101$^6$-thioxanthene-3-carbonyl-D-Ala-Pyr-NH—CH$_2$-5-(3-am)-thioph
ESI-MS [M + H]$^+$ 592
253. 9,10,10-Trioxo-9,10-dihydro-101$^6$-thioxanthene-3-carbonyl-Gly-Pyr-NH—CH$_2$-5-(3-am)-thioph
ESI-MS [M + H]$^+$ 578
254. 9,10,10-Trioxo-9,10-dihydro-101$^6$-thioxanthene-3-carbonyl-D-Val-Pyr-NH—CH$_2$-5-(3-am)-thioph
ESI-MS [M + H]$^+$ 620
255. 9,10-Dioxo-9,10-dihydro-anthracene-2-carbonyl-D-Ala-Pyr-NH—CH$_2$-5-(3-am)-thioph
ESI-MS [M + H]$^+$ 556
256. 9,10-Dioxo-9,10-dihydro-anthracene-2-carbonyl-Gly-Pyr-NH—CH$_2$-5-(3-am)-thioph
ESI-MS [M + H]$^+$ 542
257. 9,10-Dioxo-9,10-dihydro-anthracene-2-carbonyl-D-Val-Pyr-NH—CH$_2$-5-(3-am)-thioph
ESI-MS [M + H]$^+$ 584
258. 4-Benzoylbenzoyl-D-Ser-Pyr-NH—CH$_2$-5-(3-am)-thioph
ESI-MS [M + H]$^+$ 546
259. 4-Aminobenzoyl-D-Ala-Pyr-NH—CH$_2$-5-(3-am)-thioph
ESI-MS [M + H]$^+$ 441
260. 4-Methylaminobenzoyl-D-Ala-Pyr-NH—CH$_2$-5-(3-am)-thioph
ESI-MS [M + H]$^+$ 455
261. 4-Aminobenzoyl-D-Val-Pyr-NH—CH$_2$-5-(3-am)-thioph
ESI-MS [M + H]$^+$ 469
262. 4-Methylaminobenzoyl-D-Val-Pyr-NH—CH$_2$-5-(3-am)-thioph
ESI-MS [M + H]$^+$ 483
263. 3-Aminobenzoyl-D-Val-Pyr-NH—CH$_2$-5-(3-am)-thioph
ESI-MS [M + H]$^+$ 469
264. 4-(4-HOOC-Benzoyl)-benzoyl-D-Val-Pyr-NH—CH$_2$-5-(3-am)-thioph
ESI-MS [M + H]$^+$ 602

-continued 265. 4-(3-Phenyl-ureido)-benzoyl-D-Ala-Pyr-NH—
CH$_2$-5-(3-am)-thioph
ESI-MS [M + H]$^+$ 560
266. 3-(3-Benzyl-ureido)-benzoyl-D-Ala-Pyr-NH—
CH$_2$-5-(3-am)-thioph
ESI-MS [M + H]$^+$ 574
267. 3-(3-Phenyl-ureido)-benzoyl-D-Ala-Pyr-NH—
CH$_2$-5-(3-am)-thioph
ESI-MS [M + H]$^+$ 560
268. 4-(3-Phenyl-ureido)-benzoyl-Gly-Pyr-NH—CH$_2$-5-(3-am)-thioph
ESI-MS [M + H]$^+$ 546
269. 3-(3-Benzyl-ureido)-benzoyl-Gly-Pyr-NH—CH$_2$-5-(3-am)-thioph
ESI-MS [M + H]$^+$ 560
270. 3-(3-Phenyl-ureido)-benzoyl-Gly-Pyr-NH—CH$_2$-5-(3-am)-thioph
ESI-MS [M + H]$^+$ 546
271. 3-(3-Benzoyl-ureido)-benzoyl-Gly-Pyr-NH—CH$_2$-5-(3-am)-thioph
ESI-MS [M + H]$^+$ 574
272. 4-(3-Phenyl-ureido)-benzoyl-D-Val-Pyr-NH—
CH$_2$-5-(3-am)-thioph
ESI-MS [M + H]$^+$ 588
273. 3-(3-Phenyl-ureido)-benzoyl-D-Val-Pyr-NH—
CH$_2$-5-(3-am)-thioph
ESI-MS [M + H]$^+$ 588
274. 3-[3-(3-Acetyl-phenyl)-ureido]-benzoyl-D-Val-Pyr-NH—
CH$_2$-5-(3-am)-thioph
ESI-MS [M + H]$^+$ 630
275. 4-Benzyloxy-benzoyl-D-Ala-Pyr-NH—CH$_2$-5-(3-am)-thioph
ESI-MS [M + H]$^+$ 532
276. 4-(4-Chloro-benzyloxy)-benzoyl-D-Ala-Pyr-NH—
CH$_2$-5-(3-am)-thioph
ESI-MS [M + H]$^+$ 566
277. 3-(4-Benzyloxy-phenyl)-propionyl-D-Ala-Pyr-NH—
CH$_2$-5-(3-am)-thioph
ESI-MS [M + H]$^+$ 560
278. 3-[4-(4-Chloro-benzyloxy)-phenyl]-propionyl-D-Ala-Pyr-NH—
CH$_2$-5-(3-am)-thioph
ESI-MS [M + H]$^+$ 594
279. 4-Benzyloxy-benzoyl-Gly-Pyr-NH—CH$_2$-5-(3-am)-thioph
ESI-MS [M + H]$^+$ 518
280. 4-(4-Chloro-benzyloxy)-benzoyl-Gly-Pyr-NH—
CH$_2$-5-(3-am)-thioph
ESI-MS [M + H]$^+$ 552
281. 3-(4-Benzyloxy-phenyl)-propionyl-Gly-Pyr-NH—
CH$_2$-5-(3-am)-thioph
ESI-MS [M + H]$^+$ 546
282. 3-[4-(4-Chloro-benzyloxy)-phenyl]-propionyl-Gly-Pyr-NH—
CH$_2$-5-(3-am)-thioph
ESI-MS [M + H]$^+$ 580
283. 4-Benzyloxy-benzoyl-D-Val-Pyr-NH—CH$_2$-5-(3-am)-thioph
ESI-MS [M + H]$^+$ 560
284. 4-(4-Chloro-benzyloxy)-benzoyl-D-Val-Pyr-NH—
CH$_2$-5-(3-am)-thioph
ESI-MS [M + H]$^+$ 594
285. 3-(4-Benzyloxy-phenyl)-propionyl-D-Val-Pyr-NH—
CH$_2$-5-(3-am)-thioph
ESI-MS [M + H]$^+$ 588
286. 3-[4-(4-Chloro-benzyloxy)-phenyl]-propionyl-D-Val-Pyr-NH—
CH$_2$-5-(3-am)-thioph
ESI-MS [M + H]$^+$ 622
287. Phenyl-C≡C—CO-D-Chg-Pyr-NH—CH$_2$-5-(3-am)-thioph
MS [M + H]$^+$ 518
288. Phenyl-C≡C—CO-D-Abu-Pyr-NH—CH$_2$-5-(3-am)-thioph
MS [M + H]$^+$ 466
289. 4-Benzoylbenzoyl-D-Abu-Pro-NH—CH$_2$-5-(3-am)-thioph
MS [M + H]$^+$ 546
290. 4-Benzoylbenzoyl-D-Chg-Pyr-NH—CH$_2$-5-(3-am)-thioph
MS [M + H]$^+$ 598
291. HOOC-p-C$_6$H$_4$—CH$_2$-D-Pro-Pyr-NH—CH$_2$-5-(3-am)-thioph
MS [M + H]$^+$ 482
292. HOOC-p-C$_6$H$_4$—CH$_2$-D,L-Thienyl(3)glycine-Pyr-NH—
CH$_2$-5-(3-am)-thioph
MS [M + H]$^+$ 524
293. p-COOH-Benzyl-D-Abu-Pyr-NH—CH$_2$-5-(3-am)-thioph
MS [M + H]$^+$ 470
294. 4-Benzoyl-benzoyl-Acpc-Pyr-NH—CH$_2$-5-(3-am)-thioph
MS [M + H]$^+$ 570
295. 4-Benzoyl-benzoyl-N-Me-D-Val-Pyr-NH—CH$_2$-5-(3-am)-thioph
MS [M + H]$^+$ 572

-continued 296. p-Carboxy-benzyl-D-Ile-Pyr-NH—CH$_2$-5-(3-am)-thioph
MS [M + H]$^+$ 498
297. HOOC-p-C$_6$H$_4$—CH$_2$-D-Nva-Pyr-NH—CH$_2$-5-(3-am)-thioph
MS [M + H]$^+$ 484
298. HOOC-p-C$_6$H$_4$—CH$_2$-D-Leu-Pyr-NH—CH$_2$-5-(3-am)-thioph
MS [M + H]$^+$ 498
299. 4-Benzoylbenzoyl-D-Nva-Pyr-NH—CH$_2$-5-(3-am)-thioph
MS [M + H]$^+$ 558
300. p-Carboxy-benzyl-D-Ala-Pyr-NH—CH$_2$-5-(3-am)-thioph
MS [M + H]$^+$ 456
301. p-Carboxy-benzyl-Acpc-Pyr-NH—CH$_2$-5-(3-am)-thioph
MS [M + H]$^+$ 496
302. HOOC-p-C$_6$H$_4$—CH$_2$-N-Me-D-Val-Pyr-NH—CH$_2$-5-(3-am)-thioph
MS [M + H]$^+$ 498
303. p-Benzoyl-benzyl-D-Abu-Pyr-NH—CH$_2$-5-(3-am)-thioph
MS [M + H]$^+$ 530
304. 2-Carboxy-benzyl-D-Abu-Pyr-NH—CH$_2$-5-(3-am)-thioph
MS [M + H]$^+$ 470
305. (4-COOH—CH═CH)-Benzyl-D-Abu-Pyr-NH—CH$_2$-5-(3-am)-thioph
MS [M + H]$^+$ 496
306. 4-Carboxy-benzyl-D-Abu-3-Me-Pro-NH—CH$_2$-5-(3-am)-thioph
MS [M + H]$^+$ 486
307. HOOC-p-C$_6$H$_4$—CH$_2$-D-Abu-5-Me-Pro-NH—CH$_2$-5-(3-am)-thioph
MS [M + H]$^+$ 486
308. 2-(CarboxyMethoxy)-benzyl-D-Abu-Pyr-NH—CH$_2$-5-(3-am)-thioph
MS [M + H]$^+$ 500
309. Benzyl-D-Abu-Pyr-NH—CH$_2$-5-(3-am)-thioph
MS [M + H]$^+$ 426
310. 4-(CarboxyMethoxy)-benzyl-D-Abu-Pyr-NH—CH$_2$-5-(3-am)-thioph
MS [M + H]$^+$ 500
311. Benzenesulfonyl-D-Abu-Pyr-NH—CH$_2$-5-(3-am)-thioph
MS [M + H]$^+$ 490
312. HOOC-p-C$_6$H$_4$—CH$_2$-D-Abu-Pyr-NH—CH$_2$-5-(2-am)-thioph
MS [M + H]$^+$ 470
313. 4-Benzoyl-benzoyl-D-Pro-Pyr-NH—CH$_2$-5-(2-am)-thioph
MS [M + H]$^+$ 556
314. HOOC-p-C$_6$H$_4$—CH$_2$-D-Pro-Pyr-NH—CH$_2$-5-(2-am)-thioph
MS [M + H]$^+$ 482
315. HOOC-p-C$_6$H$_4$—CH$_2$-D-Pip-Pyr-NH—CH$_2$-5-(3-am)-thioph
MS [M + H]$^+$ 473
316. HOOC-p-C$_6$H$_4$—CH$_2$-D-Abu-Pro-NH—CH$_2$-5-(3-am)-thioph
MS [M + H]$^+$ 472
317. 4-Carboxy-benzyl-D-allo-Ile-Pyr-NH—CH$_2$-5-(3-am)-thioph
MS [M + H]$^+$ 498
318. 2-HOOC-thienyl(5)-CH$_2$-D-Abu-Pyr-NH—CH$_2$-5-(3-am)-thioph
MS [M + H]$^+$ 476
319. 2-COOH-furanyl(5)-CO-D-Abu-Pyr-NH—CH$_2$-5-(3-am)-thioph
MS [M + H]$^+$ 460
320. HOOC-p-C$_6$H$_4$—CH$_2$-D-Nle-Pyr-NH—CH$_2$-5-(3-am)-thioph
MS [M + H]$^+$ 498
321. Benzoyl-D-Abu-Pyr-NH—CH$_2$-5-(3-am)-thioph
MS [M + H]$^+$ 440
322. 4-MeSO$_2$—C$_6$H$_4$—CH$_2$-D-Abu-Pyr-NH—CH$_2$-5-(3-am)-thioph
MS [M + H]$^+$ 504
323. Phenylsulfonyl-D-Chg-Pyr-NH—CH$_2$-5-(3-am)-thioph
MS [M + H]$^+$ 530
324. Phenylacetyl-D-Abu-Pyr-NH—CH$_2$-5-(3-am)-thioph
MS [M + H]$^+$ 454
325. Phenylsulfonyl-D-Abu-Pyr-NH—CH$_2$-5-(3-am)-thioph
MS [M + H]$^+$ 476
326. 1-Naphthyl-CH$_2$CO-D-Abu-Pyr-NH—CH$_2$-5-(3-am)-thioph
MS [M + H]$^+$ 504
327. 2-Naphthyl-CH$_2$CO-D-Abu-Pyr-NH—CH$_2$-5-(3-am)-thioph
MS [M + H]$^+$ 504
328. 1-Indanyl-CO-D-Abu-Pyr-NH—CH$_2$-5-(3-am)-thioph
MS [M + H]$^+$ 480
329. Benzhydryl-Co-D-Abu-Pyr-NH—CH$_2$-5-(3-am)-thioph
MS [M + H]$^+$ 530
330. 2-Cl-Phenyl-CH$_2$CO-D-Abu-Pyr-NH—CH$_2$-5-(3-am)-thioph
MS [M + H]$^+$ 488
331. 2,6-Dichlorophenyl-CH$_2$CO-D-Abu-Pyr-NH—CH$_2$-5-(3-am)-thioph
MS [M + H]$^+$ 524
332. 2-Methyl-phenyl-CH$_2$CO-D-Abu-Pyr-NH—CH$_2$-5-(3-am)-thioph
MS [M + H]$^+$ 468
333. Biphenyl-CH$_2$CO-D-Abu-Pyr-NH—CH$_2$-5-(3-am)-thioph
MS [M + H]$^+$ 530
334. p-Methyl-phenyl-CH$_2$CO-D-Abu-Pyr-NH—CH$_2$-5-(3-am)-thioph
MS [M + H]$^+$ 468

-continued 335. 3-Methyl-phenyl-CH$_2$CO-D-Abu-Pyr-NH—CH$_2$-5-(3-aIn)-thioph
MS [M + H]$^+$ 468
336. 2-Nitro-phenyl-CH$_2$CO-D-Abu-Pyr-NH—CH$_2$-5-(3-am)-thioph
MS [M + H]$^+$ 499
337. 1-Fluorenyl-CH$_2$CO-D-Abu-Pyr-NH—CH$_2$-5-(3-am)-thioph
MS [M + H]$^+$ 542
338. 2-Br-Phenyl-CH$_2$CO-D-Abu-Pyr-NH—CH$_2$-5-(3-am)-thioph
MS [M + H]$^+$ 534
339. 2-Fluoro-phenyl-CH$_2$CO-D-Abu-Pyr-NH—CH$_2$-5-(3-am)-thioph
MS [M + H]$^+$ 472
340. 2-Phenyl-isobutyryl-D-Abu-Pyr-NH—CH$_2$-5-(3-am)-thioph
MS [M + H]$^+$ 482
341. p-Benzyloxy-benzoyl-D-val-Pyr-NH—CH$_2$-5-(3-am)-thioph
MS [M + H]$^+$ 560
342. 2,6-Dichlorophenyl-CH$_2$CO-D-Abu-Pyr-NH—CH$_2$-5-(2-am)-thioph
MS [M + H]$^+$ 524
343. 2,6-Dichlorophenyl-CH$_2$CO-D-Val-Pyr-NH—CH$_2$-5-(3-am)-thioph
MS [M + H]$^+$ 538
344. 2,6-Dichloro-phenyl-CH$_2$CO-D-Chg-Pyr-NH—CH$_2$-5-(3-am)-thioph
MS [M + H]$^+$ 578
345. 1-Naphthyl-CO-D-Abu-Pyr-NH—CH$_2$-5-(3-am)-thioph
MS [M + H]$^+$ 490
346. Cyclopentyl-CH$_2$CO-D-Abu-Pyr-NH—CH$_2$-5-(3-am)-thioph
MS [M + H]$^+$ 446
347. 1-Adamantyl-CO-D-Abu-Pyr-NH—CH$_2$-5-(3-am)-thioph
MS [M + H]$^+$ 498
348. Cyclohexyl-CH$_2$CO-D-Abu-Pyr-NH—CH$_2$-5-(3-am)-thioph
MS [M + H]$^+$ 460
349. 2-Thienyl-CH$_2$CO-D-Abu-Pyr-NH—CH$_2$-5-(3-am)-thioph
MS [M + H]$^+$ 460
350. 2-Naphthyl-Co-D-Abu-Pyr-NH—CH$_2$-5-(3-am)-thioph
MS [M + H]$^+$ 490
351. 1-Naphthyl-CH$_2$-D-Abu-Pyr-NH—CH$_2$-5-(3-am)-thioph
MS [M + H]$^+$ 476
352. 2-Naphthyl-CH$_2$-D-Abu-Pyr-NH—CH$_2$-5-(3-am)-thioph
MS [M + H]$^+$ 476
353. Benzyloxycarbonyl-D-Abu-Pyr-NH—CH$_2$-5-(3-am)-thioph
MS [M + H]$^+$ 470
354. 4-MeOOC-Benzyl-D-Val-Pyr-NH—CH$_2$-5-(3-ham)-thioph
MS [M + H]$^+$ 514
355. 2-Phenyl-2-hydroxy-acetyl-D-Abu-Pyr-NH—CH$_2$-5-(3-am)-thioph
MS [M + H]$^+$ 470
356. 2-Phenyl-2-methoxy-acetyl-D-Abu-Pyr-NH—CH$_2$-5-(3-am)-thioph
MS [M + H]$^+$ 484
357. 2-(p-Isobutyl-phenyl)propionyl-D-Abu-Pyr-NH—
CH$_2$-5-(3-am)-thioph
MS [M + H]$^+$ 524
358. (S)-2-Phenyl-propionyl-D-Abu-Pyr-NH—CH$_2$-5-(3-am)-thioph
MS [M + H]$^+$ 468
359. (R)-2-Phenyl-propionyl-D-Abu-Pyr-NH—CH$_2$-5-(3-am)-thioph
MS [M + H]$^+$ 468
360. 3-Pyridyl-CH$_2$CO-D-Abu-Pyr-NH—CH$_2$-5-(3-am)-thioph
MS [M + H]$^+$ 455
361. Phenyl-O—CH$_2$CO-D-Abu-Pyr-NH—CH$_2$-5-(3-am)-thioph
MS [M + H]$^+$ 470
362. 1-Adamantyl-CH$_2$CO-D-Abu-Pyr-NH—CH$_2$-5-(3-am)-thioph
MS [M + H]$^+$ 512
363. 2,4,6-Trimethylphenyl-CH$_2$CO-D-Abu-Pyr-NH—
CH$_2$-5-(3-am)-thioph
MS [M + H]$^+$ 496
364. p-Pentoxy-benzoyl-D-val-Pyr-NH—CH$_2$-5-(3-am)-thioph
MS [M + H]$^+$ 540
365. p-Benzyloxy-phenyl-CH$_2$CO-D-Val-Pyr-NH—CH$_2$-5-(3-am)-thioph
MS [M + H]$^+$ 574
366. 1-Indanyl-CO-D-Val-Pyr-NH—CH$_2$-5-(3-am)-thioph
MS [M + H]$^+$ 494
367. 2,6-Dichlorophenyl-CH$_2$CO-D-Val-Pyr-NH—CH$_2$-5-(2-am)-thioph
MS [M + H]$^+$ 538
368. 2-Benzothienyl-CO-D-Abu-Pyr-NH—CH$_2$-5-(3-am)-thioph
MS [M + H]$^+$ 496
369. HOOC-p-C$_6$H$_4$—CH$_2$-D-Nva-Pyr-NH-3-(6-am)-pico
MS [M + H]$^+$ 465
370. 2-Tetrahydronaphthyl-CO-D-Abu-Pyr-NH—CH$_2$-5-(3-am)-thioph
MS [M + H]$^+$ 494
371. 1-Indanyl-CO-D-Ile-Pyr-NH—CH$_2$-5-(3-am)-thioph
MS [M + H]$^+$ 508
372. 1-Benzocyclobutane-Co-D-Abu-Pyr-NH—CH$_2$-5-(3-am)-thioph
MS [M + H]$^+$ 466

-continued 373. 1-Benzocyclobutane-CO-D-Val-Pyr-NH—CH$_2$-5-(3-am)-thioph
MS [M + H]$^+$ 480
374. 2,4,6-Trimethylphenyl-CH$_2$CO-D-Val-Pyr-NH—
CH$_2$-5-(3-am)-thioph
MS [M + H]$^+$ 510
375. 1-Indanyl-CO-D-Chg-Pyr-NH—CH$_2$-5-(3-am)-thioph
MS [M + H]$^+$ 534
376. 1-Indanyl-CO-D-Leu-Pyr-NH—CH$_2$-5-(3-am)-thioph
MS [M + H]$^+$ 508
377. 1-Indanyl-CO-D-Phe-Pyr-NH—CH$_2$-5-(3-am)-thioph
MS [M + H]$^+$ 542
378. 1-Anthracenyl-CO-D-Abu-Pyr-NH—CH$_2$-5-(3-am)-thioph
MS [M + H]$^+$ 540
379. Benzenesulfonyl-D-Cha-Pyr-NH—CH$_2$-5-(3-am)-thioph
MS [M + H]$^+$ 558
380. p-Hexyloxy-benzoyl-D-Val-Pyr-NH—CH$_2$-5-(3-am)-thioph
MS [M + H]$^+$ 554
381. 2-(p-(Phenoxy)phenyl)-acetyl-D-val-Pyr-NH—
CH$_2$-5-(3-am)-thioph
MS [M + H]$^+$ 560
382. (R)-1-Indanyl-CO-D-Abu-Pyr-NH—CH$_2$-5-(3-am)-thioph
MS [M + H]$^+$ 480
383. 1-Indanyl-CO-D-Val-Pyr-NH—CH$_2$-5-(2-am)-thioph
MS [M + H]$^+$ 494
384. (S)-1-Indanyl-CO-D-Val-Pyr-NH—CH$_2$-5-(3-am)-thioph
MS [M + H]$^+$ 494
385. Butylsulfonyl-D-Phe-Pyr-NH—CH$_2$-5-(3-am)-thioph
MS [M + H]$^+$ 518
386. (3,5-Bistrifluoromethyl)phenyl(1)-CH$_2$CO-D-Val-Pyr-NH—
CH$_2$-5-(3-am)-thioph
MS [M + H]$^+$ 604
387. (3-Trifluoromethyl)phenyl(1)-CH$_2$CO-D-Val-Pyr-NH—
CH$_2$-5-(3-am)-thioph
MS [M + H]$^+$ 536
388. 1-Phenyl-cyclopropyl(1)-CO-D-Val-Pyr-NH—CH$_2$-5-(3-am)-thioph
MS [M + H]$^+$ 494
389. (S)-1-Indanyl-CO-D-Val-Pyr-NH—CH$_2$-5-(3-am)-thioph
MS [M + H]$^+$ 494
390. p-Isopropyl-phenyl-CH$_2$CO-D-Val-Pyr-NH—CH$_2$-5-(3-am)-thioph
MS [M + H]$^+$ 510
391. p-Butoxyphenyl-CH$_2$CO-D-Val-Pyr-NH—CH$_2$-5-(3-am)-thioph
MS [M + H]$^+$ 540
392. Phenyl-CH(iPr)-Co-D-Val-Pyr-NH—CH$_2$-5-(3-am)-thioph
MS [M + H]$^+$ 510
393. 1-(4-Cl-Phenyl)-cyclobut-1-ylCO-D-Val-Pyr-NH—
CH$_2$-5-(3-am)-thioph
MS [M + H]$^+$ 542
394. 2-Carboxy-thien-5-yl-CH$_2$-D-Val-Pyr-NH—CH$_2$-5-(3-am)-thioph
MS [M + H]$^+$ 490
395. 1-Phenyl-cyclopent-1-yl-CO-D-Val-Pyr-NH—CH$_2$-5-(3-am)-thioph
MS [M + H]$^+$ 522
396. 1-Adamantyl-CH$_2$CO-D-Val-Pyr-NH—CH$_2$-5-(3-am)-thioph
MS [M + H]$^+$ 526
397 1-Fluorenyl-CO-D-Val-Pyr-NH—CH$_2$-5-(3-am)-thioph
MS [M + H]$^+$ 542
398. Benzhydryl-CO-D-Val-Pyr-NH—CH$_2$-5-(3-am)-thioph
MS [M + H]$^+$ 544
399. (R)-1-Indanyl-CO-D-Val-Pyr-NH—CH$_2$-5-(2-am)-thioph
MS [M + H]$^+$ 494
400. (S)-1-Indanyl-CO-D-Val-Pyr-NH—CH$_2$-5-(2-am)-thioph
MS [M + H]$^+$ 494
401. p-COOH-Benzoyl-D-Val-Pyr-NH—CH$_2$-5-(3-am)-thioph
MS [M + H]$^+$ 498
402. 2-Carboxy-5-furyl-CH$_2$-D-Val-Pyr-NH—CH$_2$-5-(3-am)-thioph
MS [M + H]$^+$ 474
403. p-COOMe-Benzoyl-D-Val-Pyr-NH—CH$_2$-5-(3-am)-thioph
MS [M + H]$^+$ 512
404. m-COOH-Phenyl-SO$_2$-D-Chg-Pyr-NH—CH$_2$-5-(3-am)-thioph
MS [M + H]$^+$ 574
405. p-COOH-Phenyl-SO$_2$-D-Chg-Pyr-NH—CH$_2$-5-(3-am)-thioph
MS [M + H]$^+$ 574

The $C_{1S}$ and $C_{1R}$ inhibition values for some novel compounds are shown in the table below.

TABLE

| Example No. | $C_{1S}$ IC$_{50}$ [μmol/l] according to Example B | $C_{1R}$ IC$_{50}$ [μmol/l] according to Example A |
|---|---|---|
| 29 | 0.6 | 0.9 |
| 22 | 0.6 | 0.9 |
| 23 | 0.8 | 0.5 |
| 24 | 0.8 | >100 |
| 42 | 1 | 0.7 |
| 49 | 1 | 1 |
| 21 | 1 | 4 |
| 20 | 2 | 0.6 |
| 35 | 2 | 2 |
| 41 | 2 | 2 |
| 15 | 2 | 3 |
| 26 | 2 | >100 |
| 50 | 3 | 20 |
| 4 | 3 | 30 |
| 44 | 3 | 40 |
| 51 | 3 | 40 |
| 52 | 4 | 10 |
| 17 | 4 | 40 |
| 7 | 4 | >100 |
| 38 | 5 | 10 |
| 30 | 5 | >100 |
| 6 | 6 | |
| 25 | 6 | 50 |
| 1 | 6 | >100 |
| 8 | 6 | >100 |
| 18 | 7 | 10 |
| 54 | 8 | |
| 5 | 10 | |
| 39 | 10 | 2 |
| 31 | 10 | 3 |
| 43 | 10 | 6 |
| 13 | 10 | 30 |
| 45 | 20 | 6 |
| 53 | 20 | 8 |
| 27 | 20 | 10 |
| 46 | 20 | 40 |
| 2 | 20 | 50 |
| 34 | 20 | 70 |
| 9 | 20 | >100 |
| 28 | 20 | >100 |
| 16 | 20 | >100 |
| 10 | 20 | >100 |
| 14 | 20 | >100 |
| 32 | 30 | 10 |
| 19 | 30 | 30 |
| 48 | 30 | 50 |
| 3 | 30 | >100 |
| 11 | 30 | >100 |
| 12 | 30 | >100 |
| 35 | 40 | 20 |
| 33 | 40 | 40 |
| 47 | 50 | 10 |

The compound of Example 367 is a very particularly preferred and active complement inhibitor.

We claim:

1. A compound of the formula I

or a tautomer, a pharmacologically tolerable salt or a prodrug thereof, where:

A is

H, $C_{1-6}$-alkyl, $C_{1-6}$-alkyl-SO$_2$, $R^{A1}$OCO, $R^{A2}R^{A3}$NCO; $R^{A4}$OCONR$^{A2}$, $R^{A4}$CONR$^{A2}$, $R^{A1}$O, $R^{A2}R^{A3}$N,  phenoxy, $R^{A2}R^{A3}$N—SO$_2$, Cl, Br, F, NO$_2$, $R^{A1}$—N(OH)—CO— or $R^{A1}R^{A2}$NCONR$^{A3}$, where $R^{A1}$ is H, $C_{1-12}$-alkyl, $C_{3-8}$-cycloalkyl, $C_{3-8}$-cycloalkyl-$C_{1-3}$-alkyl or $C_{1-3}$-alkylaryl;

$R^{A2}$ is H—, $C_{1-6}$-alkyl, $C_{0-3}$-alkylaryl or $C_{0-3}$-alkylheteroaryl; $R^{A3}$ is H, $C_{1-6}$-alkyl or $C_{0-3}$-alkylaryl;

$R^{A4}$ is $C_{1-6}$-alkyl or $C_{1-3}$-alkylaryl;

where each aryl is optionally substituted with up to 2 identical or different radicals selected from the group consisting of F, Cl, Br, CF$_3$, CH$_3$, OCH$_3$ and NO$_2$,

123

B is —(CH$_2$)$_{l^B}$—L$^B$—(CH$_2$)$_{m^B}$—
  l$^B$ is 0, 1, 2 or 3;
  m$^B$ is 0, 1 or 2;
  L$^B$ is

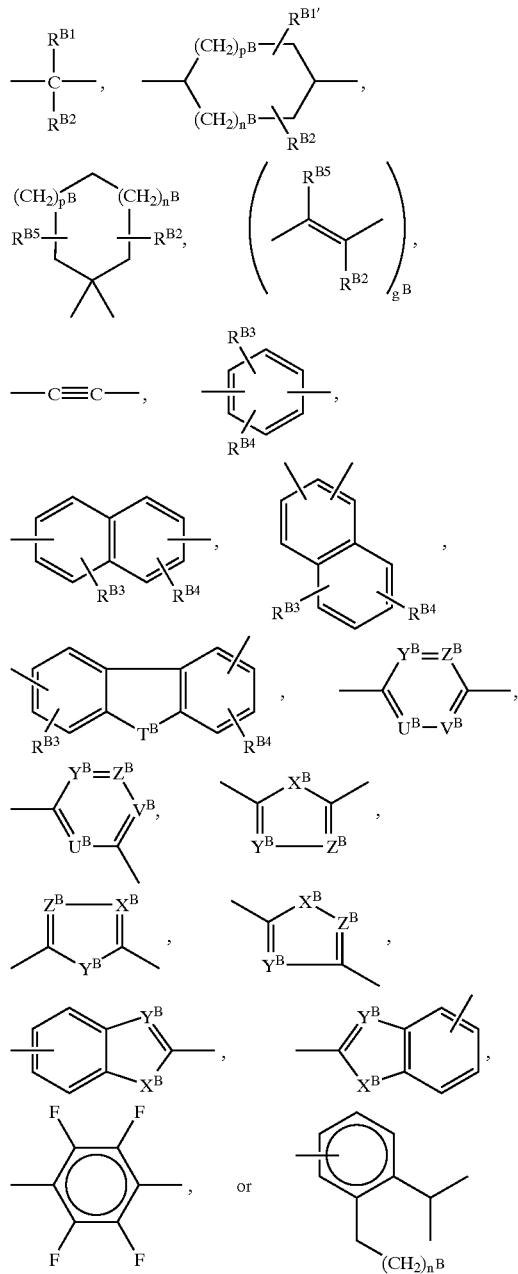

where a phenyl ring is optionally fused to the above-mentioned ring systems, which phenyl ring is optionally substituted with up to 2 identical or different radicals selected from the group consisting of CH$_3$, CF$_3$, Br, Cl and F, or is optionally substituted by R$^8$OOC—;
where
  R$^8$ is H or C$_{1-3}$-alkyl;
  n$^B$ is 0, 1 or 2;
  p$^B$ is 0, 1 or 2;
  q$^B$ is 1, 2 or 3;
  R$^{B1}$ is C$_{0-3}$-alkylaryl, C$_{0-3}$-alkylheteroaryl, C$_{0-3}$-alkyl-C$_{3-8}$-cycloalkyl or OCH$_3$;
  R$^{B2}$ is H, C$_{1-6}$-alkyl, C$_{0-3}$-alkylaryl or C$_{0-3}$-alkylheteroaryl;

124

R$^{B3}$ is H, C$_{1-6}$-alkyl, C$_{0-3}$-alkylaryl or C$_{0-3}$-alkylheteroaryl R$^{B5}$OCO, R$^{B6}$—O, F, Cl, Br, NO$_2$ or CF$_3$;
R$^{B4}$ is H, C$_{1-6}$-alkyl, R$^{B6}$—O, Cl, Br, F or CF$_3$;
R$^{B5}$ is H, C$_{1-6}$-alkyl, C$_{0-3}$-alkylaryl or C$_{0-3}$-alkylheteroaryl;
R$^{B6}$ is H or C$_{1-6}$-alkyl;
T$^B$ is CH$_2$, O, S, NH or N—C$_{1-6}$-alkyl;
R$^{B1'}$ is H, C$_{1-6}$-alkyl, C$_{0-3}$-alkylaryl, C$_{0-3}$-alkylheteroaryl or C$_{0-3}$-alkyl-C$_{3-8}$-cycloalkyl;
R$^{B1}$ and R$^{B2}$ are optionally bonded together;
X$^B$ is O, S, NH or N—C$_{1-6}$-alkyl;
Y$^B$ is

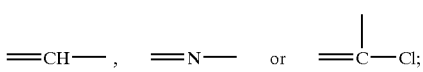

Z$^B$ is CH—,

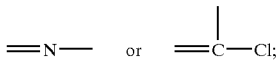

U$^B$ is =CH— or =N—;
V$^B$ is =CH— or =N—;

or

B is
  —(CH$_2$)$_{l^B}$—L$^B$—M$^B$—L$^B$—(CH$_2$)$_{m^B}$, where
  l$^B$ and m$^B$ have the abovementioned meanings and the two groups L$^B$, independently of one another, are the radicals stated under L$^B$;
  M$^B$ is a single bond, O, S, CH$_2$, CH$_2$—CH$_2$, CH$_2$—O, O—CH$_2$, CH$_2$—S, S—CH$_2$, CO, SO$_2$, CH=CH or C≡C;

or

B is -1-adamantyl-CH$_2$—, -2-adamantyl-CH$_2$—, -1-adamantyl-, -2-adamantyl-,

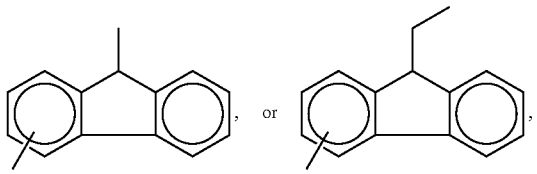

or

B is

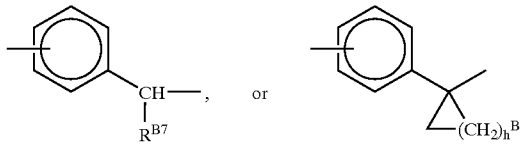

where
  $h^B$ is 1, 2, 3 or 4; and
  $R^{B7}$ is $C_{1-6}$-alkyl or $C_{3-8}$-cycloalkyl;

or

B is

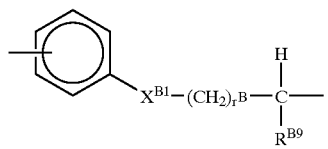

where
  $X^{B1}$ is a bond, O, S, or

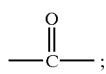

$r^B$ is 0, 1, 2 or 3;
  $R^{B9}$ is H or $C_{1-3}$-alkyl;

or

A—B together are

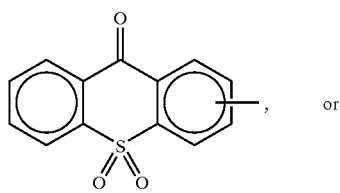, or

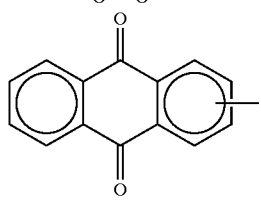

D is a single bond, CO, OCO, $NR^{D1}$—CO, $SO_2$ or $NR^{D1}SO_2$,
where
  $R^{D1}$ is H, $C_{1-4}$-alkyl or $C_{0-3}$-alkylaryl;
E is a single bond or

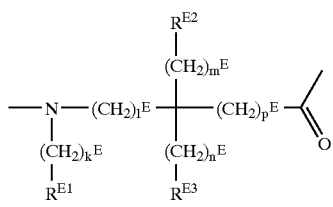

where
  $k^E$ is 0, 1 or 2;
  $l^E$ is 0, 1 or 2;
  $m^E$ is 0, 1, 2 or 3;
  $n^E$ is 0, 1 or 2;
  $p^E$ is 0, 1 or 2;
  $R^{E1}$ is H, $C_{1-6}$-alkyl, $C_{3-8}$-cycloalkyl, aryl, pyridyl, thienyl or $C_{3-8}$-cycloalkyl having a fused-on phenyl ring, the abovementioned radicals being optionally substituted with up to three identical or different substituents selected from the group consisting of $C_{1-6}$-alkyl, O—$C_{1-6}$-alkyl, F, Cl and Br;
  or
  $R^{E1}$ is $R^{E4}OCO$—$CH_2$;
  $R^{E2}$ is H, $C_{1-6}$-alkyl, $C_{3-8}$-cycloalkyl, phenyl, pyridyl, furyl, thienyl, imidazolyl, tetrahydropyranyl or tetrahydrothiopyranyl, the abovementioned radicals being optionally substituted with up to three identical or different substituents selected from the group consisting of $C_{1-6}$-alkyl, O—$C_{1-6}$-alkyl, F, Cl and Br, or is $CH(CH_3)OH$ or $CH(CF_3)_2$;
  $R^{E3}$ is H, $C_{1-6}$-alkyl, $C_{3-8}$-cycloalkyl or phenyl, the abovementioned radicals being optionally substituted with up to three identical or different substituents selected from the group consisting of $C_{1-6}$-alkyl, O—$C_{1-6}$-alkyl, F, Cl and Br;
  $R^{E4}$ is H, $C_{1-12}$-alkyl or $C_{1-3}$-alkylaryl;
  $R^{E2}$ and $R^{B1}$ together optionally form a bridge having $(CH_2)_{0-4}$, CH=CH, $CH_2$-CH=CH or CH=CH—$CH_2$ groups
  the groups stated under $R^{E1}$ and $R^{E3}$ are optionally linked to one another via a bond; the groups stated under $R^{E2}$ and $R^{E3}$ are also optionally linked to one another via a bond;
  or
  $R^{E2}$ is $COR^{E5}$;
  $R^{E5}$ is OH, O—$C_{1-6}$-alkyl or O—$C_{1-3}$-alkylaryl;

or

E is D-Asp, D-Glu, D-Lys, D-Orn, D-His, D-Dab, D-Dap or D-Arg;
G is

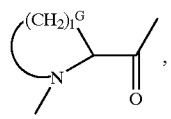

where $l^G$ is 2, 3, 4 or 5, and
where a $CH_2$ group of the ring is optionally replaced by O, S, NH, $CH(C_{1-3}$-alkyl), CHF or $CF_2$;

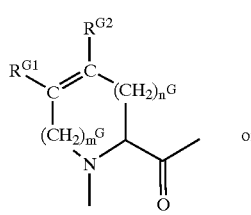 or 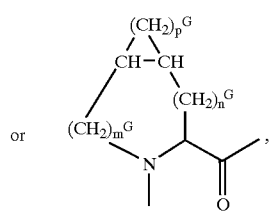, where
  $m^G$ is 0, 1 or 2;
  $n^G$ is 0, 1 or 2;

$p^G$ is 1 or 3;
$R^{G1}$ and $R^{G2}$ are each H;
or
$R^{G1}$ and $R^{G2}$ together form a CH=CH—CH=CH chain;
or
G is

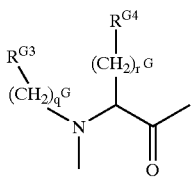

where
$q^G$ is 0, 1 or 2;
$r^G$ is 0, 1 or 2;
$R^{G3}$ is H, $C_1$–$C_6$-alkyl or $C_{3-8}$-cycloalkyl;
$R^{G4}$ is H, $C_1$–$C_6$-alkyl, $C_{3-8}$-cycloalkyl or phenyl;
K is
NH—$(CH_2)_{n^K}$—$Q^K$ where
$n^K$ is 1 or 2;
$Q^K$ is

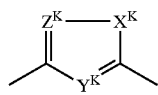 or 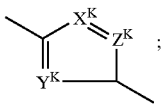;

$X^K$ is O, S, NH or N—$C_{1-6}$-alkyl;
$Y^K$ is =CH—,

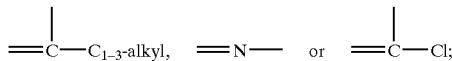

$Z^K$ is

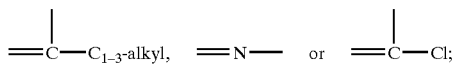

L is

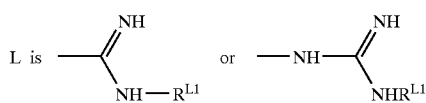

where
$R^{L1}$ is H, OH, O—$C_{1-6}$-alkyl, O—$(CH_2)_{0-3}$-phenyl, CO—$C_{1-6}$-alkyl, $CO_2$—$C_{1-6}$-alkyl or $CO_2$—$C_{1-3}$-alkylaryl.

2. The compound claimed in claim 1, or a tautomer, a pharmacologically tolearable salt, or a prodrug thereof, where:
A is
H, $C_{1-6}$-alkyl, $C_{1-6}$-alkyl-$SO_2$, $R^{A1}OCO$, $R^{A2}R^{A3}NCO$, $R^{A4}OCONR^{A2}$, $R^{A4}CONR^{A2}$, $R^{A1}O$, phenoxy, $R^{A2}R^{A3}N$, HO—$SO_2$, $R^{A2}R^{A3}N$—$SO_2$, Cl, Br, F, tetrazolyl, $H_2O_3P$, $NO_2$, $R^{A1}$—N(OH)—CO or $R^{A1}R^{A2}NCONR^{A3}$,
where
$R^{A1}$ is H, $C_{1-12}$-alkyl, $C_{3-8}$-cycloalkyl, $C_{1-3}$-alkyl-$C_{3-8}$-cycloalkyl or $C_{1-3}$-alkylaryl;

$R^{A2}$ is H, $C_{1-6}$-alkyl, $C_{0-3}$-alkylaryl or $C_{0-3}$-alkylheteroaryl; $R^{A3}$ is H, $C_{1-6}$-alkyl or $C_{0-3}$-alkylaryl;
$R^{A4}$ is $C_{1-6}$-alkyl or $C_{1-3}$-alkylaryl;
where each aryl is optionally substituted with up to 2 identical or different radicals selected from the group consisting of F, Cl, Br, $OCH_3$, $CH_3$, $CF_3$ and $NO_2$;

B is
—$(CH_2)_{l^B}$—$L^B$—$(CH_2)_{m^B}$— where
$l^B$ is 0, 1, 2 or 3;
$m^B$ is 0, 1, 2 or 3;

$L^B$ is

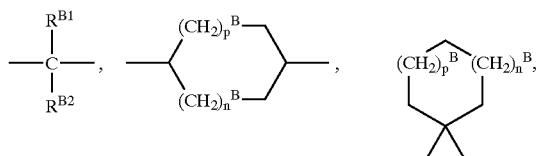

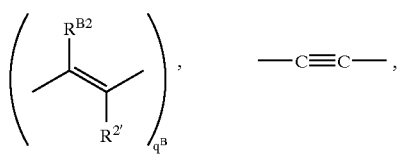

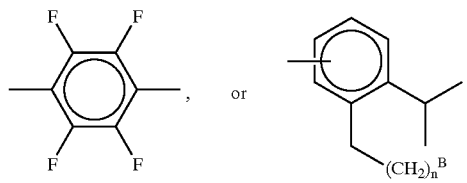

where a phenyl ring is optionally fused to the above-mentioned ring systems, which phenyl ring is optionally substituted with up to 2 identical or different radicals selected from the group consisting of $CH_3$, $CF_3$, Br, Cl and F, or is optionally substituted by $R^8OOC$—;
where
$R^8$ is H or $C_{1-3}$-alkyl
$n^B$ is 0, 1 or 2;
$p^B$ is 0, 1 or 2;
$q^B$ is 1, 2 or 3;
$R^{B1}$ is $C_{0-3}$-alkylaryl, $C_{0-3}$-alkylheteroaryl, $C_{0-3}$-alkyl-$C_{3-8}$-cycloalkyl, OH or $OCH_3$;
$R^{B2}$ is H, $C_{1-6}$-alkyl, $C_{0-3}$-alkylaryl or $C_{0-3}$-alkylheteroaryl;
$R^{B1}$ and $R^{B2}$ are optionally bonded together;
$R^{B2'}$ is H, $C_{1-6}$-alkyl, $C_{0-3}$-alkylaryl, $C_{0-3}$-alkylheteroaryl or $C_{0-3}$-alkyl-$C_{3-8}$-cycloalkyl;
or
B is -1-adamantyl-, -1-adamantyl-$CH_2$—, -2-adamantyl- or -2-adamantyl-$CH_2$—,

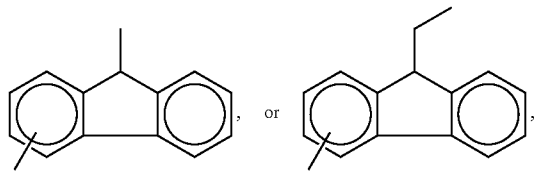

B is —(CH$_2$)$_{l^B}$—L$^{B1}$—M$^B$—L$^{B2}$—(CH$_2$)$_{m^B}$—, where l$^B$ and m$^B$ have the abovementioned meanings and the two groups L$^{B1}$ and L$^{B2}$, independently of one another, are selected from among the following radicals:

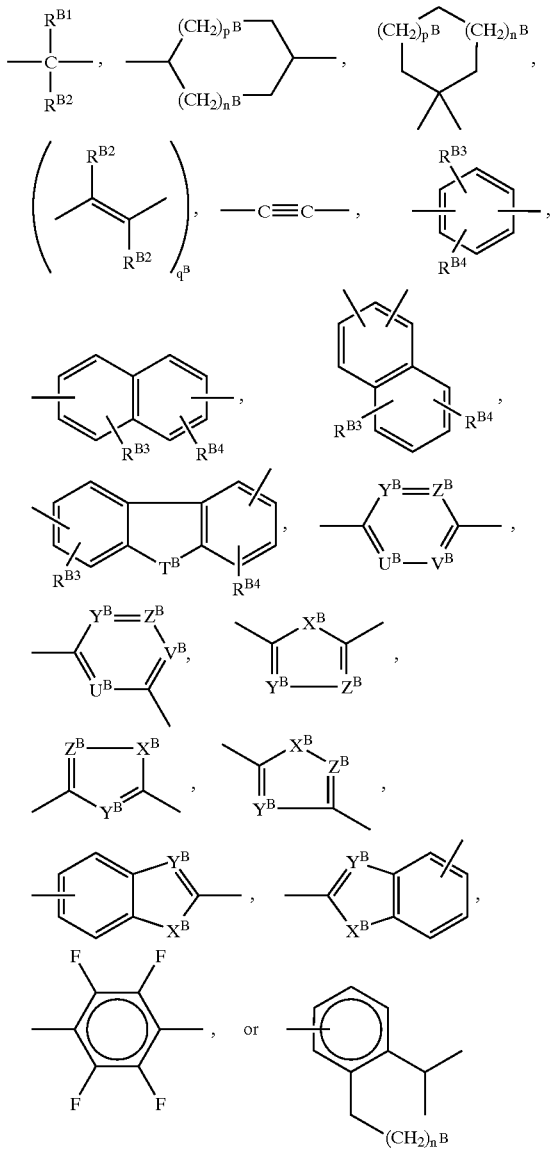

where a phenyl ring is optionally fused to the abovementioned ring systems;
where
n$^B$ is 0, 1 or 2;
p$^B$ is 0, 1 or 2;
q$^B$ is 1, 2 or 3;
R$^{B1}$ is C$_{0-3}$-alkylaryl, C$_{0-3}$-alkylheteroaryl, C$_{0-3}$-alkyl-C$_{3-8}$-cycloalkyl, OH or OCH$_3$, or in the case of L$^{B2}$, R$^{B1}$ is additionally H or C$_{1-6}$-alkyl;
R$^{B2}$ is H, C$_{1-6}$-alkyl, C$_{0-3}$-alkylaryl or C$_{0-3}$-alkylheteroaryl;
R$^{B2'}$ is H, C$_{1-6}$-alkyl, C$_{0-3}$-alkylaryl, C$_{0-3}$-alkylheteroaryl or C$_{0-3}$-alkyl-C$_{3-8}$-cycloalkyl;
R$^{B3}$ is H, C$_{1-6}$-alkyl, C$_{0-3}$-alkylaryl, C$_{0-3}$-alkylheteroaryl, R$^{B5}$OCO, R$^{B6}$—O, F, Cl, Br, NO$_2$ or CF$_3$;
R$^{B4}$ is H, C$_{1-6}$-alkyl, R$^{B6}$—O, Cl, Br, F or CF$_3$;
R$^{B5}$ is H, C$_{1-6}$-alkyl or C$_{1-3}$-alkylaryl;

R$^{B6}$ is H or C$_{1-6}$-alkyl;
T$^B$ is CH$_2$, O, S, NH or N—C$_{1-6}$-alkyl;
X$^B$ is O, S, NH or N—C$_{1-6}$-alkyl;
X$^B$ is O, S, NH or N—C$_{1-6}$-alkyl;

Y$^B$ is =CH—, =C—C$_{1-6}$-alkyl, =N— or =C—Cl;

Z$^B$ is =CH—, =C—C$_{1-6}$-alkyl, =N— or =C—Cl;

U$^B$ is =CH—, =C—C$_{1-6}$-alkyl, =N— or =C—O—C$_{1-3}$-alkyl;

V$^B$ is =CH—, =C—C$_{1-6}$-alkyl, =N— or =C—O—C$_{1-3}$-alkyl;

R$^{B1}$ and R$^{B2}$ are optionally bonded together;
M$^B$ is a single bond, O, S, CH$_2$, CH$_2$—CH$_2$, CH$_2$—O, O—CH$_2$, CH$_2$—S, S—CH$_2$, CO, SO$_2$, CH=CH or C≡C;

or

B is

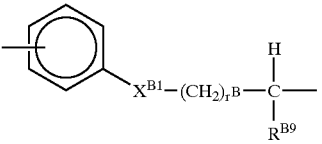

where
X$^{B1}$ is a bond, O, S or

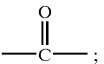

r$^B$ is 0, 1, 2 or 3;
R$^{B9}$ is H or C$_{1-3}$-alkyl;

or

A—B together are

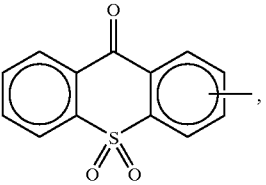

, or

-continued

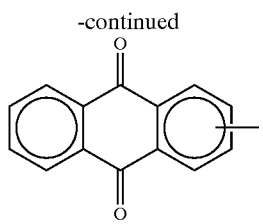

D is a single bond, CO, OCO, NR$^{D1}$—CO, SO$_2$ or NR$^{D1}$SO$_2$, where
R$^{D1}$ is H, C$_{1-4}$-alkyl or C$_{0-3}$-alkylaryl;

or

B—D together are

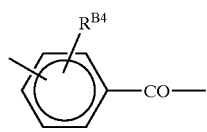

E is a single bond or

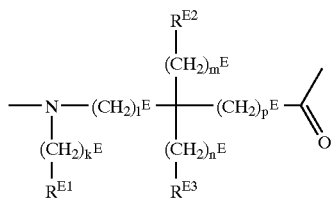

where
k$^E$ is 0, 1 or 2;
l$^E$ is 0, 1 or 2;
m$^E$ is 0, 1, 2 or 3;
n$^E$ is 0, 1 or 2;
p$^E$ is 0, 1 or 2;
R$^{E1}$ is H, C$_{1-6}$-alkyl, C$_{3-8}$-cycloalkyl, phenyl, naphthyl, pyridyl, thienyl or C$_{3-8}$-cycloalkyl having a fused-on phenyl ring, the abovementioned radicals being optionally substituted with up to three identical or different substituents selected from the group consisting of C$_{1-6}$-alkyl, O—C$_{1-6}$-alkyl, F, Cl and Br;
or
R$^{E1}$ is R$^{E4}$OCO—CH$_2$;
R$^{E2}$ is H, C$_{1-6}$-alkyl, C$_{3-8}$-cycloalkyl, phenyl, pyridyl, thienyl, furyl, imidazolyl, tetrahydropyranyl or tetrahydrothiopyranyl, the abovementioned radicals being optionally substituted with up to three identical or different substituents selected from the group consisting of C$_{1-6}$-alkyl, OH, O—C$_{1-6}$-Alkyl, F, Cl and Br, or is CH(CH$_3$)OH or CH(CF$_3$)$_2$;
R$^{E3}$ is H, C$_{1-6}$-alkyl, C$_{3-8}$-cycloalkyl or phenyl, the abovementioned radicals being optionally substituted with up to three identical or different substituents selected from the group consisting of C$_{1-6}$-alkyl, O—C$_{1-6}$-alkyl, F, Cl and Br;
R$^{E4}$ is H, C$_{1-12}$-alkyl or C$_{1-3}$-alkylaryl;
R$^{E2}$ and R$^{B1}$ together optionally form a bridge having (CH$_2$)$_{0-4}$, CH=CH, CH$_2$—CH=CH or CH=CH—CH$_2$ groups;
the groups stated under R$^{E1}$ and R$^{E3}$ are optionally linked to one another via a bond; the groups stated under R$^{E2}$ and R$^{E3}$ are also optionally linked to one another via a bond;
or
R$^{E2}$ is COR$^{E5}$;
R$^{E5}$ is OH, O—C$_{1-6}$-alkyl or O—C$_{1-3}$-alkylaryl;
or
E is D-Asp, D-Glu, D-Lys, D-Orn, D-His, D-Dab, D-Dap or D-Arg;

G is

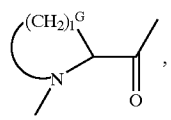

where l$^G$=2, 3, 4 or 5, and
where a CH$_2$ group of the ring is optionally replaced by O, S, NH, CHF, CF$_2$ or CH(C$_{1-3}$-alkyl);

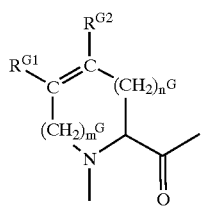

where
m$^G$ is 0, 1 or 2;
n$^G$ is 0, 1 or 2;
p$^G$ is 1 or 3;
R$^{G1}$ is H;
R$^{G2}$ is H;
or
R$^{G1}$ and R$^{G2}$ together form a CH=CH—CH=CH chain;
or
G is

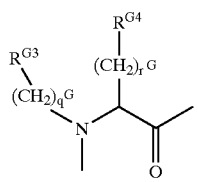

where
q$^G$ is 0, 1 or 2;
r$^G$ is 0, 1 or 2;
R$^{G3}$ is H, C$_1$–C$_6$-alkyl or C$_{3-8}$-cycloalkyl;
R$^{G4}$ is H, C$_1$–C$_6$-alkyl, C$_{3-8}$-cycloalkyl or phenyl;
K is
NH—(CH$_2$)$_{n^K}$—Q$^K$ where
n$^K$ is 1 or 2;
Q$^K$ is

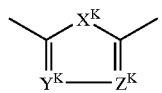

$X^K$ is O, S, NH or N—$C_{1-6}$-alkyl;

$Y^K$ is =CH—, =C—$C_{1-3}$-alkyl, =N— or =C—Cl;

$Z^K$ is =CH—, =C—$C_{1-3}$-alkyl, =N— or =C—Cl;

L is

-C(=NH)-NH-$R^{L1}$ or -NH-C(=NH)-NHR$^{L1}$ where
$R^{L1}$ is H, OH, O—$C_{1-6}$-alkyl, O—$(CH_2)_{0-3}$-phenyl, CO—$C_{1-6}$-alkyl, $CO_2$—$C_{1-6}$-alkyl or $CO_2$-$C_{1-5}$-alkylaryl.

3. The compound claimed in claim 1, or a tautomer, a pharmacologically tolearable salt, or a prodrug thereof, where:

A is
H, $C_{1-6}$-alkyl, $C_{1-6}$-alkyl-$SO_2$, $R^{A1}$OCO, $R^{A2}R^{A3}$NCO, $R^{A4}$OCONR$^{A2}$, $R^{A4}$CONR$^{A2}$, $R^{A1}$O, phenoxy, $R^{A2}R^{A3}$N, HO—$SO_2$, $R^{A2}R^{A3}$N—$SO_2$, Cl, Br, F, tetrazolyl, $H_2O_3P$, $NO_2$, $R^{A1}$—N(OH)—CO— or $R^{A1}R^{A2}$NCONR$^{A3}$, where
$R^{A1}$ is H, $C_{1-12}$-alkyl, $C_{3-8}$-cycloalkyl, $C_{1-3}$-alkyl-$C_{3-8}$-cycloalkyl or $C_{1-3}$-alkylaryl;
$R^{A2}$ is H, $C_{1-6}$-alkyl, $C_{0-3}$-alkylaryl or $C_{0-3}$-alkylheteroaryl;
$R^{A3}$ is H, $C_{1-6}$-alkyl or $C_{0-3}$-alkylaryl;
$R^{A4}$ is $C_{1-6}$-alkyl or $C_{1-3}$-alkylaryl;
where each aryl is optionally substituted by up to 2 identical or different substituents selected from the group consisting of F, Cl, Br, $CH_3$, $CF_3$, $OCH_3$ and $NO_2$;

B is —$(CH_2)_{l^B}$—$L^B$—$(CH_2)_{m^B}$— where
$l^B$ is 0, 1, 2 or 3;
$m^B$ is 0, 1, 2, 3, 4 or 5;
$L^B$ is

[chemical structures showing phenyl with $R^{B3}$, $R^{B4}$; naphthyl with $R^{B3}$, $R^{B4}$; fluorene-type with $T^B$, $R^{B3}$, $R^{B4}$; pyridine-type with $Y^B=Z^B$, $U^B-V^B$]

[continued structures with $X^B$, $Y^B$, $Z^B$; pentafluorophenyl; phenyl-$(CH_2)_n^B$-isopropyl; oxazole-type; benzoxazole-type]

where a phenyl ring is optionally fused to the abovementioned ring systems, which phenyl ring is optionally substituted with up to 2 identical or different radicals selected from the group consisting of $CH_3$, $CF_3$, F, Cl and Br, or is optionally substituted by $R^8$OOC—;

where
$R^{B3}$ is H, $C_{1-6}$-alkyl, $C_{0-3}$-alkylaryl, $C_{0-3}$-alkylheteroaryl $R^{B5}$OCO, $R^{B6}$—O, F, Cl, Br, $NO_2$ or $CF_3$;
$R^{B4}$ is H, $C_{1-6}$-alkyl, $R^{B6}$—O, Cl, Br, F or $CF_3$;
$R^{B5}$ is H, $C_{1-6}$-alkyl or $C_{1-3}$-alkylaryl;
$R^{B5}$ is H or $C_{1-6}$-alkyl;
$R^8$ is H or $C_{1-3}$-alkyl
$T^B$ is $CH_2$, O, S, NH or N—$C_{1-6}$-alkyl;
$X^B$ is O, S, NH or N—$C_{1-6}$-alkyl;

$Y^B$ is =CH—, =N— or =C—Cl;

$Z^B$ is =CH—, =N— or =C—Cl;

$U^B$ is =CH— or =N—;
$V_B$ is =CH— or =N—;

or

B is

[phenyl-CH($R^{B7}$)— or phenyl-C(CH_3)(cyclopropyl with $(CH_2)_h^B$)]

where
$h^B$ is 1, 2, 3, or 4;
$R^{B7}$ is $C_{1-6}$-alkyl or $C_{3-8}$-cycloalkyl;

or

A—B together are

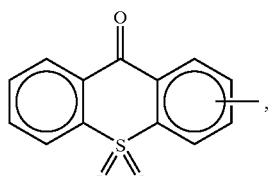, or

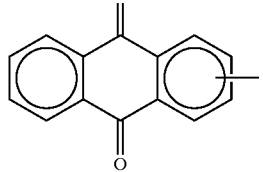

or

B is
-1-adamantyl-, -2-adamantyl-, -1-adamantyl-$CH_2$—, -2-adamantyl-$CH_2$—,

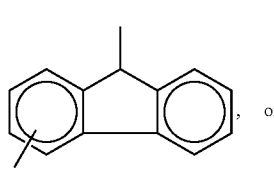, or 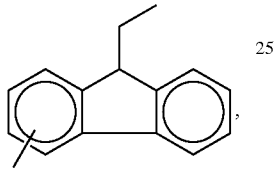, or

B is

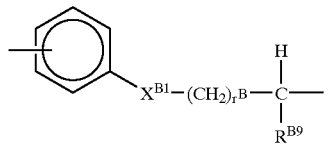

where
$X^{B1}$ is a bond, O, S, or

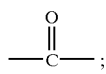;

$r^B$ is 0, 1, 2 or 3;
$R^{B9}$ is H or $C_{1-3}$-alkyl;
D is a single bond, —$NR^{D1}$—CO or —$NR^{D1}SO_2$, where
$R^{D1}$ is H, $C_{1-4}$-alkyl or $CO_3$-alkylaryl;
E is a single bond or

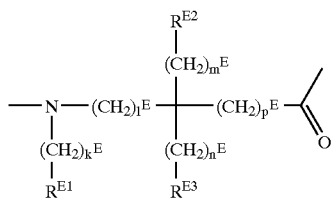

where
$k^E$ is 0, 1 or 2;
$l^E$ is 0, 1 or 2;
$m^E$ is 0, 1, 2 or 3;
$n^E$ is 0, 1 or 2;
$p^E$ is 0, 1 or 2;
$R^{E1}$ is H, $C_{1-6}$-alkyl, $C_{3-8}$-cycloalkyl, aryl, pyridyl, thienyl, $C_{3-8}$-cycloalkyl having a fused-on phenyl ring, the abovementioned radicals being optionally substituted with up to three identical or different substituents selected from the group consisting of $C_{1-6}$-alkyl, O—$Cl_6$-alkyl, F, Cl and Br;

or $R^{E1}$ is $R^{E4}OCO$—$CH_2$;
$R^{E2}$ is H, $C_{1-6}$-alkyl, $C_{3-8}$-cycloalkyl, phenyl, pyridyl, furyl, thienyl, imidazolyl, tetrahydropyranyl or tetrahydrothiopyranyl, the abovementioned radicals being optionally substituted with up to three identical or different substituents selected from the group consisting of $C_{1-6}$-alkyl, O—$C_{1-6}$-alkyl, F, Cl and Br, or is $CH(CH_3)OH$ or $CH(CF_3)_2$;
$R^{E3}$ is H, $C_{1-6}$-alkyl or $C_{3-8}$-cycloalkyl, the abovementioned radicals being optionally substituted with up to three identical or different substituents selected from the group consisting of $C_{1-6}$-alkyl, O—$C_{1-6}$-alkyl, F, Cl and Br;
$R^{E2}$ and $R^{B1}$ together optionally form a bridge having $(CH_2)_{0-4}$, CH=CH, $CH_2$—CH=CH or CH=CH—$CH_2$ groups;
the groups stated under $R^{E1}$ and $R^{E3}$ are optionally linked to one another via a bond; the groups stated under $R^{E2}$ and $R^{E3}$ are also optionally linked to one another via a bond;

or $R^{E2}$ is $COR^{E5}$;
$R^{E4}$ is H, $C_{1-12}$-alkyl or $C_{1-3}$-alkylaryl;
$R^{E5}$ is OH, O—$C_{1-6}$-alkyl or $OC_{1-3}$-alkylaryl;

or

E is D-Asp, D-Glu, D-Lys, D-Orn, D-His, D-Dab, D-Dap or D-Arg;

G is 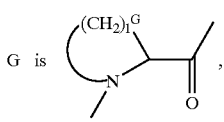, where $l^G$=2, 3, 4 or 5, and
where a $CH_2$ group of the ring is optionally replaced by O, S, NH, CHF, $CF_2$ or $CH(C_{1-3}$-alkyl);

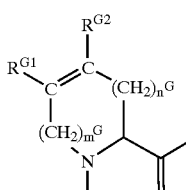 or 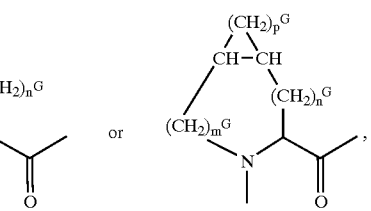, where
m$^G$ is 0, 1 or 2;
n$^G$ is 0, 1 or 2;
p$^G$ is 1 or 3;
R$^{G1}$ is H;
R$^{G2}$ is H;
or
R$^{G1}$ and R$^{G2}$ together form a CH=CH—CH=CH chain;
or
G is

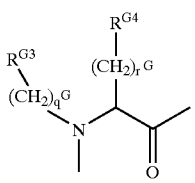

where
q$^G$ is 0, 1 or 2;
r$^G$ is 0, 1 or 2;
R$^{G3}$ is H, C$_1$–C$_6$-alkyl or C$_{3-8}$-cycloalkyl;
R$^{G4}$ is H, C$_1$–C$_6$-alkyl, C$_{3-8}$-cycloalkyl or phenyl;
K is
NH—(CH$_2$)$_{n^K}$—Q$^K$ where
n$^K$=1 or 2;
Q$^K$ is

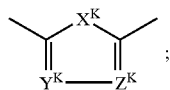

X$^K$ is O, S, NH or N—C$_{1-6}$-alkyl;

Y$^K$ is =CH—, =C—C$_{1-6}$—alkyl,
=N— or =C—Cl;

Z$^K$ is =CH—, =C—C$_{1-6}$—alkyl,
=N— or =C—Cl;

L is 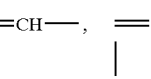 or 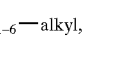

where
R$^{L1}$ is —H, —OH, —O—C$_{1-6}$-alkyl, —O—(CH$_2$)$_{0-3}$-phenyl, —CO—C$_{1-6}$-alkyl, —CO$_2$—C$_{1-6}$-alkyl or CO$_2$—C$_{1-3}$-alkylaryl.

4. The compound claimed in claim 1, or a tautomer, a pharmacologically tolerable salt, or a prodrug thereof, where
A is
H, C$_{1-6}$-alkyl, C$_{1-6}$-alkyl-SO$_2$, R$^{A1}$OCO, R$^{A2}$R$^{A3}$NCO; R$^{A4}$OCONR$^{A2}$, R$^{A4}$CONR$^{A2}$, R$^{A1}$O, R$^{A2}$R$^{A3}$N, HO—SO$_2$—, phenoxy, R$^{A2}$R$^{A3}$N—SO$_2$, Cl, Br, F, tetrazolyl, H$_2$O$_3$P—, NO$_2$, R$^{A1}$—N(OH)—CO— or R$^{A1}$R$^{A2}$NCONR$^{A3}$,
where
R$^{A1}$ is H, C$_{1-12}$-alkyl, C$_{3-8}$-cycloalkyl, C$_{3-8}$-cycloalkyl-C$_{1-3}$-alkyl or C$_{1-3}$-alkylaryl;

R$^{A2}$ is H—, C$_{1-6}$-alkyl, C$_{0-3}$-alkylaryl or C$_{0-3}$-alkylheteroaryl;
R$^{A3}$ is H, C$_{1-6}$-alkyl or C$_{0-3}$-alkylaryl;
R$^{A4}$ is C$_{1-6}$-alkyl or C$_{1-3}$-alkylaryl;
where each aryl is optionally substituted with up to 2 identical or different radicals selected from the group consisting of F, Cl, Br, CF$_3$, CH$_3$, OCH$_3$ and NO$_2$;
B is —(CH$_2$)$_{l^B}$—L$^B$—(CH$_2$)$_{m^B}$— where
l$^B$ is 0, 1, 2 or 3;
m$^B$ is 0, 1 or 2;
L$^B$ is

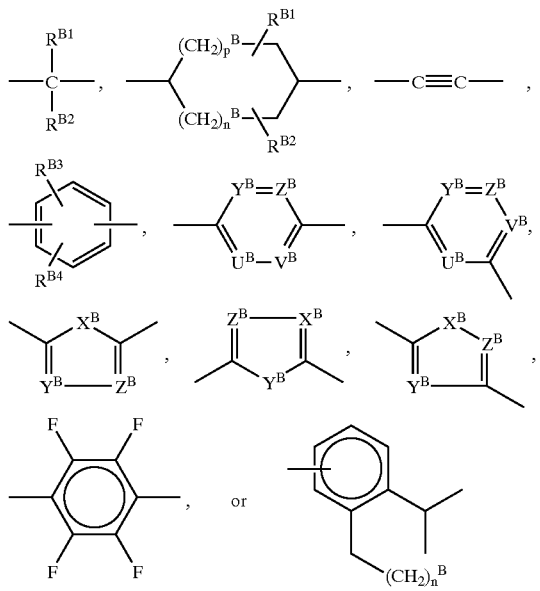

where a phenyl ring is optionally fused to the abovementioned ring systems, which phenyl ring is optionally substituted with up to 2 identical or different radicals selected from the group consisting of CH$_3$, CF$_3$, Br, Cl and F, or is optionally substituted by R$^8$OOC—;
where
R$^8$ is H or C$_{1-3}$-alkyl
n$^B$ is 0,1 or 2;
p$^B$ is 0, 1 or 2;
R$^{B1}$ is C$_{0-3}$-alkylaryl, C$_{0-3}$-alkylheteroaryl, C$_{0-3}$-alkyl-C$_{3-8}$-cycloalkyl, OH or OCH$_3$;
R$^{B2}$ is H, C$_{1-6}$-alkyl, C$_{0-3}$-alkylaryl or C$_{0-3}$-alkylheteroaryl;
R$^{B3}$ is H, C$_{1-6}$-alkyl, C$_{0-3}$-alkylaryl or C$_{0-3}$-alkylheteroaryl; R$^{B5}$OCO, R$^{B6}$—O, F, Cl, Br, NO$_2$ or CF$_3$;
R$^{B4}$ is H, C$_{1-6}$-alkyl, R$^{B6}$—O, Cl, Br, F or CF$_3$;
R$^{B5}$ is H, C$_{1-6}$-alkyl or C$_{1-3}$-alkylaryl;
R$^{B6}$ is H or C$_{1-6}$-alkyl;
R$^{B1'}$ is H, C$_{1-6}$-alkyl, C$_{0-3}$-alkylaryl, C$_{0-3}$-alkylheteroaryl or C$_{0-3}$-alkyl-C$_{3-8}$-cycloalkyl;
R$^{B1}$ and R$^{B2}$ are optionally bonded together;
X$^B$ is O, S, NH or N—C$_{1-6}$-alkyl;
Y$^B$ is
Z$^B$ is
U$^B$ is =CH— or =N—;
V$^B$ is =CH— or =N—;
or
B is —(CH$_2$)$_{l^B}$—L$^B$—M$^B$—L$^B$—(CH$_2$)$_{m^B}$—, where
l$^B$ and m$^B$ have the abovementioned meanings and the two groups L$^B$, independently of one another, are the radicals stated under L$^B$;

$M^B$ is a single bond, O, S, $CH_2$, $CH_2$—$CH_2$, $CH_2$—O, O—$CH_2$, $CH_2$—S, S—$CH_2$, CO, $SO_2$, CH=CH or C≡C;

or

B is
-1-adamantyl-$CH_2$—, -2-adamantyl-$CH_2$—, -1-adamantyl-, -2-adamantyl-,

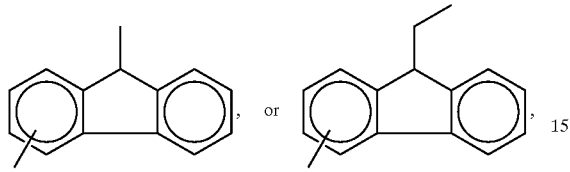

or

B is

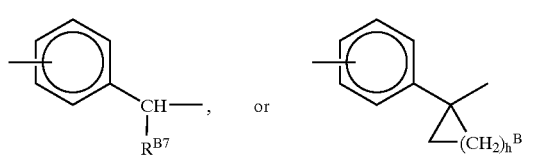

where
$h^B$ is 1, 2, 3 or 4;
$R^{B7}$ is $C_{1-6}$-alkyl or $C_{3-8}$-cycloalkyl;

or

B is

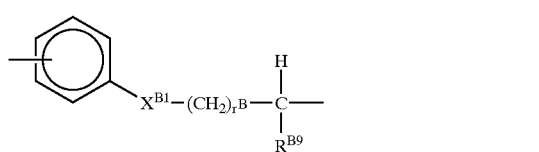

where
$X^{B1}$ is a bond, O, S or

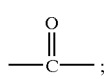

$r^B$ is 0, 1, 2 or 3;
$R^{B9}$ is H or $C_{1-3}$-alkyl;

or

A—B together are

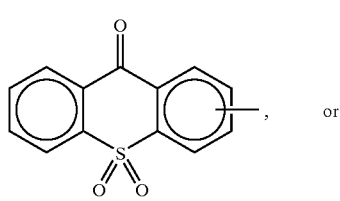, or

-continued

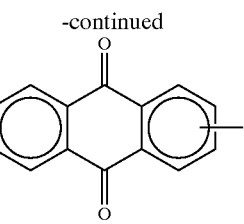

D is a single bond, CO, OCO or $NR^{D1}$—CO, $SO_2$ or $NR^{D1}SO_2$, where
$R^{D1}$ is H, $C_{1-4}$-alkyl or $C_{0-3}$-alkylaryl;

E is

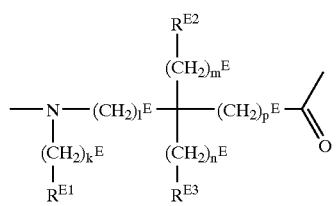

where
$k^E$ is 0 or 1;
$l^E$ is 0 or 1;
$m^E$ is 0 or 1;
$n^E$ is 0 or 1;
$p^E$ is 0 or 1;
$R^{E1}$ is H, $C_{1-6}$-alkyl, $C_{3-8}$-cycloalkyl, aryl, pyridyl, thienyl or $C_{3-8}$-cycloalkyl having a fused-on phenyl ring;
or
$R^{E1}$ is $R^{E4}OCO$—$CH_2$;
$R^{E2}$ is H, $C_{1-6}$-alkyl, $C_{3-8}$-cycloalkyl, phenyl, pyridyl, furyl, thienyl, imidazolyl, tetrahydropyranyl or tetrahydrothiopyranyl, where the abovementioned radicals optionally carry up to three identical or different substituents selected from the group consisting of $C_{1-6}$-alkyl, O—$C_{1-6}$-alkyl, F, Cl and Br, or is $CH(CH_3)OH$ or $CH(CF_3)_2$;
$R^{E3}$ is H, $C_{1-6}$-alkyl, $C_{3-8}$-cycloalkyl or phenyl;
$R^{E4}$ is H, $C_{1-12}$-alkyl or $C_{1-3}$-alkylaryl;
$R^{E2}$ and $R^{B1}$ together optionally form a bridge with $(CH_2)_{0-4}$, CH=CH, $CH_2$—CH=CH or CH=CH—$CH_2$ groups;
the groups stated under $R^{E1}$ and $R^{E2}$ may be linked to one another via a bond; the groups stated under $R^{E2}$ and $R^{E3}$ may also be linked to one another via a bond;

or

E is D-Asp, D-Glu, D-Lys, D-Orn, D-His, D-Dab, D-Dap or D-Arg;

G is

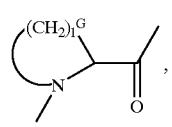

where
$l^G$ is 2, 3, or 4, and where a $CH_2$ group of the ring is optionally replaced by O, S, $CF_2$, CHF or $CH(C_{1-3}$-alkyl);

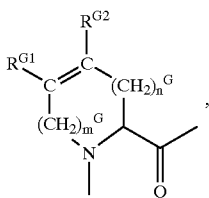

where
m<sup>G</sup> is 0, 1 or 2;
n<sup>G</sup> is 0, 1 or 2;
R<sup>G1</sup> and R<sup>G2</sup> are each H;
or
G is

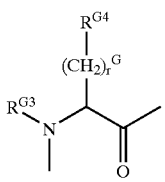

where
r<sup>G</sup> is 0 or 1;
R<sup>G3</sup> is H, $C_1$–$C_6$-alkyl or $C_{3-8}$-cycloalkyl;
R<sup>G4</sup> is H, $C_1$–$C_6$-alkyl, $C_{3-8}$-cycloalkyl or phenyl;
K is
NH—(CH$_2$)$_{n^K}$—Q$^K$, where
n<sup>K</sup> is 1 or 2;
Q<sup>K</sup> is

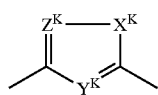

X<sup>K</sup> is O or S;

Y<sup>K</sup> is =CH—, =C—$C_{1-3}$—alkyl or =N—;

Z<sup>K</sup> is =CH—, =C—$C_{1-3}$—alkyl, or =N—;

L is $$\underset{NH-R^{L1}}{\overset{NH}{-}}\quad \text{or} \quad -NH\underset{NHR^{L1}}{\overset{NH}{-}}$$

where
R<sup>L1</sup> is H, OH, O—$C_{1-6}$-alkyl, O—(CH$_2$)$_{0-3}$-phenyl, CO—$C_{1-6}$-alkyl, CO$_2$—$C_{1-6}$-alkyl or CO$_2$—$C_{1-3}$-alkylaryl.

5. The compound claimed in claim 1, or a tautomer, a pharmacologically tolerable salt, or a prodrug thereof, where
A is
H, $C_{1-6}$-alkyl, $C_{1-6}$-alkyl-SO$_2$ or R$^{A1}$OCO, R$^{A2}$R$^{A3}$NCO; R$^{A4}$OCONR$^{A2}$, R$^{A4}$CONR$^{A2}$, R$^{A1}$O, R$^{A2}$R$^{A3}$N, HO—SO$_2$—, phenoxy, R$^{A2}$R$^{A3}$N—SO$_2$, Cl, Br, F, tetrazolyl, H$_2$O$_3$P—, NO$_2$, R$^{A1}$—N(OH)—CO— or R$^{A1}$ R$^{A2}$NCONR$^{A3}$,
where
R<sup>A1</sup> is H, $C_{1-12}$-alkyl, $C_{3-8}$-cycloalkyl, $C_{3-8}$-cycloalkyl-$C_{1-3}$-alkyl or $C_{1-3}$-alkylaryl;

R<sup>A2</sup> is H—, $C_{1-6}$-alkyl, $C_{0-3}$-alkylaryl or $C_{0-3}$-alkylheteroaryl;
R<sup>A3</sup> is H, $C_{1-6}$-alkyl or $C_{0-3}$-alkylaryl;
R<sup>A4</sup> is $C_{1-6}$-alkyl or $C_{1-3}$-alkylaryl;
where each aryl is optionally substituted with up to 2 identical or different radicals selected from the group consisting of F, Cl, Br, CF$_3$, CH$_3$, OCH$_3$ and NO$_2$,
B is
—(CH$_2$)$_{l^B}$—L$^B$—(CH$_2$)$_{m^B}$— where
l<sup>B</sup> is 0, 1 or 2;
m<sup>B</sup> is 0, 1 or 2;
L<sup>B</sup> is

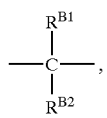 , 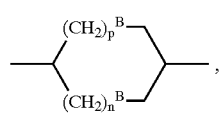 ,

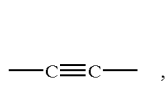 , 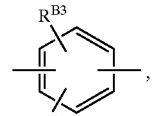 ,

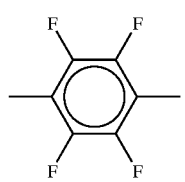 , or 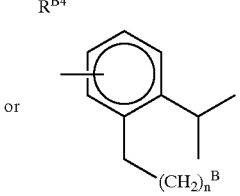

where a phenyl ring is optionally fused to the abovementioned ring systems, which phenyl ring is optionally substituted with up to 2 identical or different radicals selected from the group consisting of CH$_3$, CF$_3$, Br, Cl and F, or is optionally substituted by R$^8$OOC—;
where
R<sup>8</sup> is H or $C_{1-3}$-alkyl
n<sup>B</sup> is 0 or 1;
p<sup>B</sup> is 0 or 1;
R<sup>B1</sup> is $C_{0-3}$-alkylaryl, $C_{0-3}$-alkylheteroaryl, $C_{0-3}$-alkyl-$C_{3-8}$-cycloalkyl, OH or OCH$_3$;
R<sup>B2</sup> is H, $C_{1-6}$-alkyl, $C_{0-3}$-alkylaryl or $C_{0-3}$-alkylheteroaryl;
R<sup>B3</sup> is H, $C_{1-6}$-alkyl, R$^{B5}$OCO, R$^{B6}$—O, F, Cl, Br, NO$_2$ or CF$_3$;
R<sup>B4</sup> is H, $C_{1-6}$-alkyl, R$^{B6}$—O, Cl, Br, F or CF$_3$;
R<sup>B5</sup> is H or $C_{1-6}$-alkyl;
R<sup>B6</sup> is H or $C_{1-6}$-alkyl;
R<sup>B1</sup> and R<sup>B2</sup> are optionally bonded together;

or

B is
—(CH$_2$)$_{l^B}$—L$^B$—m$^B$—L$^B$—(CH$_2$)$_{m^B}$, where
l<sup>B</sup> and m<sup>B</sup> have the abovementioned meanings and the two groups L$^B$, independently of one another, are the radicals stated under L$^B$;

$M^B$ is a single bond, O, S, $CH_2$, $CH_2$—$CH_2$, $CH_2$—O, O—$CH_2$, $CH_2$—S, S—$CH_2$, CH=CH or C≡C;

or

B is
-1-adamantyl-$CH_2$—, -2-adamantyl-$CH_2$—,

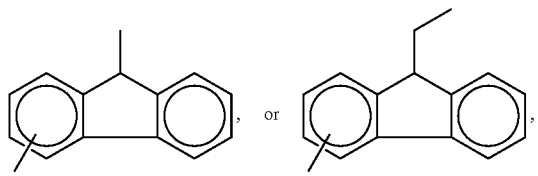

or

B is

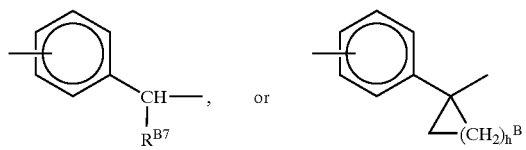

where
$h^B$ is 1, 2, 3, or 4;
$R^{B7}$ is $C_{1-6}$-alkyl or $C_{3-8}$-cycloalkyl;

or

B is

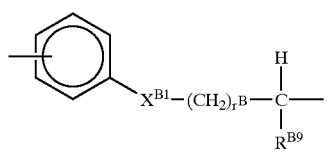

where
$X^{B1}$ is a bond, O, S or

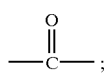;

$r^B$ is 0, 1, 2 or 3;
$R^{B9}$ is H or $C_{1-3}$-alkyl;

or

A—B together are

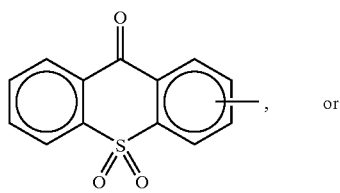, or

-continued

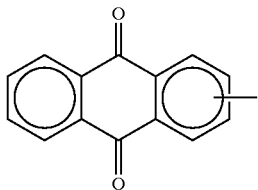

D is a single bond, CO, OCO, $NR^{D1}$—CO, $SO_2$ or $NR^{D1}SO_2$,
where
$R^{D1}$ is H, $C_{1-4}$-alkyl or $C_{0-3}$-alkylaryl;

E is

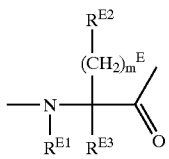

where
$m^E$ is 0, 1, 2 or 3;
$R^{E1}$ is H or $C_{1-6}$-alkyl;
$R^{E2}$ is H, $C_{1-6}$-alkyl or $C_{3-8}$-cycloalkyl, where the abovementioned radicals optionally carry up to three substituents selected from the group consisting of $C_{1-6}$-alkyl and F; or is $CH(CH_3)OH$ or $CH(CF_3)_2$;
$R^{E3}$ is H;
the groups stated under $R^{E1}$ and $R^{E2}$ are optionally linked to one another via a bond;

or

E is D-Asp, D-Glu, D-Lys, D-Orn, D-His, D-Dab, D-Dap or D-Arg;

G is

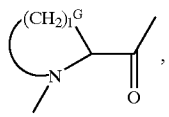

where
$l^G$ is 2 or 3, and
where a $CH_2$ group of the ring is optionally replaced by S or CHCH3; or

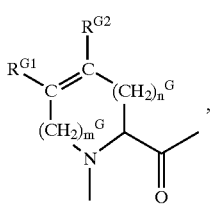

where
m$^G$ is 1;
n$^G$ is 0;
R$^{G1}$ and R$^{G2}$ are each H;
K is NH—(CH$_2$)$_{n^K}$—Q$^K$,
where
n$^K$ is 1;
Q$^K$ is

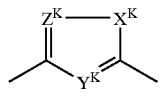 or 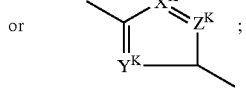 ;

X$^K$ is S;
Y$^K$ is =CH— or =N—;
Z$^K$ is =CH— or =N—;
L is

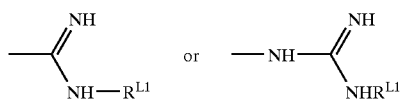

where
R$^{L1}$ is H, OH, CO—C$_{1-6}$-alkyl, CO$_2$—C$_{1-6}$-alkyl or CO$_2$—C$_{1-3}$-alkylaryl.

6. A compound of the formula I

    (I), or a tautomer, a pharmacologically tolerable salt, or a prodrug thereof, where A is
H, C$_{1-6}$-alkyl, C$_{1-6}$-alkyl-SO$_2$ or R$^{A1}$OCO, R$^{A2}$R$^{A3}$NCO; R$^{A4}$OCONR$^{A2}$, R$^{A4}$CONR$^{A2}$, R$^{A1}$O, R$^{A2}$R$^{A3}$N, HO—SO$_2$—, phenoxy, R$^{A2}$R$^{A3}$N—SO$_2$, Cl, Br, F, tetrazolyl, H$_2$O$_3$P—, NO$_2$, R$^{A1}$—N(OH)—CO— or R$^{A1}$R$^{A2}$NCONR$^{A3}$,
where
R$^{A1}$ is H, C$_{1-12}$-alkyl, C$_{3-8}$-cycloalkyl, C$_{1-3}$-cycloalkyl-C$_{1-3}$-alkyl or C$_{1-3}$-alkylaryl;
R$^{A2}$ is H—, C$_{1-6}$-alkyl, C$_{0-3}$-alkylaryl or C$_{0-3}$-alkylheteroaryl;
R$^{A3}$ is H, C$_{1-6}$-alkyl or C$_{0-3}$-alkylaryl;
R$^{A4}$ is C$_{1-6}$-alkyl or C$_{1-3}$-alkylaryl;
where each aryl is optionally substituted with up to 2 identical or different radicals selected from the group consisting of F, Cl, Br, CF$_3$, CH$_3$, OCH$_3$ and NO$_2$;

B is
—(CH$_2$)$_{l^B}$—L$^B$—(CH$_2$)$_{m^B}$— where
l$^B$ is 0 or 1;
m$^B$ is 0, 1 or 2;
L$^B$ is

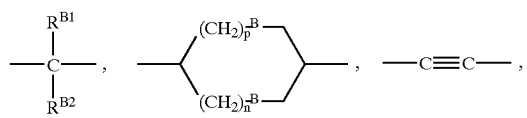

-continued

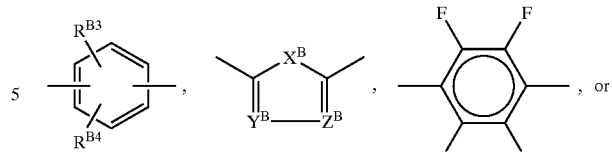

where a phenyl ring is optionally fused to the abovementioned ring systems, which phenyl ring is optionally substituted with up to 2 identical or different radicals selected from the group consisting of CH$_3$, CF$_3$, Br, Cl and F, or is optionally substituted by R$^8$OOC—;
where
R$^8$ is H or C$_{1-3}$-alkyl
n$^B$ is 0 or 1;
p$^B$ is 0 or 1;
R$^{B1}$ is C$_{0-3}$-alkylaryl, C$_{0-3}$-alkylheteroaryl, C$_{0-3}$-alkyl-C$_{3-8}$-cycloalkyl, OH or OCH$_3$;
R$^{B2}$ is H, C$_{1-6}$-alkyl, C$_{0-3}$-alkylaryl or C$_{0-3}$-alkylheteroaryl;
R$^{B3}$ is H, C$_{1-6}$-alkyl, R$^{B5}$OCO, R$^{B6}$—O, F, Cl, Br, NO$_2$ or CF$_3$;
R$^{B4}$ is H, C$_{1-6}$-alkyl, R$^{B6}$—O, Cl, Br, F or CF$_3$;
R$^{B5}$ is H or C$_{1-6}$-alkyl;
R$^{B6}$ is H or C$_{1-6}$-alkyl;
R$^{B1}$ and R$^{B2}$ are optionally bonded together;
X$^B$ is O or S;
Y$^B$ is =CH— or =N—;
Z$^B$ is =CH— or =N—;

or

B is —(CH$_2$)$_{l^B}$—L$^B$—M$^B$—L$^B$—(CH$_2$)$_{m^B}$,
where
l$^B$ and m$^B$ have the abovementioned meanings and the two groups L$^B$, independently of one another, are the radicals —C≡C—,

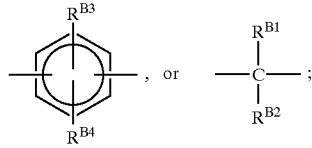 , or  ;

M$^B$ is a single bond, O, CH$_2$—S, S—CH$_2$, CO, SO$_2$ or CH$_2$—O;

or

B is

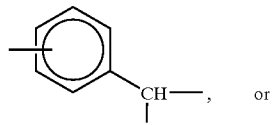 , or 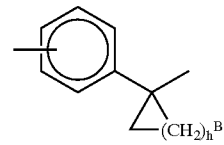

where
$h^B$ is 1, 2, 3, or 4;
$R^{B7}$ is $C_{1-6}$-alkyl or $C_{3-8}$-cycloalkyl;

or

B is 1-fluorenyl-, 1-adamantyl- or 1-adamantyl-$CH_2$—;

or

A—B together are 2-pyridyl-$CH_2$—, 2-benzothienyl-, 3-benzothienyl-,

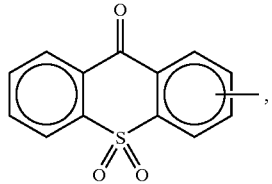, or

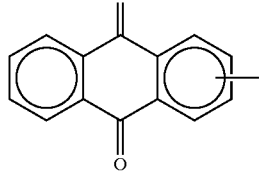

D is a single bond, CO or $SO_2$;
E is

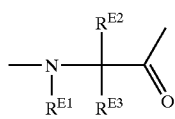

where
$R^{E1}$ is H or $CH_3$;
$R^{E2}$ is H, $C_{1-6}$-alkyl, $C_{3-8}$-cycloalkyl, thienyl, $CH(CH_3)OH$ or $CH(CF_3)_2$;
$R^{E3}$ is H;
the groups stated under $R^{E1}$ and $R^{E2}$ are optionally linked to one another via a bond; the groups stated under $R^{E2}$ and $R^{E3}$ are also optionally linked to one another via a bond;

or

E is D-Lys, D-Orn, D-Dab, D-Dap or D-Arg where Orn is ornithine, Dab is 2,4-diamino butyric acid and Dap is 2,3-diamino propionic acid;
G is

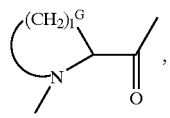

where
$l^G$ is 2 or 3, and
where a $CH_2$ group of the ring is optionally replaced by $CHCH_3$; or

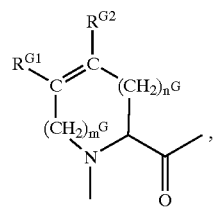

where
$m^G$ is 1;
$n^G$ is 0;
$R^{G1}$ and $R^{G2}$ are each H;
K is
NH—$(CH_2)_{n^K}$—$Q^K$, where
$n^K$ is 1;
$Q^K$ is

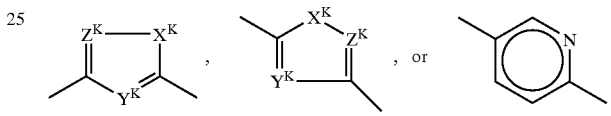

$X^K$ is S;
$Y^K$ is =CH— or =N—
$Z^K$ is =CH— or =N—

L is

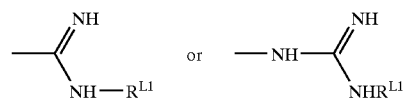

where
$R^{L1}$ is H or OH.

7. The compound claimed in claim 1, or a tautomer, a pharmacologically tolerable salt, or a prodrug thereof, where A is
H, $C_{1-6}$-alkyl, $C_{1-6}$-alkyl-$SO_2$ or $R^{A1}OCO$, $R^{A2}R^{A3}NCO$, $R^{A4}OCONR^{A2}$, $R^{A4}CONR^{A2}$, $R^{A1}O$, phenoxy, $R^{A2}R^{A3}N$, HO—$SO_2$, $R^{A2}R^{A3}N$—$SO_2$, Cl, Br, F, tetrazolyl, $H_2O_3P$, $NO_2$, $R^{A1}$—N(OH)—CO or $R^{A1}R^{A2}NCONR^{A3}$,
where
$R^{A1}$ is H, $C_{1-12}$-alkyl, $C_{3-8}$-cycloalkyl, $C_{1-3}$-alkyl-$C_{3-8}$-cycloalkyl or $C_{1-3}$-alkylaryl;
$R^{A2}$ is H, $C_{1-6}$-alkyl, $C_{0-3}$-alkylaryl or $C_{0-3}$-alkylheteroaryl;
$R^{A3}$ is H, $C_{1-6}$-alkyl or $C_{0-3}$-alkylaryl;
$R^{A4}$ is $C_{1-6}$-alkyl or $C_{1-3}$-alkylaryl;
where each aryl is optionally substituted with up to 2 identical or different radicals selected from the group consisting of F, Cl, Br, $OCH_3$, $CH_3$, $CF_3$ and $NO_2$;

B is $-(CH_2)_{l^B}-L^B-(CH_2)_{m^B}-$, where
$l^B$ is 0, 1 or 2;
$m^B$ is 0, 1 or 2;

$L^B$ is

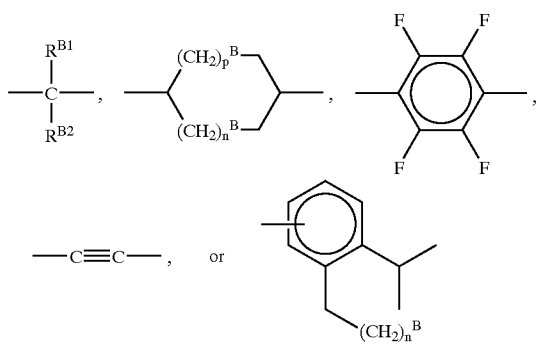

where a phenyl ring is optionally fused to the above-mentioned ring systems, which phenyl ring is optionally substituted with up to 2 identical or different radicals selected from the group consisting of $CH_3$, $CF_3$, Br, Cl and F, or is optionally substituted by $R^8OOC-$;

where
$R^8$ is H or $C_{1-3}$-alkyl;
$n^B$ is 0, 1 or 2;
$p^B$ is 0, 1 or 2;
$R^{B1}$ is $C_{0-3}$-alkylaryl, $C_{0-3}$-alkylheteroaryl, $C_{0-3}$-alkyl-$C_{3-8}$-cycloalkyl, OH or $OCH_3$;
$R^{B2}$ is H, $C_{1-6}$-alkyl, $C_{0-3}$-alkylaryl or $C_{0-3}$-alkylheteroaryl;
$R^{B1}$ and $R^{B2}$ are optionally bonded together;

or

B is -1-adamantyl-$CH_2$—, -2-adamantyl-$CH_2$—,

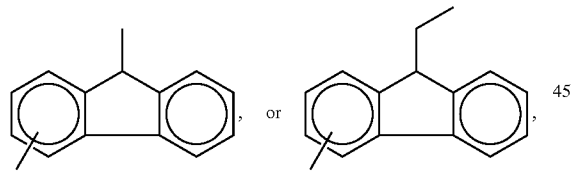

or

B is $-(CH_2)_{l^B}-L^{B1}-M^B-L^{B2}-(CH_2)_{m^B}-$, where $l^B$ and $m^B$ have the abovementioned meanings and the two groups $L^{B1}$ and $L^{B2}$, independently of one another, are the following radicals:

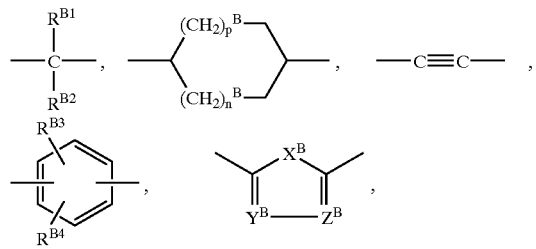

-continued

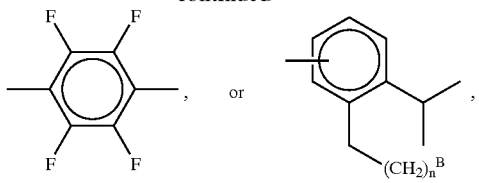

where a phenyl group is optionally fused to the above-mentioned ring systems, and where
$n^B$ is 0, 1 or 2;
$p^B$ is 0, 1 or 2;
$R^{B1}$ is H, $C_{1-6}$-alkyl, $C_{0-3}$-alkylaryl, $C_{0-3}$-alkylheteroaryl, $C_{0-3}$-alkyl-$C_{3-8}$-cycloalkyl, OH or $OCH_3$, and in the case of $L^{B2}$, $R^{B1}$ may also be H or $C_{1-6}$-alkyl;
$R^{B2}$ is H, $C_{1-6}$-alkyl, $C_{0-3}$-alkylaryl or $C_{0-3}$-alkylheteroaryl;
$R^{B3}$ is H, $C_{1-6}$-alkyl, aryl, heteroaryl, $R^{B5}OCO$, $R^{B6}-O$, F, Cl, Br, $NO_2$ or $CF_3$;
$R^{B4}$ is H, $C_{1-6}$-alkyl, $R^{B6}-O$, Cl, Br, F or $CF_3$;
$R^{B5}$ is H or $C_{1-6}$-alkyl;
$R^{B6}$ is H or $C_{1-6}$-alkyl;
$X^B$ is O or S;
$Y^B$ is =CH— or =N—;
$Z^B$ is =CH— or =N—;
$R^{B1}$ and $R^{B2}$ may also be bonded together;
$M^B$ is a single bond, O, S, $CH_2$, $CH_2-CH_2$, $CH_2-O$, $O-CH_2$, $CH_2-S$, $S-CH_2$, CO, $SO_2$, CH=CH or C≡C;

or

B is

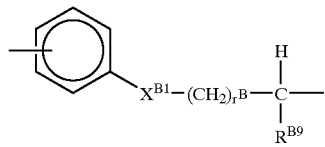

where
$X^{B1}$ is a bond, O, S or

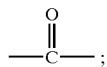

$r^B$ is 0, 1, 2 or 3;
$R^{B9}$ is H or $C_{1-3}$-alkyl;

or

A—B together are

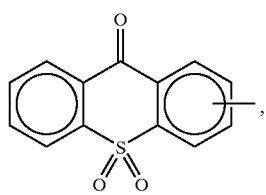

-continued

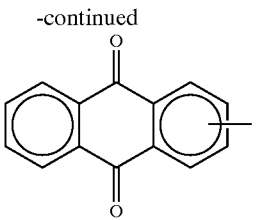

D is a single bond, CO, OCO, $NR^{D1}$—CO, $SO_2$ or $NR^{D1}SO_2$, where
$R^{D1}$ is H, $C_{1-4}$-alkyl or $C_{0-3}$-alkylaryl;

or

B—D together are

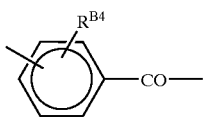

E is

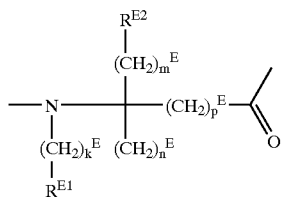

where
$k^E$ is 0 or 1;
$m^E$ is 0 or 1;
$n^E$ is 0 or 1;
$p^E$ is 0 or 1;
$R^{E1}$ is H, $C_{1-6}$-alkyl, $C_{3-8}$-cycloalkyl, phenyl, naphthyl, pyridyl, thienyl or $C_{3-8}$-cycloalkyl having a fused-on phenyl ring;
$R^{E2}$ is H, $C_{1-6}$-alkyl, $C_{3-8}$-cycloalkyl, phenyl, pyridyl, thienyl, furyl, imidazolyl, tetrahydropyranyl, tetrahydrothiopyranyl, $CH(CH_3)OH$ or $CH(CF_3)_2$;
$R^{E3}$ is H, $C_{1-6}$-alkyl, $C_{3-8}$-cycloalkyl or phenyl;
the groups stated under $R^{E1}$ and $R^{E2}$ are optionally linked to one another via a bond; the groups stated under $R^{E2}$ and $R^{E3}$ are also optionally linked to one another via a bond;

or

E is D-Asp, D-Glu, D-Lys, D-Orn, D-His, D-Dab, D-Dap or D-Arg;

G is

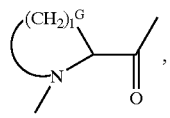

where
$l^G$ is 2, 3 or 4, and
where a $CH_2$ group of the ring is optionally replaced with $CHCH_3$; or

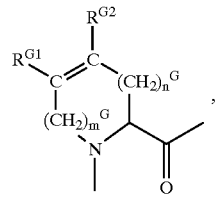

where
$m^G$ is 1;
$n^G$ is 0 or 1;
$R^{G1}$ is H;
$R^{G2}$ is H;

or

G is

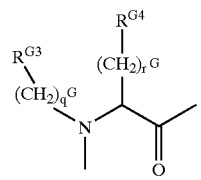

where
$q^G$ is 0 or 1;
$r^G$ is 0 or 1;
$R^{G3}$ is H, $C_1$–$C_6$-alkyl or $C_{3-8}$-cycloalkyl;
$R^{G4}$ is H, $C_1$–$C_6$-alkyl, $C_{3-8}$-cycloalkyl or phenyl;

K is
NH—$(CH_2)_{n^K}$—$Q^K$, where
$n^K$ is 1;
$Q^K$ is

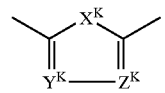

$X^K$ is O or S;
$Y^K$ is =CH— or =N—;
$Z^K$ is =CH— or =N—;

L is

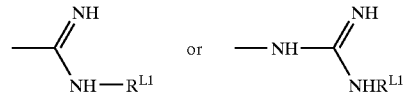

where
$R^{L1}$ is H, OH, CO—$C_{1-6}$-alkyl, $CO_2$—$C_{1-6}$-alkyl or $CO_2$—$C_{1-5}$-alkylaryl.

8. The compound claimed in claim 1, or a tautomer, a pharmacologically tolearable salt, or a prodrug thereof, where A is
H, $C_{1-6}$-alkyl, $C_{1-6}$-alkyl-$SO_2$, $R^{A1}OCO$, $R^{A2}R^{A3}NCO$, $R^{A4}OCONR^{A2}$,
$R^{A4}CONR^{A2}$, $R^{A1}O$, phenoxy, $R^{A2}R^{A3}N$, HO—$SO_2$, $R^{A2}R^{A3}N$—$SO_2$, Cl, Br, F, tetrazolyl, $H_2O_3P$, $NO_2$, $R^{A1}$—N(OH)—CO or $R^{A1}R^{A2}NCONR^{A3}$,
where
$R^{A1}$ is H, $C_{1-12}$-alkyl, $C_{3-8}$-cycloalkyl, $C_{1-3}$-alkyl-$C_{3-8}$-cycloalkyl or $C_{1-3}$-alkylaryl;

$R^{A2}$ is H, $C_{1-6}$-alkyl, $C_{0-3}$-alkylaryl or $C_{0-3}$-alkylheteroaryl;

$R^{A3}$ is H, $C_{1-6}$-alkyl or $C_{0-3}$-alkylaryl $R^{A4}$ is $C_{1-6}$-alkyl or $C_{1-3}$-alkylaryl;

where each aryl is optionally substituted with up to 2 identical or different radicals from the group consisting of F, Cl, Br, $OCH_3$, $CH_3$, $CF_3$ and $NO_2$, B is —$(CH_2)_{p^B}$—$L^B$—$(CH_2)_{m^B}$—, where $l^B$ is 0 or 1;

$m^B$ is 0, 1 or 2;

$L^B$ is

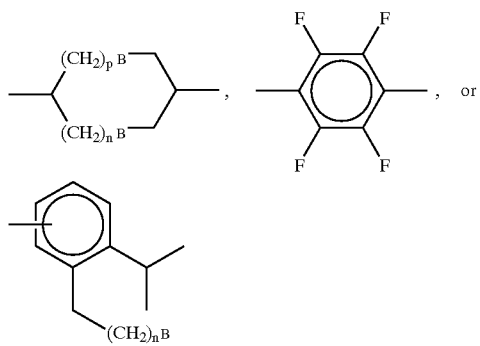, or where a phenyl ring is optionally fused to the above-mentioned ring systems, which phenyl ring is optionally substituted with up to 2 identical or different radicals selected from the group consisting of $CH_3$, $CF_3$, Br, Cl and F, or is optionally substituted by $R^8OOC$—;

where $R^8$ is H or $C_{1-3}$-alkyl;

$n^B$ is 0 or 1;

$p^B$ is 0 or 1;

or

B is -1-adamantyl-$CH_2$—, -2-adamantyl-$CH_2$—, or

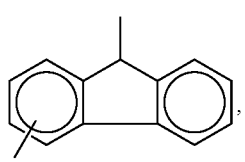, or

B is —$(CH_2)_{p^B}$—$L^{B1}$—$M^B$—$L^{B2}$—$(CH_2)_{m^B}$—, where $l^B$ and $m^B$ have the abovementioned meanings and the two groups $L^{B1}$ and $L^{B2}$, independently of one another, are the following radicals:

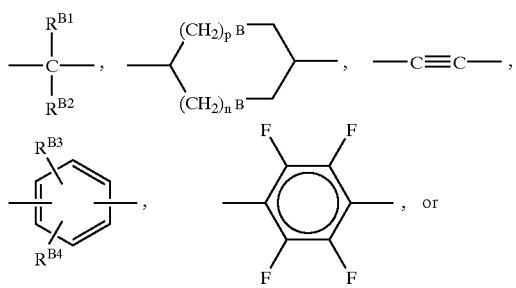

-continued

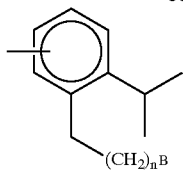

where a phenyl ring is optionally fused to the above-mentioned ring systems;

where $n^B$ is 1;

$p^B$ is 0 or 1;

$R^{B1}$ is H, $C_{0-3}$-alkylaryl, $C_{0-3}$-alkylheteroaryl, $C_{0-3}$-alkyl-$C_{3-8}$-cycloalkyl, OH or $OCH_3$, or in the case of $L^{B2}$, $R^{B1}$ is additionally H or $C_{1-6}$-alkyl;

$R^{B2}$ is H, $C_{1-6}$-alkyl, $C_{0-3}$-alkylaryl or $C_{0-3}$-alkylheteroaryl;

$R^{B3}$ is H, $C_{1-6}$-alkyl, $R^{B6}$—O, F, Cl, Br, $NO_2$ or $CF_3$;

$R^{B4}$ is H, $C_{1-6}$-alkyl, $R^{B6}$—O, Cl, Br, F or $CF_3$; $R^{B6}$ is H, $C_{1-6}$-alkyl;

$R^{B1}$ and $R^{B2}$ are optionally bonded together;

$M^B$ is a single bond, O, S, $CH_2$, $CH_2$—$CH_2$, $CH_2$—O, O—$CH_2$, $CH_2$—S, S—$CH_2$, CO or $SO_2$;

or

A—B together are 2-pyridyl-$CH_2$—, 2-benzothienyl-,

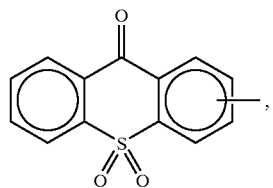, or

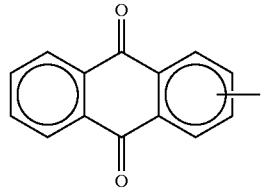

D is a single bond, CO or $SO_2$;

or

B—D together are

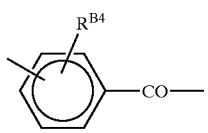

E is

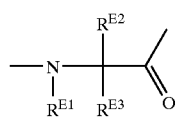

where
$R^{E1}$ is H;
$R^{E2}$ is H, $C_{1-6}$-alkyl, $C_{3-8}$-cycloalkyl, phenyl, pyridyl, thienyl, furyl, imidazolyl, tetrahydropyranyl, tetrahydrothiopyranyl, $CH(CH_3)OH$ or $CH(CF_3)_2$;
$R^{E3}$ is H;
the groups stated under $R^{E1}$ and $R^{E2}$ are optionally linked to one another via a bond;

or

E is D-Lys, D-Orn, D-Dab, D-Dap or D-Arg;
G is

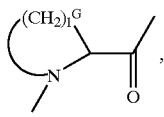

where
$l^G$ is 2 or 3, and
where a $CH_2$ group of the ring is optionally replaced with $CHCH_3$; or

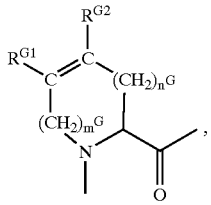

where
$m^G$ is 1;
$n^G$ is 0;
$R^{G1}$ is H;
$R^{G2}$ is H;
K is
NH—$(CH_2)_{n^K}$—$Q^K$, where
$n^K$ is 1;
$Q^K$ is

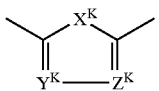

$X^K$ is S;
$Y^K$ is =CH— or =N—;
$Z^K$ is =CH— or =N—;

L is

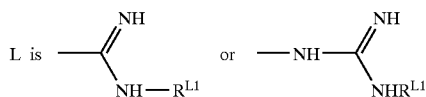

where
$R^{L1}$ is H or OH.

9. The compound claimed in claim 1, or a tautomer, a pharmacologically tolerable salt, or a prodrug thereof, where A is
H, $C_{1-6}$-alkyl, $C_{1-6}$-alkyl-$SO_2$, $R^{A1}OCO$, $R^{A2}R^{A3}NCO$, $R^{A4}OCONR^{A2}$,
$R^{A4}CONR^{A2}$, $R^{A1}O$, phenoxy, $R^{A2}R^{A3}N$, HO—$SO_2$, $R^{A2}R^{A3}N$—$SO_2$, Cl, Br, F, tetrazolyl, $H_2O_3P$, $NO_2$, $R^{A1}$—N(OH)—CO— or $R^{A1}R^{A2}NCONR^{A3}$, where
$R^{A1}$ is H, $C_{1-12}$-alkyl, $C_{3-8}$-cycloalkyl, $C_{1-3}$-alkyl-$C_{3-8}$-cycloalkyl or $C_{1-3}$-alkylaryl;
$R^{A2}$ is H, $C_{1-6}$-alkyl, $C_{0-3}$-alkylaryl or $C_{0-3}$-alkylheteroaryl;
$R^{A3}$ is H, $C_{1-6}$-alkyl or $C_{0-3}$-alkylaryl;
$R^{A4}$ is $C_{1-6}$-alkyl or $C_{1-3}$-alkylaryl;
where each aryl is optionally substituted with up to 2 identical or different substituents selected from the group consisting of F, Cl, Br, $CH_3$, $CF_3$, $OCH_3$ and $NO_2$, B is
—$(CH_2)_{l^B}$—$L^B$—$(CH_2)_{m^B}$—, where
$l^B$ is 0 or 1;
$m^B$ is 0, 1 or 2;

$L^B$ is

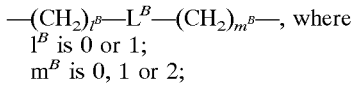

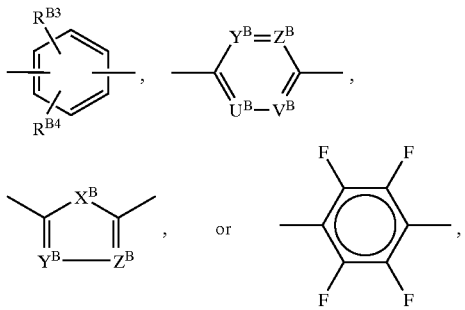

where a phenyl ring is optionally fused to the above-mentioned ring systems;
$R^{B3}$ is H, $C_{1-6}$-alkyl, aryl, $R^{B5}OCO$, $R^{B6}$—O, F, Cl, Br, $NO_2$ or $CF_3$;
$R^{B4}$ is H, $C_{1-6}$-alkyl, $R^{B6}$—O, Cl, Br, F or $CF_3$;
$R^{B5}$ is H, $C_{1-6}$-alkyl or $C_{1-3}$-alkylaryl;
$R^{B6}$ is H or $C_{1-6}$-alkyl;
$X^B$ is O or S;
$Y^B$ is =CH— or =N—;
$Z^B$ is =CH— or =N—;
$U^B$ is =CH— or =N—;
$V^B$ is =CH— or =N—;

or

B is

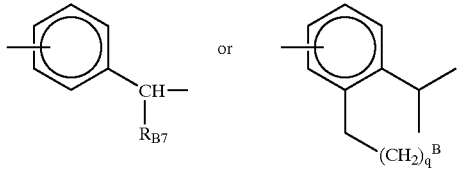

$q^B$ is 0, 1, or 2;
$R^{B7}$ is $C_{1-6}$-alkyl or $C_{3-8}$-cycloalkyl;

or

A—B together are

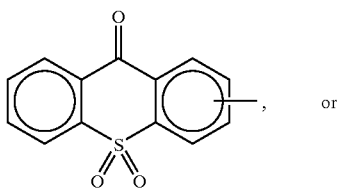

or

-continued

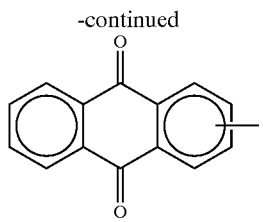

D is a single bond;
E is

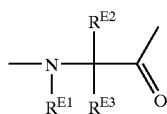

where
$R^{E1}$ is H;
$R^{E2}$ is H, $C_{1-6}$-alkyl, $C_{3-8}$-cycloalkyl, phenyl, pyridyl, furyl, thienyl, imidazolyl, tetrahydropyranyl or tetrahydrothiopyranyl, where the abovementioned radicals are optionally substituted with up to three identical or different substituents selected from the group consisting of O—$C_{1-6}$-alkyl and F; or is $CH(CH_3)OH$ or $CH(CF_3)_2$;
$R^{E3}$ is H;
the groups stated under $R^{E1}$ and $R^{E2}$ are optionally linked to one another via a bond;

or

E is D-Lys, D-Orn, D-Dab, D-Dap or D-Arg;
G is

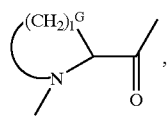

where
$l^G$ is 2 or 3, and
where a $CH_2$ group of the ring is optionally replaced with $CHCH_3$; or

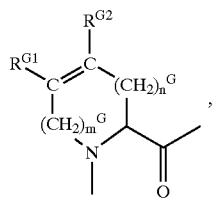

where
$m^G$ is 1;
$n^G$ is 0;
$R^{G1}$ is H;
$R^{G2}$ is H;
K is
NH—$(CH_2)_{n^K}$—$Q^N$, where
$n^K$ is 1;
$Q^K$ is

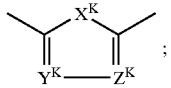

$X^K$ is O or S;
$Y^K$ is =CH— or =N—;
$Z^K$ is =CH— or =N—;
L is

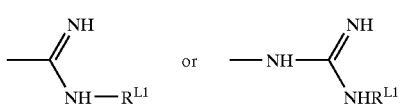

where
$R^{L1}$ is —H or —OH.

10. A composition comprising a compound according to claim 1 and a pharmaceutically acceptable carrier.

11. A method of inhibiting C1s comprising contacting C1s with an effective amount of a compound according to claim 1.

12. A method of inhibiting C1s comprising administering an effective amount of a compound according to claim 1 to a patient in need thereof.

13. A method of inhibiting C1r comprising contacting C1r with an effective amount of a compound according to claim 1.

14. A method of inhibiting C1r comprising administering an effective amount of a compound according to claim 1 to a patient in need thereof.

15. A method of inhibiting complement activation comprising administering an effective amount of a compound according to claim 1 to a patient in need thereof.

16. A method of inhibiting formation of complement factor C5a comprising administering an effective amount of a compound according to claim 1 to a patient in need thereof.

* * * * *